United States Patent

Seno et al.

[11] Patent Number: 6,147,100
[45] Date of Patent: Nov. 14, 2000

[54] PYRROLIDINE DERIVATIVES HAVING PHOSPHOLIPASE A$_2$ INHIBITORY ACTIVITY

[75] Inventors: Kaoru Seno, Hyogo; Mitsuaki Ohtani; Fumihiko Watanabe, both of Nara, all of Japan

[73] Assignee: Shionogi & Co., Ltd., Osaka, Japan

[21] Appl. No.: 09/355,008

[22] PCT Filed: Jan. 27, 1998

[86] PCT No.: PCT/JP98/00307

§ 371 Date: Jul. 22, 1999

§ 102(e) Date: Jul. 22, 1999

[87] PCT Pub. No.: WO98/33797

PCT Pub. Date: Jun. 8, 1998

[30] Foreign Application Priority Data

Jan. 31, 1997 [JP] Japan ................................. 9-17962

[51] Int. Cl.[7] ..................... A61K 31/426; C07D 417/12
[52] U.S. Cl. ................................... 514/369; 548/183
[58] Field of Search ........................... 548/183; 514/369

[56] References Cited

U.S. PATENT DOCUMENTS

| | | | |
|---|---|---|---|
| 5,317,016 | 5/1994 | Nishitani et al. | 514/210 |
| 5,955,616 | 9/1999 | Ohtani | 514/369 |

FOREIGN PATENT DOCUMENTS

| | | |
|---|---|---|
| 0 528 734 | 2/1993 | European Pat. Off. . |
| 0 675 114 | 10/1995 | European Pat. Off. . |
| 0 780 389 | 6/1997 | European Pat. Off. . |
| 0 848 004 | 6/1998 | European Pat. Off. . |
| 5-306224 | 11/1993 | Japan . |
| 7-138258 | 5/1995 | Japan . |
| 97/41119 | 11/1997 | WIPO . |
| 97/41120 | 11/1997 | WIPO . |
| 97/41121 | 11/1997 | WIPO . |

OTHER PUBLICATIONS

F.J. Allan et al., "The Condensation of Rhodanine With Aromatic Dialdehydes and Some Related Compounds", Canadian J. Chem., vol. 36, 1958, pp. 1579–1583.

G.L. Baker et al., "Transition–Metal–Catalzyed . . . via Catalytic Hydrogenation", J. Org. Chem, vol. 46, 1981, pp. 2954–2960.

J.M. Dayer et al., "Cachectin/Tumor Necrosis Factor Stimulates Collagenase . . . and Dermal Fibroblasts", J. Exp. Med., vol. 162, Dec. 1985, pp. 2163–2168.

D.L. Flynn et al., "A mild Two–Step Method for the Hydrolysis/Methanolysis of Secondary Amides and Lactams", J. Org. Chem., vol. 48, 1983, pp. 2424–2426.

C. Pedregal et al., "Highly Chemoselective Reduction of N–Boc Protected Lactams", Tetrahedron Letters, vol. 35, No. 13, 1994, pp. 2053–2056.

J. Ezauerra et al., "Stereoselective Reactions of Lithium Enolates Derived from N–BOC Protected Pyroglutamic Esters", Tetrahedron Letters, vol. 49, No. 38, 1993, pp. 8665–8678.

R.M. Kramer et al., "The Ca$^{2+}$–sensitive Cytosolic Phospholipase . . . Monoblast U937 Cells", J. Biol. Chem., vol. 266, No. 8, Mar. 15, 1991, pp. 5268–5272.

V.P. Dole et al., "Microdetermination of Long–chain Fatty Acids in Plasma and Tissues", J. Biol. Chem., vol. 235, No. 9, 1960, pp. 2595–2599.

Oyo Mitsunobu, "The Use of Diethy Azodicarboxylate and Triphenylphosphine in Synthesis and Transformation of Natural Products",Synthesis, 1981, pp. 1–28.

A. Zask et al., "Synthesis of 3–Mercapto–2(5H)–furanones via Reaction of Dilithio–2,4–thiazolidinedione with α–Halo Ketones" Tetrahedron Letters, vol. 34, No. 17, 1993, pp. 2719–2722.

Primary Examiner—Robert Gerstl
Attorney, Agent, or Firm—Foley & Lardner

[57] ABSTRACT

A compound represented by the formula (I):

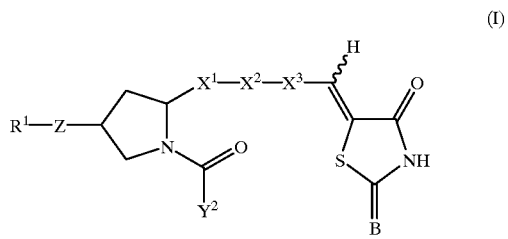

wherein, for example, $R^1$ is optionally substituted aralkyl, Z is nitrogen atom which optionally substituted with alkyl, $X^1$ is —CH$_2$NHCO—, $X^2$ is phenylene, $X^3$ is a bond, $Y^2$ is optionally substituted aryl, B is oxygen atom, its pharmaceutically acceptable salt, or hydrate thereof and a pharmaceutical composition which contains them as an active ingredient.

23 Claims, No Drawings

PYRROLIDINE DERIVATIVES HAVING PHOSPHOLIPASE $A_2$ INHIBITORY ACTIVITY

TECHNICAL FIELD

The present invention relates to novel pyrrolidine derivatives having activity of inhibiting cytosolic phospholipase $A_2$, and the pharmaceutical composition for inhibiting the cytosolic phospholipase $A_2$ which contains a novel pyrrolidine derivative as an active ingredient.

BACKGROUND ART

Phospholipase $A_2$ ($PLA_2$) is a protein capable of specifically hydrolyzing the ester bond at the sn-2-position of phospholipids, and includes cytosolic $PLA_2$ ($cPLA_2$) and secretory type $PLA_2$ ($sPLA_2$) which are clearly distinguishable from each other. It is known that $cPLA_2$ can selectively hydrolyze phospholipids which is esterified with arachidonic acid the 2-position. Accordingly, the prevention of $cPLA_2$ activity would inhibit the release of arachidonic acid from phospholipids. Arachidonic acid is a precursor of prostaglandins and leulotrienes which are endobiotic substances known to be participating in the onset of inflammation. These inflammation inducers are produced through a series of processes, so called, "arachidonate cascade". Therefore, it is assumed that the inhibition of the release of arachidonic acid would suppress the production of various substances involved in inflammation and is useful for the prevention or treatment of inflammatory diseases. Examples of such diseases include rheumatoid arthritis, asthma, inflammatory bowel diseases, injury due to ischemic reperfusion, allergic rhinitis, psoriasis, and the like. The compounds having thiazolidinedion and pyrrolidine rings are disclosed in WO97/41120, WO97/41121, EP-780389-A1, JP 7-138258 (A1), and EP-528734-A1. However, there is no description about the cytosolic phospholipase $A_2$ inhibitory activity therein. WO97/05135 discloses the cytosolic phospholipase $A_2$ inhibitor but not compounds of the present invention.

DISCLOSURE OF INVENTION

The present inventors have intensively studied for developing specific $cPLA_2$ inhibitors and found that certain kinds of novel pyrrolidine derivatives possess potent $cPLA_2$ inhibitory activity. Thus, the present invention provides I) a compound of the formula (I):

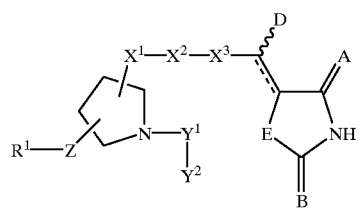

(I)

wherein $R^1$ is hydrogen atom, lower alkyl, optionally substituted aryl, aryl fused with a non-aromatic hydrocarbon ring or a non-aromatic heterocyclic ring, optionally substituted aralkyl, optionally substituted arylcarbonyl, or optionally substituted heteroaryl; Z is —S—, —SO—, —O—, —OCH$_2$—, —CONH—, CONHCH$_2$—, —N(R$^{16}$)— (wherein R$^{16}$ is hydrogen atom, alkyl, or aralkyl), or a bond; $X^1$ is —(CH$_2$)$_q$—CO— (wherein q is an integer of 0 to 3), —(CH$_2$)$_r$—CO—N(R$^{17}$)— (wherein R$^{17}$ is hydrogen atom or lower alkyl, and r is an integer of 0 to 3), —CH$_2$NSO$_2$—, —(CH$_2$)$_s$—N(R$^{18}$)—CO— (wherein R$^{18}$ is hydrogen atom or lower alkyl, s is an integer of 0 to 3), —CH$_2$NHCOCH$_2$O—, —CH$_2$N(R$^{19}$)COCH=CH— (wherein R$^{19}$ is hydrogen atom or lower alkyl), —(CH$_2$NHCS—, —CH$_2$O—, —OCH$_2$—, —CH$_2$OCH$_2$—, —CH$_2$—N(R$^{20}$)—CH$_2$— (wherein R$^{20}$ is hydrogen atom, lower alkyl, or acyl), alkylene, alkenylene, or a bond; $X^2$ is optionally substituted arylene, optionally substituted heteroarylene, heterocyclediyl, —C≡C—, or a bond; $X^3$ is alkylene, alkenylene, or a bond; A, B, and E are each independently oxygen atom or sulfur atom; D is hydrogen atom or hydroxy lower alkyl; $Y^1$ is —(CH$_2$)$_m$CO—, —(CH$_2$)$_m$CONH—, —(CH$_2$)$_m$CSNH—, —(CH$_2$)$_m$SO$_2$—, —(CH$_2$)$_m$COO—, —(CH$_2$)$_n$NHCO—, —(CH$_2$)$_n$NHSO$_2$—, or a bond; m is an integer of 0 to 3; n is an integer of 1 to 3; $Y^2$ is a substituent represented by the formula:

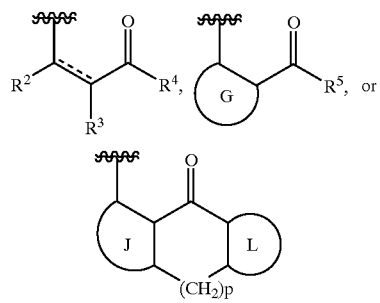

wherein $R^2$ and $R^3$ are both hydrogen atoms or one is optionally substituted aryl, optionally substituted heteroaryl, or optionally substituted cycloalkyl, and the other is hydrogen atom or lower alkyl; $R^4$, $R^5$, G ring, J ring, and L ring are each independently optionally substituted aryl, optionally substituted heteroaryl, optionally substituted cycloalkyl, or cycloalkenyl; a broken line (— — —) represents the presence or absence of a bond; and p is an integer of 0 to 2;

a broken line (— — —) represents the presence or absence of a bond; a wavy line (~) represents cis or trans configuration of D to E; provided that $X^1$ is alkylene and $X^2$ and $X^3$ are both bonds when the carbon atom adjacent, to D and the carbon atom consisting the ring are linked by a single bond, and $Y^1$ is not a bond when $X^1$ is —CH$_2$O—, its pharmaceutically acceptable salt, or hydrate thereof.

Mentioned in more detail, the invention relates to II) a compound represented by formula (II):

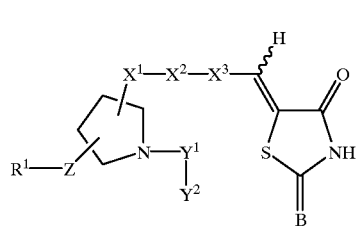

(II)

wherein $R^1$, Z, $X^1$, $X^2$, $X^3$, $Y^1$, $Y^2$, and B are as defined above, a wavy line represents cis or trans configuration of hydrogen atom to sulfur atom, provided that $Y^1$ is not a bond when $X^1$ is —CH$_2$O—, its pharmaceutically acceptable salt, or hydrate thereof.

III) A compound represented by the formula (III):

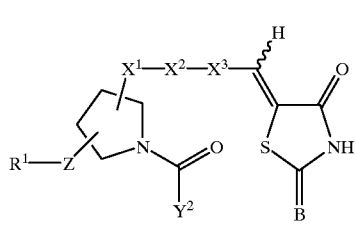
(III)

wherein $R^1$, Z, $X^1$, $X^2$, $X^3$, $Y^2$, B, and a wavy line are as defined above, its pharmaceutically acceptable salt, or hydrate thereof.

IV) A compound represented by the formula (IV):

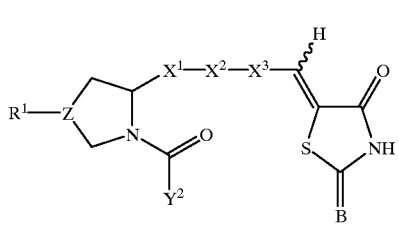
(IV)

wherein $R^1$, Z, $X^1$, $X^2$, $X^3$, $Y^2$, B, and a wavy line are as defined above its pharmaceutically acceptable salt, or hydrate thereof.

V) A compound represented by the formula (V):

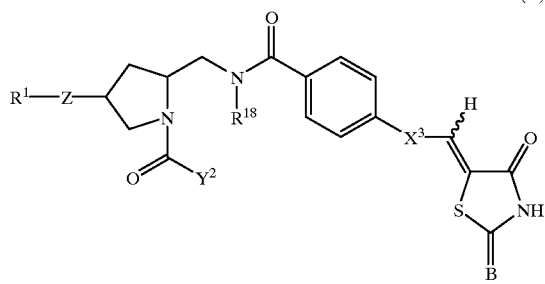
(V)

wherein $R^1$, Z, $R^{18}$, $X^3$, $Y^2$, B, and a wavy line are as defined above, its pharmaceutically acceptable salt, or hydrate thereof.

VI) A compound represented by the formula (VI):

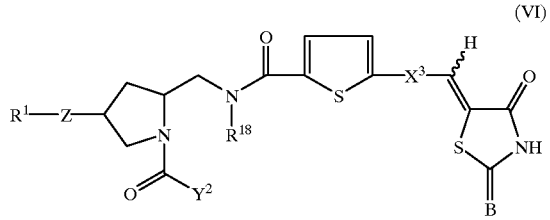
(VI)

wherein $R^1$, Z, $R^{18}$, $X^3$, $Y^2$, B, and a wavy line are as defined above, its pharmaceutically acceptable salt, or hydrate thereof.

VII) A compound represented by the formula (VII):

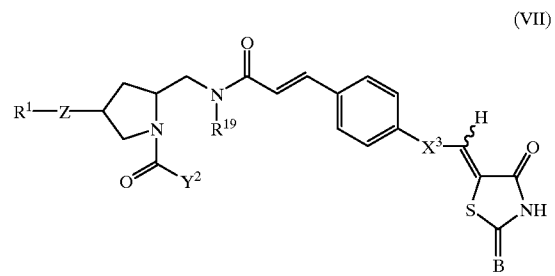
(VII)

wherein $R^1$, Z, $R^{19}$, $X^3$, $Y^2$, B, and a wavy line are as defined above, its pharmaceutically acceptable salt, or hydrate thereof.

VIII) A compound represented by the formula (VIII):

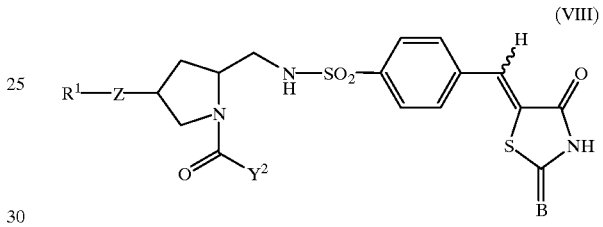
(VIII)

wherein $R^1$, Z, $Y^2$, B, and a wavy line are as defined above, its pharmaceutically acceptable salt, or hydrate thereof.

IX) A compound represented by the formula (IX):

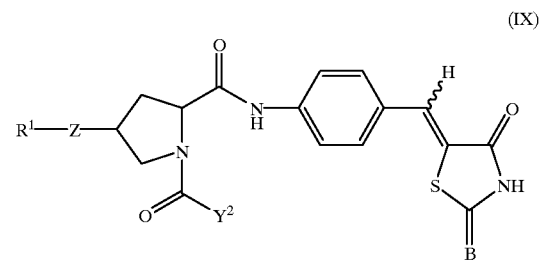
(IX)

wherein $R^1$, Z, $Y^2$, B, and a wavy line are as defined above, its pharmaceutically acceptable salt, or hydrate thereof.

X) A compound represented by the formula (X):

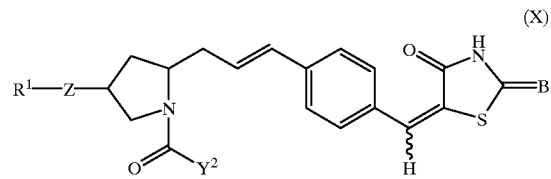
(X)

wherein $R^1$, Z, $Y^2$, B, and a wavy line are as defined above, its pharmaceutically acceptable salt, or hydrate thereof.

XI) A compound represented by the formula (I):

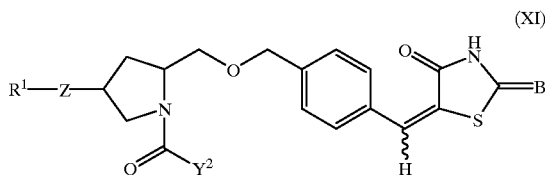

(XI)

wherein $R^1$, Z, $Y^2$, B, and a wavy line are as defined above, its pharmaceutically acceptable salt, or hydrate thereof.

XII) The compound of any one of I) to III), wherein Z is —$N(R^{16})$—, its pharmaceutically acceptable salt, or hydrate thereof.

XIII) The compound of any one of V) to VII), wherein $R^{18}$ is hydrogen atom and $X^3$ is a bond, its pharmaceutically acceptable salt, or hydrate thereof.

XIV) The compound of any one of I) to XIII), wherein $R^1$ is optionally substituted aryl, aryl fused with a non-aromatic hydrocarbon ring or a non-aromatic heterocyclic ring, or optionally substituted aralkyl, its pharmaceutically acceptable salt, or hydrate thereof.

XV) The compound of any one of I) to XIV), wherein $Y^2$ is a substituent represented by the formula:

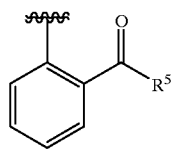

wherein $R^5$ is optionally substituted aryl, its pharmaceutically acceptable salt, or hydrate thereof.

XVI) A compound represented by the formula (I'):

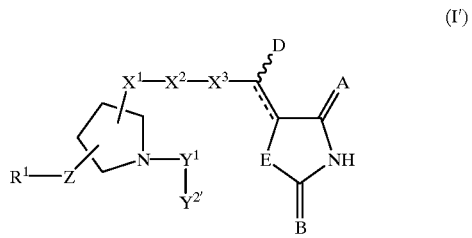

(I')

wherein Z is —$N(R^{16})$—, $Y^{2'}$ is optionally substituted aryl, and $R^1$, $X^1$, $X^2$, $X^3$, $Y^1$, A, B, a wavy line, and a broken line are as defined above, its pharmaceutically acceptable salt, or hydrate thereof.

XVII) A pharmaceutical composition which contains a compound of any one of I) to XVI) as an active ingredient.

XVIII) A composition for inhibiting phospholipase $A_2$ which contains a compound of any one of I) to XVI) as an active ingredient.

XIX) A composition for inhibiting the production of arachidonic acid which contains a compound of any one of I) to XVI) as an active ingredient.

XX) A composition for inhibiting the production of prostaglandin $E_2$ which contains a compound of any one of I) to XVI) as an active ingredient.

XXI) A composition for inhibiting the production of leukotriene $C_4$ which contains a compound of any one of I) to XVI) as an active ingredient.

All of the compounds of the present invention have superior phospholipase $A_2$ inhibitory activity and its accompanied activity of inhibiting the production of the compounds which are produced in the arachidonate cascade such as prostaglandin $E_2$ and the like. Particularly, the following compounds are preferable.

i) A compound represented by the formula (i):

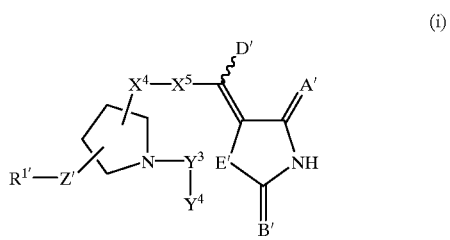

(i)

wherein $R^{1'}$ is hydrogen atom, optionally substituted lower alkyl, optionally substituted aryl, or optionally substituted aralkyl; Z' is —S—, —SO—, —O—, —NH—, —CONH—, —CONHCH$_2$—, or a bond; $X^4$ is —CO—, —CONH—, —CH$_2$NHSO$_2$—, —CH$_2$NHCO—, —CH$_2$NHCS—, —CH$_2$O—, —OCH$_2$—, —CH$_2$OCH$_2$—, alkylene, alkenylene, or a bond; $X^5$ is optionally substituted arylene, optionally substituted indolediyl, or a bond; A', B', and E' are each independently oxygen atom or sulfur atom; D' is hydrogen atom or hydroxy lower alkyl; $Y^3$ is —(CH$_2$)$_m$'CO—, —(CH$_2$)$_m$'CONH—, —(CH$_2$)$_m$'CSNH—, —(CH$_2$)$_m$'SO$_2$, —(CH$_2$)$_m$'COO—, —(CH$_2$)$_n$'NHCO—, —(CH$_2$)$_n$'NHSO$_2$—, or a bond, m' is an integer of 0 to 3, n' is an integer of 1 to 3; $Y^4$ is a substituent represented by the formula:

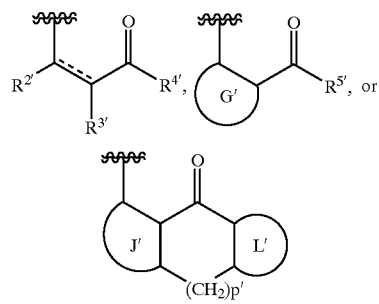

wherein $R^{2'}$ and $R^{3'}$ are both hydrogen atoms or one is optionally substituted aryl, optionally substituted heteroaryl, or optionally substituted cycloalkyl and the other is hydrogen atom or lower alkyl; $R^{4'}$, $R^{5'}$, G' ring, J' ring, and L' ring are each independently optionally substituted aryl, optionally substituted heteroaryl, optionally substituted cycloalkyl, or cycloalkenyl; a broken line (— — —) represents the presence or absence of a bond; and p' is an integer of 0 to 2; a wavy line (~) cis or trans configuration of D' to E', its pharmaceutically acceptable salt, or hydrate thereof.

ii) The following compounds represented by the formula (IV), its pharmaceutically acceptable salt, or hydrate thereof; when $R^A$ is optionally substituted aralkyl or optionally substituted aryl, $R^B$ is optionally substituted aralkyl, and $R^C$ is optionally substituted aryl as $R^1$; $R^D$ is —O—, —OCH$_2$—, —NH—, —N($R^{16}$)— wherein $R^{16}$ is hydrogen atom, alkyl or benzyl, —S—, or a bond, $R^E$ is —O— or —N($R^{16}$)— wherein $R^{16}$ is alkyl or benzyl, and $R^F$ is —O— or —N($R^{16}$)— wherein $R^{16}$ is alkyl as Z; $R^G$ is a substituent represented by the formula:

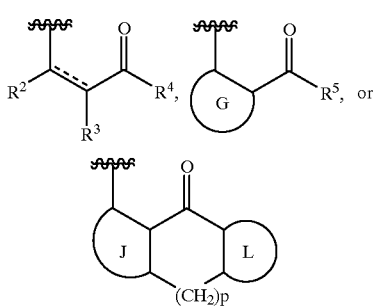

wherein $R^2$, $R^3$, $R^4$, $R^5$, G ring, J ring, L ring, p, and a broken line are as defined above, $R^H$ is a substituent represented by the formula:

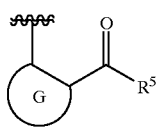

wherein $R^5$ and G are as defined above, and $R^I$ is a substituent represented by the formula:

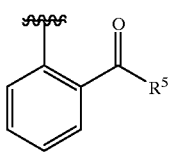

wherein $R^5$ is as defined above as $Y^2$; $R^J$ is —$CH_2N(R^{18})$CO— wherein $R^{18}$ is hydrogen atom or lower alkyl, —$CH_2N(R^{18})COCH=CH$— wherein $R^{18}$ is hydrogen atom or lower alkyl, —$CH_2NHSO_2$—, —CONH—, —$CH_2CH=CH$—, or —$CH_2OCH_2$— as $X^1$; $R^K$ is 1,4-phenylene or 2,5-thiophendiyl, and $R^L$ is 1,4-phenylene as $X^2$; $R^M$ is a bond or ethenylenyl, and $R^N$ is a bond as $X^3$; B is oxygen atom or sulfur atom; and a wavy line is as defined above, the compounds represented by the following combinations are preferred; $(R^1, Z, Y^2, X^1, X^2, X^3)$=$(R^A, R^D, R^G, R^J, R^K, R^M)$, $(R^A, R^D, R^G, R^J, R^K, R^N)$, $(R^A, R^D, R^G, R^J, R^L, R^M)$, $(R^A, R^D, R^G, R^J, R^L, R^N)$, $(R^A, R^D, R^H, R^J, R^K, R^M)$, $(R^A, R^D, R^H, R^J, R^K, R^N)$, $(R^A, R^D, R^H, R^J, R^L, R^M)$, $(R^A, R^D, R^H, R^J, R^L, R^N)$, $(R^A, R^D, R^I, R^J, R^K, R^M)$, $(R^A, R^D, R^I, R^J, R^K, R^N)$, $(R^A, R^D, R^I, R^J, R^L, R^M)$, $(R^A, R^D, R^I, R^J, R^L, R^N)$, $(R^A, R^E, R^G, R^J, R^K, R^M)$, $(R^A, R^E, R^G, R^J, R^K, R^N)$, $(R^A, R^E, R^G, R^J, R^L, R^M)$, $(R^A, R^E, R^G, R^J, R^L, R^N)$, $(R^A, R^E, R^H, R^J, R^K, R^M)$, $(R^A, R^E, R^H, R^J, R^K, R^N)$, $(R^A, R^E, R^H, R^J, R^L, R^M)$, $(R^A, R^E, R^H, R^J, R^L, R^N)$, $(R^A, R^E, R^I, R^J, R^K, R^M)$, $(R^A, R^E, R^I, R^J, R^K, R^N)$, $(R^A, R^E, R^I, R^J, R^L, R^M)$, $(R^A, R^E, R^I, R^J, R^L, R^N)$, $(R^A, R^F, R^G, R^J, R^K, R^M)$, $(R^A, R^F, R^G, R^J, R^K, R^N)$, $(R^A, R^F, R^G, R^J, R^L, R^M)$, $(R^A, R^F, R^G, R^J, R^L, R^N)$, $(R^A, R^F, R^H, R^J, R^K, R^M)$, $(R^A, R^F, R^H, R^J, R^K, R^N)$, $(R^A, R^F, R^H, R^J, R^L, R^M)$, $(R^A, R^F, R^H, R^J, R^L, R^N)$, $(R^A, R^F, R^I, R^J, R^K, R^M)$, $(R^A, R^F, R^I, R^J, R^K, R^N)$, $(R^A, R^F, R^I, R^J, R^L, R^M)$, $(R^A, R^F, R^I, R^J, R^L, R^N)$, $(R^B, R^D, R^G, R^J, R^K, R^M)$, $(R^B, R^D, R^G, R^J, R^K, R^N)$, $(R^B, R^D, R^G, R^J, R^L, R^M)$, $(R^B, R^D, R^G, R^J, R^L, R^N)$, $(R^B, R^D, R^H, R^J, R^K, R^M)$, $(R^B, R^D, R^H, R^J, R^K, R^N)$, $(R^B, R^D, R^H, R^J, R^L, R^M)$, $(R^B, R^D, R^H, R^J, R^L, R^N)$, $(R^B, R^D, R^I, R^J, R^K, R^M)$, $(R^B, R^D, R^I, R^J, R^K, R^N)$, $(R^B, R^D, R^I, R^J, R^L, R^M)$, $(R^B, R^D, R^I, R^J, R^L, R^N)$, $(R^B, R^E, R^G, R^J, R^K, R^M)$, $(R^B, R^E, R^G, R^J, R^K, R^N)$, $(R^B, R^E, R^G, R^J, R^L, R^M)$, $(R^B, R^E, R^G, R^J, R^L, R^N)$, $(R^B, R^E, R^H, R^J, R^K, R^M)$, $(R^B, R^E, R^H, R^J, R^K, R^N)$, $(R^B, R^E, R^H, R^J, R^L, R^M)$, $(R^B, R^E, R^H, R^J, R^L, R^N)$, $(R^B, R^E, R^I, R^J, R^K, R^M)$, $(R^B, R^E, R^I, R^J, R^K, R^N)$, $(R^B, R^E, R^I, R^J, R^L, R^M)$, $(R^B, R^E, R^I, R^J, R^L, R^N)$, $(R^B, R^F, R^G, R^J, R^K, R^M)$, $(R^B, R^F, R^G, R^J, R^K, R^N)$, $(R^B, R^F, R^G, R^J, R^L, R^M)$, $(R^B, R^F, R^G, R^J, R^L, R^N)$, $(R^B, R^F, R^H, R^J, R^K, R^M)$, $(R^B, R^F, R^H, R^J, R^K, R^N)$, $(R^B, R^F, R^H, R^J, R^L, R^M)$, $(R^B, R^F, R^H, R^J, R^L, R^N)$, $(R^B, R^F, R^I, R^J, R^K, R^M)$, $(R^B, R^F, R^I, R^J, R^K, R^N)$, $(R^B, R^F, R^I, R^J, R^L, R^M)$, $(R^B, R^F, R^I, R^J, R^L, R^N)$, $(R^C, R^D, R^G, R^J, R^K, R^M)$, $(R^C, R^D, R^G, R^J, R^K, R^N)$, $(R^C, R^D, R^G, R^J, R^L, R^M)$, $(R^C, R^D, R^G, R^J, R^L, R^N)$, $(R^C, R^D, R^H, R^J, R^K, R^M)$, $(R^C, R^D, R^H, R^J, R^K, R^N)$, $(R^C, R^D, R^H, R^J, R^L, R^M)$, $(R^C, R^D, R^H, R^J, R^L, R^N)$, $(R^C, R^D, R^I, R^J, R^K, R^M)$, $(R^C, R^D, R^I, R^J, R^K, R^N)$, $(R^C, R^D, R^I, R^J, R^L, R^M)$, $(R^C, R^D, R^I, R^J, R^L, R^N)$, $(R^C, R^E, R^G, R^J, R^K, R^M)$, $(R^C, R^E, R^G, R^J, R^K, R^N)$, $(R^C, R^E, R^G, R^J, R^L, R^M)$, $(R^C, R^E, R^G, R^J, R^L, R^N)$, $(R^C, R^E, R^H, R^J, R^K, R^M)$, $(R^C, R^E, R^H, R^J, R^K, R^N)$, $(R^C, R^E, R^H, R^J, R^L, R^M)$, $(R^C, R^E, R^H, R^J, R^L, R^N)$, $(R^C, R^E, R^I, R^J, R^K, R^M)$, $(R^C, R^E, R^I, R^J, R^K, R^N)$, $(R^C, R^E, R^I, R^J, R^L, R^M)$, $(R^C, R^E, R^I, R^J, R^L, R^N)$, $(R^C, R^F, R^G, R^J, R^K, R^M)$, $(R^C, R^F, R^G, R^J, R^K, R^N)$, $(R^C, R^F, R^G, R^J, R^L, R^M)$, $(R^C, R^F, R^G, R^J, R^L, R^N)$, $(R^C, R^F, R^H, R^J, R^K, R^M)$, $(R^C, R^F, R^H, R^J, R^K, R^N)$, $(R^C, R^F, R^H, R^J, R^L, R^M)$, $(R^C, R^F, R^H, R^J, R^L, R^N)$, $(R^C, R^F, R^I, R^J, R^K, R^M)$, $(R^C, R^F, R^I, R^J, R^K, R^N)$, $(R^C, R^F, R^I, R^J, R^L, R^M)$, and $(R^C, R^F, R^I, R^J, R^L, R^N)$.

The term "halogen" herein used means fluoro, chloro, bromo, and iodo.

The term "lower alkyl" herein used means $C_1$–$C_6$ straight or branched chain alkyl. Examples of the lower alkyl are methyl, ethyl, n-propyl, iso propyl, n-butyl, iso butyl, sec-butyl, tert-butyl, and the like.

Methyl, ethyl, n-propyl, and iso propyl are preferred as the lower alkyl for $R^1$, $R^2$, $R^3$, $R^{17}$, $R^{18}$, $R^{19}$, and $R^{20}$. Particularly, methyl is preferred.

The term "alkyl" for $R^{16}$ herein used means the above mentioned "lower alkyl" and "$C_3$–$C_8$ cycloalkyl lower alkyl". Examples of the alkyl are methyl, ethyl, iso propyl, iso butyl, iso pentyl, cyclopropylmethyl, and cyclobutylmethyl. Iso-propyl, iso butyl, iso pentyl, and cycloalkylmethyl are preferred.

The term "cycloalkyl" herein used means $C_3$–$C_7$ cycloalkyl. Examples of the cycloalkyl are cyclopropyl, cyclobutyl, cyclopentyl, cyclohexyl, and cycloheptyl. Cyclopentyl, cyclohexyl, and cycloheptyl are preferred. Particularly, cyclopentyl and cyclohexyl are preferred.

The term "cycloalkenyl" herein used means $C_3$–$C_7$ cycloalkenyl having one or more unsaturated bond(s) in the ring. Examples of the cycloalkenyl are cyclopropenyl, cyclopentacdienyl, cyclohexenyl, and the like. Cyclohexenyl is preferred.

The term "a non-aromatic heterocyclic ring" herein used means a 5 to 7 membered non-aromatic ring which contains one or more hetero atoms selected from the group consisting of nitrogen, oxygen and sulfur atoms in the ring or a fused ring comprising of two or more of such rings. Examples of the non-aromatic heterocyclic ring are pyrrolidine, piperidine, piperazine, octahydroquinoline, tetrahydrofuran, tetrahydropyrane, and the like.

The term "aryl" herein used means a monocyclic or fused aromatic hydrocarbon ring or a group containing continuously bonded two or more of the monocyclic aromatic hydrocarbon rings. Examples of the aryl are phenyl, 1-naphthyl, 2-naphthyl, biphenylyl, indenyl, 2-p-terphenyl, 2-m-terphenyl, 2-o-terphenyl, anthryl, phenathryl, and the like. Phenyl, 1-naphthyl, 2-naphthyl, anthryl, phenanthryl, 2-biphenylyl, 3-biphenylyl, 4-biphenylyl, 2-p-terphenyl, 2-m-terphenyl, 2-o-terphenyl are preferred.

The term "aryl fused with a non-aromatic hydrocarbon ring" herein used means phenyl, 1-naphthyl, and 2-naphthyl which are fused with the above mentioned "cycloalkyl". Examples of it are indanyl, 1,2,3,4-tetrahydronaphthyl, acenaphtyl, and the like. Indanyl and 1,2,3,4-tetrahydronaphthyl are preferred.

The term "aryl fused with a non-aromatic heterocyclic ring" herein used means phenyl, 1-naphthyl, and 2-naphthyl which are fused with the above mentioned "a non-aromatic heterocyclic ring". Examples of it are indolyl, isoindolyl, 2,3,6,7-tetrohydro-1H, 5H-pyrido[3,2,1-ij]quinolyl, isochromanyl, chromanyl, and the lile. 2,3,6,7-tetrohydro-1H, 5H-pyrido[3,2,1-ij]quinolyl is preferred.

The term "aralkyl" herein used means the above mentioned "lower alkyl" substituted with the above mentioned "aryl". Examples of the aralkyl are benzyl, phenethyl, phenylpropyl, benzhydryl, naphthylmethyl, naphthylethyl, and the like. Benzyl, benzhydryl, phenethyl, and naphthylmethyl are preferred. Particularly, benzyl and benzhydryl are preferred.

The term "alkylene" herein used means a group derived from $C_1$–$C_5$ alkyl. Examples of the alkylene are methylene, ethylene, trimethylene, tetramethylene, and pentamethylene.

The term "alkenylene" herein used means a group derived from $C_2$–$C_4$ alkenyl. Examples of the alkenylene are vinylene, propenylene, and butenylene.

The term "arylene" herein used means a group derived from the above mentioned "aryl". Examples of the arylene are phenylene, naphthylene, and the like. Mentioned in more detail, it is exemplified by 1,2-phenylene, 1,3-phenylene, 1,4-phenylene, and the like.

The term "heteroarylene" herein used means a group derived from the "heteroaryl" mentioned below. Examples of the heteroarylene are thiophendiyl, furandiyl, and the like. Mentioned in more detail, it is exemplified by 2,5-thiophendiyl, 2,5-furandiyl, and the like.

The term "heterocyclediyl" herein used means a group derived from the above mentioned "a non-aromatic heterocyclic ring". Examples of the heterocyclediyl are pyrrolidinediyl, piperidinediyl, piperazinediyl, and the like. Mentioned in more detail, it is exemplified by 1,4-piperidinediyl and the like.

The term "hydroxy lower alkyl" herein used means the above mentioned "lower alkyl" substituted with hydroxy. Examples of the hydroxy lower alkyl are hydroxymethyl, hydroxyethyl, and the like.

The term "heteroaryl" herein used means a 5 to 6 membered aromatic mono heterocyclic group which contains one or more hetero atoms selected from the group consisting of nitrogen, oxygen and sulfur atoms in the ring or the heterocyclic group fused with phenyl. Examples of the heteroaryl are pyrrole, pyrrolyl, pyridyl, thienyl, furyl, benzofuryl, benzothienyl, indolyl, and the like. Pyridyl, thienyl, furyl, benzo[b]thienyl, benzo[b]furanyl, and indolyl are preferred.

The term "lower alkyloxy" herein used means alkyloxy of which alkyl part is the above mentioned "lower alkyl". Examples of the alkyloxy are methyloxy, ethyloxy, n-propyloxy, iso propyloxy, n-butyloxy, iso butyloxy, sec-butyloxy, t-butyloxy, and the like. Methyloxy, ethyloxy, and n-propyloxy are preferred.

The term "optionally substituted aryl" herein used for $R^1$ means the above mentioned "aryl" which may be substituted with one or more substituents selected from the group consisting of phenyl $C_2$–$C_4$ alkenyl (e.g., phenylethenyl), lower alkyl (e.g., methyl, ethyl, iso propyl, iso butyl, and t-butyl), cycloalkyl (e.g., cyclopentanyl and cyclohexenyl), halogen (e.g., fluoro, chloro, bromo, and iodo), lower alkyloxy (e.g., methyloxy and ethyloxy), trihalo lower alkyl (e.g., trifluoromethyl and trichloromethyl), nitro, phenyl, naphthyl (e.g., 1-naphthyl and 2-naphthyl), phenanthryl (e.g., 9-phenanthryl), benzo-1,3-dioxolanyl (e.g., 4-benzo-1,3,-dioxolanyl and 5-benzo-1,3-dioxolanyl), heteroaryl (e.g., 3-pyridyl, 3-thienyl, and 2-benzothienyl), aralkyl (e.g., benzyl and phenethyl), aryloxy (e.g., phenyloxy), hydroxy, amino, mono- or di-substituted amino (e.g., dimethylamino, diethylamino, phenylamino, N-methyl-N-phenylamino, and N-methyl-N-benzylamino), piperazinyl which may be substituted with the above mentioned lower alkyl (e.g., 4-methylpiperazinyl), and the like. Examples of optionally substituted aryl for $R^1$ are phenyl, 2-biphenylyl, 3-biphenylyl, 4-biphenylyl, 1-naphthyl, 2-naphthyl, 2-p-terphenyl, 2-m-terphenyl, 2-o-terphenyl, 2-isopropylphenyl, 2-t-butylphenyl, 2-isobutylphenyl, 2-cyclopentylphenyl, 2-bromophenyl, 3-bromophenyl, 2-iodophenyl, 2-(4-benzo-1,3-dioxolanyl)phenyl, 2-(5-benzo-1,3-dioxolanyl)phenyl, 2-phenoxyphenyl, 2-benzylphenyl, 2-(3-pyridyl)phenyl, 3-dimethylaminophenyl, 3-diethylaminophenyl, 3-phenylaminophenyl, 3-N-methyl-N-phenylamino)phenyl, 2-(1-naphthyl)phenyl, 2-(2-naphthyl)phenyl, 3-(1-naphthyl)phenyl, 3-(2-naphthyl)phenyl, 4-ethenylphenyl)phenyl, 2-bromo-6-isopropylphenyl, 2-isopropyl-6-phenyl-phenyl, 2-isopropyl-6-(1-naphthyl)phenyl, 2-bromo-6-nitrophenyl, 2-methyloxy-6-(1-naphthyl)phenyl, 2'-methyl-2-biphenylyl, 2'-isopropyl-2-biphenylyl, 2'-methyloxy-2-biphenylyl, 3'-methyl-2-biphenylyl, 3'-trifluoromethyl-2-biphenylyl, 3'-nitoro-2-biphenylyl, 3'-methyloxy-2-biphenylyl, 3'-ethyloxy-2-biphenylyl, 3'-hydroxy-2-biphenylyl, 3-methyloxy-2-biphenylyl, 6-phenyl-2-naphthyl, 1-bromo-6-phenyl-2-naphthyl, 1,6-diphenyl-2-naphthyl, 4-phenyl-1-naphthyl, 2-(4-methylpiperazinyl)phenyl, and the like.

The term "optionally substituted aryl" herein used for $R^2$, $R^3$, $R^4$, $R^5$, G ring, J ring, and L ring means the above mentioned "aryl" which may be substituted with one or more substituents selected from the group consisting of halogen (e.g. fluoro, chloro, bromo, and iodo), lower alkyl (e.g., methyl, ethyl, n-propyl, and iso propyl), lower alkyloxy (e.g., methyloxy and ethyloxy), trihaloalkyl (e.g., trifluoromethyl), alkyloxycarbonyl (e.g., mehtyloxycarbonyl), acyl (e.g., acetyl), amino, mono- or di-substituted amino (e.g., acylamino and methylamino), and the like.

The term "optionally substituted aryl" herein used for $Y^{2'}$ means the above mentioned "aryl" which may be substituted with one or more substituents selected from the group consisting of halogen (e.g., fluoro, chloro, bromo, and iodo), lower alkyl (e.g., methyl, ethyl, n-propyl, and iso propyl), lower alkyloxy (e.g., methyloxy and ethyloxy), trihaloalkyl (e.g., trifluoromethyl), alkyloxycarbonyl (e.g., methyloxycarbonyl), acyl (e.g. acetyl), amino, mono- or di-substituted amino (e.g., acylamino and methylamino), and the like. Examples of the optionally substituted aryl for $Y^{2'}$ are phenyl, biphenylyl, 2,5-dichlorophenyl, 4-bromophenyl, and the like.

The term "optionally substituted aralkyl" herein used for $R^1$ means the above mentioned "lower alkyl" substituted with one or more of the above mentioned "optionally substituted aryl" for $R^1$. Examples of the optionally substituted aralkyl for $R^1$ are benzyl, phenethyl, 2-biphenylmethyl, 3-biphenylmethyl, 4-biphenylmethyl, 1-naphthylmethyl, 2-naphthylmethyl, 2-p-terphenylmethyl, 2-m-terphenylmethyl, 2-o-terphenylmethyl, diphenylmethyl, 2-isopropylphenyl, 2-t-butylphenylmethyl, 2-isobutylphenylmethyl, 2-cyclopentylphenylmethyl, 2-bromophenylmethyl, 3-bromophenylmethyl, 2-iodophenylmethyl, 2-(4-benzo-1,3-dioxolanyl) phenylmethyl, 2-(5-benzo-1,3-dioxolanyl)phenylmethyl, 2-phenoxyphenylmethyl, 2-benzylphenylmethyl, 2-phenethylmethyl, 2-(3-thienyl)phenylmethyl, 2-(2-benzothienyl)phenylmethyl, 2-(3-pyridyl)phenylmethyl, 3-dimethylaminophenylmethyl, 3-diethylaminophenylmethyl, 3-phenylaminophenylmethyl, 3-(N-methyl-N-phenylamino)phenylmethyl, 2-(1-naphthyl) phenylmethyl, 2-(2-naphthyl)phenylmethyl, 3-(1-naphthyl) phenylmethyl, 3-(2-naphthyl)phenylmethyl, 2-(9-phenanthryl)phenylmethyl, 4-ethenylphenyl)phenylmethyl, 2-bromo-6-isopropylphenylmethyl, 2-isopropyl-6-phenyl-phenylmethyl, 2-isopropyl-6-(1-naphthyl)phenylmethyl, 2-bromo-6-nitrophenylmethyl, 2-methyloxy-6-(1-naphthyl) phenylmethyl, 2'-methyl-2-biphenylmethyl, 2'-isopropyl-2-biphenylmethyl, 2'-methyloxy-2-biphenylmethyl, 3'-methyl-2-biphenylmethyl, 4'-fluoro-2-biphenylmethyl, 3'-trifluoromethyl-2-biphenylmethyl, 3'-nitro-2-biphenylmethyl, 3'-methyloxy-2-biphenylmethyl, 3'-ethyloxy-2-biphenylmethyl, 3'-hydroxy-2-biphenylmethyl, 3-methyloxy-2-biphenylmethyl, 6-phenyl-2-naphthylmethyl, 1-bromo-6-phenyl-2-naphthylmethyl, 1,6-diphenyl-2-naphthylmethyl, 4-phenyl-1-naphthylmethyl, 1-phenyl-2-naphthylmethyl, and the like.

The term "optionally substituted heteroaryl" herein used for $R^1$ means the above mentioned "heteroaryl" which may be substituted with one or more substituents as exemplified for the above mentioned "optionally substituted aryl" for $R^1$.

The term "optionally substituted heteroaryl" herein used for $R^2$, $R^3$, $R^4$, $R^5$, G ring, J ring, and L ring means the above mentioned "heteroaryl" in which any of the carbon atoms in the ring may be substituted with one or more substituents selected from the group consisting of halogen (e.g., fluoro, chloro, bromo, and iodo), lower alkyl (e.g., methyl and ethyl), lower alkyloxy (e.g., methyloxy and ethyloxy), alkyloxycarbonyl (e.g., methyloxycarbonyl), and the like. When the hetero atom is nitrogen, the nitrogen atom is optionally substituted with optionally substituted alkyl, acyl, and the like.

The term "optionally substituted arylene" herein used means the above mentioned "arylene" which may be substituted with the substituents as exemplified for "optionally substituted aryl" for $R^2$, $R^3$, $R^4$, $R^5$, G ring, J ring, and L ring. Examples of the optionally substituted arylene are 1,4-phenylene, 2-hydroxy-1,4-phenylene, and the like. 1,4-Phenylene is preferred.

The term "optionally substituted heteroarylene" herein used means the above mentioned "hetoroarylene" which may be substituted with the substituents as exemplified for substituents of "optionally substituted aryl" for $R^2$, $R^3$, $R^4$, $R^5$, G ring J ring, and L ring. Examples of the optionally substituted arylene are 2,5-thiophendiyl, 2,5-furandiyl, 2,5-pyridinediyl. 2,5-Thiophendiyl is preferred.

The term "optionally substituted arylcarbonyl" herein used means arylcarbonyl of which "optionally substituted aryl" part is the above mentioned "optionally substituted aryl".

The substituents of "optionally substituted lower alkyl", "optionally substituted cycloalkyl", and "optionally substituted cycloalkenyl" are exemplified by lower alkyloxy, lower alkyloxycarbonyl, carboxy, monoalkyl-substituted amino, dialkyl-substituted amino, and the like.

The term "optionally substituted lower alkyloxy" herein used means the above mentioned "lower alkyloxy" which may be substituted with the substituents as exemplified for "optionally substituted alkyl". Examples of the optionally substituted lower alkyloxy are methyloxycarbonylmethyloxy, methyloxycarbonylethyloxy, ethyloxycacrbonylmethyloxy, ethtyloxycarbonylethyloxy, dimethylaminomethyloxy. dimethylaminoehtyloxy, and the like.

The term "acyl" herein used means alkylcarbonyl of which alkyl part, is the above mentioned "lower alkyl" and arylcarbonyl of which aryl part is the above mentioned "aryl". Examples of the acyl are acetyl, propionyl, benzoyl, toluoyl, and the like. The aryl part of "arylcarbonyl" is optionally substituted with lower alkyl, halogen, and the like.

BEST MODE FOR CARRYING OUT THE INVENTION

Although the compound of the present invention can be prepared in a conventional manner, it is conveniently prepared according to any of the processes shown below depending on the type of the aimed compounds. The following processes are, however, provided just for illustrative purpose and compounds of the present invention prepared by any other methods also fall within the scope of the invention.

1) Compounds having oxygen atom at the 4-position of pyrrolidine ring (Z=—O—)

Method A: Compounds having methylene at the 2-position of pyrrolidine ring (for example, $X^1$=—$CH_2NHCO$—, —$CH_2NHSO_2$—, —$CH_2NHCS$—, —$CH_2NHCOCH$=$CH$—, and —$CH_2NHCOCH_2O$—).

Method B: Compounds having an amide group at the 2-position of pyrrolidine ring ($X^1$=—CONH—).

Method C: Compounds which do not have an amide bond at the 2-position of pyrrolidine ring but have an ether bond ($X^1$=—$CH_2OCH_2$—).

Method D: Compounds having a hydroxy lower alkyl group on the double bond (D=hydroxy lower alkyl).

Method E: Compounds which do not have an amide bond at the 2-position of the pyrrolidine ring but have only a carbon chain ($X^1$=—$CH_2CH_2$—, —CH=CH—, —$CH_2CH_2CH_2$—, and —$CH_2CH$=CH—).

Method F: Compounds having an amide bond intervened a carbon chain at the 2-position of the pyrrolidine ring ($X^1$=—$CH_2CH_2CH_2NHCO$—, —$CH_2CH_2NHCO$—, —$CH_2CONH$—, and $CH_2CH_2CONH$—)

Method G: Compounds having an amide bond or an amine group which does not have hydrogen atom at the 2-position of the pyrrolidine ring ($X^1$=—$CH_2N(CH_3)$ CO—, —$CH_2N(CH_3)CH_2$—, —$CH_2N(R^{20})CH_2$—, and —$CON(CH_3)$—).

Method H: Compounds which do not have an amide bond at the 2-position of the pyrrolidine ring but have the thiazolidine ring intervened by one carbon atom ($X^1$=$X^2$=$X^3$=a bond).

2) Compounds having sulfur atom at the 4-position of the pyrrolidine ring (Z=—S—).

Method I: Compounds having methylene at the 2-position of the pyrrolidine ring ($X^1$=$CH_2NHCO$—, —$CH_2NHSO_2$—, —$CH_2NHCS$—, —$CH_2NHCOCH$=CH—, and —$CH_2NHCOCH_2O$—).

Method J: Compounds having an amide group at the 2-position of the pyrrolidine ring ($X^1$=—CONH—).

Method K: Compounds which do not have an amide bond at the 2-position of the pyrrolidine ring but have only a carbon chain ($X^1$=—$CH_2CH_2$—, —CH=CH—, —$CH_2CH_2CH_2$—, and —$CH_2CH$=CH—).

Method L: Compounds having an amide bond intervened by a carbon chain at the 2-position of the pyrrolidine ring (X$^1$=CH$_2$CH$_2$CH$_2$NHCO—, —CH$_2$CH$_2$NHCO—, —CH$_2$CONH—, and —CH$_2$CH$_2$CONH—).

3) Compounds having nitrogen atom at the 4-position of the pyrrolidine ring (Z=—N(R$^{16}$)—)

Method M: Compounds having methylene at the 2-position of the pyrrolidine ring (X$^1$=CH$_2$NHCO—, —CH$_2$NHSO$_2$—, —CH$_2$NHCS—, CH$_2$NHCOCH=CH—, and —CH$_2$NHCOCH$_2$O—).

Method N: Compounds having an amide group at the 2-position of the pyrrolidine ring (X$^1$=—CONH—).

4) Compounds having carbon atom at the 4-position of the pyrrolidine ring (Z=a bond)

Method O: Compounds having methylene at the 2-position of the pyrrolidine ring (X$^1$=CH$_2$NHCO—, —CH$_2$NHSO$_2$—, —CH$_2$NHCS—, —CH$_2$NHCOCH=CH—, and —CH$_2$NHCOCH$_2$O—).

5) Proline derivatives (Z and X are a bond and R$^1$ is hydrogen atom)

Method P: Compounds wherein the pyrrolidine ring has no substituent at the 4-position.

6) Compounds having sulfur or oxygen atom at the 4-position of pyrrolidine ring and having different configuration at the 2- and 4-positions of the pyrrolidine ring.

Method Q: Compounds of the configuration of (2β, 4α), (2β, 4β), (2α, 4α), or (2α, 4β) having sulfur atom or oxygen atom at the 4-position of the pyrrolidine. The configuration of the compounds having oxygen atom at the 4-position of the pyrrolidine ring synthesized in accordance with the above mentioned method is (2β, 4α) and that, of the compounds having sulfur atom is (2β, 4α) or (2β, 4β).

The compounds of the present invention can be synthesized in accordance with the above mentioned or similar methods. These methods are hereinafter described in more detail.

Method A-1

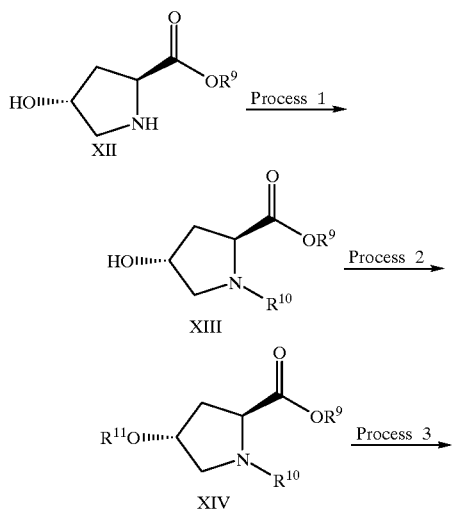

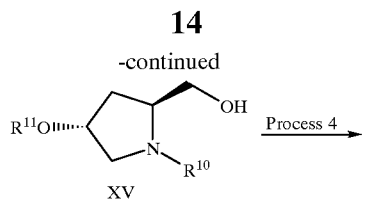

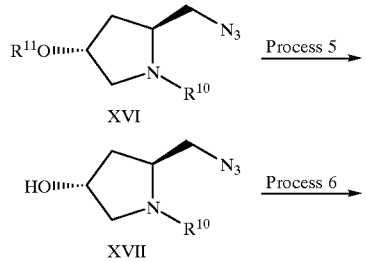

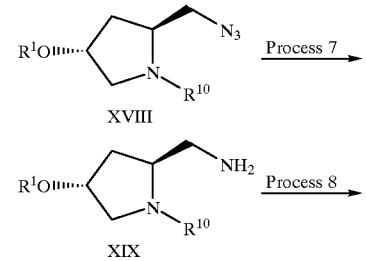

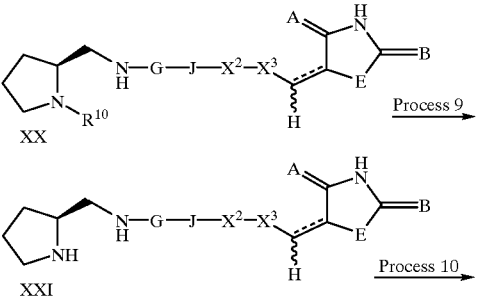

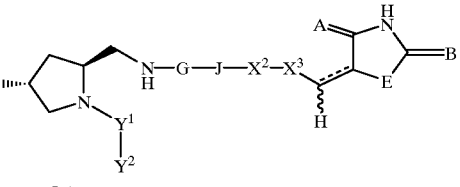

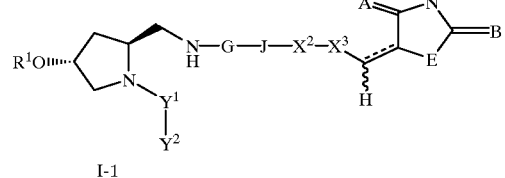

Wherein A, B, E, R$^1$, X$^2$, X$^3$, Y$^1$, Y$^2$, a wavy line, and a broken line are as defined above, R$^9$ is lower alkyl such as methyl, ethyl, tert-butyl, and the like or aralkyl such as benzyl, R$^{10}$ is an amino protecting group, R$^{11}$ is a hydroxy-protecting group, G is —CO—, —CS—, or —SO$_2$—, and J is —CH=CH—, —CH$_2$O—, or a bond.

Process 1 (XII→XIII)

This process involves the protection of secondary amine on the pyrrolidine ring (Protective Groups in Organic Synthesis, Theodora W. Green (John Wiley & Sons)). For example, the compound (XII) which is commercially available is reacted in a solvent such as tetrahydrofuran, dichloromethane, benzene, or the like in the presence of triethylamine, pyridine, or the like with a BOC-protecting agent such as 2-tert-butyloxycarbonylimino)-2-phenylacetonitrile, di-tert-butyldicarbonate [(BOC)$_2$O], tert-butyloxycarbonylazide (BOC-N$_3$), or the like a PMZ-protecting agent such as 4-methyloxycarbonylazide, 4-methyloxycarbonyl-S-(4,6-dimethylpyrimidine-2-yl) thiocarbonate, and the like, or a PNZ-protecting agent such as p-nitrobenzylchloroformate and the like so as to form a carbamate.

Process 2 (MIII→XIV)

This process involves the protection of hydroxy group (Protective Groups in Organic Synthesis, Theodora W. Green (John Wiley & Sons)). As the protective group of hydroxy, generally used one is usable. For example, a starting material is reacted with 3,4-dihydro-2H-pyran in dichloromethane in the presence of p-toluenesulfonic acid as a catalyst at room temperature for 5 to 8 hours to obtain a tetrahydropyranyl-protected derivative.

Process 3 (XIV→XV)

In this process, an ester is reduced to an alcohol. For example, the reduction is carried out in a solvent such as tetrahydrofuran, and the like using a reducing agent such as lithium aluminum hydride, lithium borohydride, and the like.

Process 4 (XV→XVI)

In this process, a hydroxy is converted into a leaving group and further converted into an azide group. Examples of leaving group include O-mesyl O-tosyl, O-trifluoromethansulfonyl, halogen, and the like. The introduction of the leaving group is carried out according to conventional methods using mesyl chloride, tosyl chloride, trifluoromethansulfonyl chloride, phosphorous trichloride, phosphorus pentachloride, and the like.

The successive conversion into an azide derivative is carried out according to conventional methods in a solvent such as dichloromethane, hexamethylphosphoric triamide, dimethylformamide, and the like using a reagent such as sodium azide, and the like.

Process 5 (XVI→XVII)

This process involves the removal of the hydroxy protecting group (Protective Groups in Organic Synthesis, Theodora W. Green (John Wiley & Sons)). This reaction is carried out according to conventional methods used for the deprotection of the above mentioned protecting group. When the protecting group is tetrahydropyranyl, for example, the reaction is carried out in a solvent such as methanol, and the like in the presence of p-toluenesulfonic acid in acetic acid-tetrahydrofuran-water, and the like.

Process 6 (XVII→XVIII)

This reaction involves the formation of an ether bond. For example, this reaction is carried out in a solvent such as dimethylformamide and the like in the presence of an alkyl halide such as methyl iodide or benzylchloride by adding a strong base such as sodium hydride and the like.

Process 7 (XVIII→XIX)

This reaction involves the reduction of azide to amine. For example, this reaction is carried out in ethanol-water, tetrahydrofuran-water, and the like in the presence of a base such as sodium hydroxide and the like by reacting with stannic chloride.

Process 8 (XIX→XX)

In this process, an amine derivative is reacted with a carboxylic acid derivative, a thiocarboxylic acid derivative, or a sulfonic acid derivative according to the activated ester method, the acid chloride method, the mixed acid anhydride method and the like to obtain an amide derivative, a thioamide derivative, or a sulfonamide derivative. This process is carried out in a solvent such as tetrahydrofuran, dichloromethane, toluene, benzene, and the like. In the activated ester method, the reaction is carried out using a condensing agent such as 1-hydroxybenzotriazole, hydroxysuccinimide, dimethylaminopyridine, and the like and dicyclohexylcarbodiimide, 1-ethyl-3-(3-dimethylaminopropyl)carbodiimide hydrochloride, and the like. In the acid chloride method, a free acid is converted into an acid chloride using a reagent such as thionyl chloride and oxaryl chloride to obtain an aimed compound. In the mixed acid anhydride method, a carboxylic acid is converted into mixed acid anhydride using ethylchloroformate, isobutylchloroformate, and the like. These reactions are carried out in the presence of a base such as triethylamine, pyridine, and the like, if necessary. This process is, for example, carried out in a solvent such as N,N-dimethylformamide and the like by reacting a starting material with 4-(4-oxo-2-thioxothiazolidine-5-ylidenmethyl) benzoic acid, 4-(2,4-dioxothiazolidine-5-ylidenemethyl) benzoic acid, and the like which are described in JP05306224 and Can. J. Chem., 1958, 36, 1579. in the presence of 1-hydroxybenzotriazole, 1-ethyl-3-(3-dimethylaminopropyl)carbodiimide hydrochloride, and the like.

Process 9 (XX→XXI)

This process involves the deprotection of the protected N-atom of the pyrrolidine ring (Protective Groups in Organic Synthesis, Theodora W. Green (John Wiley & Sons)). This reaction is carried out by usual methods used for the deprotection of the above mentioned protecting group. When the protecting group is tert-butyloxycarbonyl, the reaction is, for example, carried out in a solvent such as methanol, ethyl acetate, and the like by reacting with 5 to 20 equivalents of a mineral acid such as hydrochloric acid, hydrobromic acid, and the like for 2 to 6 hours. The reaction mixture is concentrated in vacuo to give a corresponding acid salt of the aimed compound.

Process 10 (XX→I-1)

This reaction involves the formation of an amide, a sulfonamide, an urea, or a thiourea. For example, the formation of an amide bond is carried out by reacting with an acyl halide in the presence of a base such as triethylamine or pyridine, if necessary. When the acylating agent is a carboxylic acid, the reaction can be conducted in a manner similar to that described in above process 8.

Method A-2

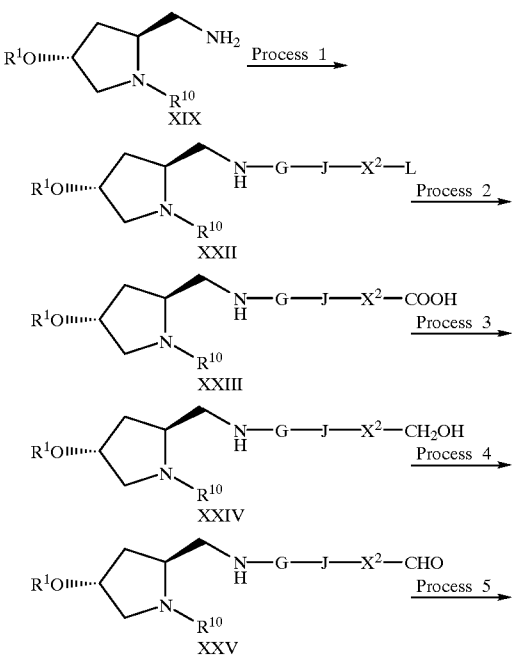

-continued

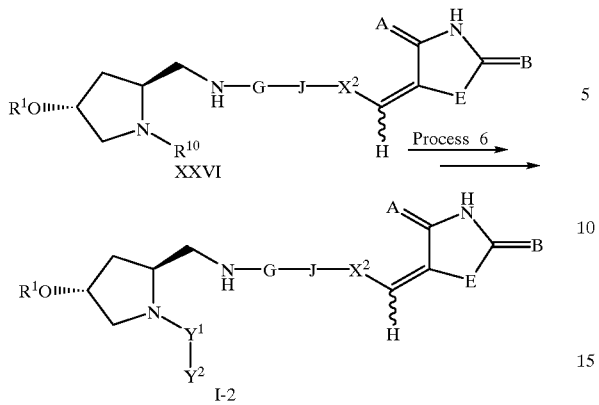

Method A-3

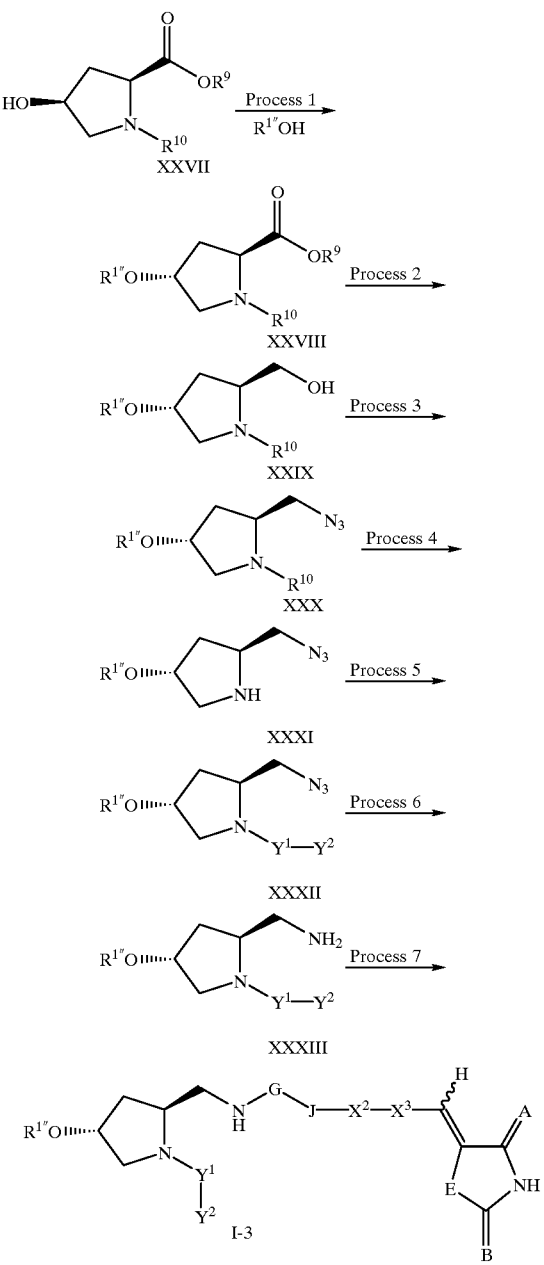

Wherein A, B, E, $R^1$, $X^2$, $Y^1$, $Y^2$, $R^9$, $R^{10}$, G, J, and a wavy line are as defined above and L is a protected carboxyl group.

Process 1 (XIX→XXII)

In this process, an amine derivative is reacted with a carboxylic acid derivative, a thiocarboxylic acid derivative, or a sulfonic acid derivative in accordance with the activated ester method, the acid chloride method, the mixed acid anhydride method, and the like to give an amide derivative, a thioamide derivative, or a sulfonamide derivative. This process can be carried out in a manner similar to that described in Process 8 of Method A-1.

Process 2 (XXII→XXIII)

This process involves the deprotection of the carboxy protecting group of the side chain of the pyrrolidine ring (Protective Groups in Organic Synthesis, Theodora W. Green (John Wiley & Sons)). This reaction is carried out by usual methods for the deprotection of the carboxy protecting group. When the carboxy is protected as methyl ester, this reaction is carried out by hydrolysis in a solvent such as methanol and the like.

Process 3 (XXIII→XXIV)

In this process, the carboxylic acid derivative is reduced to the alcohol derivative. For example, a starting material is converted into an acid anhydride by reacting with ethyl chlorocarbonate and the like in a solvent such as tetrahydrofuran and the like and the acid anhydride is converted into a hydroxymethyl derivative by using a reducing agent such as sodium borohydride and the like.

Process 4 (XXIV→XXV)

This process involves the oxidation of the alcohol derivative to the aldehyde derivative. This process is carried out by usual methods for the oxidation of alcohols to aldehydes such as Swern oxidation, Dess-Martin oxidation, and the like. This reaction is, for example, carried out by reacting with a dimethylsulfoxide solution of Dess-Martin reagent and the like in a solvent such as tetrahydrofuran and the like.

Process 5 (XXV→XXVI)

This process involves the production of a benzylidene derivative by reacting an aldehyde derivative with 2,4-thiazolidinedione, 2-thioxo-4-thiazolidinedione (Rhodanine), 2,4-oxazolidinedione, and the like. This reaction is, for example, carried out in a solvent such as benzene, toluene, and the like under the condition for Knoevenagel reaction using acetic acid, pyridine, and the like as a catalyst.

Process 6 (XXVI→I-2)

This process can be carried out in a manner similar to those described in Processes 9 and 10 of Method A-1.

Wherein A, B, E, $X^2$, $X^3$, $y^1$, $Y^2$, $R^9$, $R^{10}$, G, J, and a wavy line are as defined above and $R^{1''}$ is optionally substituted aryl or optionally substituted heteroaryl.

Process 1 (XXVII→XXVIII)

This process involves the inversion of the configuration of the 4-position of the pyrrolidine ring by Mitsunobu reaction (Synthesis. 1981, 1) and the introduction of —$OR^{1''}$ at the same time. In this process, for example, the compound (XXVII) is dissolved in a solvent such as tetrahydrofuran and the like, triphenylphosphine and diethylazocarboxylate are added to the mixture, and then $R^{1''}OH$ is added to the resulting mixture.

Process 2 (XXVIII→XXVIX)

This process can be carried out in a manner similar to that described in Process 3 of Method A-1.

Process 3 (XXVIX→XXX)
This process can be carried our in a manner similar to that described in Process 4 of Method A-1.
Process 4 (XXX→XXXI)
This process can be carried out in a manner similar to that described in Process 9 of Method A-1.
Process 5 (XXI→XXXII)
This process can be carried out in a manner similar to that described in Process 10 of Method A-1.
Process 6 (XXXII→XXXIII)
This process can be carried out in a manner similar to that described in Process 7 of Method A-1.
Process 7 (XXXIII→I-3)
This process can be carried out in a manner similar to that described in Process 8 of Method A-1.

Method A-3'

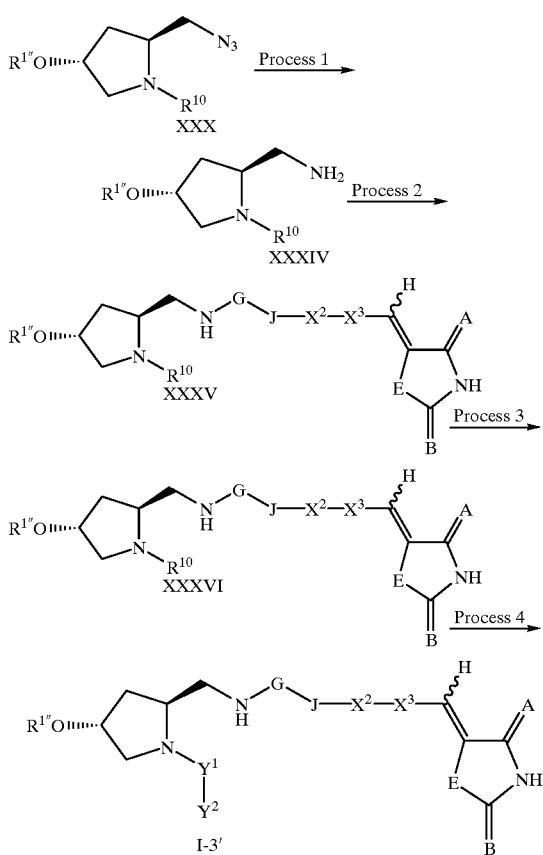

Wherein A, B, E, $X^2$, $X^3$, $Y^1$, $Y^2$, $R^{1''}$, $R^9$, $R^{10}$, G, J, and a wavy line are as defined above.
Process 1 (XXX→XXXIV)
This process can be carried out in a manner similar to that described in Process 7 of Method A-1.
Process 2 (XXXIV→XXXV)
This process can be carried out in a manner similar to that described in Process 8 of Method A-1.
Process 3 (XXXV→XXXVI)
This process can be carried out in a manner similar to that described in Process 9 of Method A-1.
Process 4 (XXXVI→I-3')
This process can be carried out in a manner similar to that described in Process 10 of Method A-1.

Method B-1

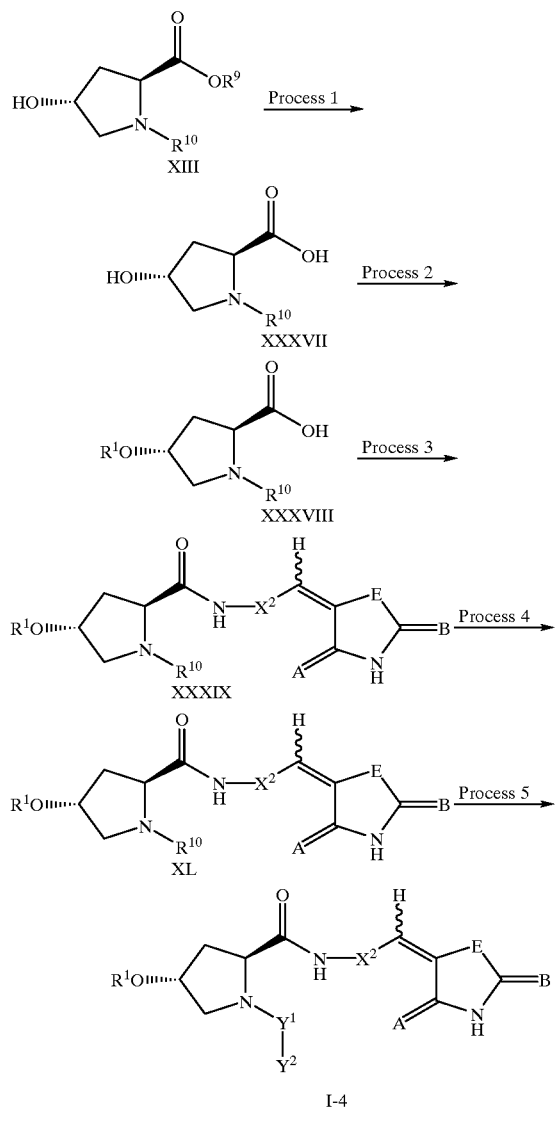

Wherein A B, E, $R^1$, $R^{10}$, $X^2$, $Y^1$, $Y^2$, and a wavy line are as defined above.
Process 1 (XIII→XXXVII)
This process can be carried out in a manner similar to that described in Process 1 of Method A-1.
Process 2 (XXXVII→XXXVIII)
This process can be carried our in a manner similar to that described in Process 6 of Method A-1.
Process 3 (XXXVIII→XXXIX)
In this process, an amide bond is formed by reacting an amine derivative with a carboxylic acid derivative using the activated ester method, the acid chloride method, the mixed acid anhydride method, and the like. This reaction can be carried out in a manner similar to that described in Process 8 of Method A-1.
Process 4 (XXXIX→XL)
This process can be carried out in a manner similar to that described in Process 9 of Method A-1.
Process 5 (XL→I-4)
This process can be carried out in a manner similar to that described in Process 10 of Method A-1.

Method B-2

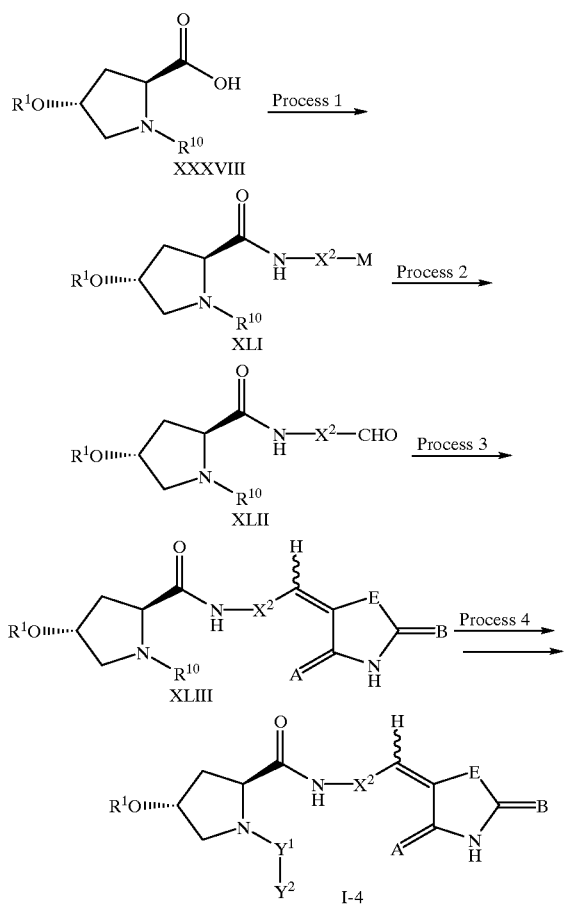

Wherein A, B, E, $R^1$, $R^{10}$, $X^2$, $Y^1$, $Y^2$, and a wavy line are as defined above and M is a formyl group or a precursor of an aldehyde such as a protected carboxyl group and the like.

Process 1 (XXXVIII→XLI)

This process can be carried out in a manner similar to that described in Process 1 of Method A-2.

Process 2 (XLI→XLII)

This process can be carried out in a manner similar to those described in Processes 2 to 4 of Method A-2.

Process 3 (YLII→XLIII)

This process can be carried out in a manner similar to that described in Process 5 of Method A-2.

Process 4 (YLIII→I-4')

This process can be carried out in a manner similar to those described in Processes 9 and 10 of Method A-1.

Method C

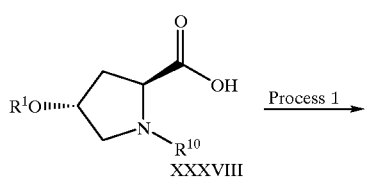

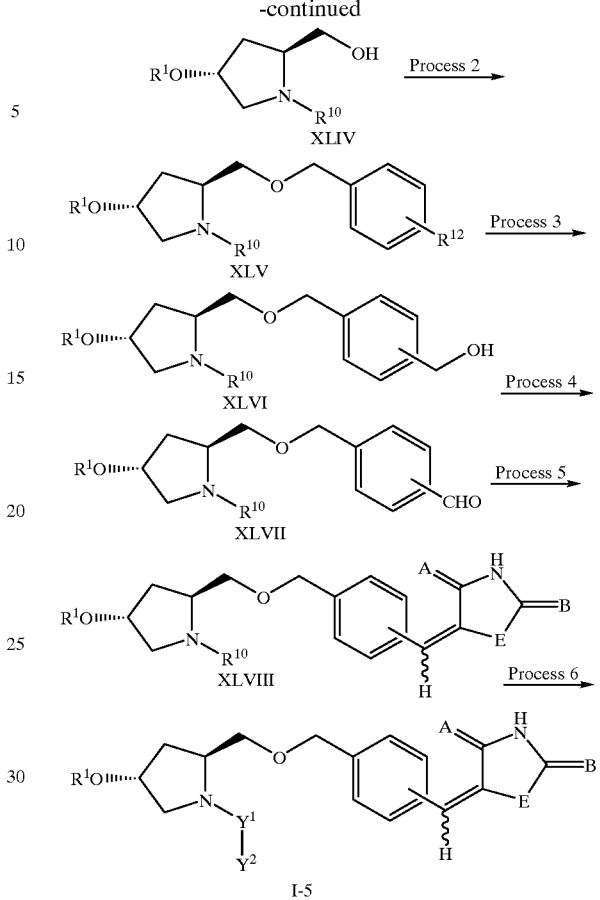

Wherein A, B, E, $R^1$, $R^{10}$, $Y^1$, $Y^2$, and a wavy line are as defined above and $R^{12}$ is alkyloxycarbonyl.

Process 1 (XXXVIII→XLIV)

This process can be carried out in a manner similar to that described in Process 3 of Method A-1.

Process 2 (XLIV→XLV)

This process can be carried out in a manner similar to that described in Process 6 of Method A-1.

Process 3 (XLV→XLVI)

This process involves the reduction of an ester to an alcohol. This reaction is, for example, carried out in a solvent such as ether, tetrahydrofuran, and the like or in a mixed solvent of ether and tetrahydrofuran, and the like by reacting with lithium aluminum hydride.

Process 4 (XLVI→XLVII)

This process can be carried out in a manner similar to that described in Process 4 of Method A-2.

Process 5 (XLVII→XLVIII)

This process can be carried out in a manner similar to that described in Process 5 of Method A-2.

Process 6 (XLVIII→I-3)

This process can be carried out in a manner similar to those described in Processes 9 and 10 of Method A-1.

Method D

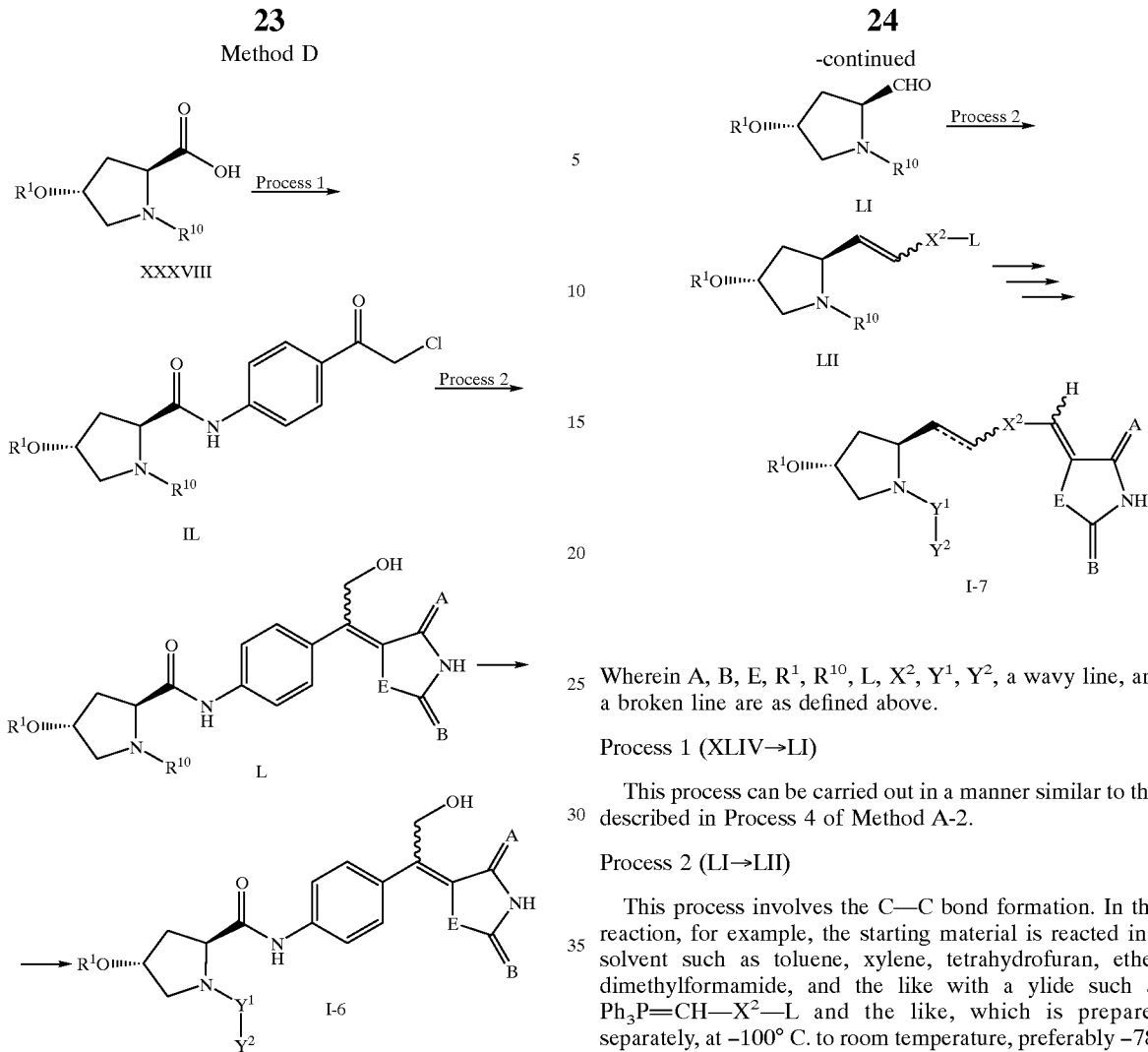

Wherein A, B, E, $R^1$, $R^{10}$, $Y^1$, $Y^2$, and a wavy line are as defined above.

Process 1 (XXXVII→IL)

This process can be carried out in a manner similar to that described in Process 8 of Method A-1. p-Chloroacetylaniline can be prepared in accordance with the method described in Arie Zask et al. 1993, Tet. Lett., 34, 2719.

Process 2 (IL→L)

This process involves the formation of a bond with a thiazolidinedione derivative. In this reaction, for example, 2,4-thiazolidinedione is first converted into an anion with a base such as n-butyllithium, and then reacted with the starting material in a solvent such as tetrahydrofuran.

The aimed compound can be obtained by further reacting in accordance with the methods described in Processes 9 and 10 of Method A-1.

Method E-1

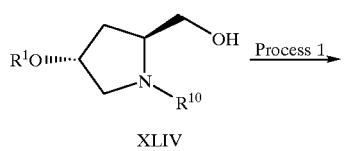

Wherein A, B, E, $R^1$, $R^{10}$, L, $X^2$, $Y^1$, $Y^2$, a wavy line, and a broken line are as defined above.

Process 1 (XLIV→LI)

This process can be carried out in a manner similar to that described in Process 4 of Method A-2.

Process 2 (LI→LII)

This process involves the C—C bond formation. In this reaction, for example, the starting material is reacted in a solvent such as toluene, xylene, tetrahydrofuran, ether, dimethylformamide, and the like with a ylide such as $Ph_3P=CH-X^2-L$ and the like, which is prepared separately, at $-100°$ C. to room temperature, preferably $-78°$ C. to ice-cooling for 1 to 20 hours, preferably 1 to 5 hours with stirring to give an aimed intermediate.

Successively, the obtained compound is reacted in accordance with the methods described in Processes 2 to 6 of Method A-2 to give the aimed compound (the reduction of double bond is carried out by usual catalytic hydrogenation).

Method E-2

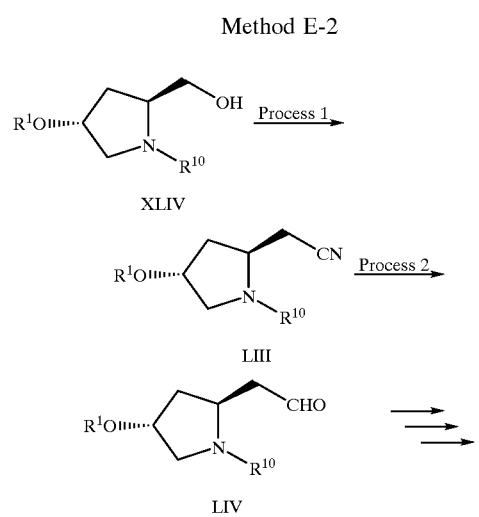

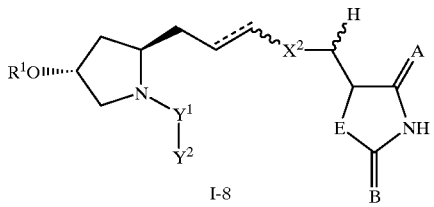

I-8

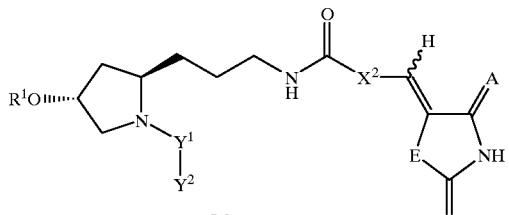

I-9

Wherein A, B, E, $R^1$, $R^{10}$, $X^2$, $Y^1$, $Y^2$, a wavy line, and a broken line are as defined above.

Process 1 (XLIV→LIII)

This process involves the conversion of a hydroxyl group to a leaving group such as mesyloxy, tosyloxy and the like, and the successive introduction of a cyano group. This reaction is, for example, carried out in a solvent such as N,N-dimethylformamide, ethanol, propanol, and the like by reacting with a cyanating agent such as sodium cyanide, potassium cyanide, and the like at ice-cooling to 100° C.

Process 2 (LIII→LIV)

This process involves the reduction of a nitrile to an aldehyde. This reaction is carried out in a solvent such as ether, benzene, toluene, cyclohexane and the like, by reacting with a reducing agent such as diisobutylaluminum hydride.

Successively, the aimed compound can be obtained in accordance with the method described in Process 2 of Method E-1.

Wherein A, B, E, $R^1$, $R^{10}$, L, $X^2$, $Y^1$, $Y^2$, and a wavy line are as defined above.

Process 1 (LI→LV)

This process can be carried out in a manner similar to that described in Process 2 of Method E-2.

Process 2 (LV→LVI)

This process can be carried out in a manner similar to those described in Process 3 of Method A-1 or Processes 2 and 3 of Method A-2.

Process 3 (LVI→LVII)

This process can be carried out in a manner similar to that described in Process 4 of Method A-1.

Process 4 (LVI→LVII)

This process involves the reduction of a double bond and the reduction of an azide derivative to an amine derivative at the same time. This reaction is, for example, carried out in a solvent such as methanol, ethanol, ethyl acetate, acetic acid and the like by hydrogenating with a catalyst such as Pd-C, $PtO_2$, $Rh-Al_2O_3$, Raney Nickel, and the like in 1 to 3 atm. at 0° C. to 100° C.

Successively, the aimed compound can be obtained in accordance with the methods described in Processes 8 to 10 of Method A-1.

Method F-1

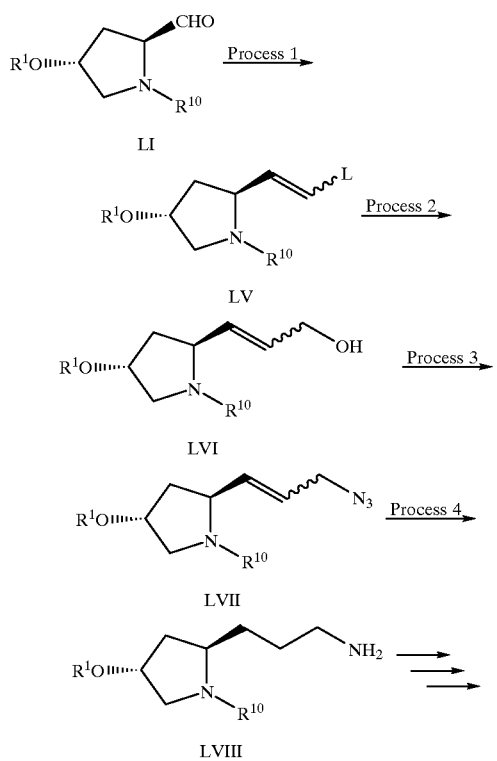

Method F-2

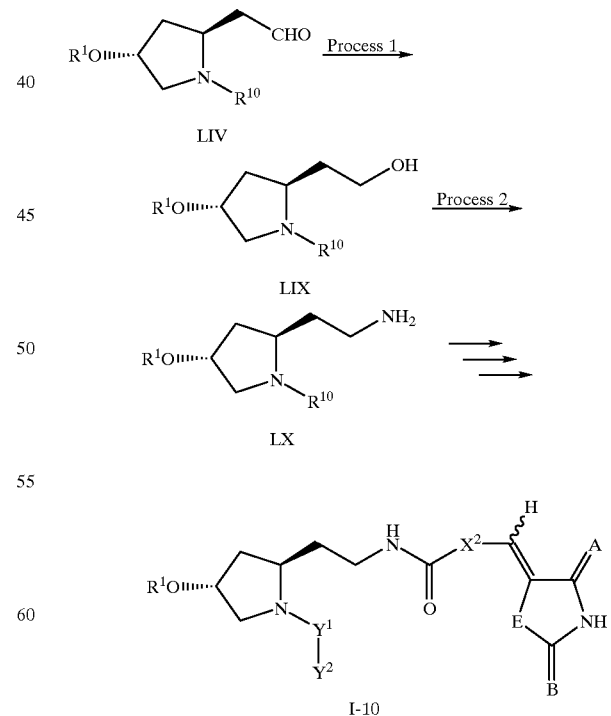

I-10

Wherein A, B, E, $R^1$, $R^{10}$, $X^2$, $Y^1$, $Y^2$, and a wavy line are as defined above.

Process 1 (LIV→LIX)

This process involves the reduction of an aldehyde to an alcohol. This process can be carried out by usual methods, for example, catalytic hydrogenating (Process 4 of Method F-1) and reacting with a reducing agent such as sodium borohydride, lithium borohydride, diisobutylaluminum hydride, lithium aluminum hydride, and the like in a solvent such as ether, benzene, toluene, cyclohexane, and the like.

Process 2 (LIX→LIX)

This process can be carried out in a manner similar to those described in Processes 4 and 7 of Method A-1.

Successively, the aimed compound can be obtained in accordance with the methods described in Processes 8 to 10 of Method A-1.

Method F-3

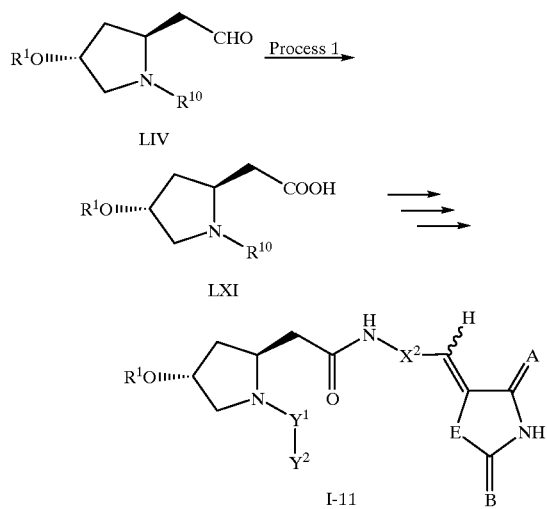

Wherein A, B, E, $R^1$, $R^{10}$, $X^2$, $Y^1$, $Y^2$, and a wavy line are as defined above.

Process 1 (LIV→LXI)

This process involves the oxidation of an aldehyde to a carboxylic acid. This process can be carried out by the usual oxidation. This reaction is, for example, carried out by reacting with ruthenium tetroxide-sodium periodate in tetrachloromethane-acetonitrile-water or reacting with hypochlorite in acetic acid-water.

Successively, the aimed compound can be obtained in accordance with the methods described in Process 3 to 5 of Method B-1.

Method F-4

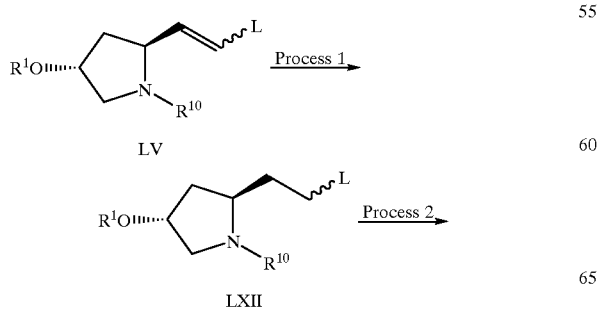

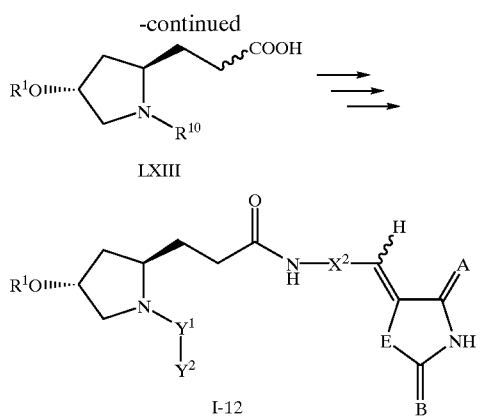

Wherein A, B, E, $R^1$, $R^{10}$, $X^2$, $Y^1$, $Y^2$, and a wavy line are as defined above.

Process 1 (LV→LXII)

This process involves the reduction of a double bond. For example, this process can be carried out in a manner similar to that described in Process 4 of Method F-1.

Process 2 (LXII→LXIII)

This process can be carried out in a manner similar to that described in Process 2 of Method A-2.

The aimed compound can be obtained in accordance with the methods described in Processes 3 to 5 of Method B-1.

Method G-1

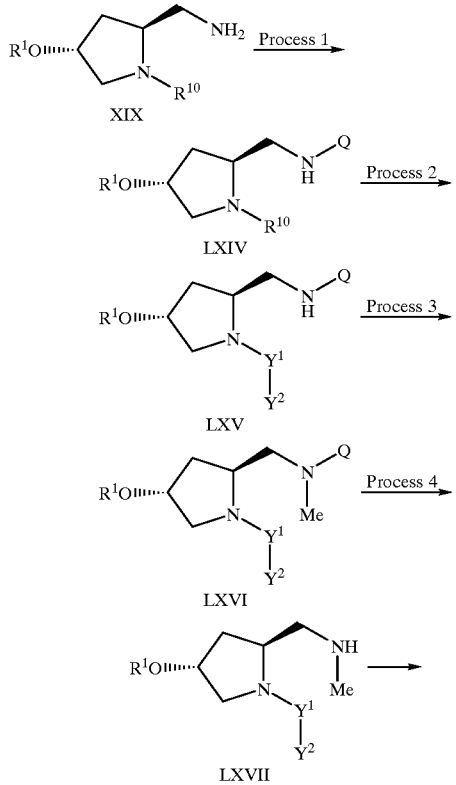

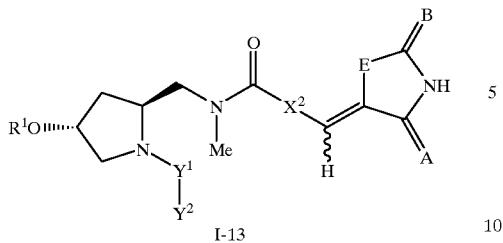

I-13

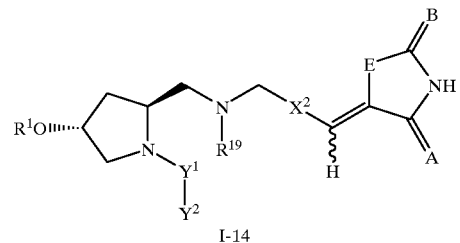

I-14

Wherein A, B, E, $R^1$, $R^{10}$, $X^2$, $Y^1$, $Y^2$, and a wavy line are as defined above and Q is an amino-protecting group distinguishable from $R^{10}$. For example, when $R^{10}$ is Boc, Q is $CF_3CO-$.

Process 1 (XIX→LXIV)

This process involves the protection of an amino group of the side chain. This protecting group must be distinguishable from $R^{10}$. When the protecting group is trifluoromethyl carbonyl, this process can be carried out by reacting with anhydrous trifluoroacetic anhydride-pyridine in dichloromethane, trifluoroacetic acid ethyl ester-triethylamine in methanol, and the like.

Process 2 (LXIV→LXV)

This process can be carried out in a manner similar to that described in Process 9 and 10 of Method A-1.

Process 3 (LXV→LXVI)

This process involves the N-alkylation. This process can be carried out in a solvent such as dimethylformamide and the like in the presence of a base such as sodium hydride by reacting with an alkyl halide such as methyl iodide.

Process 4 (LXVI→LXVII)

This process involves the deprotection of protecting group Q. For example, when the protecting group is trifluoromethylcarbonyl, this process can be carried out in a solvent such as methanol, ethanol, and the like by reacting with sodium hydroxide, potassium hydroxide, potassium carbonate, sodium carbonate, ammonia, and the like.

Successively, the aimed compound can be obtained in accordance with the method described in Process 8 of Method A-1.

Method G-2

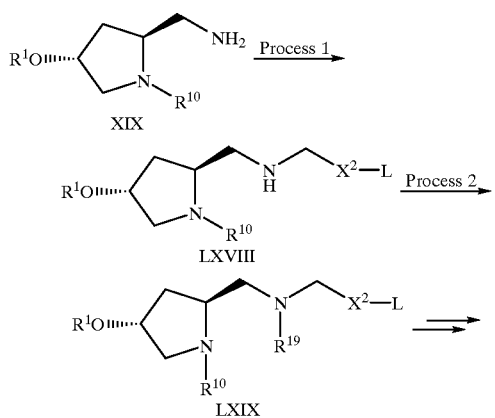

Wherein A, B, E, $R^1$, $R^{10}$, $R^{19}$, L, $X^2$, $Y^1$, $Y^2$, and a wavy line are as defined above.

Process 1 (XIX→LXVIII)

This process involves the reduction of Schiff's base, which is produced in the dehydration of an amine derivative and an aldehyde derivative, by reacting with sodium borohydride and the like.

Process 2 (LXVIII→LXIX)

This process involves the N-alkylation or N-acylation. The N-Alkylation can be carried out in the presence of a base such as triethylamine, pyridine, and the like by reacting a starting material with an alkyl halide or, as described in Process 1, by reacting with an aldehyde derivative under reducing condition. The N-acylation can be carried out in dichloromethane in the presence of pyridine, triethylamine, and the like by reacting with acetic anhydride or benzoyl-chloride when the acyl is acetyl or benzoyl.

Successively, the aimed compound can be obtained in accordance with the methods described in Processes 2 to 6 of Method A-2.

Method G-3

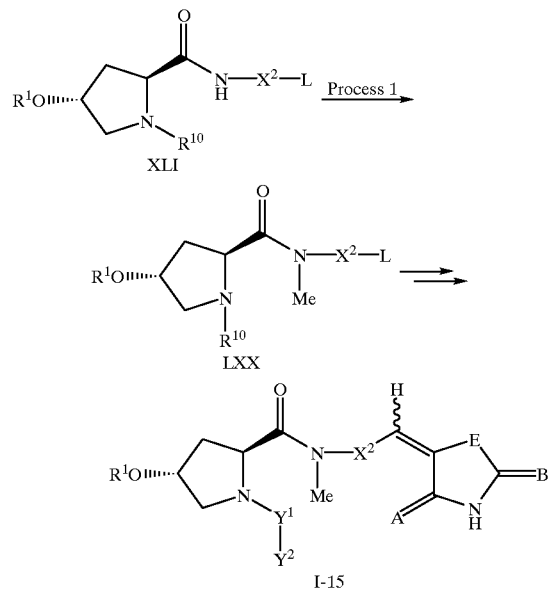

Wherein A, B, E, $R^1$, $R^{10}$, $X^2$, $Y^1$, $Y^2$, and a wavy line are as defined above.

Process 1 (XLI→LXX)

This process can be carried out in a manner similar to that described in Process 3 of Method G-1.

Successively, the aimed compound can be obtained in accordance with the methods described in Processes 2 to 6 of Method A-2.

Method H

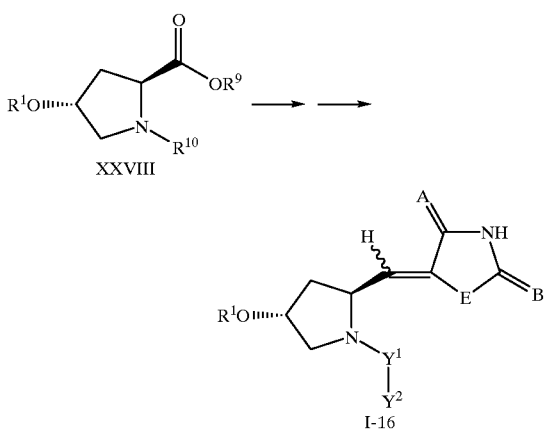

Wherein A, B, E, R$^1$, R$^9$, R$^{10}$, L, Y$^1$, Y$^2$ and a wavy line are as defined above.

After an aldehyde derivative which is prepared by the method described in Process 1 of Method E-1 is synthesized, the aimed compound can be obtained in accordance with the methods described in Processes 5 and 6 of Method A-2.

Method I-1

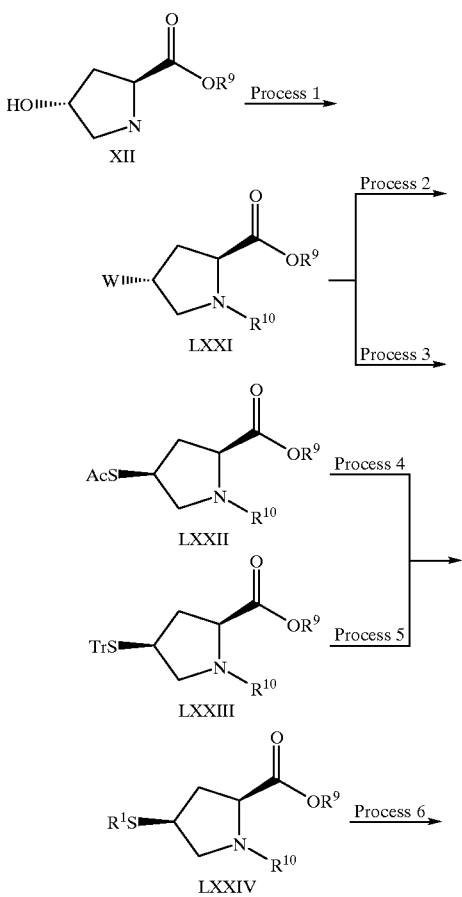

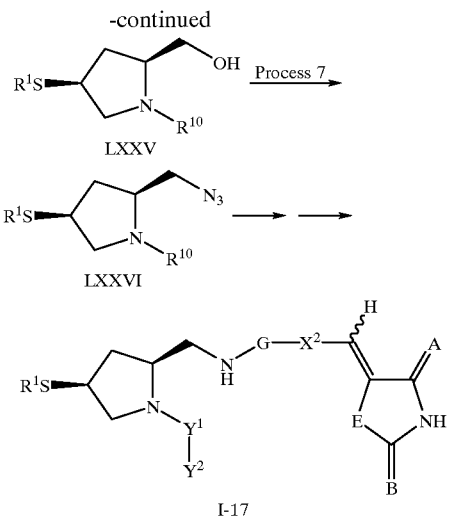

Wherein A, B, E, G, R$^1$, R$^9$, R$^{10}$, Y$^1$, Y$^2$, and a wavy line are as defined above, W is a leaving group, Ac is acetyl, and Tr is trityl.

Process 1 (XII→LXXI)

This process involves the protection of a secondary amine of the pyrrolidine ring, followed by conversion of a 4-hydroxy group to a leaving group. N-protecting reaction can be carried out in a manner similar to that described in Process 1 of Method A-1.

Successively, a hydroxy group is converted into a leaving group. Examples of the leaving group are O-mesyl, O-tosyl, O-trifluoromethansulfonyl, halogen, and the like. This introduction of these leaving groups is carried out by usual methods using mesyl chloride, tosyl chloride, trifluoromethansulfonyl chloride, phosphorous trichloride, phosphorous pentachloride, and the like (JP-5-294970(A1)).

Process 2 (LXXI→LXXII)

This process involves the conversion of the leaving group at the 4-position of the pyrrolidine ring to a substituted thio group such as acetylthio. This process is, for example, carried out in a solvent such as dimethylformamide and the like by reacting with potassium thioacetate and the like.

Process 3 (LXXI→LXXIII)

The purpose of this process is the same as Process 2 except that tritylthio is introduced instead of acetylthio. This process is, for example, carried out in a solvent such as dimethylformamide, tetrahydrofuran, and the like by reacting with sodium tritylthilate and the like.

Processes 4 and 5 (LXXII, LXXIII→XXIV)

In this process, —S—R$^1$ derivative is obtained by reacting a sodium salt, which is prepared by the deprotection of a sulfur substituent, with a haloid such as an alkyl halide (e.g., iodomethane and 2-bromopropane), an alkenyl halide (geranyl halide), an aralkyl halide (benzyl bromide), and the like. For example, the Process 4 is carried out in a solvent such as methanol, toluene, dimethylformamide, and the like by reacting with sodium methylate and the like, and successively adding the above mentioned haloid to give a derivative having —S—R$^1$ group at the 4-position.

In the Process 5, the trityl group is deprotected by using silver nitrate to give a silver salt, which is treated with hydrogen sulfide to give a thiol derivative. This is converted into S-sodium salt derivative, which then is reacted with the above mentioned haloid to give —S—R$^1$ derivative. This process is, for example, carried out in a solvent such as methanol and the like by adding silver nitrate and collecting precipitated crystals or extracting the silver salt. Successively, the silver salt is reacted with hydrogen sulfide in a solvent such as dichloromethane, tetrahydrofuran, and the like to give a 4-thiol derivative, which is reacted with sodium methylate in a solvent such as toluene, methanol, dichloromethane, and the like to produce an S-sodium salt, which may optionally be concentrated to dryness for isolation, then the salt is reacted with the above mentioned haloid to give —S—$R^1$ derivative.

Process 6 (LXXIV→LXXV)

This process can be carried out in a manner similar to that described in Process 3 of Method A-1.

Process 7 (LXXV→LXXVI)

This process can be carried out in a manner similar to that described in Process 4 of Method A-1.

Successively, the aimed compound can be obtained in accordance with the methods described in Processes 5 to 10 of Method A-1.

Method I-2

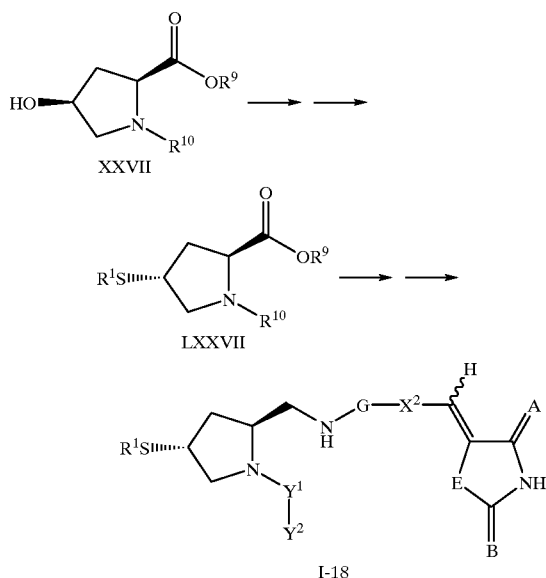

Wherein A, B, E, G, $R^1$, $R^9$, $R^{10}$, $Y^1$, $Y^2$, and a wavy line are as defined above.

In this process, the aimed compound is obtained in a manner similar to that described in Method I-1 using a starting compound which has a different configuration at the 4-position of the pyrrolidine ring from that of the starting compound of Method I-1.

Method J-1

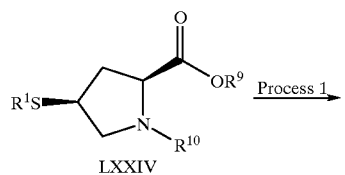

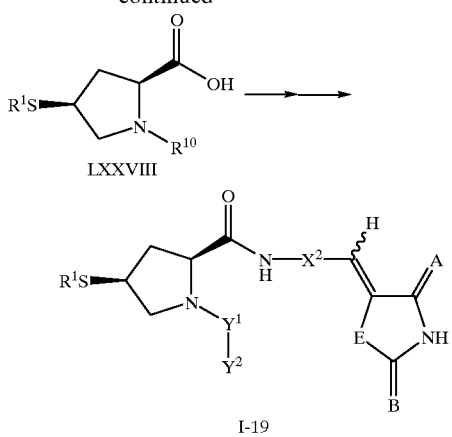

Wherein A, B, E, $R^1$, $R^9$, $R^{10}$, $Y^1$, $Y^2$, and a wavy line are as defined above.

Process 1 (LXXIV→LXXVIII)

This process can be carried out in a manner similar to that described in Process 1 of Method B-1.

Successively, the aimed compound can be obtained in accordance with the methods described in Processes 3 to 5 of Method B-1.

Method J-2

Wherein A, B, E, $R^1$, $R^9$, $R^{10}$, $Y^1$, $Y^2$, and a wavy line are as defined above.

In this process, the aimed compound is obtained in a manner similar to that described in Method J-1 using a starting compound which has a different configuration at the 4-position of the pyrrolidine ring from that of the starting compound of Method J-1.

Method K

This method is for the synthesis of the compound which has a sulfur atom at the 4-position of the pyrrolidine ring and a carbon chain at the 2-position in a manner similar to that described in Method E-1 or E-2 using the compound (LXXV) prepared in Method I or the compound of which configuration of a sulfur substituent at the 4-position is reversed as a starting material.

Method L

This method relates to the synthesis of the compound which has a substituted thio group at the 4-position of the pyrrolidine ring and an amide bond intervened by a carbon chain at the 2-position of the pyrrolidine ring in a manner similar to those described in Methods F-1 to F-4 using the compounds (LI), (LIV), and (LV) as a starting material.

Method M

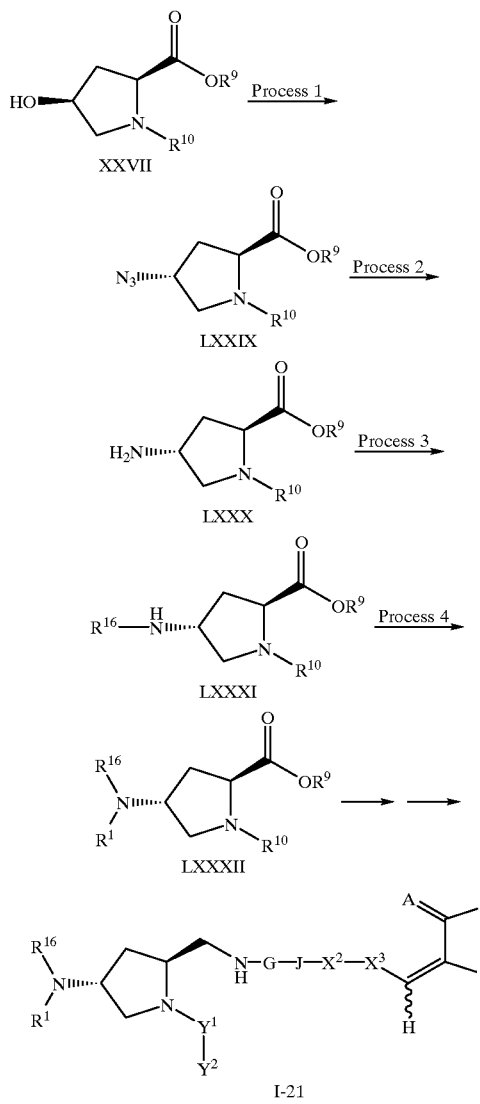

Wherein A, B, E, G, J, $R^1$, $R^9$, $R^{10}$, $R^{16}$, $X^2$, $X^3$, $Y^1$, $Y^2$, and a wavy line are as defined above.

Process 1 (XXVII→LXXIX)

This process can be carried out in a manner similar to that described in Process 4 of Method A-1.

Process 2 (LXXIX→LXXX)

This process can be carried out in a manner similar to that described in Process 7 of Method A-1.

Processes 3 and 4(LXXX→LXXXI, LXXXI→LXXXII)

These processes involve N-alkylation. For example, these processes can be carried out in a manner similar to that described in Process 2 of Method G-2.

The resultant compound is treated in a manner similar to those described in Processes 2 to 7 of Method A-3 to give the aimed compound.

Method N

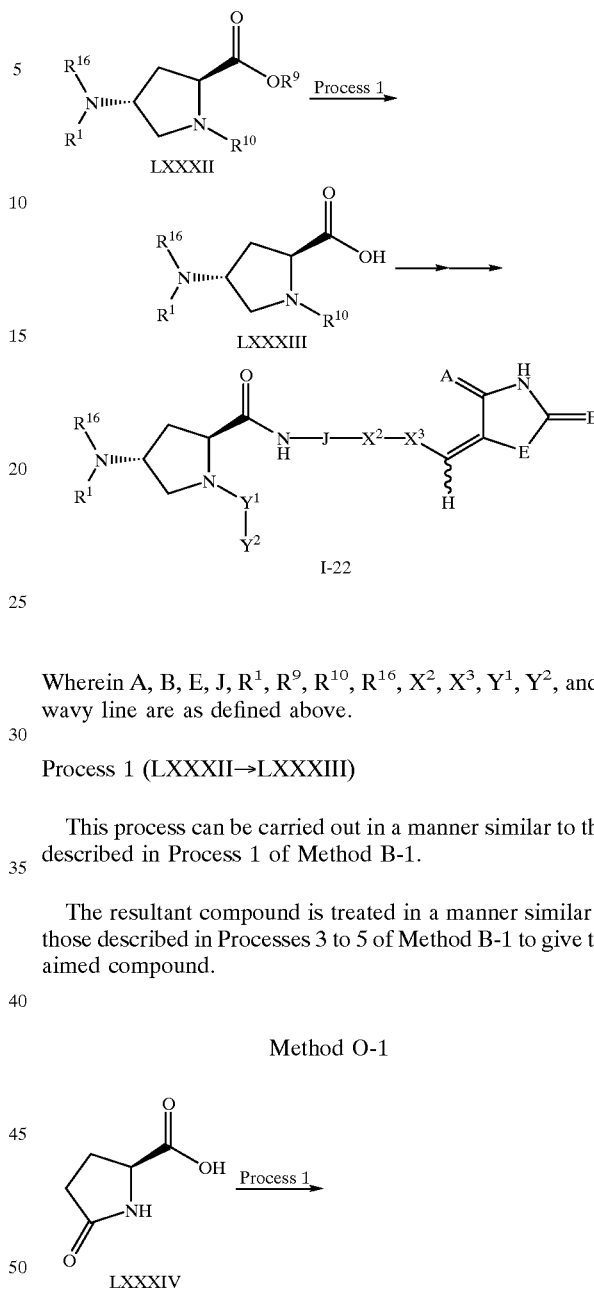

Wherein A, B, E, J, $R^1$, $R^9$, $R^{10}$, $R^{16}$, $X^2$, $X^3$, $Y^1$, $Y^2$, and a wavy line are as defined above.

Process 1 (LXXXII→LXXXIII)

This process can be carried out in a manner similar to that described in Process 1 of Method B-1.

The resultant compound is treated in a manner similar to those described in Processes 3 to 5 of Method B-1 to give the aimed compound.

Method O-1

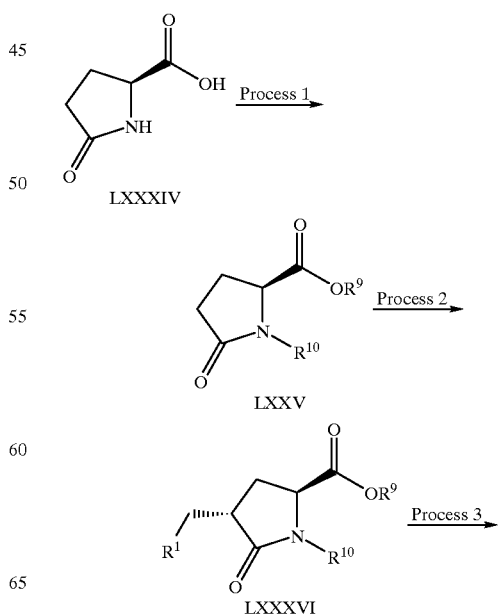

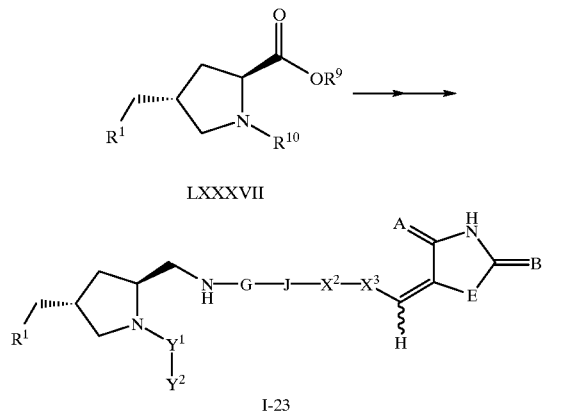

LXXXVII

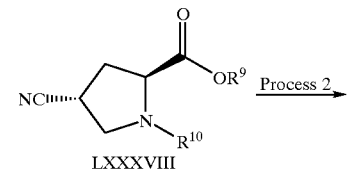

I-23

Wherein A, B, E, G, J, $R^1$, $R^9$, $R^{10}$, $X^2$, $X^3$, $Y^1$, $Y^2$, and a wavy line are as defined above.

Process 1 (LXXXIV→LXXXV)

This process involves the protection of a secondary amine of the pyrrolidine ring after protecting the carboxyl group; for example, 1) the starting material is reacted with thionyl chloride in a solvent such as toluene, dichloromethane, tetrahydrofuran, and the like to give an acid halide, and successively adding an alcohol such as methanol, ethanol, and the like to give a methyl ester derivative, an ethyl ester derivative, and the like, 2) when $R^{10}$ is Boc, this process is carried out by adding dimethylaminopyridine as a catalyst in a manner similar to that described in Process 1 of Method A-1 (P. A. Grieco et. al., J, Org. Chem., 1983, 48, 2424–2426.).

Process 2 (LXXXV→LXXXVI)

This process involves the introduction of "optionally substituted aralkyl" at the α-position of carbonyl (i.e. the 4-position of the pyrrolidine ring). For example, this process can be carried out by reacting with an alkyl halide such as benzyl chloride in a solvent such as tetrahydrofuran and the like in the presence of a base such as lithium hexamethyldisilazane (J, Ezquerra et. al. Tetrahedron, 1993, 49(38), 8665–8678.).

Process 3 (LXXXVI→LXXXVII)

This process involves the reduction of a ketone at the 5-position of the pyrrolidine ring. For example, this process is carried out by reacting with a reductant such as lithium triethylborohydride and the like in a solvent such as ether, toluene, and the like, and further reacting with triethylsilane in the presence of Lewis acid such as $BF_3$ ethelate (C. Pedregal et. al., Tetrahedron Letters, 1994, 35(13), 2053–2056.).

The resultant compound is treated in a manner similar to those described in Processes 2 to 7 of Method A-3 and Processes 7 to 10 of Method A-1 to give the aimed compound.

Method O-2

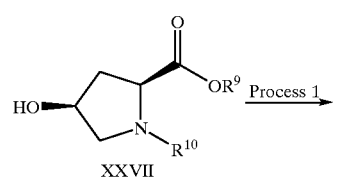

XXVII

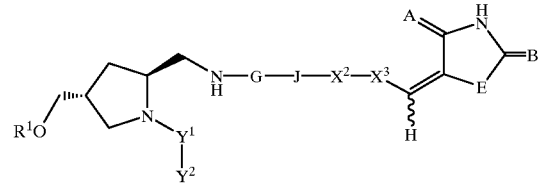

LXXXVIII

XCI

XCII

I-24

Wherein A, B, E, G, J, $R^1$, $R^9$, $R^{10}$, $R^{11}$, $X^2$, $X^3$, $Y^1$, $Y^2$, and a wavy line are as defined above.

Process 1 (XXVII→LXXXVIII)

This process can be carried out in a manner similar to that described in Process 1 of Method E-2.

Process 2 (LXXXVIII→LXXXX)

This process involves the conversion to the hydroxy derivative in a manner similar to that described in Process 3 of Method A-1 and the protection of this hydroxy group. For example, when the protecting group is t-butyldimethylsilyl group, this process can be carried out by reacting with a sililation agent such as t-butyldimethylsilyl chloride and the like in a solvent such as dimethylformamide and the like in the presence of imidazole.

Process 3 (LXXXVIX→XC)

This process can be carried out in a manner similar to that described in Process 2 of Method E-2.

Process 4 (XC→XCI)

This process can be carried out in a manner similar to that described in Process 1 of Method F-2.

Process 5 (XCI→XCII)

This process can be carried out in a manner similar to that described in Process 1 of Method A-3.

Successively, the aimed compound can be obtained in a manner similar to those described in Processes 3 to 7 of Method A-3, after deprotection of the protecting group of hydroxy. For example, when the protecting group is t-butyldimethylsilyl group, this deprotection can be carried out by treating with tetrabutylammonium fluoride in a solvent such as tetrahydrofuran and the like.

Method O-3

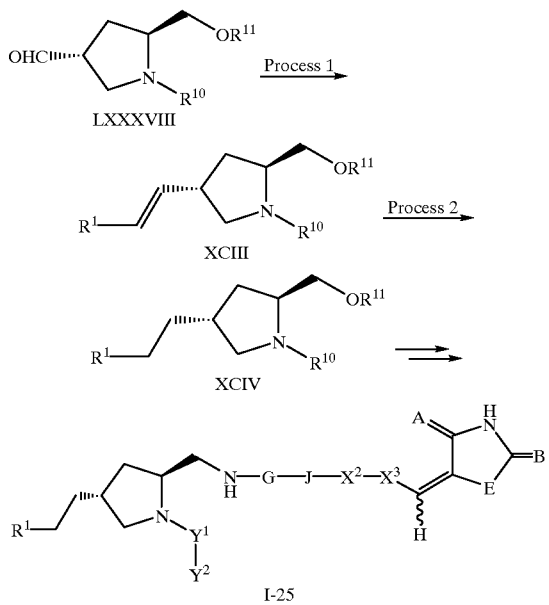

Wherein A, B, E, G, J, $R^1$, $R^{10}$, $R^{11}$, $X^2$, $X^3$, $Y^1$, $Y^2$, and a wavy line are as defined above.

Process 1 (LXXXVIII→XCIII)

This process can be carried out in a manner similar to that described in Process 2 of Method E-1.

Process 2 (XCIII→XCIV)

This process can be carried out in accordance with the above mentioned catalytic hydrogenation.

Successively, the aimed compound can be obtained in a manner similar to those described in Processes 3 to 7 of Method A-3, after deprotection of the protecting group of hydroxy. For example, when the protecting group is t-butyldimethylsilyl group, the deprotection can be carried out by treating with tetrabutylammonium fluoride in a solvent such as tetrahydrofuran and the like.

Method P

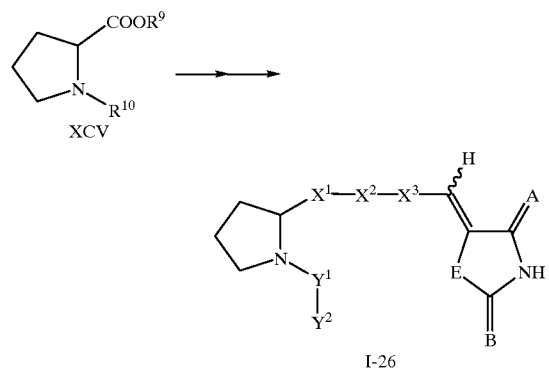

Wherein A, B, E, $R^9$, $R^{10}$, $X^1$, $X^2$, $X^3$, $Y^1$, $Y^2$, and a wavy line are as defined above.

This method is related to the synthesis of the compound which has no substituent at the 4-position of the pyrrolidine ring. The aimed compound can be prepared in a manner similar to that described in the above mentioned methods except for using proline as a starting compound.

Method Q

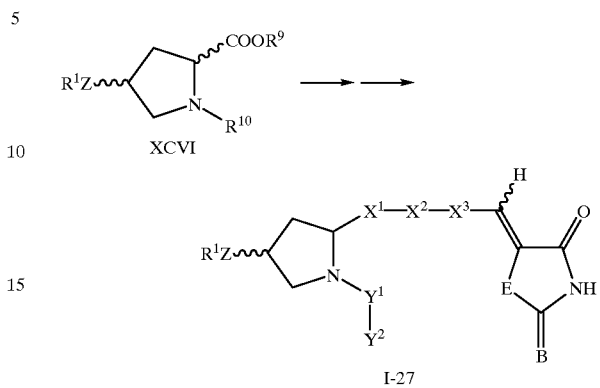

Wherein A, B, E, $R^9$, $R^{10}$, $X^1$, $X^2$, $Y^1$, and $Y^2$ are as defined above, a wavy line on the pyrrolidine ring represents the bond is R or S configuration, and a wavy line on the double bond represents hydrogen atom is cis or trans against E.

This method is related to the synthesis of the compounds which correspond to those described in Methods A, I, and the like, but are in different configuration(s) at the 2- and/or 4-position. The compound having oxygen atom at the 4-position obtained in the above is in (2β, 4α) configuration and that having sulfur atom at the 4-position is in (2β, 4β) or (2β, 4α) configuration. In the Method Q, the compounds having oxygen or sulfur atom at the 4-position and (2β, 4β), (2α, 4β), or (2α, 4α) configuration are synthesized.

All of the starting compounds are known in J. Org. Chem., 1981, 46, 2954–2960(J. K. Still et. al.) and Japanese Patent Publication (KOKAI) No. 294970/1993 (U.S. Pat. No. 5,317,016). The conversion of respective functional groups can be carried out in a manner similar to that described in the above. When a compound contains a functional group(s) possibly interfering the reaction, it can previously be protected and deprotected at an appropriate stage in accordance with the literature such as Protective Groups in Organic Synthesis, Theodora W. Green (John Wiley & Sons).

All of the above mentioned methods are definitely shown by the concrete substituent(s) and the substituted position, but the compound of this invention can be prepared by using the above mentioned Methods A to Q appropriately.

The term "the compounds of the present invention" herein used includes pharmaceutically acceptable salts and hydrates of the compounds. For example, salts with alkali metals (e.g., lithium, sodium, and potassium), alkaline earth metals (e.g., magnesium and calcium), ammonium, organic bases, amino acids, mineral acids (e.g., hydrochloric acid, hydrobromic acid, phosphoric acid, and sulfuric acid), or organic acids (e.g. acetic acid, citric acid, maleic acid, fumaric acid, benzenesulfonic acid, and p-toluenesulfonic acid) and hydrates of them are exemplified. These salts and hydrates can be formed by usual methods. The hydrates may coordinate with an arbitrary number of water molecules.

The present invention is not restricted to any particular isomers but includes all possible isomers and racemic modifications.

The compound of the present invention has activity of inhibiting the production of arachidonic acid, prostaglandin $E_2$, and leukotriene $C_4$ each based on the inhibition of $cPLA_2$ activity and is useful for the prevention or treatment of diseases attributable to prostaglandin or leukotriene.

Definitely, the compounds of this invention are useful for the prevention or treatment of diseases such as rheumatoid arthritis, asthma, inflammatory bowel disease, injury by ischemia-reperfusion, allergic rhinitis, and proriasis.

When the compound of this invention is administered to a patient for the treatment or prevention of the above diseases, it can be administered by oral administration such as powder, granules, tablets, capsules, pilulae, and liquid medicine, or by parenteral administration such as injections, suppository, percutaneous formulations, insufflation, or the like. An effective amount of the compound of this invention is formulated by being mixed with appropriate medicinal admixture such as excipient, binder, penetrant, disintegrators, lubricant, and the like, if necessary. When parenteral injection is prepared, the compound of this invention and an appropriate carrier are sterilized to prepare it.

An appropriate dosage varies with the conditions of the patients, an administration route, their age, and their body weight. The dosage is finally decided by a doctor. In the case of oral administration to an adult, the dosage can generally be between 1–100 mg/kg/day, preferably 10–50 mg/kg/day, and in the case of parenteral administration to an adult, the dosage can generally be between 0.1–10 mg/kg/day, preferably 1–5 mg/kg/day, which may be administrated in one to several divisions.

The following examples are provided to further illustrate the present invention and are not to be construed as limiting the scope thereof.

EXAMPLE

Example 1 (Method A-1)

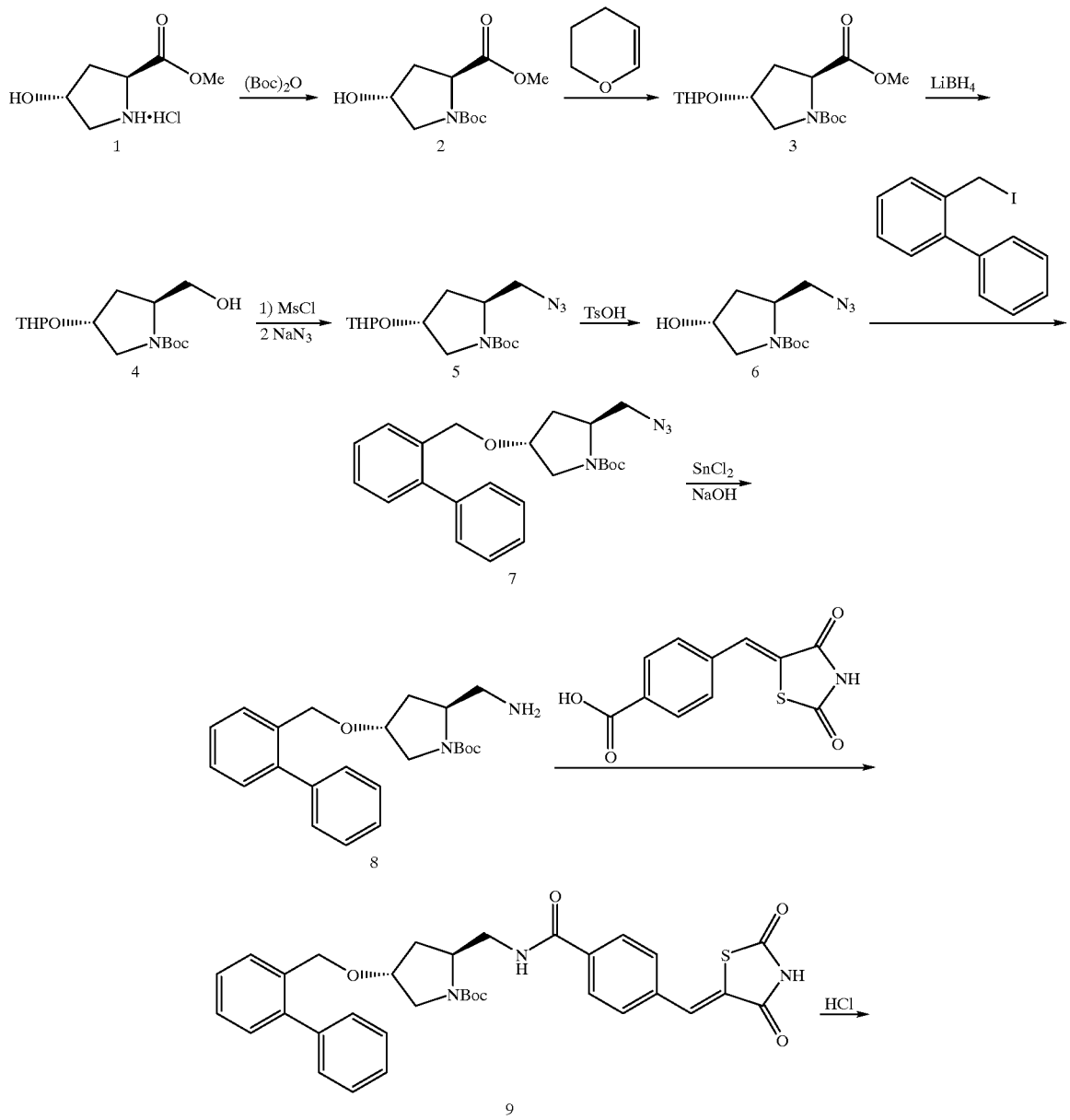

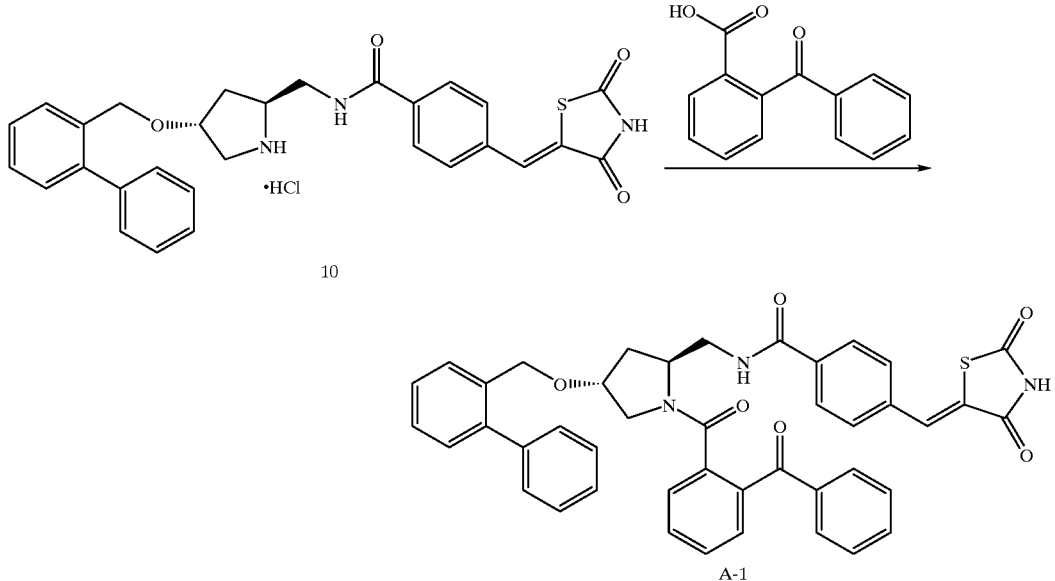

(1) 1→2

To a solution of 4-hydroxy-L-proline methylester hydrochloride (1) (18.14 g, 99.88 mmol) in dioxane (150 ml) was added 10% sodium hydrogencarbonate aq. (120 ml) 5 and 26.19 g (120.0 mmol) of di-t-butylcarbonate under ice-cooling with stirring and the resulting mixture was stirred for 2 h at the same temperature. The reaction mixture was allowed to warm to room temperature and stirred for 17 h. The insoluble material was filtered off and the filtrate was extracted with ethyl acetate (300 ml). The organic layer was washed with water and brine, dried over sodium sulphate, and concentrated in vacuo to give 24.0 g (98.0%) of the compound (2) as an oil.

NMR (CDCl$_3$) δ ppm: 1.42 (⅔×9H, s), 1.46 (⅓×9H, s), 1.81–2.38 (3H), 3.40–3.68 (2H), 3.71 (1H, s), 3.73 (3H, s), 4.36–4.55 (2H).

(2) 2→3

To a solution of the compound (2) (24.0 g, 97.85 mmol) in chloroform (300 ml) was added 10.0 g (118.9 mmol) of dihydropyrane and 350 mg of p-toluenesulfonic acid under ice-cooling with stirring, the resulting mixture was stirred for 1 h at the same temperature, allowed to warm to room temperature, and was stirred for 5 h. The reaction mixture was washed with 5% sodium hydrogencarbonate aq., water, and brine, dried over sodium sulphate, and concentrated in vacuo. The residue was subjected to silica gel column chromatography (hexane:ethyl acetate=2:1) to give 22.2 g (68.9%) of an aimed compound (3).

NMR (CDCl$_3$) δ ppm: 1.41 (⅔×9H, s), 1.46 (⅓×9H, s), 1.53 (4H, m), 1.60–1.90 (2H), 1.98–2.50 (2H), 3.39–3.75 (3H), 3.73 (⅔×3H, s), 3.74(⅓×3H, s), 3.83 (1H, m), 4.27–4.47 (2H), 4.61–4.70 (1H).

(3) 3→4

To a solution of the compound (3) (22.2 g, 67.4 mmol) in tetrahydrofuran (300 ml) was added 2.2 g (101 mmol) of lithium borohydride under ice-cooling with stirring and the resulting mixture was stirred for 3 h at the same temperature, allowed to warm to room temperature, and stirred for 17 h. To the reaction mixture was added methanol (1 ml), iced water (500 ml), and 10% hydrochloric acid aq. (35 ml), and the resulting mixture was extracted with ethyl acetate (500 ml). The organic layer was washed with water and brine, dried over sodium sulphate, and concentrated in vacuo to give 18.9 g (93.1%) of the compound (4) as an oil.

NMR (CDCl$_3$) δ ppm: 1.42–1.90 (16H), 2.02–2.24 (1H), 3.34–3.92 (6H), 4.11 (1H, s), 4.28 (1H, br s), 4.88 (1H, m).

(4) 4→5

To a solution of the compound (4) (18.9 g, 62.71 mmol) in tetrahydrofuran (150 ml) was added 12 ml of triethylamine and 8.71 g (76.04 mmol) of methanesulfonyl chloride under ice-cooling with stirring and the resulting mixture was stirred for 30 min at the same temperature. Ethyl acetate (400 ml) was added to the reaction mixture. The organic layer was washed with water and brine, dried over sodium sulphate, and concentrated in vacuo. The residue was subjected to silica gel column chromatography (hexane:ethyl acetate=2:1) to give 15.48 g of the aimed compound (5) as an oil.

NMR (CDCl$_3$) δ ppm: 1.47 (9H, s), 1.53 (3H, m), 1.60–1.88 (2H), 1.93–2.25 (2H), 1.93–2.25 (2H), 3.20–3.92 (7H), 4.08 (1H, m), 4.38 (1H, m), 4.65 (1H, m).

(5) 5→6

To a solution of 15.48 g (47.43 mmol) of the compound (5) in methanol (400 ml) was added 400 mg of p-toluenesulfonic acid and the resulting mixture was stirred for 15 h at room temperature. Triethylamine (1 ml) was added to the reaction mixture and the resulting mixture was concentrated in vacuo. The residue was dissolved in 200 ml of ethyl acetate and the organic layer was washed with water and brine, dried over sodium sulphate, and concentrated in vacuo. The obtained oily material (11.5 g) was used in next step.

NMR (CDCl$_3$) δ ppm: 1.48 (9H, s), 1.70 (1H, br s), 2.05 (2H, m), 3.08–4.20 (5H), 4.46 (1H, m).

(6) 6→7

To a solution of the compound (6) (19.16 g, 79.08 mmol) in N, N-dimethylformamide (160 ml) was added 60% sodium hydride (3.48 g, 86.99 mmol) and the resulting mixture was stirred for 20 min at 50° C. To the reaction mixture was added a solution of 2-phenylbenzyl iodide (23.26 g, 79.08 mmol) in N, N-dimethylformamide (40 ml) under ice-cooling with stirring, and the resulting mixture was stirred for 1 h 40 min at room temperature. The reaction mixture was dissolved in ethyl acetate (200 ml). The organic layer was washed with water and brine, dried over sodium sulphate, and concentrated in vacuo. The residue was subjected to silica gel column chromatography (hexane:ethyl acetate=4:1) to give 23.89 g (74%) of the aimed compound (7).

NMR (CDCl$_3$) δ ppm: 1.46 (9H, s), 1.72–2.15 (2H), 3.06–4.14 (6H), 4.38 (2H, d, J=2.4 Hz), 7.20–7.56 (9H). IR ν$_{max}$ (Film): 2103, 1649, 1394, 1256, 1164, 1121 cm$^{-1}$. Elemental analysis (C$_{23}$H$_{28}$N$_4$O$_3$); Calcd.: C, 67.63; H, 6.91; N, 13.72%. Found: C, 67.43; H, 6.97; N, 13.64%.

(7) 7→8

Stannous chloride dihydrate (19.32 g, 47.30 mmol) was dissolved in 2N sodium hydroxide aq. (142 ml) and the solution was added to a solution of the compound (7) (19.32 g, 47.30 mmol) in ethanol (194 ml) under ice-cooling with stirring and the resulting mixture was stirred for 1 h at the same temperature. The precipitate was filtered off and the filtrate was concentrated in vacuo. Ethyl acetate (200 ml) was added to the residue and the organic layer was washed with water and brine, dried over sodium sulphate, and concentrated in vacuo to give 18.09 g (100%) of the aimed compound (8) as an oil.

NMR (CDCl$_3$) δ ppm: 1.31 (2H, s), 1.45 (9H, s), 1.78–2.12 (2H), 2.68–2.90 (2H), 3.19–4.05 (4H), 4.38 (2H, d, J=3.0 Hz), 7.23–7.54 (9H). IR ν$_{max}$ (Film): 3372, 1691, 1397, 1254, 1168, 1118 cm$^{-1}$. Elemental analysis (C$_{23}$H$_{30}$N$_2$O$_3$·0.5H$_2$O$_3$); Calcd.: C, 70.56; H, 7.98; N, 7.16%. Found: C, 70.45; H, 7.89; N, 7.07%.

(8) 8→9

To a solution of the compound (8) (13.84 g, 36.18 mmol) in N, N-dimethylformamide (200 ml) were added 4-(2,4-dioxothiazolidine-5-ylidenemethyl) benzoic acid (9.02 g, 36.18 mmol), and 1-hydroxybenzotriazole hydrate (5.54 g, 36.18 mmol), and 1-ethyl-3-(3-dimethylaminopropyl) carbodiimide hydrochloride (7.63 g, 39.80 mmol) at room temperature and the resulting mixture was stirred for 1 h. Ethyl acetate (400 ml) was added to the reaction mixture. The organic layer was washed with water and brine, dried over sodium sulphate, and concentrated in vacuo. The residue was subjected to silica gel column chromatography (chloroform:methanol=49:1) to give 20.20 g (100%) of the aimed compound (9).

NMR (CDCl$_3$) δ ppm: 1.60–1.83 (1H), 2.05–2.25 (1H), 3.05–4.30 (6H), 4.37 (1H, d$_{AB}$, J=11.0 Hz), 4.42 (1H, d$_{AB}$, J=11.0 Hz), 7.20–7.60 (9H), 7.53 (2H, d$_{AB}$, J=8.3 Hz), 7.82 (1H, s), 7.96 (2H, s), d$_{AB}$, J=8.3 Hz), 8.68 (1H, br s), 9.07 (1H, br s). IR ν$_{max}$ (KBr): 3411, 1750, 1708, 1667, 1611, 1542, 1405, 1318, 1296, 1162, 1120 cm$^{-1}$. Elemental analysis (C$_{34}$H$_{35}$N$_3$SO$_6$); Calcd.: C, 66.54; H, 5.75; N, 6.85; S, 5.22%. Found: C, 66.33; H, 5.83; N, 6.76; S, 5.07%.

(9) 9→10

To a solution of the compound (9) (21.87 g, 35.63 mmol) in ethyl acetate (100 ml) was added 4N hydrochloric acid in ethyl acetate (80 ml) at room temperature with stirring and the resulting mixture was stirred for 2 h. The precipitation was collected to give 17.23 g (88%) of the hydrochloride derivative (10).

NMR (DMSO-d$_6$) δ ppm: 1.72 (1H, m), 2.07 (1H, m), 3.00–3.92 (5H), 4.12–4.22 (1H), 4.36 (1H, d$_{AB}$, J=11.3 Hz), 4.39 (1H, d$_{AB}$, J=11.3 Hz), 7.20–7.59 (9H), 7.71 (2H, d$_{AB}$, J=8.2 Hz), 7.84 (1H, s), 8.05 (2H, d$_{AB}$, J=8.2 Hz), 9.05 (1H, t, J=5.6 Hz), 9.22–9.72 (1H, br), 11.80–12.10 (1H, br), 12.43–13.00 (1H, br). IR ν$_{max}$ (KBr): 3421, 3237, 1748, 1705, 1637, 1610, 1541, 1300, 1153 cm$^{-1}$. Elemental analysis (C$_{29}$H$_{28}$N$_3$ClSO$_4$·1.1H$_2$O); Calcd.: C, 61.12; H, 5.34; N, 7.37; Cl, 6.22; S, 5.63%. Found: C, 61.17; H, 5.14; N, 7.33; Cl, 6.29; S, 5.49%.

(10) 10→A-1

To a solution of the compound (10) (111.4 mg, 0.202 mmol) in N, N-dimethylformamide (2 ml) were added 2-benzoyl benzoic acid (50.4 mg, 0.223 mmol), 1-hydroxybenzotirazole hydrate (34.1 mg, 0.223 mmol), 1-ethyl-3-(3-dimethylaminopropyl) carbodiimide hydrochloride (42.7 mg, 0.223 mmol), and triethylamine (0.042 ml, 0.303 mmol) at room temperature and the resulting mixture was stirred for 2 h. Ethyl acetate (30 ml) was added to the reaction mixture. The organic layer was washed with water and brine, dried over sodium sulphate, and concentrated in vacuo. The residue was subjected to silica gel column chromatography (chloroform:methanol=100:1) to give 94.1 mg (64.6%) of the aimed compound (A-1).

NMR (CDCl$_3$) δ ppm: 1.81 (1H, ddd, J=5.0, 7.6, 13.8 Hz), 2.19–2.28 (1H), 3.25 (1H dd, J=4.1, 12.0 Hz), 3.34 (1H, d, J=12.0 Hz), 3.41 (1H, ddd, J=5.4, 6.9, 14.1 Hz), 3.87–3.95 (2H), (4.24 (1H, d$_{AB}$, J=11.1 Hz), 4.35 (1H, d$_{AB}$, J=11.1 Hz), 4.52 (1H, dq, J=2.6, 7.3 Hz), 7.24–7.62 (18H), 7.74 (2H, d, J=7.8 Hz), 7.78 (1H, s), 7.94 (2H, d, J=8.5 Hz), 8.25 (1H, t, J=5.0 Hz). IR ν$_{max}$ (KBr): 3405, 3058, 1749, 1708, 1655, 1624, 1577, 1317, 1152 cm$^{-1}$. Elemental analysis (C$_{43}$H$_{35}$N$_3$SO$_6$·0.5H$_2$O); Calcd.: C, 70.67; H, 4.97; N, 5.75; S, 4.39%. Found: C, 70.75; H, 4.98; N, 5.68; S, 4.49%.

The compounds (A-2) to (A-57) were synthesized in a manner similar to that described in the above method. The results were shown in Tables 1 to 6.

TABLE 1

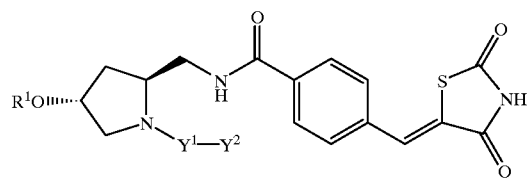

| Compound No. | R$^1$ | —Y$^1$—Y$^2$ | NMR (CDCl$_3$) δ ppm |
|---|---|---|---|
| A-1 | (2-biphenylmethyl) | (2-benzoylbenzoyl) | 4.24(1H, d$_{AB}$, J=11.1Hz)<br>4.35(1H, d$_{AB}$, J=11.1Hz)<br>7.78(1H, s) |

TABLE 1-continued
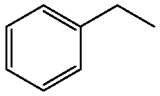
| Compound No. | R¹ | —Y¹—Y² | NMR (CDCl$_3$) δ ppm |
|---|---|---|---|
| A-2 | 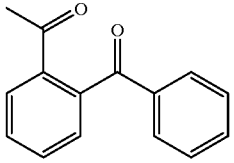 | 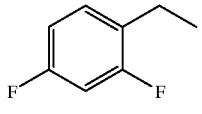 | 4.34(1H, d$_{AB}$, J=11.8Hz)<br>4.48(1H, d$_{AB}$, J=11.8Hz)<br>7.77(1H, s) |
| A-3 | 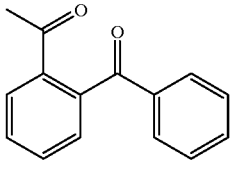 | 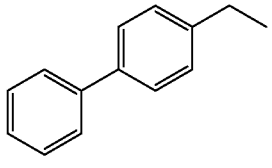 | 4.41(2H, s)<br>7.78(1H, s) |
| A-4 | 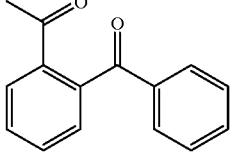 | 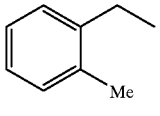 | 4.41(1H, d$_{AB}$, J=12.0Hz)<br>4.50(1H, d$_{AB}$, J=12.0Hz)<br>7.77(1H, s) |
| A-5 | 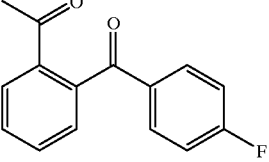 | 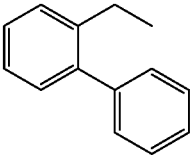 | 4.35(1H, d$_{AB}$, J=11.8Hz)<br>4.46(1H, d$_{AB}$, J=11.8Hz)<br>7.78(1H, s) |
| A-6 | 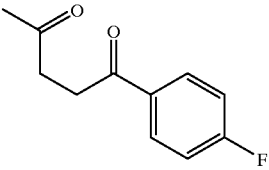 | 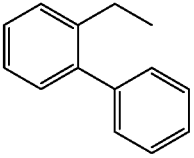 | 4.40(1H, d$_{AB}$, J=11.1Hz)<br>4.48(1H, d$_{AB}$, J=11.1Hz)<br>7.71(1H, s) |
| A-7 | 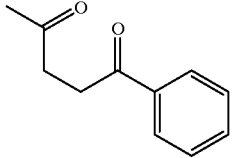 | 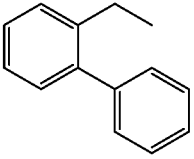 | 4.41(1H, d$_{AB}$, J=11.1Hz)<br>4.47(1H, d$_{AB}$, J=11.1Hz)<br>7.70(1H, s) |
| A-8 | 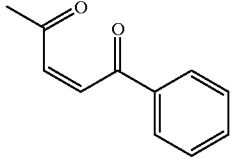 | | 4.39(1H, d$_{AB}$, J=11.0Hz)<br>4.48(1H, d$_{AB}$, J=11.0Hz)<br>7.79(1H, s) |

TABLE 1-continued

| Compound No. | R¹ | —Y¹—Y² | NMR (CDCl₃) δ ppm |
|---|---|---|---|
| A-9 | 2-phenylphenyl-CH₂- | -C(=O)-C(CH₃)=CH-C(=O)-phenyl | 4.34(1H, d_AB, J=11.3Hz) 4.45(1H, d_AB, J=11.3Hz) 7.80(1H, s) |
| A-10 | 2-phenylphenyl-CH₂- | acetyl-cyclohexyl-C(=O)-phenyl | 4.33(½×1H, d_AB, J=11.4Hz) 4.37(½×1H, d_AB, J=11.7Hz) 4.43(½×1H, d_AB, J=11.4Hz) 4.49(½×1H, d_AB, J=11.7Hz) 7.79(½×1H, s) 7.82(½×1H, s) |

TABLE 2

| Compound No. | —Y¹—Y² | B | NMR (CDCl₃) δ ppm |
|---|---|---|---|
| A-11 | 2-acetyl-3-benzoylpyridyl | O | (DMSO-d₆) 4.33(2H, s) 7.82(1H, s) |
| A-12 | 2-acetyl-3-benzoylthienyl | O | 4.22(1H, d_AB, J=11.4Hz) 4.33(1H, d_AB, J=11.4Hz) 7.82(1H, s) |
| A-13 | — | — | — |
| A-14 | 2-acetyl-(cyclohexylcarbonyl)phenyl | O | 4.22(1H, d_AB, J=11.4Hz) 4.33(1H, d_AB, J=11.4Hz) 7.81(1H, s) |

TABLE 2-continued

| Compound No. | —Y¹—Y² | B | NMR (CDCl₃) δ ppm |
|---|---|---|---|
| A-15 | — | — | — |
| A-16 | (2-acetylphenyl)(4-fluorophenyl) ketone group | O | 4.25(1H, d$_{AB}$, J=11.3Hz)<br>4.36(1H, d$_{AB}$, J=11.3Hz)<br>7.77(1H, s) |
| A-17 | (2-acetylphenyl)(furan-3-yl) ketone group | O | 4.24(1H, d$_{AB}$, J=11.1Hz)<br>4.34(1H, d$_{AB}$, J=11.1Hz)<br>7.78(1H, s) |
| A-18 | (2-acetylphenyl)(thiophen-3-yl) ketone group | O | 4.25(1H, d$_{AB}$, J=11.1Hz)<br>4.36(1H, d$_{AB}$, J=11.1Hz)<br>7.79(1H, s) |
| A-19 | (2-acetylphenyl)(thiophen-2-yl) ketone group | O | 4.23(1H, d$_{AB}$, J=11.4Hz)<br>4.34(1H, d$_{AB}$, J=11.4Hz)<br>7.80(1H, s) |
| A-20 | (2-acetylphenyl)(4-fluorophenyl) ketone group | S | 4.25(1H, d$_{AB}$, J=11.2Hz)<br>4.36(1H, d$_{AB}$, J=11.2Hz)<br>7.58(1H, s) |

TABLE 3

| Compound No. | —Y¹—Y² | B | NMR (CDCl₃) δ ppm |
|---|---|---|---|
| A-21 | 2-acetyl-(4-methylbenzoyl)benzene group | O | 4.22(1H, d$_{AB}$, J=11.1Hz)<br>4.33(1H, d$_{AB}$, J=11.1Hz)<br>7.78(1H, s) |
| A-22 | 2-acetyl-(4-chlorobenzoyl)benzene group | O | 4.26(1H, d$_{AB}$, J=11.1Hz)<br>4.36(1H, d$_{AB}$, J=11.1Hz)<br>7.77(1H, s) |
| A-23 | 2-acetyl-(2-aminobenzoyl)benzene group | O | 4.25(1H, d$_{AB}$, J=11.3Hz)<br>4.33(1H, d$_{AB}$, J=11.3Hz)<br>7.77(1H, s) |
| A-24 | 2-acetyl-(2-acetamidobenzoyl)benzene group | O | 4.34(1H, d$_{AB}$, J=11.4Hz)<br>4.41(1H, d$_{AB}$, J=11.4Hz)<br>7.69(1H, s) |
| A-25 | 2-acetyl-(2,4-difluorobenzoyl)benzene group | O | 4.23(1H, d$_{AB}$, J=11.3Hz)<br>4.41(1H, d$_{AB}$, J=11.3Hz)<br>7.69(1H, s) |
| A-26 | 1-acetyl-9-fluorenone group | O | 4.20(1H, d$_{AB}$, J=11.3Hz)<br>4.33(1H, d$_{AB}$, J=11.3Hz)<br>7.83(1H, s) |

TABLE 3-continued
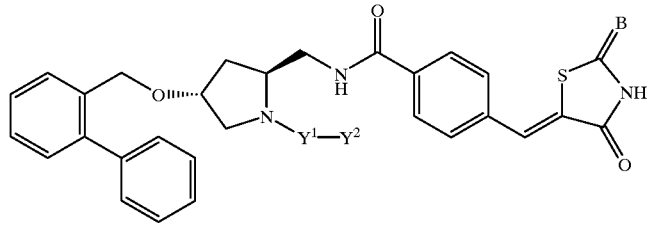
| Compound No. | —Y¹—Y² | B | NMR (CDCl₃) δ ppm |
|---|---|---|---|
| A-27 | 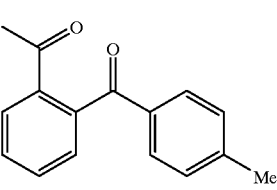 | S | 2.30(3H, s)<br>4.22(1H, d_{AB}, J=11.2Hz)<br>4.34(1H, d_{AB}, J=11.3Hz)<br>7.58(1H, s) |
| A-28 | 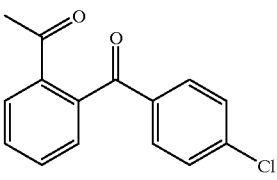 | S | 4.26(1H, d_{AB}, J=11.4Hz)<br>4.37(1H, d_{AB}, J=11.4Hz)<br>7.56(1H, s) |
TABLE 4
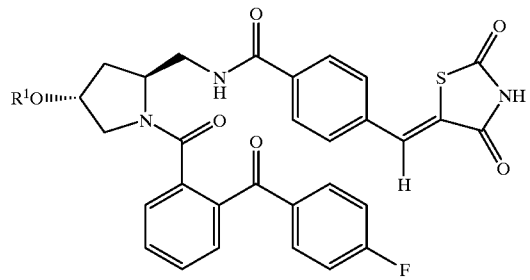
| Compound No. | R¹ | NMR (CDCl₃) δ ppm |
|---|---|---|
| A-29 | 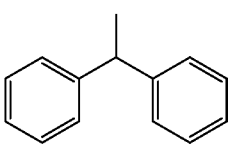 | 5.27(1H, s)<br>7.78(1H, s) |
| A-30 | 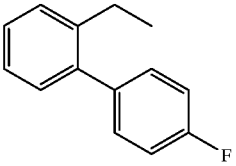 | 4.23(1H, d_{AB}, J=11.1Hz)<br>4.31(1H, d_{AB}, J=11.1Hz) |

TABLE 4-continued
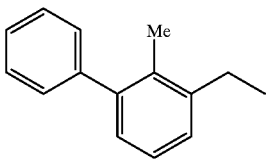
| Compound No. | R¹ | NMR (CDCl₃) δ ppm |
|---|---|---|
| A-31 | 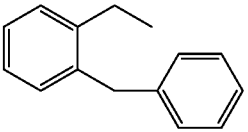 | 4.42(1H, d$_{AB}$, J=11.7Hz)<br>4.51(1H, d$_{AB}$, J=11.7Hz)<br>7.78(1H, s) |
| A-32 | 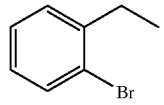 | 4.32(1H, d$_{AB}$, J=11.9Hz)<br>4.41(1H, d$_{AB}$, J=11.9Hz)<br>7.78(1H, s) |
| A-33 | 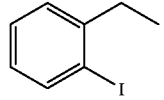 | 4.45(1H, d$_{AB}$, J=12.9Hz)<br>4.50(1H, d$_{AB}$, J=12.9Hz)<br>7.75(1H, s) |
| A-34 | 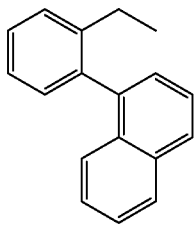 | 4.36(1H, d$_{AB}$, J=12.5Hz)<br>4.42(1H, d$_{AB}$, J=12.5Hz)<br>7.77(1H, s) |
| A-35 | 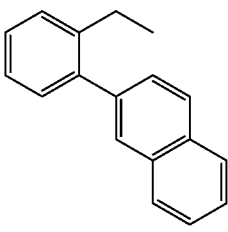 | 4.05(1H, d$_{AB}$, J=12.3Hz)<br>4.10(1H, d$_{AB}$, J=12.3Hz)<br>7.69(1H, s) |
| A-36 | 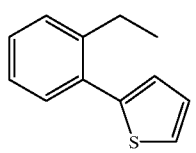 | 4.30(1H, d$_{AB}$, J=11.4Hz)<br>4.39(1H, d$_{AB}$, J=11.4Hz) |
| A-37 |  | 4.38(1H, d$_{AB}$, J=11.6Hz)<br>4.49(1H, d$_{AB}$, J=11.6Hz)<br>7.76(1H, s) |

TABLE 4-continued
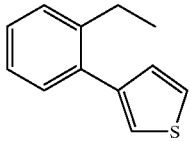
| Compound No. | R¹ | NMR (CDCl₃) δ ppm |
|---|---|---|
| A-38 | 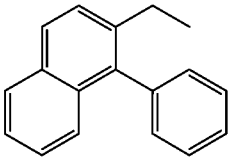 | 4.31(1H, d_{AB}, J=11.3Hz)<br>4.41(1H, d_{AB}, J=11.3Hz)<br>7.76(1H, s) |
TABLE 5
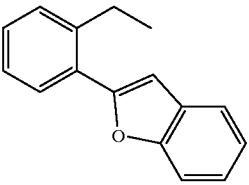
| Compound No. | R¹ | NMR (CDCl₃) δ ppm |
|---|---|---|
| A-39 | 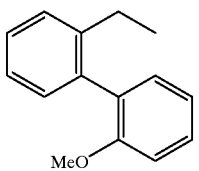 | 4.24(1H, d_{AB}, J=11.7Hz)<br>4.33(1H, d_{AB}, J=11.7Hz)<br>7.74(1H, s) |
| A-40 | 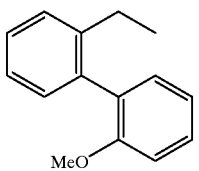 | 4.62(1H, d_{AB}, J=12.3Hz)<br>4.73(1H, d_{AB}, J=12.3Hz)<br>7.75(1H, s) |
| A-41 | 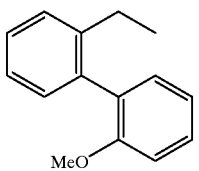 | 3.68(3H, s)<br>7.75(1H, s) |

TABLE 5-continued
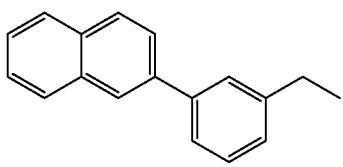
| Compound No. | R¹ | NMR (CDCl₃) δ ppm |
|---|---|---|
| A-42 | 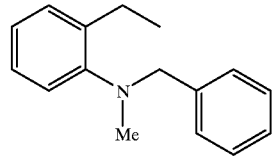 | 4.48(1H, d_{AB}, J=12.0Hz)<br>4.56(1H, d_{AB}, J=12.0Hz)<br>7.70(1H, s) |
| A-43 | 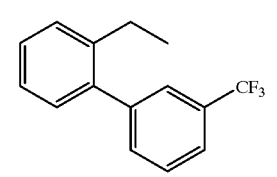 | 4.51(1H, d_{AB}, J=11.7Hz)<br>4.63(1H, d_{AB}, J=11.7Hz)<br>7.78(1H, s) |
| A-44 | 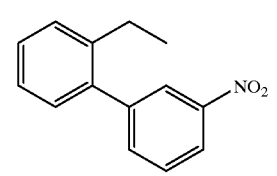 | 4.20(1H, d_{AB}, J=11.1Hz)<br>4.29(1H, d_{AB}, J=11.1Hz)<br>7.75(1H, s) |
| A-45 | 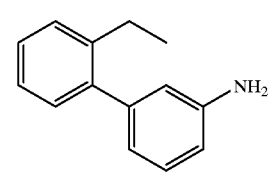 | 4.20(1H, d_{AB}, J=11.1Hz)<br>4.32(1H, d_{AB}, J=11.1Hz)<br>7.75(1H, s) |
| A-46 | 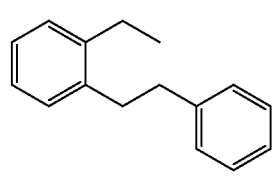 | 4.25(1H, d_{AB}, J=11.1Hz)<br>4.39(1H, d_{AB}, J=11.1Hz)<br>7.72(1H, s) |
| A-47 | | 4.29(1H, d_{AB}, J=11.7Hz)<br>4.40(1H, d_{AB}, J=11.7Hz)<br>7.77(1H, s) |

TABLE 5-continued
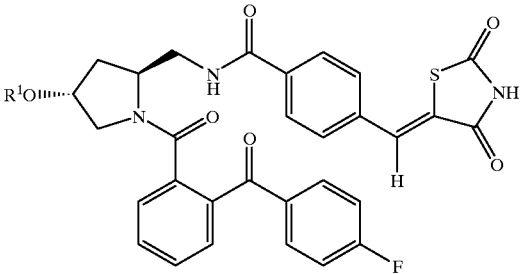
| Compound No. | R¹ | NMR (CDCl₃) δ ppm |
|---|---|---|
| A-48 | 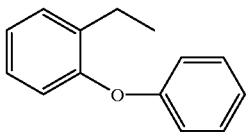 | 4.45(1H, d_AB, J=12.3Hz)<br>4.50(1H, d_AB, J=12.3Hz)<br>7.77(1H, s) |
TABLE 6
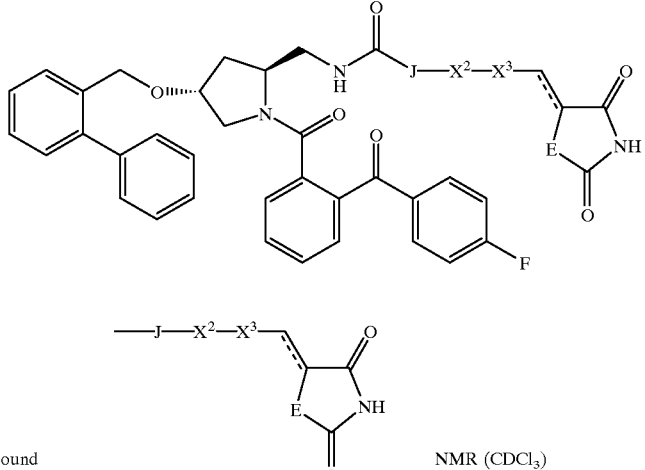
| Compound No. | —J—X²—X³ | NMR (CDCl₃) δ ppm |
|---|---|---|
| A-49 | 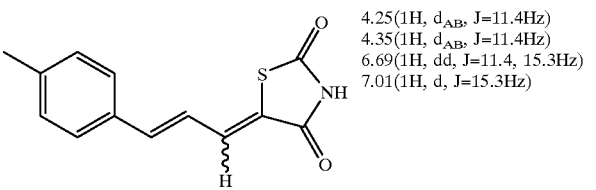 | 4.25(1H, d_AB, J=11.4Hz)<br>4.35(1H, d_AB, J=11.4Hz)<br>6.69(1H, dd, J=11.4, 15.3Hz)<br>7.01(1H, d, J=15.3Hz) |
| A-50 | 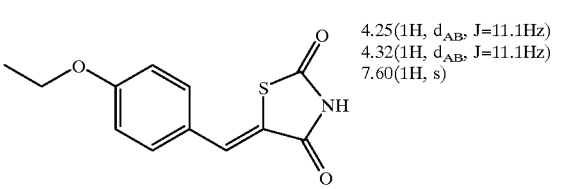 | 4.25(1H, d_AB, J=11.1Hz)<br>4.32(1H, d_AB, J=11.1Hz)<br>7.60(1H, s) |

TABLE 6-continued
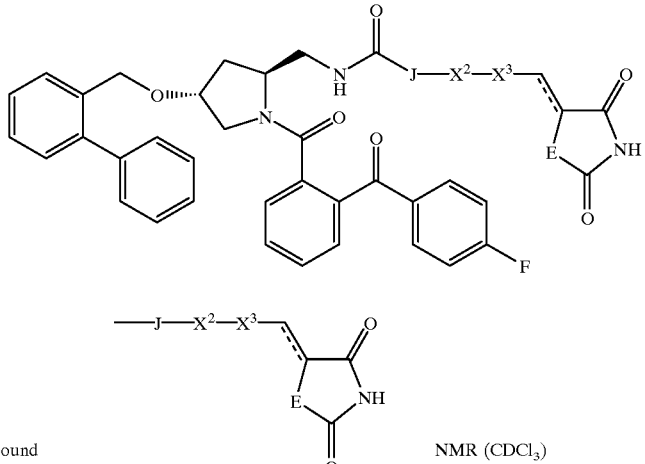
| Compound No. | | NMR (CDCl₃) δ ppm |
|---|---|---|
| A-51 | 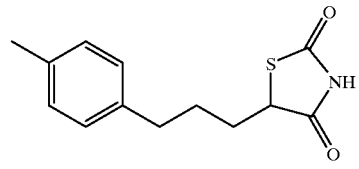 | 1.60–2.25(4H, m), 2.69(2H, m)<br>4.23(1H, d$_{AB}$, J=11.1Hz)<br>4.34(1H, d$_{AB}$, J=11.1Hz)<br>4.46(1H, m) |
| A-52 | 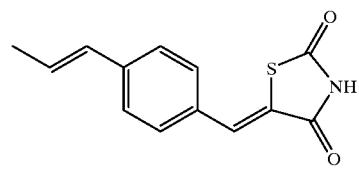 | 4.25(1H, d$_{AB}$, J=11.7Hz)<br>4.36(1H, d$_{AB}$, J=11.7Hz)<br>6.54(1H, d, J=12.6Hz)<br>7.75(1H, s) |
| A-53 | 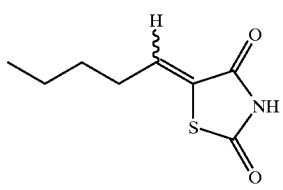 | 4.25(1H, d$_{AB}$, J=12.0Hz)<br>4.34(1H, d$_{AB}$, J=12.0Hz)<br>6.92(1H, t, J=7.5Hz) |
| A-54 | 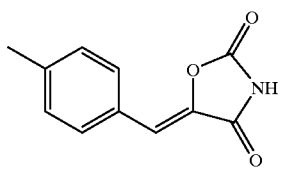 | 4.25(1H, d$_{AB}$, J=11.4Hz)<br>4.36(1H, d$_{AB}$, J=11.4Hz)<br>6.64(1H, s) |
| A-55 | 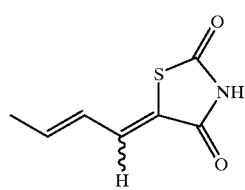 | 4.25(1H, d$_{AB}$, J=11.1Hz)<br>4.34(1H, d$_{AB}$, J=11.1Hz)<br>6.46(1H, d, J=14.4Hz) |
| A-56 | 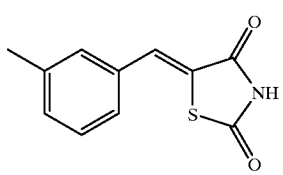 | 4.26(1H, d$_{AB}$, J=11.4Hz)<br>4.36(1H, d$_{AB}$, J=11.4Hz)<br>7.79(1H, s)<br>8.03(1H, s) |

TABLE 6-continued
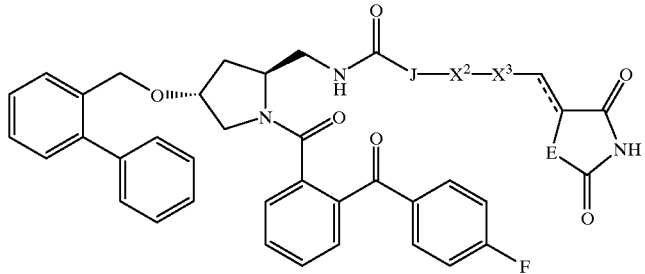
| Compound No. | | NMR (CDCl$_3$) δ ppm |
|---|---|---|
| A-57 | 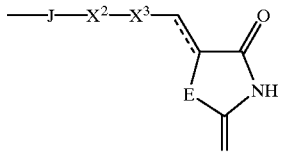 | 4.23(1H, d$_{AB}$, J=11.4Hz)<br>4.34(1H, d$_{AB}$, J=11.4Hz) |
Example 58 (Method A-2)
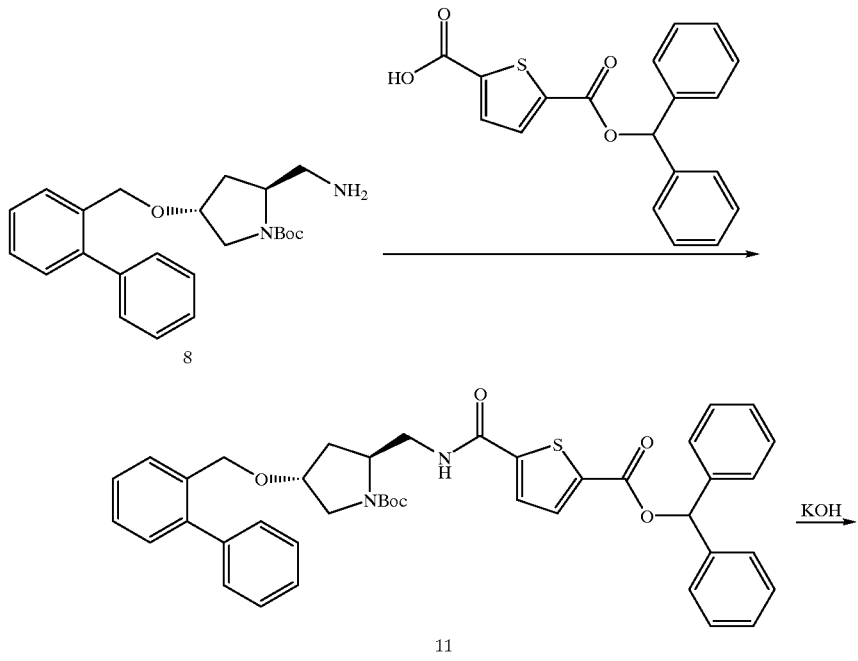

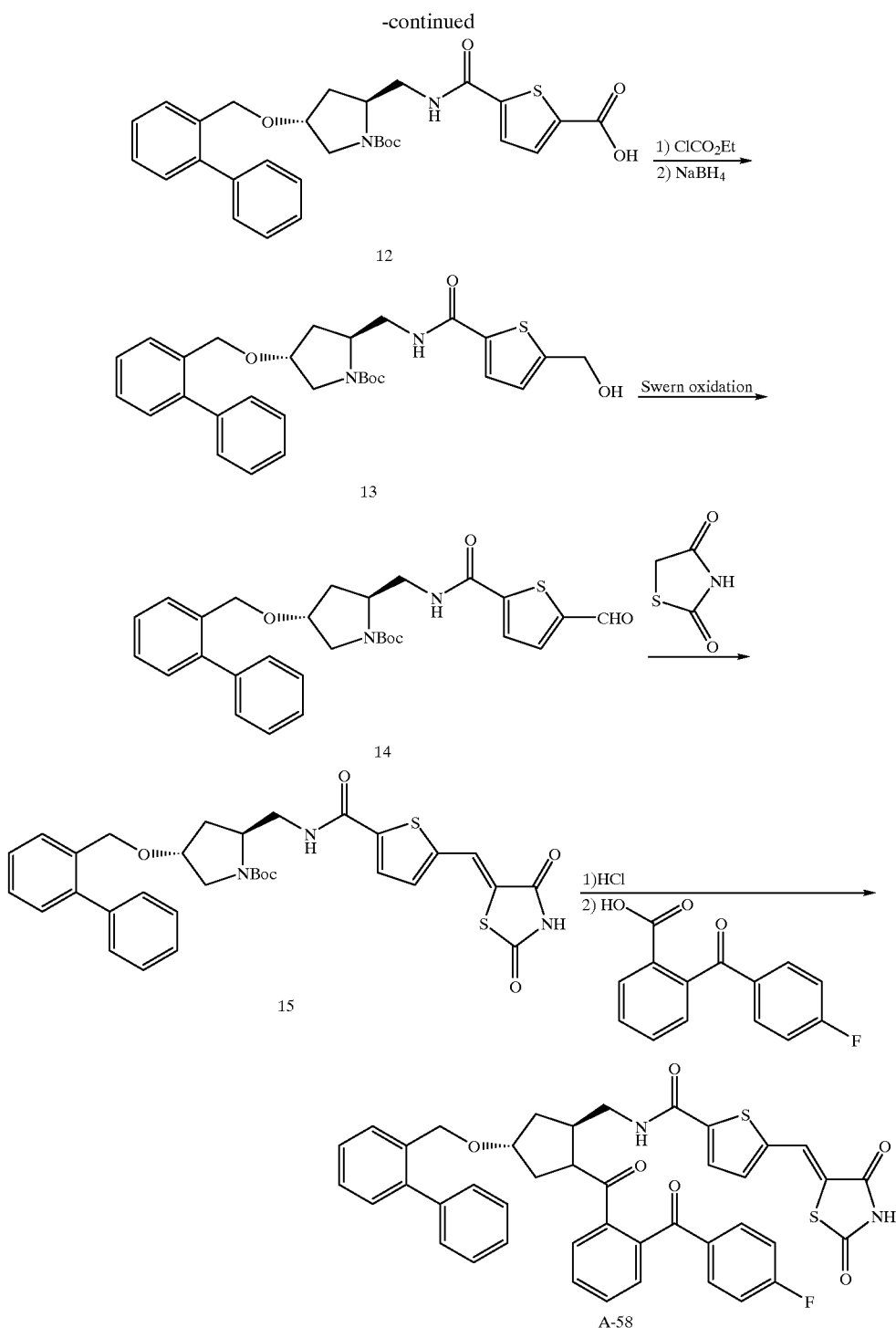

(1) 8→11

To a solution of the compound (8) (1.16 g, 3.0 mmol) which was prepared in Example 1 in dimethylformamide (30 ml) were added thiophen-2,5-dicarboxylic acid monodiphenylmethylester (1.0 g, 3.0 mmol), 1-hydroxybenzotriazole hydrate (450 mg, 3.3 mmol), and 1-ethyl-3-(3-dimethylaminopropyl)carbodiimide hydrochloride (640 mg, 3.3 mmol) at room temperature and the resulting mixture was stirred for 17 h. The reaction mixture was poured into water. To this mixture was added 2N hydrochloric acid aq. for adjusting acidic condition and resulting mixture was extracted with ethyl acetate. The organic layer was washed with 5% sodium hydrogencarbonate aq., water, and brine, dried over sodium sulphate, and concentrated in vacuo. The residue was subjected to silica gel column chromatography (hexane:ethyl acetate=3:1) to give 1.51 g (71%) of the aimed compound (11).

NMR (CDCl$_3$) δ ppm: 1.46 (9H, s), 1.70 (1H, m), 2.18 (1H, m), 3.10–3.40 (2H), 3.45–3.70 (2H), 3.90–4.05 (1H), 4.05–4.25 (1H), 4.35 (1H, d$_{AB}$, J=11.1 Hz), 4.42 (1H, d$_{AB}$, J=11.1 Hz), 7.05 (1H, s), 7.20–7.50 (20H), 7.79 (1H, d, J=4.0 Hz), 8.75 (1H, m).

(2) 11→12

To a solution of the compound (11) (1.51 g, 2.15 mmol) in methanol (15 ml) and dimethylsulfoxide (5 ml) was added iN potassium hydroxide aq. (4 ml) and the resulting mixture was stirred for 17.5 h at room temperature. Methanol was removed by concentrating in vacuo, the residue was dissolved in water, and the mixture was washed with ether. To the aqueous layer was added 2N hydrochloric acid aq. for adjusting acidic condition and the mixture was extracted with ethyl acetate. The organic layer was washed with water and brine, dried over sodium sulfate, and concentrated in vacuo to give 1.16 g (100%) of the compound (12).

NMR (CDCl$_3$) δ ppm: 1.47 (9H, s), 1.79 (1H, m), 2.13 (1H, m), 3.20–3.45 (2H), 3.45–3.70 (2H), 3.90–4.05 (1H), 4.05–4.25 (1H), 4.34 (1H, d$_{AB}$, J=11.1 Hz), 4.41 (1H, d$_{AB}$, J=11.1 Hz), 7.20–7.60 (10H), 7.77 (1H, d, J=4.0 Hz), 8.65 (1H, m).

(3) 12→13

To a solution of the compound (12) (1.15 g, 2.1 mmol) in tetrahydrofuran (20 ml) were added triethylamine (0.3 ml) and ethyl chlorocarbonate (0.2 ml) under ice-cooling with stirring and the resulting mixture was stirred for 1 h at the same temperature. The precipitated salts were filtered off and the filtrate was added dropwise to the suspension of sodium borohydride (0.24 g, 6.3 mmol) in water at room temperature and the resulting mixture was stirred for 3.5 h. The reaction mixture was poured into water. To the mixture was added 2N hydrochloric acid aq. for adjusting acidic condition and the resulting mixture was extracted with ethyl acetate. The organic layer was washed with water, 5% sodium hydrogencarbonate aq., water, and brine, dried over sodium sulfate. and concentrated in vacuo to give 1.11 g (99%) of the alcohol derivative (13).

NMR (CDCl$_3$) δ ppm: 1.46 (9H, s), 1.65–1.80 (1H), 2.50 (1H, m), 3.10–3.40 (2H), 3.45–3.65 (2H), 3.90–4.25 (2H), 4.38 (2H, m), 4.82 (2H, s), 6.95 (1H, d, J=3.8 Hz), 7.25–7.50 (10H), 8.34(1H, m).

(4) 13→14

To a solution of oxaryl chloride (0.282 ml, 3.2 mmol) in dichloromethane (5 ml) was added dropwise a solution of dimethylsulfoxide (0.45 ml, 6.3 mmol) in dichloromethane (1 ml) at −78° C. After this mixture was stirred for 10 min at the same temperature, to this mixture was added dropwise a solution of the compound (13) (1.1 g, 2.1 mmol) in dichloromethane (5 ml) over 15 min and the resulting mixture was stirred for 1.5 h at room temperature. The reaction mixture was diluted with chloroform. The organic layer was washed with 2N hydrochloric acid aq., 5% sodium hydrogencarbonate aq., water, and brine, dried over sodium sulfate, concentrated in vacuo. The residue was subjected to silica gel column chromatography (hexane:ethyl acetate=3:1 to 1:1) to give 0.91 g (83%) of the compound (14).

Thin layer chromatography: Rf=0.4 (hexane:ethyl acetate=1:1); NMR (CDCl$_3$) δ ppm: 1.47 (9H, s), 1.60–1.80 (1H), 2.14 (1H, m), 3.10–3.40 (2H), 3.50–3.70 (2H), 3.98 (1H, 1 m), 4.05–4.25 (1H), 4.39 (2H, m), 7.25–7.55 (9H), 7.58 (1H, d, J=4.0 Hz), 7.71 (1H, d, J=3.8 Hz), 8.84(1H, m), 9.93 (1H, s).

(5) 14→15

To a solution of the compound (14) (900 mg, 1.73 mmol) in toluene (20 ml) were added thiazolidiendion (240 mg, 2.1 mmol), 1M solution of piperidine in toluene (0.17 ml), and 1M solution of acetic acid in toluene (0.17 ml) and the resulting mixture was heated at reflux for 16.5 h. After removing the solvent by concentrating in vacuo, the residue was subjected to silica gel column chromatography (chloroform:methanol=100:1) to give 610 mg (57%) of the aimed compound (15).

Thin layer chromatography: Rf=0.2 (hexane:ethyl acetate=1:1)

(6) 15→A-58

The compound (A-58) was synthesized in a manner similar to that described in the synthesis of the compound (A-1) from the compound (9) in Example 1 using the compound (15) as a starting material.

NMR (CDCl$_3$) δ ppm: 1.76–1.96 (1H), 2.14–2.32 (1H), 3.20–3.55 (3H), 3.70–4.19 (2H), 4.25 (1H, d$_{AB}$, J=11.2 Hz), 4.36 (1H, d$_{AB}$, J=11.2 Hz), 4.40–4.60 (1H), 7.08 (1H, m), 7.17 (1H, d, J=4.0 Hz), 7.20–7.70 (15H), 7.57 (1H, d, J=4.0 Hz), 7.79 (1H, m), 7.89 (1H, s), 8.18, 1H, m), 8.89 (1H, m). IR ν$_{max}$ (nujol): 1747 1706, 1597, 1293 cm$^{-1}$. Elemental analysis (C$_{41}$H$_{32}$N$_3$O$_6$S$_2$F. 0.5H$_2$O); Calcd.: C, 65.24; H, 4.41; N, 5.57; S, 8.50; F, 2.52%. Found: C, 65.25; H, 4.49; N, 5.61, S, 8.64; F, 2.48%.

The compounds (A-59) to (A-66) were synthesized in a manner similar to that described in the above method. The results were shown in Table 7.

TABLE 7

| Compound No. | —G—J—X$^2$— | B | NMR (CDCl$_3$) δ ppm |
|---|---|---|---|
| A-58 | (acetyl-5-methylthiophene) | O | 4.25(1H, d$_{AB}$, J=11.2Hz) 4.36(1H, d$_{AB}$, J=11.2Hz) 7.89(1H, s) |

TABLE 7-continued

| Compound No. | —G—J—X²— | B | NMR (CDCl₃) δ ppm |
|---|---|---|---|
| A-59 | (1-acetyl-5-methylthiophene) | S | 4.25(1H, d$_{AB}$, J=11.2Hz)<br>4.36(1H, d$_{AB}$, J=11.2Hz)<br>7.70(1H, s) |
| A-60 | (methylsulfonyl-5-methylthiophene) | O | 4.28(1H, d$_{AB}$, J=11.4Hz)<br>4.34(1H, d$_{AB}$, J=11.4Hz)<br>7.71(1H, s) |
| A-61 | (methylsulfonyl-5-methylthiophene) | S | 4.28(1H, d$_{AB}$, J=11.1Hz)<br>4.39(1H, d$_{AB}$, J=11.1Hz)<br>7.50(1H, s) |
| A-62 | (methylsulfonyl-4-methylphenyl) | O | 4.27(1H, d$_{AB}$, J=11.0Hz)<br>4.39(1H, d$_{AB}$, J=11.0Hz) |
| A-63 | (methylsulfonyl-4-methylphenyl) | S | 4.26(1H, d$_{AB}$, J=11.2Hz)<br>4.39(1H, d$_{AB}$, J=11.2Hz) |
| A-64 | (1-acetyl-5-methylfuran) | O | 4.25(1H, d$_{AB}$, J=11.1Hz)<br>4.33(1H, d$_{AB}$, J=11.1Hz)<br>6.76(1H, d, J=3.3Hz)<br>7.50(1H, s) |
| A-65 | (pent-3-yn-2-one) | O | 4.25(1H, d$_{AB}$, J=11.3Hz)<br>4.35(1H, d$_{AB}$, J=11.3Hz)<br>6.77(1H, s) |
| A-66 | (hex-3-en-5-yn-2-one) | O | 4.24(1H, d$_{AB}$, J=11.1Hz)<br>4.35(1H, d$_{AB}$, J=11.1Hz)<br>6.92(1H, d, J=2.8Hz)) |

Example 67 (Method A-3)

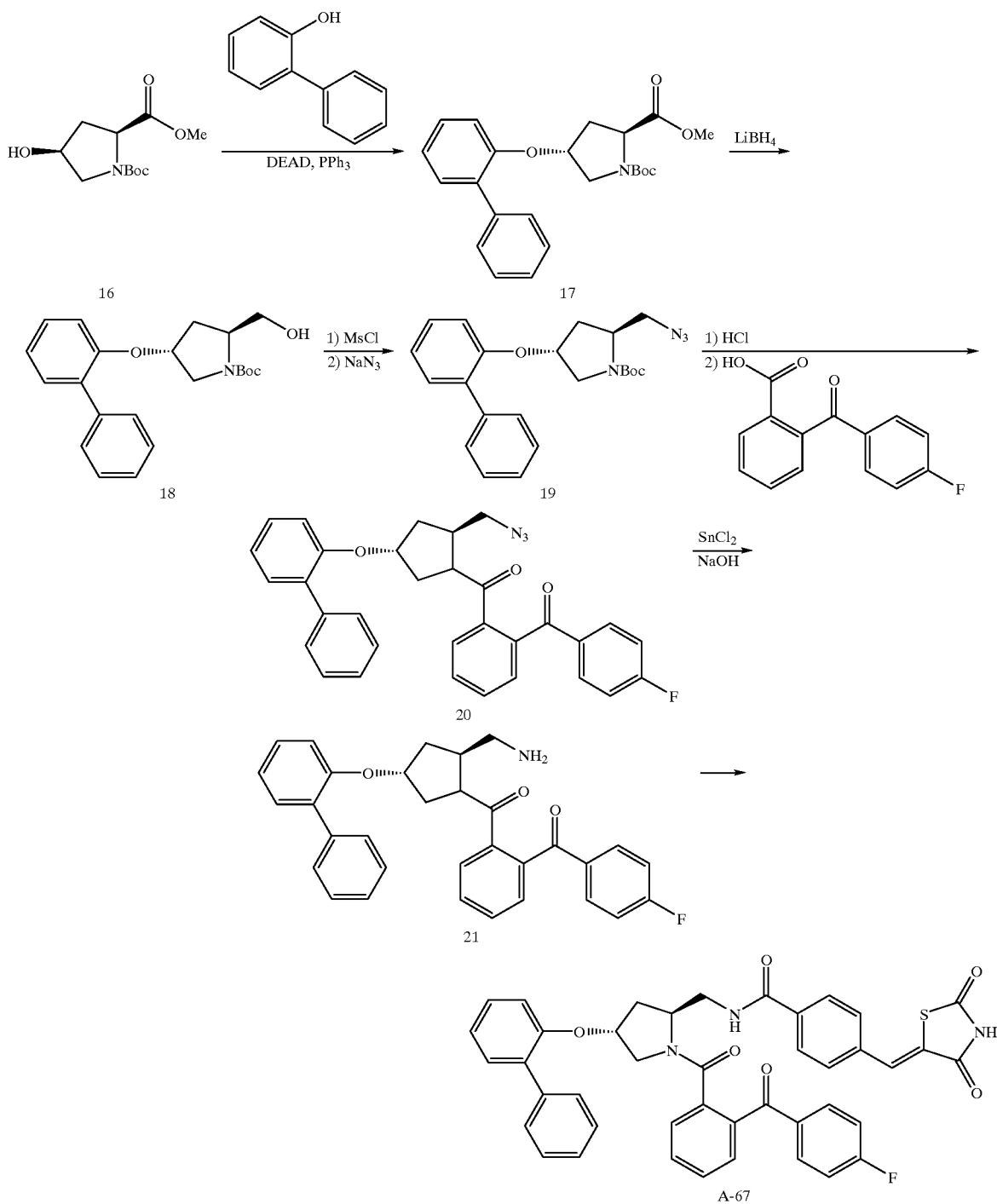

(1) 16→17

To a solution of N-Boc-cis-4-hydroxy-L-proline methylester (16) (5.46 g, 22.26 mmol), 2-phenylphenol (4.17 g, 24.50 mmol), and triphenylphosphine (6.60 g, 24.50 mmol) in tetrahydrofuran (100 ml) was added dropwise a solution of azodicarboxylic acid diethylester (4.27 g, 24.52 mmol) in tetrahydrofuran (30 ml) under ice-cooling with stirring. The mixture was stirred for 18 h at room temperature, concentrated in vacuo. The residue was dissolved in ether (100 ml). The precipitated crystal was filtered off and the filtrate was concentrated in vacuo. The residue was subjected to silica gel column chromatography (hexane:ethyl acetate=3:1) to give 6.19 g (67%) of the compound (17).

NMR (CDCl$_3$) δ ppm: 1.40(⅔×9H, s), 1.43 (⅓×9H, s), 1.97–2.18 (1H), 2.34–2.42 (1H), 3.56–3.87 (5H), 4.09–4.40 (1H), 4.82 (1H, br s), 6.94 (1H, d, J=8.2 Hz), 7.08 (1H, t, J=7.4 Hz), 7.22–7.51 (7H). IR ν$_{max}$ (CHCl$_3$): 1747, 1694 cm$^{-1}$. Elemental analysis (C$_{23}$H$_{27}$NO$_5$.0.1H$_2$O); Calcd.: C, 69.19; H, 6.87; N, 3.51%. Found: C, 69.13; H, 6.96; N, 3.63%.

(2) 17→18

To a solution of the compound (17) (6.04 g, 15.20 mmol) in tetrahydrofuran (60 ml) was added lithium borohydride (497 mg, 22.82 mmol) under ice-cooling and the resulting mixture was stirred for 1 h at room temperature. To the reaction mixture was added methanol (20 ml) and the resulting mixture was stirred for 30 min and was added ethyl acetate (300 ml). The organic layer was washed with water and brine and concentrated in vacuo to give 6.37 g (100%) of the crude compound (18).

IR $\nu_{max}$ (CHCl$_3$): 3361, 1670 cm$^{-1}$.

(3) 18→19

The compound (19) was obtained (98% yield) in a manner similar to that described in the synthesis of the compound (5) from the compound (4) using in Example 1 the crude compound (18) as a starting material.

NMR (CDCl$_3$) δ ppm: 1.44 (9H, s), 1.95–2.28 (2H), 3.11–4.18 (5H), 4.79 (1H, m), 6.99 (1H, dd, J=8.2, 1.2 Hz), 7.07 (1H, td, J=7.4, 1.2 Hz), 7.23–7.50 (7H). IR $\nu_{max}$ (CHCl$_3$): 2107, 1686 cm$^{-1}$. Elemental analysis (C$_{22}$H$_{26}$N$_4$O$_3$); Calcd.: C, 66.99; H, 6.64; N, 14.20%. Found: C, 66.81; H, 6.83; N, 14.40%.

(4) 19→20

The compound (20) was synthesized in a manner similar to that described in the synthesis of the compound (A-1) from the compound (9) in Example 1 using the compound (19) as a starting material.

NMR (CDCl$_3$) δ ppm: 2.06 (1H, ddd, J=14.0, 7.8, 4.8 Hz), 2.25 (1H, m), 3.33 (1H, dd, J=12.6, 2.8 Hz), 3.50 (2H, d, J=2.8 Hz), 3.62 (1H, dd, J=12.6, 5.0 Hz), 4.28 (1H, m), 7.40 (1H, m), 6.87 (1H, dd, J=8.2. 0.8 Hz), 6.99–7.53 (14H), 7.76–7.90 (2H), 7.83 (2H, m). IR $\nu_{max}$ (CHCl$_3$): 2106, 1663, 1632, 1598 cm$^{-1}$. Elemental analysis (C$_{31}$H$_{25}$N$_4$FO$_3$); Calcd.: C, 71.53; H, 4.84; N, 10.76; F, 3.65%. Found: C, 71.47; H, 4.99; N, 10.81; F, 3.88%.

(5) 20→21

The compound (21) was synthesized in a manner similar to that described in the synthesis of the compound (8) from the compound (7) in Example 1 using the compound (20) as a starting material.

IR $\nu_{max}$ (CHCl$_3$): 1661, 1627, 1599 cm$^{-1}$.

(6) 21→A-67

The compound (A-67) was synthesized in a manner similar to that described in the synthesis of the compound (9) from the compound (8) in Example 1 using the compound (21) as a starting material.

NMR (CDCl$_3$) δ ppm: 2.01 (1H, m), 2.51 (1H, m), 3.38–3.65 (3H), 3.92 (1H, m), 4.49 (1H, m), 4.74 (1H, br s), 6.86 (1H, d, J=8.1 Hz), 6.95–7.13 (4H), 7.21–7.64 (12H), 7.69–7.92 (2H), 7.81 (1H, s), 7.98 (2H, d, J=8.1 Hz), 8.23 (1H, t, J=5.1 Hz), 8.73 (1H, br s). IR $\nu_{max}$ (CHCl$_3$): 2106, 1663, 1632, 1598 cm$^{-1}$. Elemental analysis (C$_{42}$H$_{32}$N$_3$FO$_6$S.0.3H$_2$O); Calcd.: C, 68.99; H, 4.49; N, 5.75; F, 2.60; S, 4.39%. Found: C, 69.02; H, 4.77; N, 5.72; F, 2.67; S, 4.24%.

The compounds (A-68) to (A-141) were synthesized in a manner similar to that described in the above method. The results were shown in Tables 8 to 15.

TABLE 8

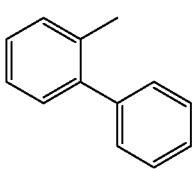

| Compound No. | R$^1$ | B | NMR (CDCl$_3$) δ ppm |
|---|---|---|---|
| A-67 | 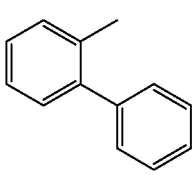 | O | 7.81(1H, s)<br>7.98(2H, d, J=8.1Hz)<br>8.73(1H, s) |
| A-68 | 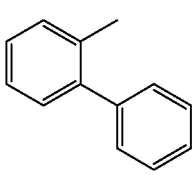 | S | 7.60(1H, s)<br>7.98(2H, d, J=8.4Hz)<br>9.77(1H, s) |

TABLE 8-continued
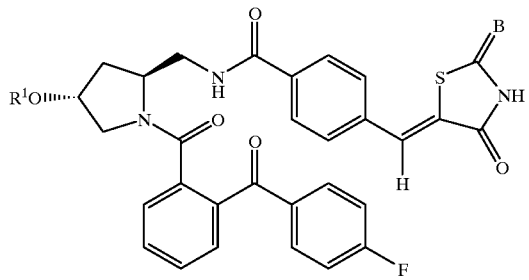
| Compound No. | R¹ | B | NMR (CDCl₃) δ ppm |
|---|---|---|---|
| A-69 | 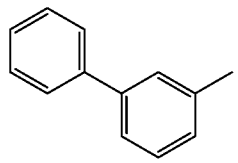 | O | 6.89(1H, d, J=8.7Hz) 7.78(1H, s) 7.98(2H, d, J=8.4Hz) |
| A-70 | 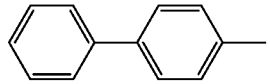 | O | 6.89(1H, d, J=8.7Hz) 7.80(1H, s) 7.99(2H, d, J=8.7Hz) |
| A-71 | 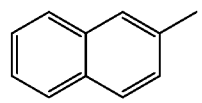 | O | 7.78(1H, s) 8.00(2H, d, J=8.6Hz) 9.14(1H, s) |
| A-72 | 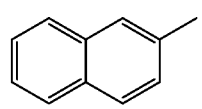 | S | 7.57(1H, s) 8.00(2H, d, J=8.2Hz) 10.17(1H, s) |
| A-73 | 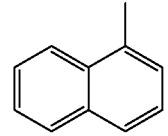 | O | 6.67(1H, d, J=7.8Hz) 7.06(2H, t, J=8.6Hz) 7.79(1H, s) 7.99(2H, d, J=8.2Hz) |
| A-74 | 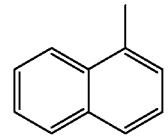 | S | 6.67(1H, d, J=7.4Hz) 7.06(2H, t, J=8.6Hz) 7.59(1H, s) 8.00(2H, d, J=8.2Hz) |
| A-75 | 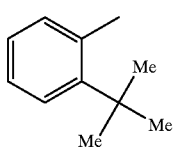 | O | 1.39(9H, s) 7.81(1H, s) 8.01(2H, d, J=8.4Hz) |
| A-76 | 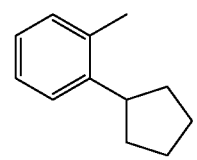 | O | 6.64(1H, d, J=7.8Hz) 7.81(1H, s) 7.99(2H, d, J=8.4Hz) |

TABLE 9

| Compound No. | R¹ | B | NMR (CDCl₃) δ ppm |
|---|---|---|---|
| A-77 | (5,6,7,8-tetrahydronaphthalen-1-yl)methyl | O | 6.48(1H, d, J=8.2Hz)<br>7.79(1H, s)<br>7.98(2H, d, J=8.1Hz) |
| A-78 | (5,6,7,8-tetrahydronaphthalen-1-yl)methyl | S | 6.46(1H, d, J=8.4Hz)<br>6.70(1H, d, J=7.8Hz)<br>7.56(1H, s) |
| A-79 | (6-phenylnaphthalen-2-yl)methyl | O | 7.78(1H, s)<br>7.97(1H, s)<br>8.00(2H, d, J=8.2Hz)<br>8.30(1H, t, J=5.1Hz) |
| A-80 | (6-phenylnaphthalen-2-yl)methyl | S | 7.56(1H, s)<br>7.97(1H, s)<br>8.00(2H, d, J=8.5Hz)<br>8.31(1H, t, J=5.1Hz) |
| A-81 | (4-phenylnaphthalen-2-yl)methyl | O | 6.74(1H, d, J=7.9Hz)<br>7.79(1H, s)<br>7.88(1H, d, J=8.2Hz)<br>8.00(2H, d, J=8.2Hz) |
| A-82 | (E)-4-styrylbenzyl | O | 6.96(1H, d, J=16.5Hz)<br>7.04(1H, d, J=16.5Hz)<br>7.76(1H, s) |
| A-83 | 2-benzylbenzyl | O | 3.96(2H, s)<br>7.77(1H, s) |

TABLE 9-continued

| Compound No. | R¹ | B | NMR (CDCl₃) δ ppm |
|---|---|---|---|
| A-84 | 3-(2-naphthyl)phenyl | O | 7.06(2H, dd, J=8.7, 8.1Hz)<br>7.20(1H, s)<br>7.74(1H, s) |
| A-85 | 1-bromo-2-methylnaphthyl | O | 7.78(1H, s)<br>7.99(2H, d, J=8.2Hz)<br>8.29(1H, t, J=5.1Hz) |
| A-86 | 1-phenyl-2-methylnaphthyl | O | 7.81(1H, s)<br>7.96(2H, d, J=8.5Hz)<br>8.23(1H, t, J=4.8Hz) |

TABLE 10

| Compound No. | R¹ | B | NMR (CDCl₃) δ ppm |
|---|---|---|---|
| A-87 | 3-(N,N-dimethylamino)phenylmethyl | O | 2.92(6H, s)<br>7.78(1H, s)<br>7.98(2H, d, J=8.5Hz)<br>8.29(1H, t, J=5.1Hz) |

TABLE 10-continued

| Compound No. | R¹ | B | NMR (CDCl₃) δ ppm |
|---|---|---|---|
| A-88 | 3-(N,N-dimethylamino)phenylmethyl (Me₂N-C₆H₄-Me) | S | 2.92(6H, s)<br>7.57(1H, s)<br>7.99(2H, d, J=8.2Hz)<br>8.29(1H, t, J=5.0Hz) |
| A-89 | 3-(N,N-diethylamino)phenylmethyl | O | 7.78(1H, s)<br>7.98(2H, d, J=8.5Hz)<br>8.29(1H, t, J=5.1Hz) |
| A-90 | 3-(N-phenylamino)phenylmethyl | O | 5.75(1H, s)<br>7.77(1H, s)<br>7.97(2H, d, J=8.5Hz)<br>8.27(1H, t, J=5.0Hz) |
| A-91 | 3-(N-methyl-N-phenylamino)phenylmethyl | O | 3.28(3H, s)<br>7.79(1H, s)<br>7.97(2H, d, J=8.5Hz)<br>8.27(1H, t, J=5.1Hz) |
| A-92 | julolidinyl | O | 5.93(1H, d, J=8.2Hz)<br>6.65(1H, d, J=8.2Hz)<br>7.80(1H, s)<br>7.97(2H, d, J=8.5Hz)<br>8.28(1H, t, J=5.1Hz) |
| A-93 | 2-iodophenylmethyl | O | 7.06(2H, t, J=8.7Hz)<br>7.80(1H, s)<br>8.00(2H, d, J=8.4Hz) |
| A-94 | 2-(1-naphthyl)phenylmethyl | O | 7.00(2H, t, J=8.1Hz)<br>7.92(2H, d, J=8.7Hz) |

TABLE 10-continued
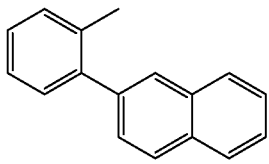
| Compound No. | R¹ | B | NMR (CDCl₃) δ ppm |
|---|---|---|---|
| A-95 | 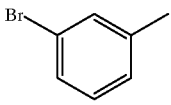 | O | 7.02(2H, t, J=8.6Hz)<br>7.77(1H, s)<br>7.95(2H, d, J=8.4Hz) |
| A-96 | 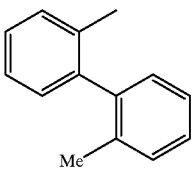 | O | 7.00(1H, s)<br>7.77(1H, s)<br>7.98(2H, d, J=8.1Hz) |
TABLE 11
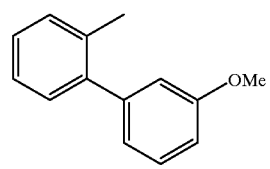
| Compound No. | R¹ | NMR (CDCl₃) δ ppm |
|---|---|---|
| A-97 | (2,2'-dimethylbiphenyl) | 2.13(3H, s)<br>7.76(1H, s)<br>7.93(2H, d, J=8.4Hz) |
| A-98 | (3'-methoxybiphenyl with 2-Me) | 3.83(3H, s)<br>7.78(1H, s)<br>7.97(2H, d, J=8.1Hz) |

TABLE 11-continued

| Compound No. | R¹ | NMR (CDCl₃) δ ppm |
|---|---|---|
| A-99 | 3-methyl-3'-methoxybiphenyl | 3.86(3H, s)<br>7.76(1H, s)<br>7.98(2H, d, J=8.4Hz) |
| A-100 | 1-(3-bromo-2-methylphenyl)-1-methylethyl | 1.12(3H, d, J=6.9Hz)<br>1.21(3H, d, J=6.9Hz)<br>7.77(1H, s) |
| A-101 | 2-methylphenyl-benzo[1,3]dioxol-5-yl | 5.99(1H, d, J=1.5Hz)<br>6.01(1H, d, J=0.9Hz)<br>7.77(1H, s) |
| A-102 | 2-methylphenyl-benzo[1,3]dioxol-4-yl | 5.88(1H, d, J=1.5Hz)<br>6.06(1H, d, J=1.2Hz)<br>7.76(1H, s) |
| A-103 | 2-methyl-2'-phenylbiphenyl | 7.75(1H, s)<br>7.91(2H, d, J=8.4Hz) |
| A-104 | 3-(1-methylethyl)-2-methylbiphenyl | 1.22(3H, d, J=6.9Hz)<br>1.27(3H, d, J=6.6Hz)<br>7.77(1H, s) |

TABLE 11-continued
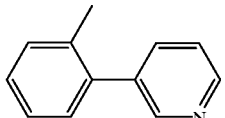
| Compound No. | R[1] | NMR (CDCl$_3$) δ ppm |
|---|---|---|
| A-105 | 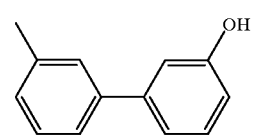 | 8.66(1H, dd, J=5.0, 1.7Hz)<br>8.86(1H, d, J=2.1Hz) |
| A-106 | 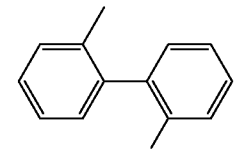 | 6.78(1H, dd, J=7.8, 3.2Hz)<br>7.77(1H, s)<br>7.97(2H, d, J=8.1Hz) |
TABLE 12
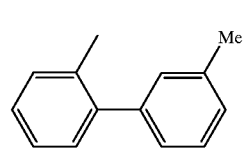
| Compound No. | R[1] | NMR (CDCl$_3$) δ ppm |
|---|---|---|
| A-107 | 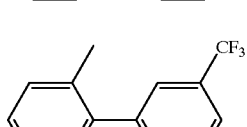 | 3.76(3H, s)<br>6.67(1H, d, J=6.9Hz)<br>6.82(1H, d, J=8.4Hz)<br>7.76(1H, s) |
| A-108 | | 2.41(3H, s)<br>6.84(1H, d, J=7.2Hz)<br>7.79(1H, s)<br>7.97(2H, d, J=8.1Hz) |
| A-109 | | 6.86(1H, d, J=8.1Hz)<br>7.97(2H, d, J=8.4Hz) |

TABLE 12-continued
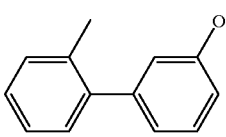
| Compound No. | R¹ | NMR (CDCl₃) δ ppm |
|---|---|---|
| A-110 | 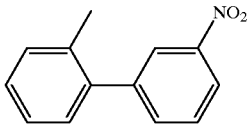 | 1.41(3H, t, J=6.9Hz)<br>6.85(1H, d, J=7.5Hz)<br>7.78(1H, s)<br>7.97(2H, d, J=8.4Hz) |
| A-111 | 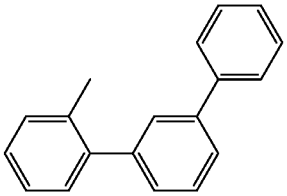 | 6.89(1H, d, J=8.4Hz)<br>7.97(2H, d, J=8.4Hz))<br>8.36(1H, t, J=2.0Hz) |
| A-112 | 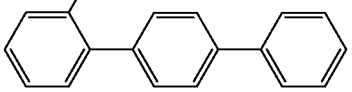 | 6.88(1H, d, J=8.1Hz)<br>7.96(2H, d, J=8.4Hz) |
| A-113 | 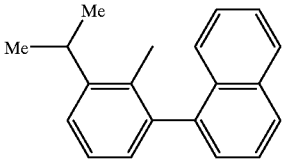 | 6.88(1H, d, J=7.8Hz)<br>7.94(2H, d, J=8.4Hz) |
| A-114 | 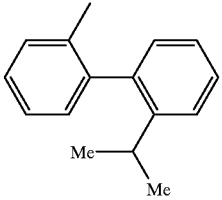 | 7.76(1H, s) |
| A-115 | 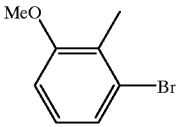 | 1.05(3H, d, J=6.9Hz)<br>6.84(1H, t, J=7.7Hz) |
| A-116 |  | 3.77(3H, s)<br>7.79(1H, s)<br>7.97(2H, d, J=8.1Hz) |

TABLE 13

| Compound No. | R¹ | NMR (CDCl₃) δ ppm |
|---|---|---|
| A-117 | 3-MeO, 2-Me biphenyl | 3.83(3H, s)<br>7.79(1H, s)<br>7.90(2H, d, J=8.4Hz) |
| A-118 | 3-MeO, 2-Me-1-naphthyl phenyl | 3.88(3H, s)<br>7.77(1H, s) |
| A-119 | 2-Me phenoxyphenyl | 7.79(1H, s)<br>7.97(2H, d, J=8.5Hz) |
| A-120 | 3-MeO, 2-Me, 2'-iPr biphenyl | 0.97(3H, d, J=6.6Hz)<br>1.26(3H, d, J=6.6Hz)<br>3.79(3H, s)<br>7.91(2H, d, J=8.7Hz) |
| A-121 | 2-Me, 2'-iPrO biphenyl | 1.07(3H, d, J=6.3Hz)<br>1.16(3H, d, J=6.0Hz)<br>7.77(1H, s)<br>7.93(2H, d, J=8.4Hz) |
| A-122 | 3-MeO, 2-Me, 2'-iPrO biphenyl | 1.17(3H, d, J=6.0Hz)<br>1.22(3H, d, J=6.0Hz)<br>3.81(3H, s)<br>7.76(1H, s)<br>7.89(2H, d, J=8.1Hz) |

TABLE 13-continued

| Compound No. | R¹ | NMR (CDCl₃) δ ppm |
|---|---|---|
| A-123 | Me-CH(Me)-CH₂-(2-Me,3-Br-phenyl) | 0.87(3H, d, J=6.6Hz) 0.88(3H, d, J=6.6Hz) 7.79(1H, s) 7.97(2H, d, J=8.4Hz) |
| A-124 | Me-CH(Me)-CH₂-(2-Me-biphenyl-3-yl) | 0.95(3H, d, J=6.6Hz) 0.96(3H, d, J=6.6Hz) 7.77(1H, s) 7.91(2H, d, J=8.4Hz) |
| A-125 | Me-CH(Me)-CH₂-(2-Me-3-(1-naphthyl)phenyl) | 1.01(3H, d, J=6.3Hz) 7.75(1H, s) |

TABLE 14

| Compound No. | R¹ | X | NMR (CDCl₃) δ ppm |
|---|---|---|---|
| A-126 | Me-CH(Me)-CH₂-(2-Me-3-(2-isopropylphenyl)phenyl) | H | 7.77(1H, s) |

TABLE 14-continued
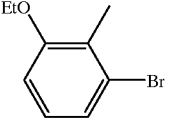
| Compound No. | R[1] | X | NMR (CDCl$_3$) δ ppm |
|---|---|---|---|
| A-127 | 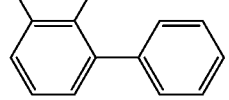 | H | 1.35(3H, t, J=6.9Hz)<br>3.99(2H, q, J=6.9Hz)<br>7.97(2H, d, J=8.4Hz) |
| A-128 | 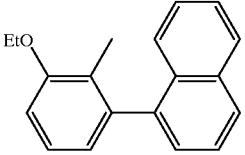 | H | 1.38(3H, t, J=6.9Hz)<br>4.05(2H, q, J=6.9Hz)<br>7.77(1H, s)<br>7.90(2H, d, J=8.4Hz) |
| A-129 | 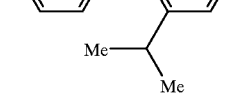 | H | 7.77(1H, s) |
| A-130 | 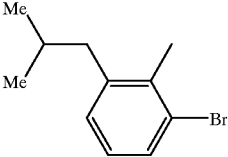 | H | 7.76(1H, s)<br>7.90(2H, d, J=8.7Hz) |
| A-131 | 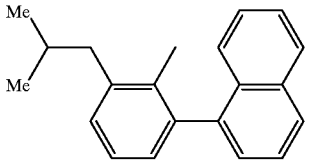 | F | 0.86(3H, d, J=6.6Hz)<br>0.87(3H, q, J=6.6Hz)<br>7.78(1H, s)<br>8.03(2H, d, J=8.7Hz) |
| A-132 |  | F | 7.93(2H, d, J=8.1Hz) |

TABLE 14-continued
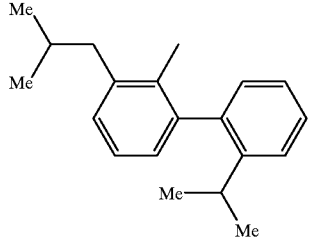
| Compound No. | R¹ | X | NMR (CDCl₃) δ ppm |
|---|---|---|---|
| A-133 | 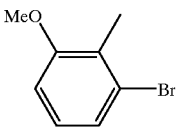 | F | 7.78(½×1H, s)<br>7.79(½×1H, s) |
| A-134 | 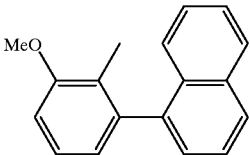 | F | 3.76(3H, s)<br>7.15(1H, dd, J=7.8, 1.5Hz)<br>7.78(1H, s)<br>8.04(2H, d, J=8.1Hz) |
TABLE 15
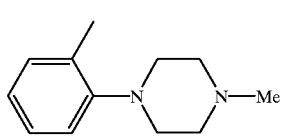
| Compound No. | R¹ | X | J | NMR (CDCl₃) δ ppm |
|---|---|---|---|---|
| A-135 | (MeO-methyl-naphthyl) | F | — | 3.87(3H, s)<br>7.78(1H, s) |
| A-136 | (methyl-phenyl-N-methylpiperazine) | H | — | 2.70(3H, s)<br>4.48(1H, d, J=11.8Hz)<br>7.53(2H, d, J=8.4Hz) |

TABLE 15-continued

| Compound No. | R¹ | X | J | NMR (CDCl₃) δ ppm |
|---|---|---|---|---|
| A-137 | 2-phenylphenyl (2-biphenyl) | H | -CH=CH-CH₃ | 6.57(1H, d, J=15.8Hz)<br>7.78(1H, s) |
| A-138 | 3-bromo-2-methyl-6-isopropoxyphenyl | H | — | 1.26(3H, d, J=6.3Hz)<br>1.28(3H, d, J=6.3Hz)<br>7.80(1H, s)<br>7.97(2H, d, J=8.1Hz) |
| A-139 | 3-isopropoxy-2-methyl-biphenyl | H | — | 1.30(3H, d, J=6.0Hz)<br>1.31(3H, d, J=6.0Hz)<br>7.78(1H, s)<br>7.90(2H, d, J=8.4Hz) |
| A-140 | 3-isopropoxy-2-methyl-1-(naphthalen-1-yl)phenyl | H | — | 1.33(3H, d, J=6.3Hz)<br>1.36(3H, d, J=6.3Hz)<br>7.76(1H, s) |
| A-141 | 3-isopropoxy-2-methyl-2'-isopropyl-biphenyl | H | — | 7.77(1H, s)<br>7.90(2H, d, J=8.1Hz) |

Example 142 (Method B-1)

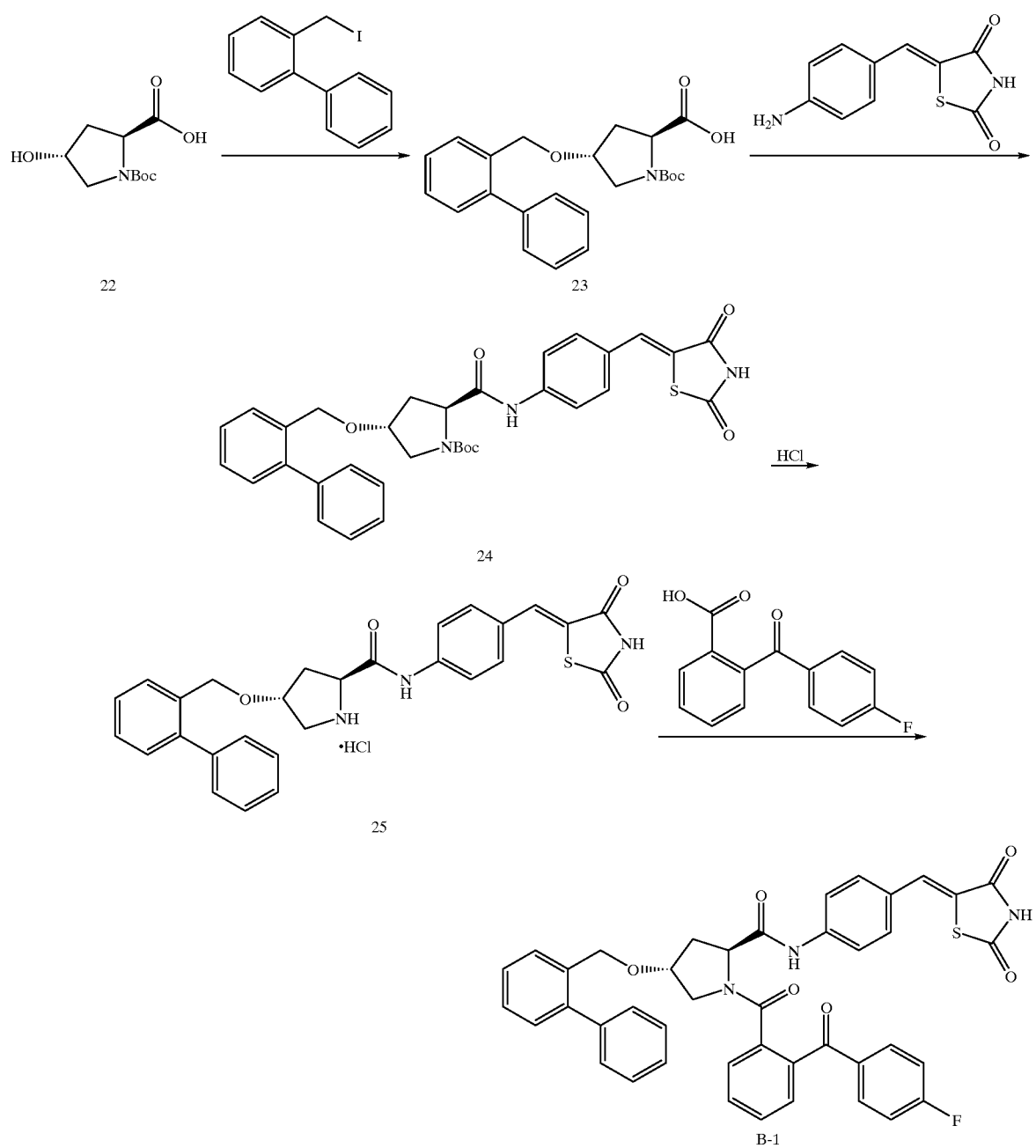

(1) 22→23

The compound (23) was synthesized in a manner similar to that described in the synthesis of the compound (7) in Example 1 using N-Boc-4-hydroxy-L-proline (22) as a starting material.

NMR (CDCl$_3$) δ ppm: 1.47 (9H, s), 2.02–2.42 (2H), 3.30–3.62 (2H), 4.01 (1H, m), 4.24–4.50 (3H), 7.23–7.55 (9H). IR $\nu_{max}$ (CHCl$_3$): 1757, 1722, 1696, 1621 cm$^{-1}$. Elemental analysis (C$_{23}$H$_{27}$NO$_5$); Calcd.: C, 69.50; H, 6.85; N, 3.52%. Found: C, 69.77; H, 6.71; N, 3.72%.

(2) 23→24

The compound (24) was obtained in a manner similar to that described in the synthesis of the compound (9) in Example 1 using the above mentioned compound (23) as a starting material.

NMR (CDCl$_3$) δ ppm: 1.47 (9H, s), 1.85–2.00 (1H), 2.30–2.60 (1H), 3.40–3.55 (2H), 4.05–4.22 (1H), 4.40 (1H, d$_{AB}$, J=11.2 Hz), 4.44 (1H, d$_{AB}$, J=11.2 Hz), 7.20–7.80 (14H), 9.08 (1H, br s), 9.77 (1H, br s). IR $\nu_{max}$ (Nujol): 1741, 1703, 1589 cm$^{-1}$.

(3) 24→B-1

The amine hydrochloride derivative (25) was obtained in a manner similar to that described in the synthesis of the compound (10) in Example 1 using the compound (24) as a starting material. Successively, the compound (B-1) was obtained in a manner similar to that described in the synthesis of (A-1) in Example 1 using the hydrochloride derivative (25) as a starting material.

NMR (CDCl$_3$) δ ppm: 2.21–2.40 (1H), 2.43–2.59 (1H), 3.39 (2H, d, J=3.8 Hz) 4.00–4.12 (1H), 4.29 (1H, d$_{AB}$, J=11.2 Hz), 4.42 (1H, d$_{AB}$, J=11.2 Hz), 4.93 (1H, dd, J=5.8, 8.4 Hz), 7.11 (2H, m), 7.24 (15H, m), 7.76 (1H, s), 7.74–7.87 (4H, m), 8.68 (1H, s), 9.43 (1H, s). IR ν$_{max}$ (Nujol): 1740, 1704, 1619, 1596 cm$^{-1}$. MS (m/z): 726 ([MH]$^+$). Elemental analysis (C$_{42}$H$_{32}$N$_3$FSO$_6$·0.4H$_2$O); Calcd.: C, 68.82; H, 4.51; N, 5.73; F, 2.59; S, 4.37%. Found: C, 68.86; H, 4.67; N, 5.76; F, 2.52; S, 4.25%.

The compounds (B-2) to (B-7) were synthesized in a manner similar to that described in the above method. The results were shown in Tables 16 and 17.

TABLE 16

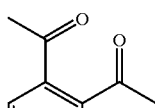

| Compound No. | —Y$^1$—Y$^2$ | B | NMR(CDCl$_3$) δ ppm |
|---|---|---|---|
| B-1 | 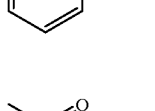 | O | 4.29(1H, d$_{AB}$, J=11.2Hz) 4.42(1H, d$_{AB}$, J =11.2Hz) 7.76(1H, s) |
| B-2 | | S | 4.29(1H, d$_{AB}$, J=11.1Hz) 4.42(1H, d$_{AB}$, J=11.1Hz) 7.58(1H, s) |
| B-3 | 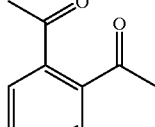 | O | 4.29(1H, d$_{AB}$, J=11.3Hz) 4.42(1H, d$_{AB}$, J=11.3Hz) 7.77(1H, s) |
| B-4 | | S | 4.30(1H, d$_{AB}$, J=11.2Hz) 4.42(1H, d$_{AB}$, J=11.2Hz) 7.56(1H, s) |

TABLE 16-continued

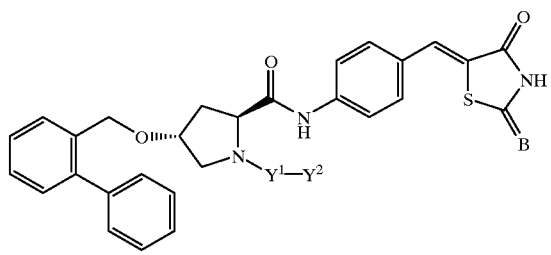

| Compound No. | —Y$^1$—Y$^2$ | B | NMR(CDCl$_3$) δ ppm |
|---|---|---|---|
| B-5 | | O | 2.40(3H, s) 4.28(1H, d$_{AB}$, J=11.2Hz) 4.41(1H, d$_{AB}$, J=11.2Hz) 7.78(1H, s) |
| B-6 | | S | 2.41(3H, s) 4.28(1H, d$_{AB}$, J=11.2Hz) 4.41(1H, d$_{AB}$, J=11.2Hz) 7.58(1H, s) |

TABLE 17

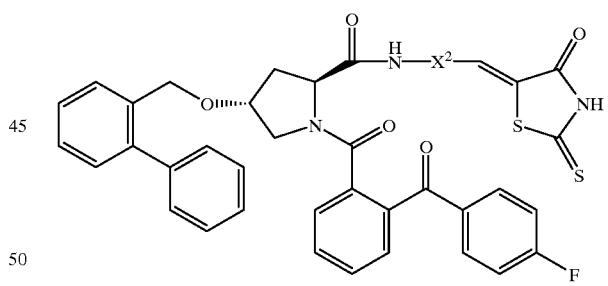

| Compound No. | —X$^2$— | NMR(CDCl$_3$) δ ppm |
|---|---|---|
| B-7 | | 4.31(1H, d$_{AB}$, J=11.2Hz) 4.44(1H, d$_{AB}$, J=11.2Hz) 7.74(1H, s) |

Example 149 (Method B-2)

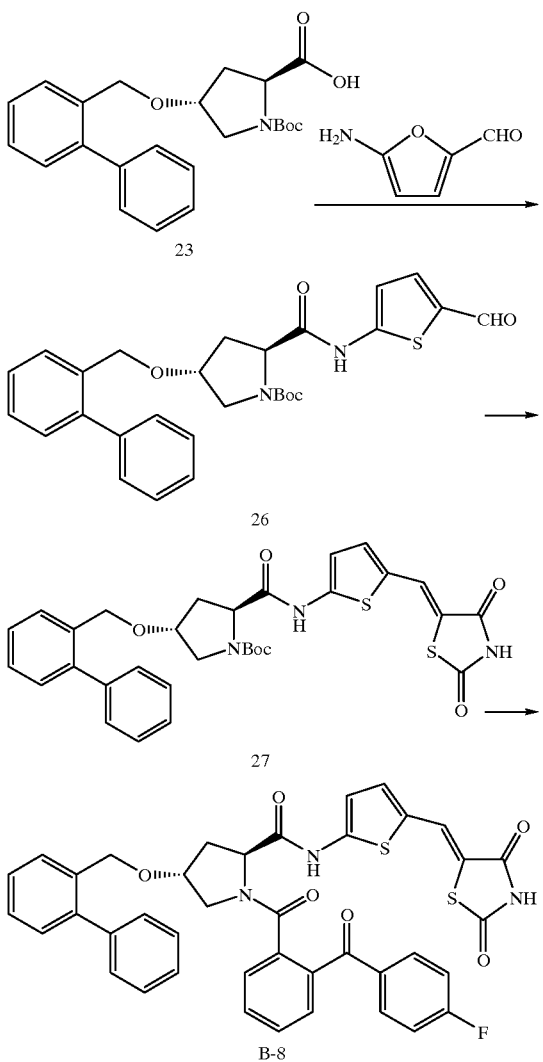

(1) 23→26

To a solution of the above mentioned compound (23) (826 mg, 2.08 mmol) in Example 149 and 2-aminothiophen-5-carbardehyde (240 mg, 1.89 mmol) in chloroform (50 ml) were added triethylamine (0.82 ml, 5.88 mmol) and 2-chloro-1,3-dimethylimidazolinium chloride (DMC) (479 mg, 2.83 mmol) under ice-cooling with stirring and the resulting mixture was stirred for 4 h at room temperature. The reaction mixture was washed with 2N hydrochloric acid, water, and brine. The organic layer was dried over sodium sulfate and concentrated in vacuo. The residue was subjected to silica gel column chromatography (hexane:ethyl acetate=1:1) to give 498 mg(52%) of the compound (26).

NMR (CDCl$_3$) δ ppm: 1.48 (9H, s), 2.03 (1H, m), 2.59 (1H, m), 3.44 (1H, m), 4.15 (1H, m), 4.40 (1H, d$_{AB}$, J=11.1 Hz), 4.45 (1H, d$_{AB}$, J=11.1 Hz), 4.56 (1H, m), 6.61 (1H, m), 7.23–7.53 (11H), 9.76 (1H, s), 10.89 (1H, s). IR ν$_{max}$ (CHCl$_3$): 3234, 1695, 1658, 1599 cm$^{-1}$. FAB-MS (m/z): 507 ([MH]$^+$).

(2) 26→27

The compound (27) was synthesized in a manner similar to that described in the synthesis of the compound (15) in Example 58 using the compound (26) as a starting material.

NMR (CDCl$_3$) δ ppm: 1.51 (9H, s), 2.21 (2H, m), 3.45 (1H, m), 3.64 (1H, m), 4.20 (1H, m), 4.42 (2H, s), 4.62 (1H, m), 6.48 (1H, d, J=4.4 Hz), 7.09 (1H, d, J=4.0 Hz), 7.25–7.54 (9H), 7.82 (1H, s), 10.18 (1H, br s), 10.97 (1H, s). IR ν$_{max}$ (CHCl$_3$): 3394, 3220, 1733, 1690, 1665, 1595 cm$^{-1}$. FAB-MS (m/z): 605 (M$^+$).

(3) 27→B-8

The compound (B-8) was obtained in a manner similar to that described in the synthesis of the compound (A-1) from the compound (9) in Example 1 using the compound (27) as a starting material.

NMR (CDCl$_3$) δ ppm: 2.32 (1H, m), 2.50 (1H, m), 3.39 (2H, d, J=3.8 Hz), 4.05 (1H, m), 4.31 (1H, d$_{AB}$, J=11.1 Hz), 4.42 (1H, d$_{AB}$, J=11.1 Hz), 4.98 (1H, dd, J=5.8, 8.6 Hz), 6.90 (1H, d, J=4.0 Hz), 7.08–7.70 (16H), 7.85 (2H, m), 7.90 (1H, s), 8.52 (1H, s), 10.46 (1H, s). IR ν$_{max}$ (CHCl$_3$): 3308, 1737, 1697, 1651, 1597 cm$^{-1}$. Elemental analysis (C$_{40}$H$_{30}$N$_3$FS$_2$O$_6$.0.6H$_2$O); Calcd.: C, 64.69; H, 4.23; N, 5.66; F, 2.56; S, 8.64%. Found: C, 64.77; H, 4.38; N, 5.69; F, 2.52; S, 8.63%.

Example 150 (Method B-2)

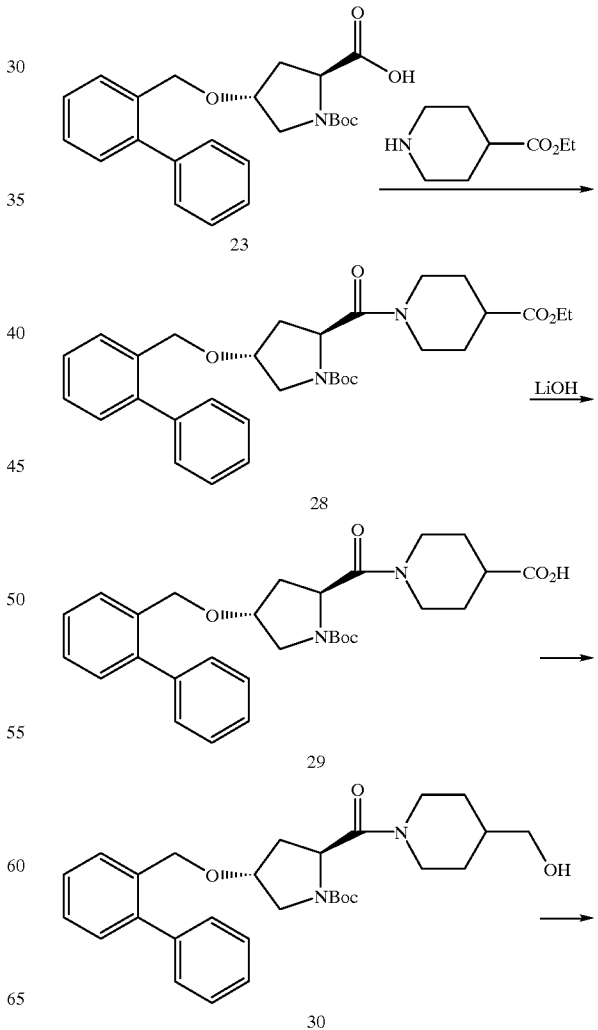

-continued

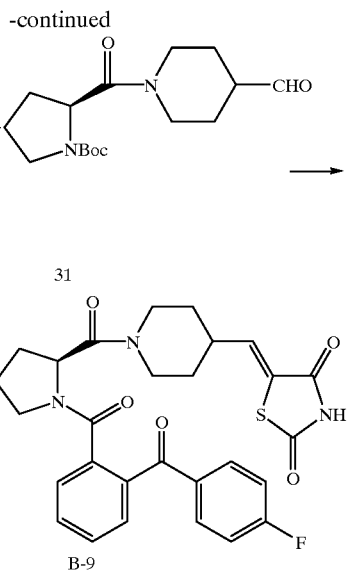

(1) 23→28

The compound (28) was obtained in a manner similar to that described in the synthesis of the compound (9) in Example 1 using the compound (23) described in Example 142 and piperidine-4-carboxylic acid ethylester as a starting material.

NMR (CDCl₃) δ ppm: 126 (3H, t, J=7.2 Hz), 1.38–1.45 (9H), 1.53–1.79 (2H), 1.84–2.02 (3H), 2.03–2.25 (1H), 2.46–2.60 (1H), 2.75–2.91 (1H), 2.99–3.27 (1H), 3.43–3.95 (3H), 4.00–4.15 (1H), 4.15 (2H, q, J=7.2 Hz), 4.26–4.46 (3H), 4.60–4.79 (1H), 7.24–7.52 (9H). IR $\nu_{max}$ (Film): 1730, 1698, 1655 cm⁻¹.

(2) 28→30

To a solution of the compound (28) (4.20 g, 7.83 mmol) in methanol (100 ml) was added lithium hydroxide monohydrate (1.20 g, 28.6 mmol) and the resulting mixture was stirred for 30 h at room temperature. To the reaction mixture was added 2N hydrochloric acid aq. (15 ml) and methanol was removed by concentrating in vacuo. The residue was dissolved in ethyl acetate and the organic layer was washed with water and brine, dried over sodium sulfate, and concentrated in vacuo to give the crude compound (29). The compound (30) was obtained by treating the compound (29) in a manner similar to that described in the synthesis of the compound (13) in Example 58.

NMR (CDCl₃) δ ppm: 1.00–1.29 (2H), 1.37–1.45 (9H), 1.68–1.99 (4H), 2.04–2.26 (1H), 2.50–2.67 (1H), 2.89–3.19 (1H), 3.43–3.69 (4H), 3.79–4.17 (2H), 4.30–4.47 (2H), 4.51–4.79 (2H), 7.26–7.52 (9H). IR $\nu_{max}$ (KBr): 3437, 1698, 1645 cm⁻¹.

(3) 30→31

The compound (31) was obtained in a manner similar to that described in the synthesis of the compound (14) in Example 58 using the compound (30) as a starting material.

NMR (CDCl₃) δ ppm: 1.40 (½×9H, s), 1.44 (½×9H, s), 1.49–1.71 (2H), 1.83–2.26 (4H), 2.43–2.59 (1H), 2.83–3.35 (2H), 3.44–4.17 (4H), 4.18–4.35 (1H), 4.34 (½×1H $d_{AB}$, J=11.1 Hz), 4.38 (½×2H, s), 4.44 (½×1H, $d_{AB}$, J=11.1 Hz), 4.60–4.79 (1H), 7.26–7.52 (9H), 9.63–9.71(1H). IR $\nu_{max}$ (KBr): 3432, 1725, 1698, 1655 cm⁻¹. Elemental analysis (C₂₉H₃₆N₂O₅.0.5H₂O); Calcd.: C, 69.44; H, 7.43; N, 5.58%. Found: C, 69.50; H, 7.30; N, 5.66%.

(3) 31→B-9

The compound (B-9) was obtained in a manner similar to that described in the synthesis of the compound (A-58) in Example 58 using the compound (31) as a starting material.

NMR (CDCl₃) δ ppm: 1.23–1.73 (3H), 1.73–2.50 (4H), 2.58–2.90 (1H), 3.01–3.28 (1H), 3.39–3.69 (2H), 3.90–4.17 (2H), 4.28–4.59 (3H), 4.70–4.77 (⅕×1H), 4.95–5.08 (⅘× 1H), 6.57 (⅕×1H, d, J=9.7 Hz), 6.75–6.90 (⅘×1H), 6.94 (⅕×2H, t, J=8.6 Hz), 7.02–7.12 (⅘×2H), 7.23–7.65(13H), 7.68–7.75(⅕×2H), 7.79–7.88 (⅘×2H), 8.50–8.62 (½×1H), 9.18 (½×1H, br s). IR $\nu_{max}$ (KBr): 3438, 3118, 1748, 1708, 1635, 1597 cm⁻¹. Elemental analysis (C₄₁H₃₆N₃SFO₆.0.5H₂O); Calcd.: C, 67.92; H, 5.12; N, 5.80; S, 4.42; F, 2.62%. Found: C, 67.86; H, 5.01; N, 5.73; S, 4.44; F, 2.56%.

Example 151 (Method C)

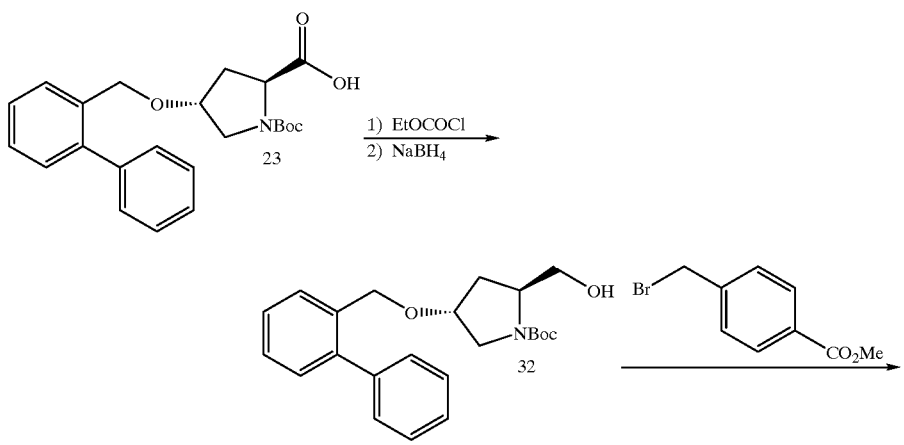

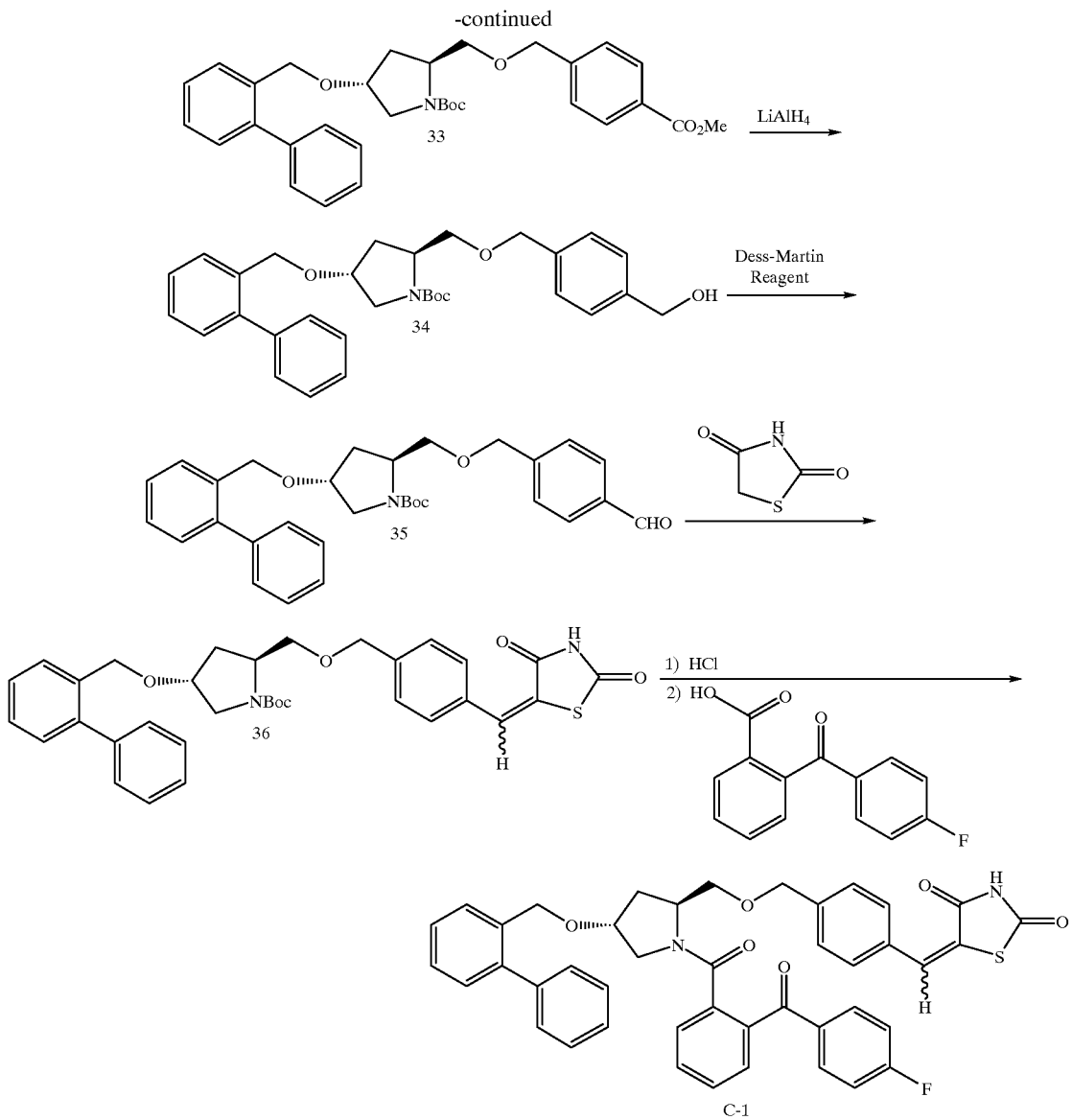

-continued (1) 23→32

To a solution of the compound (23) (2 g, 5.03 mmol) and triethylamine (0.7 ml, 5.02 mmol) in tetrahydrofuran (10 ml) was added ethyl chlorocarbonate (0.75 ml, 7.88 ml) under ice-cooling with stirring and the resulting mixture was stirred for 5 h at the same temperature. The precipitation was filtered off, and the filtrate was added dropwise to the suspension of sodium borohydride (0.57 g, 5.1 mmol) in water (10 ml) under ice-cooling with stirring. The reaction mixture was allowed to warm to room temperature and stirred for 2 h. The mixture was partitioned between ethyl acetate and 2N hydrochloric acid aq. The organic layer was washed with 5% sodium hydrogencarbonate aq., water, and brine, dried over sodium sulfate, and concentrated in vacuo to give 1.93 g (100%) of the crude compound (32).

(2) 32→33

To a solution of the compound (32) (1.33 g, 3.47 mmol) in N,N-dimethylformamide (10 ml) was added 60% sodium hydride (140 mg, 3.5 mmol) under ice-cooling with stirring and the resulting mixture was stirred for 30 min. To the reaction mixture was added 4-bromomethylbenzoic acid methylester (790 mg, 3.54 mmol) at the same temperature with stirring and the resulting mixture was allowed to warm to room temperature and stirred for 24 h. The mixture was partitioned between ethyl acetate and 2N hydrochloric acid aq. The organic layer was washed with 5% sodium hydrogencarbonate aq., water, and brine, dried over sodium sulfate, and concentrated in vacuo. The residue was subjected to silica gel column chromatography (hexane:ethyl acetate=5:1) to give 480 mg (26%) of the aimed compound.

NMR (CDCl$_3$) δ ppm: 1.43 (9H, s), 1.90–2.15 (2H), 3.25–3.75 (4H), 3.91 (3H, s), 3.95–4.20 (2H), 4.38 (2H, s), 4.55 (2H, s), 7.20–7.55 (11H), 8.00 (2H, d, J=8.2 Hz). IR $\nu_{max}$ (Film): 1721, 1694, 1613, 1395, 1279, 1108, 755 cm$^{-1}$. Elemental analysis (C$_{32}$H$_{37}$NO$_6$·0.3C$_6$H$_6$); Calcd.: C, 73.14:14; 7.05; N, 2.52%. Found: C, 73.01; H, 7.10; N, 2.61%.

(3) 33→34

A solution of the compound (33) (480 mg, 0.90 mmol) in tetrahydrofuran (2 ml) was added dropwise to a suspension of lithium aluminium hydride (34 mg, 0.9 mmol) in ether (5 ml) with stirring at room temperature and the resulting mixture was stirred for 1.5 h. The reaction mixture was partitioned between ethyl acetate and 2N hydrochloric acid aq. The organic layer was washed with 5% sodium hydrogencarbonate aq., water, and brine, dried over sodium sulfate, and concentrated in vacuo to give 410 mg (91.1%) of the compound (34) as an oil.

NMR (CDCl$_3$) δ ppm: 1.43 (9H, s), 1.65–1.80 (2H), 1.90–2.15 (1H), 3.30–3.80 (4H), 4.20 (2H), 4.36 (2H, m), 4.49 (2H, s), 4.68 (2H, s), 7.20–7.60 (13H).

(4) 34→35

A solution of the compound (34) (410 mg, 0.81 mmol) in tetrahydrofuran (2 ml) was added dropwise to a solution of Dess-Martin reagent (510 mg, 1.20 mmol) in dimethylsulfoxide (4 ml) at room temperature and the resulting mixture was stirred for 2 h. The reaction mixture was diluted with ethyl acetate (30 ml) and washed with water and brine. The organic layer was dried over sodium sulfate and concentrated in vacuo to give 390 mg (95.1%) of the compound (35).

NMR (CDCl$_3$) δ ppm: 1.43 (9H, s), 1.50–1.65 (1H), 1.95–2.15 (1H), 3.30–3.80 (4H), 3.80–4.20 (2H), 4.38 (2H, m), 4.54 (2H, s), 7.20–7.55 (11H), 7.84 (2H, d, J=8.0 Hz), 10.00 (1H, s).

(5) 35→36

To a solution of the compound (35) (390 mg, 0.78 mmol) in toluene (12 ml) were added 2,4-thiazolidinedione (100 mg, 0.85 mmol), 1M-piperidine in toluene (78 μl, 0.078 mmol), and 1M-acetic acid in toluene (78 μl, 0.078 mmol) and the resulting mixture was heated at reflux for 24 h. The solvent was removed by concentrating in vacuo. The residue was subjected to silica gel column chromatography (chloroform:methanol=50:1) to give 267 mg (57.2%) of the aimed compound (36).

NMR (CDCl$_3$) δ ppm: 1.44 (9H, s), 1.50–1.70 (1H), 1.95–2.20 (1H), 3.10–3.75 (4H), 3.90–4.20 (2H), 4.38 (2H, m), 4.54 (2H, s), 7.20–7.55 (13H), 7.83 (1H, s), 8.73 (1H, br s).

(6) 36→C-1

The compound (C-1) was synthesized in a manner similar to that described in the synthesis of the compound (A-1) from the compound (9) in Example 1 using the compound (36) as a starting material.

NMR (CDCl$_3$) δ ppm: 2.05–2.25 (2H), 3.20–3.60 (4H), 3.95–4.10 (1H), 4.27 (1H, d$_{AB}$, J=11.2 Hz), 4.33 (1H, d$_{AB}$, J=11.2 Hz), 4.34–4.58 (3H), 7.03 (2H, m), 7.81 (1H, s), 8.81 (1H, br s). IR ν$_{max}$ (Nujol): 1744, 1706, 1662, 1598 cm$^{-1}$. MS (m/z): 727 ([MH]$^+$). Elemental analysis (C$_{43}$H$_{35}$N$_2$FSO$_6$·0.3C$_6$H$_{14}$·0.3H$_2$O); Calcd.: C, 70.98; H, 5.29; N, 3.70; F, 2.51; S, 4.23%. Found: C, 70.94; H, 5.35; N, 3.79; F, 2.63; S, 4.21%.

The compound (C-2) was synthesized in a manner similar to that described in the above method. The result was shown in Table 18.

TABLE 18

| Compound No. | B | NMR(CDCl$_3$) δ ppm |
|---|---|---|
| C-1 | O | 4.27(1H, d$_{AB}$, J=11.2Hz) 4.33(1H, d$_{AB}$, J=11.2Hz) 7.81(1H, s) |
| C-2 | S | 4.27(1H, d$_{AB}$, J=11.4Hz) 4.34(1H, d$_{AB}$, J=11.4Hz) 7.61(1H, s) |

Example 153 (Method E-1)

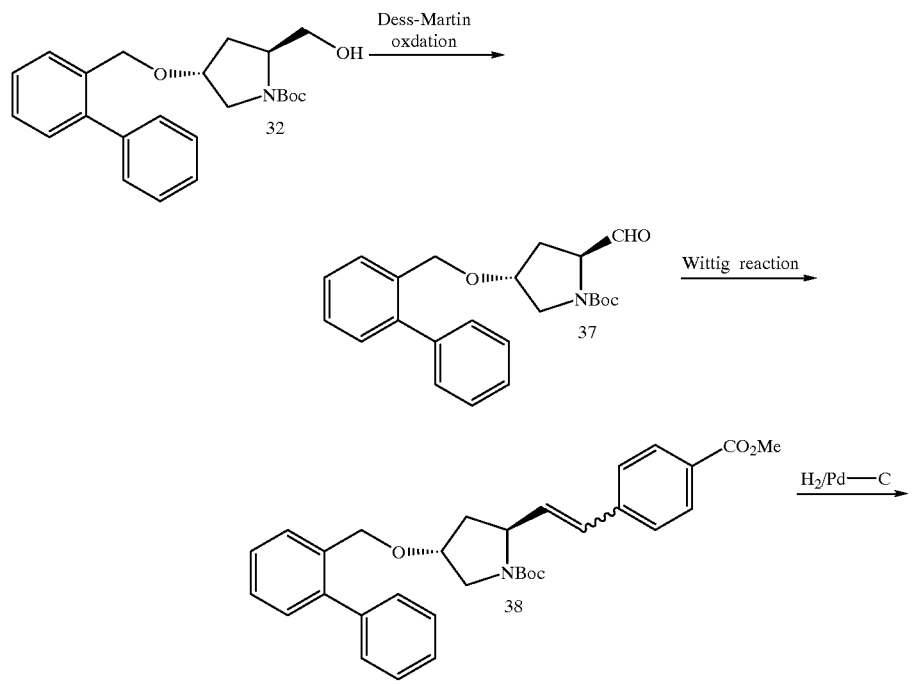

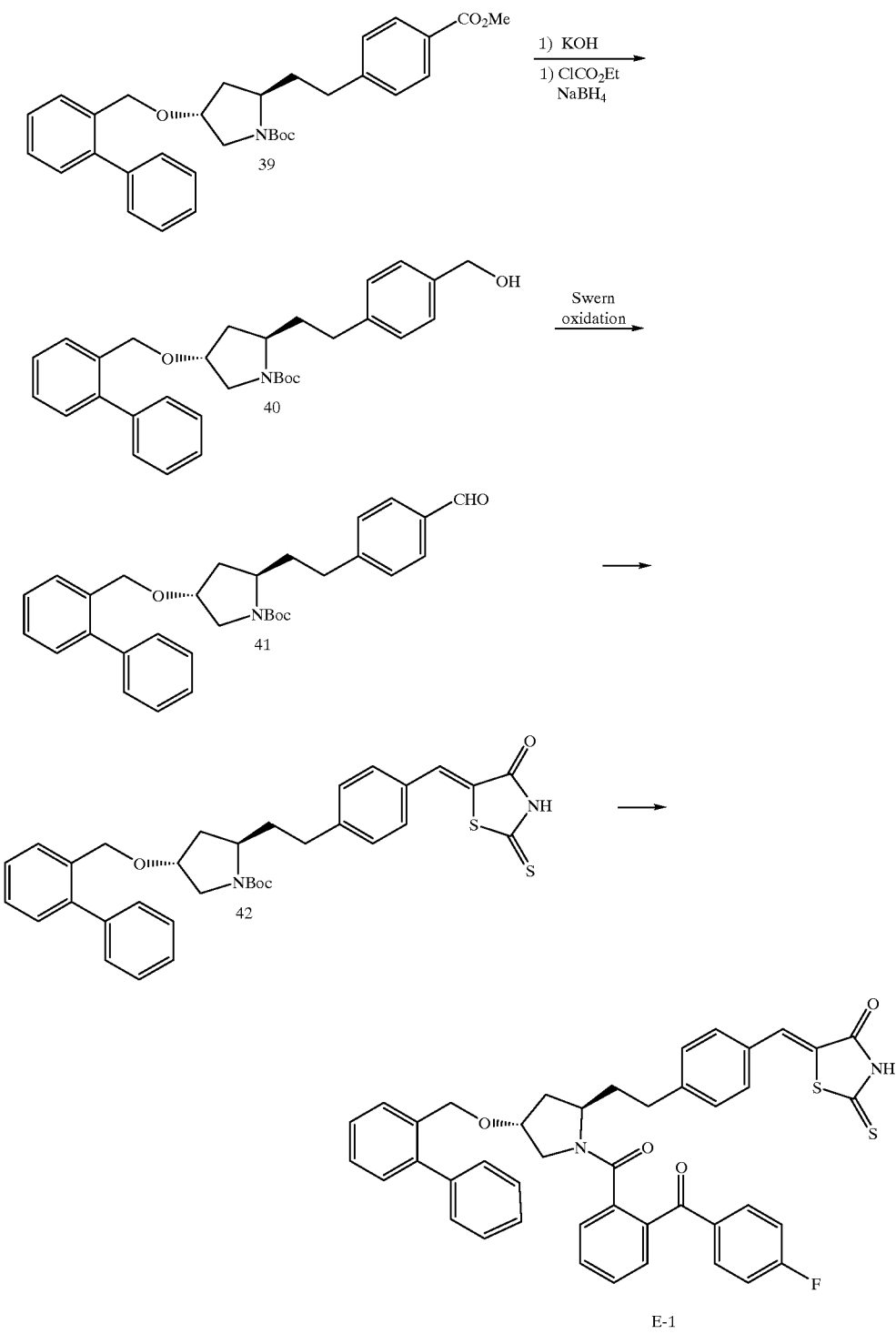

E-1

(1) 32→37

The compound (37) was obtained in a manner similar to that described in the synthesis of the compound (35) in Example 151 using the compound (32) described in Example 151 as a starting material.

NMR (CDCl$_3$) δ ppm: 1.43 and 1.46 (9H, each s), 1.70–1.95 (1H), 1.95–2.20 (1H), 3.40–3.75 (2H), 3.90–4.30 (2H), 4.40 (2H, s), 7.20–7.40 (9H), 9.39 and 9.50 (1H, each d, J=3.8 and 3.6 Hz). IR ν$_{max}$ (Film): 1737, 1697, 1395 cm$^{-1}$. Elemental analysis (C$_{23}$H$_{27}$NO$_4$.0.2H$_2$O); Calcd.: C, 71.74; H, 7.17; N, 3.64%. Found: C, 71.83; H, 7.24; N, 3.53%.

(2) 37→38

To a solution of the compound (37) (3.00 g, 7.9 mmol) in ethanol (60 ml) were added to 4-methoxycarbonylbenzyltriphenylphosphoniumbromide (7.70 g, 15.7 mmol) and triethylamine (3.3 ml, 23.7 mmol) and the resulting mixture was heated at reflux for 6.5 h.

Ethanol was removed by concentrating in vacuo. The mixture was partitioned between ethyl acetate and 2N hydrochloric acid aq. The organic layer was washed with 5% sodium hydrogencarbonate aq., water, and brine, dried over sodium sulfate, and concentrated in vacuo. The obtained oily residue was subjected to silica gel column chromatography (hexane:ethyl acetate=5:1) to give 3.0 g (74%) of the aimed compound (38).

NMR (CDCl$_3$) δ ppm: 1.34 and 1.40 (9H, each s), 1.70–1.95 (1H), 2.10–2.35 (1H) 3.30–3.75 (2H), 3.90–4.10 (1H), 3.91 and 3.92 (3H, each s), 4.10–4.95 (3H), 5.50–6.50 (2H), 7.20–7.40 (11H), 7.97 and 7.99 (2H, each d, J=8.2 Hz). Elemental analysis (C$_{32}$H$_{35}$NO$_5$.0.2C$_6$H$_6$); Clacd: C, 75.34; H, 6.89; N, 2.65%. Found: C, 75.31; H, 7.10; N, 2.74%.

(3) 38→39

To a solution of the compound (38) (2.98 g, 5.80 mmol) in methanol (30 ml) was added 5% palladium-carbon (0.3 g) and the resulting mixture was hydrogenated at 1 atm. The catalyst was filtered off and the filtrate was concentrated in vacuo. The obtained oily residue was subjected to silica gel column chromatography (hexane:ethyl acetate=5:1) to give 2.35 g (86%) of the aimed compound (39).

NMR (CDCl$_3$) δ ppm: 1.44 (9H, s), 1.60–1.80 (2H), 1.95–2.30 (2H), 2.50–2.30 (2H), 2.50–2.70 (2H), 3.20–3.80 (3H), 3.90 (3H, s), 3.90–4.05 (1H), 4.37 (2H, br s), 7.15–7.55 (11H), 7.94 (2H, d, J=8.2 Hz). IR ν$_{max}$ (Film): 1720, 1692, 1395, 1280 cm$^{-1}$. Elemental analysis (C$_{32}$H$_{37}$NO$_5$); Calcd.: C, 74.53; H, 7.23; N, 2.72%. Found: C, 74.80; H, 7.29; N, 2.63%.

(4) 39→40

The compound (40) was obtained in a manner similar to that described in the synthesis of the compound (13) from the compound (11) in Example 58 using the compound (39) as a starting material.

NMR (CDCl$_3$) δ ppm: 1.45 (9H, s), 1.60–1.90 (2H), 1.95–2.35 (2H), 2.54 (2H, m), 3.30 (1H, m), 3.35–4.05 (3H), 4.37 (2H, s), 4.65 (2H, s), 7.05–7.55 (13H). IR ν$_{max}$ (Film): 3431, 1691, 1402 cm$^{-1}$.

(5) 40→41

The compound (41) was obtained in a manner similar to that described in the synthesis of the compound (14) in Example 58 using the compound (40) as a starting material.

NMR (CDCl$_3$) δ ppm: 1.44 (9H, s), 1.60–1.85 (2H), 1.95–2.30 (2H), 2.64 (2H, m), 3.29 (1H, m), 3.35–4.05 (3H), 4.38 (2H, m), 7.25–7.55 (11H), 7.79 (2H, d, J=8.0 Hz), 9.97 )1H, s).

(6) 41→42

The compound (42) was obtained in a manner similar to that described in the synthesis of the compound (15) in Example 58 using the compound (41) as a starting material.

NMR (CDCl$_3$) δ ppm: 1.45 (9H, s), 1.67–1.81 (2H), 2.00–2.13 (2H), 2.53–2.67 (2H), 3.23–3.55 (2H), 3.96 (2H, m), 4.38 (2H, br s), 7.30–7.61 (14H). IR ν$_{max}$ (Nujol): 1717, 1692 cm$^{-1}$. Elemental analysis (C$_{34}$H$_{36}$N$_2$O$_4$S$_2$.0.8H$_2$O); Calcd.: C, 66.38; H, 6.16; N, 4.55; S, 10.42%. Found: C, 66.15; H, 6.15; N, 4.88; S, 10.31%.

(7) 42→E-1

The compound (E-1) was obtained in a manner similar to that described in the synthesis of the compound (A-1) from the compound (9) in Example 1 using the compound (42) as a starting material.

NMR (CDCl$_3$) δ ppm: 1.88–2.00 (1H), 2.11–2.21 (1H), 3.27 (2H, d, J=3.3 Hz), 3.76 (1H, t, J=6.6 Hz), 3.93 (1H, s), 4.23–4.29 (3H), 7.02 (3H, t, J=8.3 Hz), 7.21–7.60 (20H), 7.78–7.83 (2H). IR ν$_{max}$ (KBr): 1717, 1661, 1630 cm$^{-1}$. Elemental analysis (C$_{43}$H$_{35}$N$_2$O$_4$S$_2$F.0.6C$_6$H$_{14}$.0.8H$_2$O); Calcd.: C, 70.72; H, 5.83; N, 3.49; S, 8.00; F, 2.37%. Found: C, 70.62; H, 5.91; N, 3.61; S, 7.99; F, 2.30%.

The compounds (E-2) to (E-8) were synthesized in a manner similar to that described in the above method. The results were shown in Table 19.

TABLE 19

| Compound No. | —X$^1$—X$^2$— | B | NMR(CDCl$_3$) δ ppm |
|---|---|---|---|
| E-1 | (CH$_2$CH$_2$-phenyl-CH$_3$) | S | 3.27(2H, d, J=3.3Hz) 3.76(1H, t, J=6.6Hz) |
| E-2 | (CH$_2$CH$_2$-phenyl-CH$_3$) | O | 4.27(2H, m) 7.80(1H, s) |
| E-3 | (CH=CH-phenyl-CH$_3$) | S | 1.80–1.93(1H, m) 7.73–7.88(2H, m) |
| E-4 | (CH=CH-phenyl-CH$_3$) | O | 4.28–4.54(2H, m) 7.50–7.63(2H, m) |
| E-5 | (CH=CH-thienyl-CH$_3$) | S | 4.41(1H, d$_{AB}$, J=15.3Hz) 4.48(1H, d$_{AB}$, J=16.2Hz) |
| E-6 | (CH=CH-thienyl-CH$_3$) | O | 4.33–4.52(2H, m) 7.76–7.78(7H, m) |
| E-7 | (CH=CH-thienyl-CH$_3$) | S | 4.36(1H, s) 4.44(1H, s) 7.76–7.88(lH, m) |
| E-8 | (CH=CH-thienyl-CH$_3$) | O | 1.81–1.92(1H, m) 4.33–4.43(2H, m) 7.74–7.86(2H, m) |

Example 161 (Method E-2)

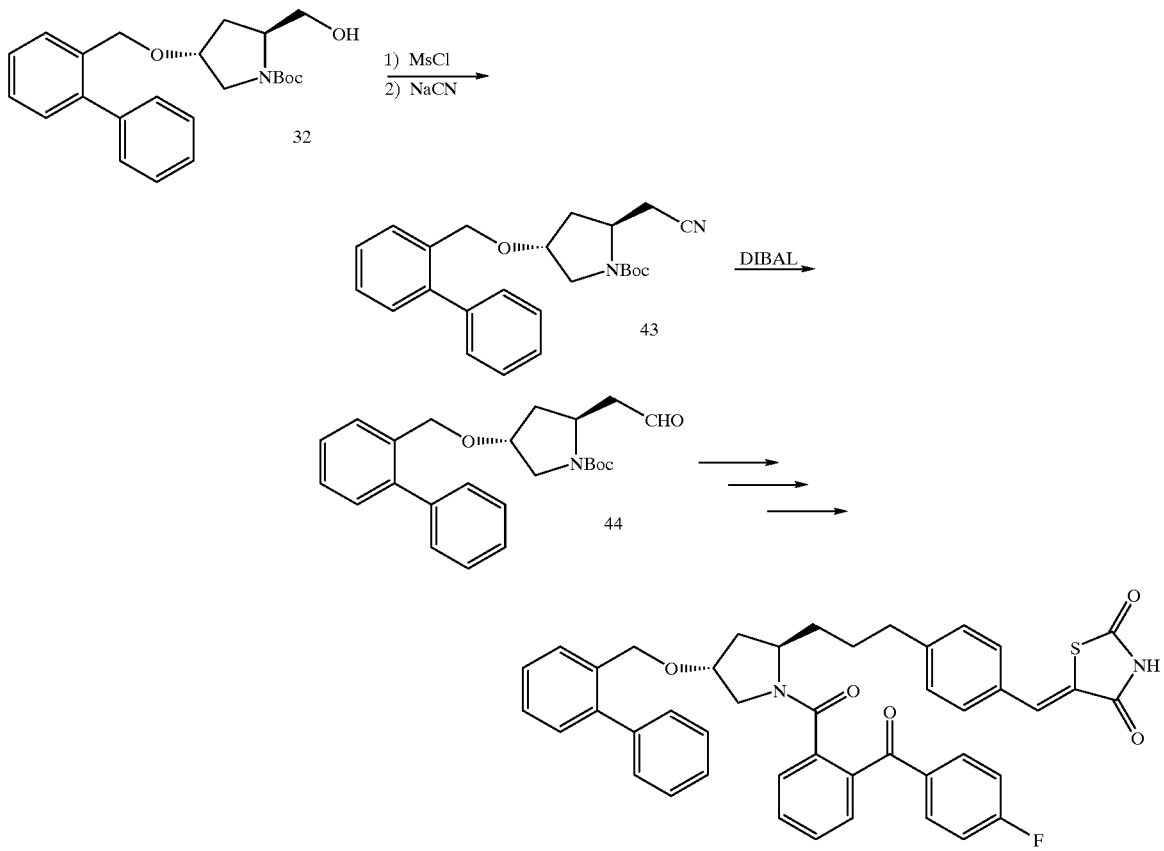

(1) 32→43

To a solution of the compound (32) (17.5 g) described in Example 151 in dichloromethane (120 ml) were added triethylamine (9.54 ml) and methanesulfonyl chloride (4.24 ml) under ice-cooling and the resulting mixture was stirred for 30 min. The reaction mixture was poured into water-ethyl acetate. The organic layer was separated and the aqueous layer was extracted with ethyl acetate. The fused organic layer was washed with sat. sodium hydrogencarbonate aq., and brine, dried over magunesium sulfate, and concentrated in vacuo. The residue was dissolved in N,N-dimethylformamide (100 ml). To this solution was added sodium cyanide (3.35 g) at room temperature and the resulting mixture was stirred for 6 h at 70° C. The reaction mixture was cooled and poured into water-ethyl acetate. The organic layer was separated and the aqueous layer was extracted with ethyl acetate. The fused organic layer was washed with 1N hydrochloric acid aq., sat. sodium hydrogencarbonate, and brine, dried over magunesium sulfate, and concentrated in vacuo. The residue was subjected to silica gel column chromatography to give 16.2 g(90%) of the aimed compound (43).

NMR (CDCl$_3$) δ ppm: 1.45 (9H, s), 1.80–2.36 (2H), 2.55–3.20 (2H), 3.28–3.85 (2H), 3.93–4.12 (2H), 4.36 (1H, d$_{AB}$, J=11.3 Hz), 4.41 (1H, d$_{AB}$, J=11.3 Hz), 7.23–7.53 (9H. IR ν$_{max}$ (CHCl$_3$): 2246, 1684 cm$^{-1}$. FAB-MS (M/z): 415 ([M+Na]$^+$).

(2) 43→44

To a solution of the compound (43) in toluene (150 ml) was added 1.0 M diisobutylaluminumhydride in toluene (61.9 ml) at −78° C., and the resulting mixture was stirred for 2 h. To this mixture was added 1.0 M diisobutylaluminumhydride in toluene (12.4 ml) and the resulting mixture was stirred for 3 h. To the reaction mixture was added 25% sodium hydroxide aq. (24.3 ml) and the resulting mixture was allowed to warm to room temperature. The reaction mixture was diluted with ethyl acetate and filtered and the organic layer was separated. The organic layer was washed with brine, dried over magnesium sulfate and concentrated in vacuo. The residue was dissolved in ethyl acetate (300 ml) and silica gel (32.4 g) was added to this solution. The mixture was stirred for 3 h at room temperature and filtered and the filtrate was concentrated in vacuo. The residue was subjected to silica gel column chromatography to give 8.72 g (53%) of the compound (44).

NMR (CDCl$_3$) δ ppm: 1.44 (9H, s), 1.57–1.78 (1H), 2.11–2.35 (1H), 2.52 (1H, ddd, J=1.8, 7.4, 16.7 Hz), 2.76–3.03 (1H), 3.22–3.78 (2H), 3.87–4.00 (1H), 4.35 (1H, d$_{AB}$, J=11.4 Hz), 4.40 (1H, d$_{AB}$, J=11.4 Hz), 7.23–7.53 (9H), 9.74 (1H, t, J=1.8 Hz). IR ν$_{max}$ (CHCl$_3$): 1720, 1682 cm$^{-1}$. HR-FAB-MS (M/z): C$_{24}$H$_{30}$NO$_4$ [M+H]$^+$; Calcd.: 396.2175. Found: 396.2186.

(3) 44→E-9

The compound (E-9) was synthesized in a manner similar to that described in the synthesis of the compound (E-1) from the compound (37) in Example 153 using the compound (44) as a starting material.

NMR (CDCl$_3$) δ ppm: 0.92–2.18 (6H), 2.57 (2H, t, J=7.7 Hz), 3.17–3.82 (2H), 3.82–3.94 (1H), 4.10–4.39 (1H), 4.23 (1H, d$_{AB}$, J=11.3 Hz), 4.27 (1H, d$_{AB}$, J=11.3 Hz), 7.00–7.57 (19H), 7.80 (1H, s), 7.82 (2H, dd, J=5.3, 8.9 Hz). IR ν$_{max}$ (KBr): 1742, 1706, 1662 cm$^{-1}$. Elemental analysis ($C_{44}H_{37}N_2O_5SF$); Calcd.: C, 72.91; H, 5.14; N, 3.86; S, 4.42; F, 2.62%. Found: C, 72.71; H, 5.35; N, 3.77; S, 4.29; F, 2.53%.

The compounds (E-10) to (E-14) were synthesized in a manner similar to that described in the above method. The results were shown in Table 20.

TABLE 20

| Compound No. | —$X^1$—$X^2$— | B | NMR(CDCl$_3$) δ ppm |
|---|---|---|---|
| E-9 | propyl-phenyl linker | O | 4.23(1H, d$_{AB}$, J=11.3Hz)<br>4.27(1H, d$_{AB}$, J=11.3Hz)<br>7.80(1H, s) |
| E-10 | propyl-phenyl linker | S | 4.23(1H, d$_{AB}$, J=11.3Hz)<br>4.27(1H, d$_{AB}$, J=11.3Hz)<br>7.63(1H, s) |
| E-11 | cis-allyl-phenyl linker | S | 4.23(1H, d$_{AB}$, J=11.3Hz)<br>4.28(1H, d$_{AB}$, J=11.3Hz)<br>5.60(1H, dt, J=11.9, 7.4Hz)<br>6.46(1H. d. J=11.9Hz)<br>7.63(1H, s) |
| E-12 | cis-allyl-phenyl linker | O | 4.23(1H, d$_{AB}$, J=11.1Hz)<br>4.28(1H, d$_{AB}$, J=11.1Hz)<br>5.58(1H, dt, J=11.7, 7.4Hz)<br>6.46(1H, d, J=11.7Hz) |
| E-13 | trans-allyl-phenyl linker | S | 4.27(1H, d$_{AB}$, J=11.3Hz)<br>4.31(1H, d$_{AB}$, J=11.3Hz)<br>6.26(1H, dt, J=15.9, 6.9Hz)<br>6.38(1H, d, J=15.9Hz)<br>7.57(1H, s) |
| E-14 | trans-allyl-phenyl linker | O | 4.26(1H, d$_{AB}$, J=11.1Hz)<br>4.31(1H, d$_{AB}$, J=11.1Hz)<br>6.24(1H, dt, J=15.9, 6.9Hz)<br>6.38(1H, d, J=15.9Hz)<br>7.77(1H, s) |

Example 167 (Method F-1)

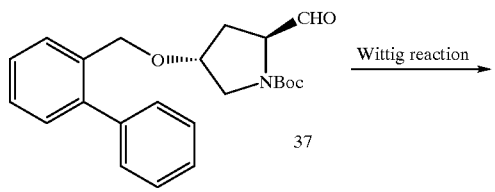

Wittig reaction

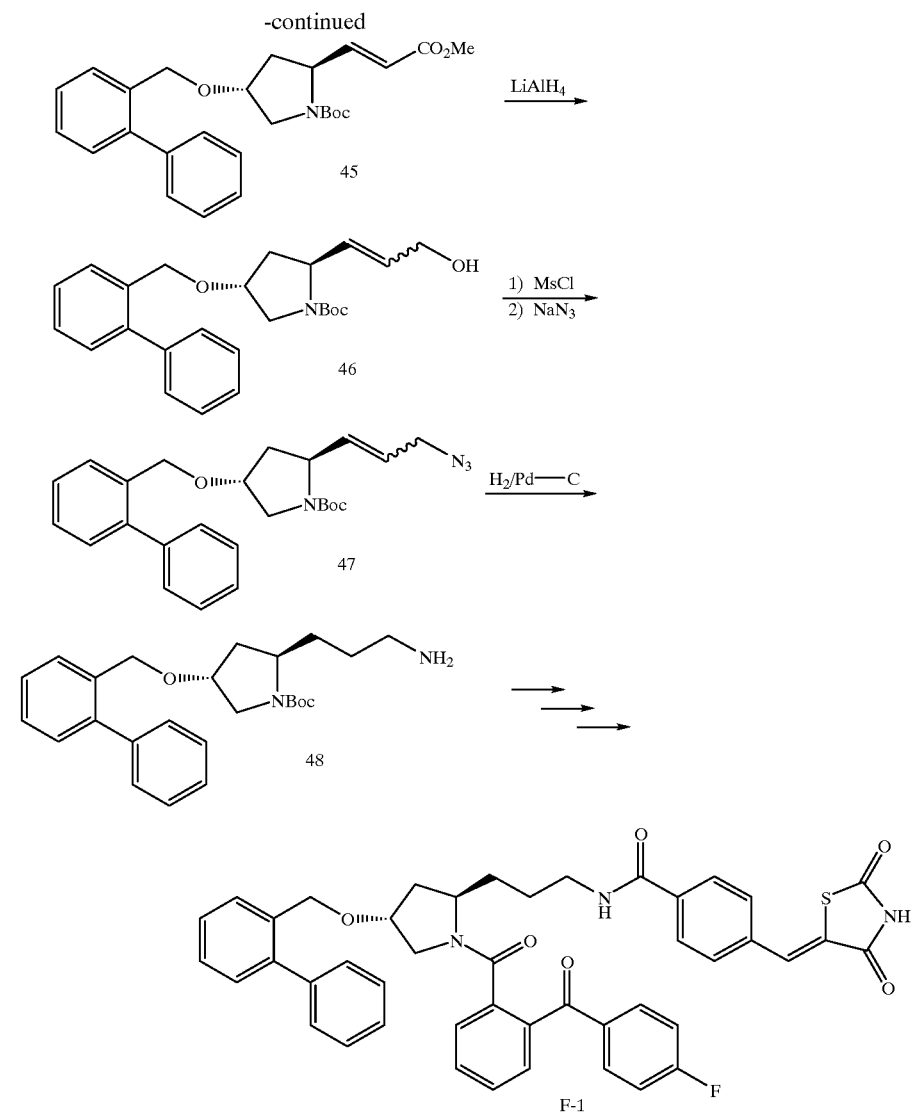

(1) 37→45

To a solution of triphenylphosphoniummethoxy-carbonylmethylenebromide (6.363 g, 15.32 mmol) in anhydrous ethanol (40 ml) was added trietbylamine (4.27 ml, 30.64 mol) and the resulting mixture was stirred for 15 min under ice-cooling, To this mixture was added a solution of the compound (37) (3.043 g, 7.66 mmol) described in Example 153 in anhydrous ethanol (10 ml) and the resulting mixture was stirred for 15 min at the same temperature, allowed to warm to room temperature, and stirred for 1 h. The reaction mixture was partitioned between ethyl acetate and water. The organic layer was washed with water and brine, dried over sodium sulfate, and concentrated in vacuo. The residue was subjected to silica gel column chromatography (bexane:ethyl acetate=7:1) to give 2.73 g (79%) of the compound (45).

NMR (CDCl$_3$) δ ppm: 1.41 (9H, s), 1.76 (1H, ddd, J=4.9, 7.3, 12.5 Hz), 2.04–2.22 (1H), 3.38 (1H, dd, J=4.9, 11.6 Hz), 3.60–3.76 (1H), 3.73 (3H, s), 3.90–4.00 (1H), 4.33–4.43 (3), 5.83 (1H, d, J=16.1 Hz), 6.72–6.84 (1H), 7.27–7.50 (11H). IR ν$_{max}$ (Film): 1723, 1697, 1598 cm$^{-1}$. Elemental analysis (C$_{26}$H$_{31}$NO$_5$.0.7H$_2$O); Calcd.: C, 69.37; H, 7.25; N, 3.11%. Found: C, 69.42; H, 6.96; N, 3.26%.

(2) 45→46

To a solution of the compound (45) (2.654 g, 5.881 mmol) in tetrahydrofuran (30 ml) was added lithiumaluminumhydride (446.4 mg, 11.76 mmol) and the resulting mixture was stirred for 40 min under ice-cooling. To this mixture were added water (30 ml) and 2N hydrochloric acid aq. (6 ml) and the resulting mixture was stirred for 30 min at the same temperature. This reaction mixture was partitioned between water and ethyl acetate. The organic layer was washed with water and brine, dried over sodium sulfate, and concentrated in vacuo. The residue was subjected to silica gel column chromatography (hexane:ethyl acetate=4:1) to give 169 mg of the compound (46).

NMR (CDCl$_3$) δ ppm: 1.42 (9H, s), 1.66 (1H, ddd, J=5.0, 6.7, 13.2 Hz), 2.07–2.17 (1H), 3.36 (1H, dd, J=4.8, 11.9 Hz), 3.42–4.03 (4H), 4.35–4.48 (1H), 4.37 (1H, d$_{AB}$, J=11.1 Hz), 4.40 (1H, d$_{AB}$, J=11.1 Hz), 4.72–4.85 (1H), (19H), 7.80 (1H, s), 7.82, 5.22–5.32 (1H), 5.73–5.87 (1H), 7.26–7.53 (1H). IR ν$_{max}$ (Film): 1682, 1599 cm$^{-1}$. Elemental analysis (C$_{25}$H$_{31}$NO$_4$.0.2H$_2$O); Calcd.: C, 71.87; H, 7.89; N, 3.49%. Found: C, 72.02; H, 7.65; N, 3.51%.

(3) 46→47

The compound (47) was obtained in a manner similar to that described in the synthesis of the compound (5) in Example 1 using the compound (46) as a starting material.

NMR (CDCl$_3$) δ ppm: 1.43 (9H, s), 1.63–1.73 (1H), 2.09–2.20 (1H), 3.35 (1H, dd, J=4.3, 12.2 Hz), 3.41–4.07 (4H), 4.39 (2H, s), 4.48–4.65 (1H), 5.45–5.60 (2H), 7.26–7.55 (9H). IR ν$_{max}$ (Film): 1694, 1599 cm$^{-1}$. Elemental analysis (C$_{25}$H$_{30}$N$_4$O$_3$·0.1H$_2$O); Calcd.: C, 68.82; H, 6.98; N, 12.84%. Found: C, 69.05; H, 7.04; N, 12.52%.

(4) 47→48

To a solution of the compound (47) (99.8 mg, 0.223 mmol) in methanol (2 ml) was added 10% palladium-carbon (10 mg) and the resulting mixture was hydrogenated. The catalyst was filtered off and the solvent was removed by concentrating in vacuo to give the crude compound (48).

NMR (CDCl$_3$) δ ppm: 1.33–1.57 (2H), 1.44 (9H, s), 1.63–2.14 (3H), 2.69–3.05 (5H), 3.05–4.00 (4H), 4.36 (2H, s), 7.25–7.51 (9H).

(5) 48→F-1

The compound (F-1) was synthesized in a manner similar to that described in the synthesis of the compound (A-1) from the compound (8) in Example 1 using the compound (48) as a starting material.

NMR (CDCl$_3$) δ ppm: 1.33–1.85 (5H), 2.10–2.22 (1H), 3.32 (2H, d, J=3.5 Hz), 3.35–3.63 (2H), 3.93–4.01 (1H), 4.27–4.39 (1H), 4.28 (1H, d$_{AB}$, J=11.3 Hz), 4.34 (1H, d$_{AB}$, J=11.3 Hz), 7.02 (2H, t, J=8.5 Hz), 7.24–7.62 (16H), 7.62 (1H, s), 7.75–7.83 (2H), 7.86 (2H, d, J=8.5 Hz), 9.92 (1H, s). IR ν$_{max}$: 3422, 1748, 1707, 1659, 1617, 1598 cm$^{-1}$. Elemental analysis (C$_{45}$H$_{38}$N$_3$O$_6$SF·0.8H$_2$O); Calcd.: C, 69.09; H, 5.10; N, 5.37; S, 4.10; F, 2.43%. Found: C, 69.04; H, 5.10; N, 3.36; S, 4.22; F, 2.61%.

Example 168 (Method F-2)

(1) 44→49

To a solution of the compound (44) (1.539 g, 3.892 mmol) described in Example 161 in tetrahydrofuran (10 ml) was added sodium borohydride (299.4 mg, 7.783 mmol) under ice-cooling and the resulting mixture was stirred for 45 min at the same temperature. The reaction was stopped by adding the dilute hydrochloric acid aq. The reaction mixture was partitioned between water and ethyl acetate. The organic layer was washed with water and brine, dried over sodium sulfate, and concentrated in vacuo. The residue was subjected to silica gel column chromatography (hexane:ethyl acetate=3:1) to give 1.134 g (73.3%) of the compound (49).

NMR (CDCl$_3$) δ ppm: 1.45 (9H, s), 1.61–1.72 (1H), 1.75 (1H, ddd, J=4.0, 5.7, 12.8 Hz), 2.01–2.12 (1H), 3.31 (1H, dd, J=5.9, 11.7 Hz), 3.43–3.53 (1H), 3.53–3.60 (1H), 3.98–4.08 (1H), 4.11–4.23 (1H), 4.36 (1H, d$_{AB}$, J=11.1 Hz), 4.38 (1H, dAB, J=11.1 Hz), 7.26–7.51 (9H). IR ν$_{max}$ (Film): 1691, 1673, 1599 cm$^{-1}$. Elemental analysis (C$_{24}$H$_{31}$NO$_4$·0.7H$_2$O); Calcd.: C, 70.29; H, 7.96; N, 3.42%. Found: C, 70.41; H, 7.69; N, 3.48%.

(2) 49→F-2

The compound (F-2) was obtained in a manner similar to that described in the synthesis of the compound (A-67) from the compound (18) in Example 67 using the ompound (49) as a starting material.

NMR (CDCl$_3$) δ ppm: 1.51–1.64 (1H), 1.67–1.85 (2H), 2.17 (1H, ddd, J=4.5, 8.4, 13.1 Hz), 2.80–2.93 (1H), 3.26–3.38 (2H), 3.69–3.83 (1H), 3.94–4.03 (1H), 4.25 (1H, d$_{AB}$, J=11.3 Hz), 4.32 (1H, d$_{AB}$, J=11.3 Hz), 4.38–4.51 (1H), 7.12 (2H, t, J=8.5 Hz), 7.23–7.61 (15H), 7.74 (1H, s), 7.80–7.88 (1H), 7.92 (2H, d, J=8.85 Hz), 8.02–8.09 (1H), 9.06 (1H, s). IR ν$_{max}$ (KBr): 3421, 1748, 1707, 1658, 1618, 1597 cm$^{-1}$. Elemental analysis (C$_{44}$H$_{36}$N$_3$O$_6$SF·0.3H$_2$O); Calcd.: C, 69.61; H, 4.86; N, 5.53; S, 4.22; F, 2.50%. Found: C, 69.61; H, 4.94; N, 5.53; S, 4.36; F, 2.50%.

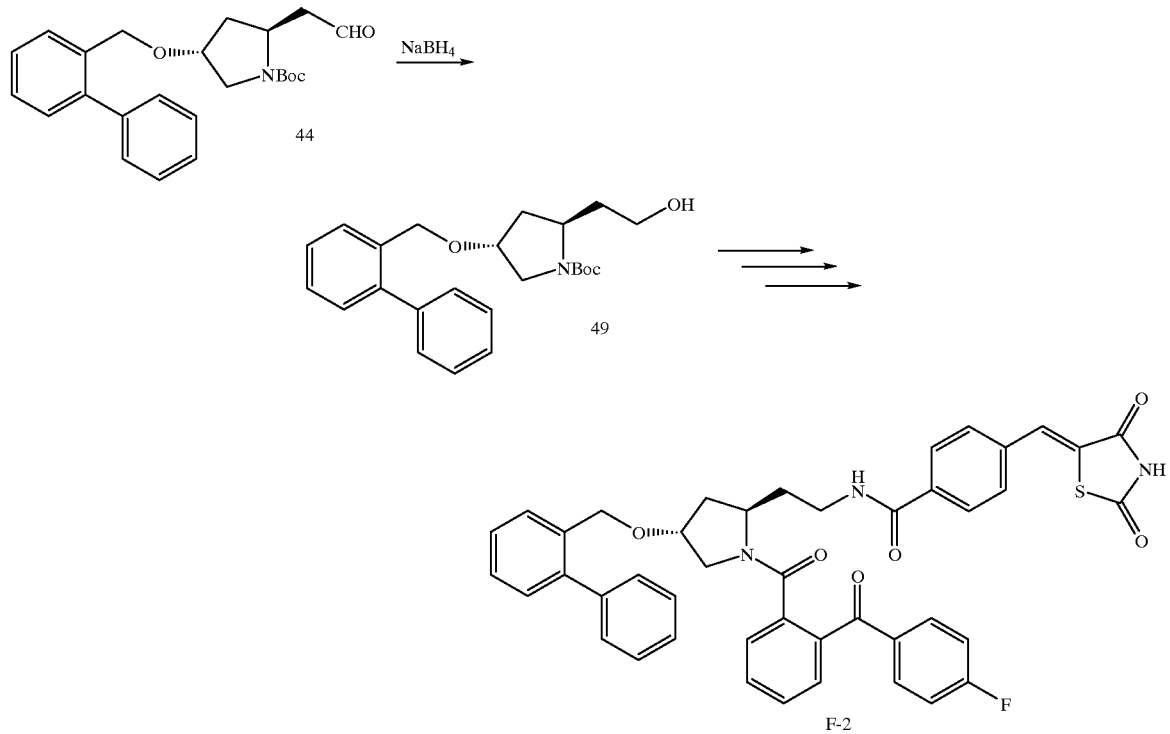

F-2

Example 169 (Method F-3)

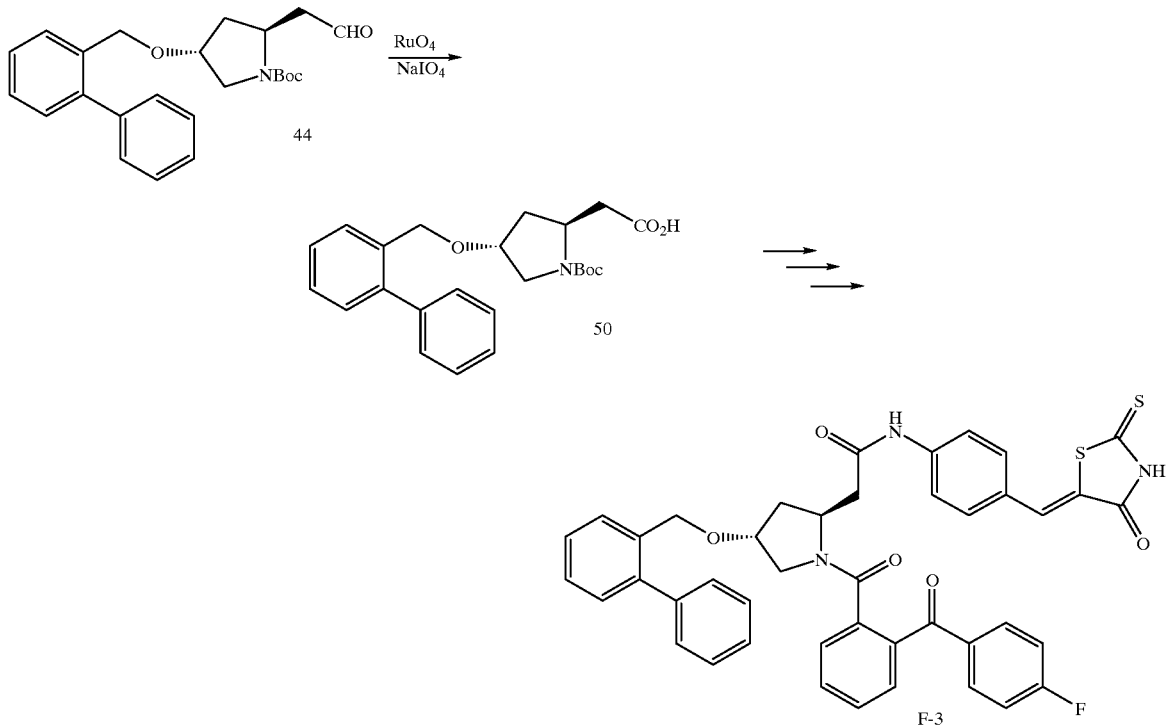

(1) 44→50

To a solution of the compound (44) (3.0 g) described in Example 161 in carbon tetrachloride (30 ml)-acetone (7.5 ml)-water (42 ml) were added sodium periodate (6.49 g) and ruthenium dioxide (20 mg) under ice-cooling and the resulting mixture was stirred for 4 h. To the reaction mixture was added 2-propanol (7.5 ml) and the resulting mixture was filtered with celite. The filtrate was concentrated in vacuo. The residue was diluted with ethyl acetate. The organic layer was dried over magnesium sulphate and concentrated in vacuo. The residue was subjected to silica gel column chromatography to give 2.06 g (66%) of the compound (50).

NMR (CDCl$_3$) δ ppm: 1.45 (9H, s), 1.70–2.31 (2H), 2.42 (1H, dd, J=8.3. 15.8 Hz), 2.78–3.08 (1H), 3.20–4.00 (3H), 4.10–4.44 (3H), 7.23–7.57 (9H). IR ν$_{max}$ (CHCl$_3$): 1710, 1685 cm$^{-1}$. FAB-MS (M/z): 412([M+H]$^+$).

(2) 50→F-3

The compound (F-3) was obtained in a manner similar to that described in the synthesis of the compound (B-1) from the compound (23) in Example 142 using the compound (50) as a starting material.

NMR (CDCl$_3$) δ ppm: 2.08–2.35 (2H), 2.51–2.80 (2H), 3.27–3.44 (2H), 3.91–4.66 (2H), 4.29 (1H, d$_{AB}$, J=11.1 Hz), 4.36 (1H, d$_{AB}$, J=11.1 Hz), 7.09 (2H, t, J=8.7 Hz), 7.14–8.00 (19H), 9.44 (1H, s), 10.00 (1H, br s). IR ν$_{max}$ (KBr): 1698, 1661 cm$^{-1}$. HR-FAB-MS (M/z): C$_{43}$H$_{35}$N$_3$O$_5$S$_2$F [M+H]$^+$; Calcd: 756.2003. Found: 756.2000. Elemental analysis (C$_{43}$H$_{34}$N$_3$O$_5$S$_2$F.1.2H$_2$O); Calcd.: C, 66.43; H, 4.72; N, 5.40; S, 8.25; F, 2.44%. Found: C, 66.27; H, 4.71; N, 5.44; S, 8.60; F, 2.55%.

The compounds (F-4) and (F-5) were synthesized in a manner similar to that described in the above method. The results were shown in Table 21.

TABLE 21

| Compound No. | —X$^2$— | B | NMR(CDCl$_3$) δ ppm |
|---|---|---|---|
| F-1 | 1,4-phenylene | S | 4.29(1H, d$_{AB}$, J=11.1Hz)<br>4.36(1H, d$_{AB}$, J=11.1Hz)<br>7.09(2H, t, J=8.7Hz) |
| F-2 | 1,4-phenylene | O | 4.30(1H, d$_{AB}$, J=11.3Hz)<br>4.34(1H, d$_{AB}$, J=11.3Hz)<br>7.08(2H, t, J=8.7Hz) |
| F-3 | 2,5-thienylene | O | 4.30(1H, d$_{AB}$, J=11.1Hz)<br>4.37(1H, d$_{AB}$, J=11.1Hz)<br>7.68(1H, s) |

Example 172 (Method G-1)
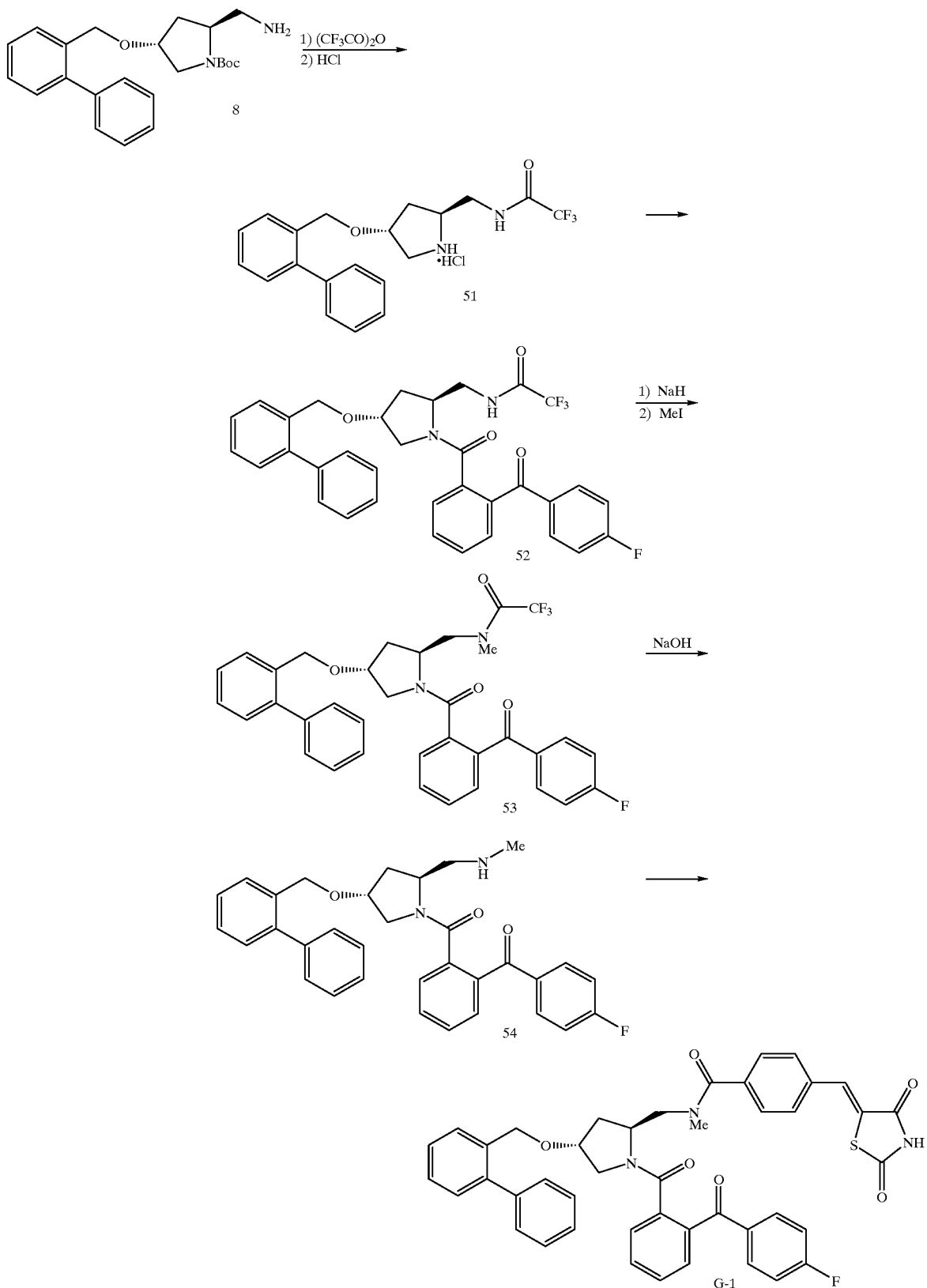

(1) 8→51

To a solution of the compound (8) (12.36 g, 32.31 mmol) in dichloromethane (50 ml) were added trifluoroacetic anhydride (10 g, 47.61 mmol) and pyridine (7 ml, 86.55 mmol) under ice-cooling with stirring and the resulting mixture was stirred for 2 h at room temperature. The reaction mixture was diluted with ether (200 ml), washed with water, 5% hydrochloric acid aq., and brine, dried over sodium sulfate, and concentrated in vacuo to give trifluoroacetamide. It was dissolved in ethyl acetate (25 ml). To this solution was added 4N hydrochloric acid in ethyl acetate (23 ml) under ice-cooling with stirring and the resulting mixture was stirred for 3 h at room temperature. The mixture was diluted with ethyl acetate (50 ml) and precipitated crystals were collected by filtration to give 8.43 g (62.9%) of hydrochloride derivative (51).

Melting point: 193–195° C. NMR (DMSO-$d_6$) δ ppm: 1.67 (1H, ddd, J=4.7, 11.4, 13.8 Hz), 2.04 (1H, dd, J=5.9, 13.8 Hz), 3.16 (1H, d, J=12.9 Hz), 3.39 (1H, dd, J=4.7, 12.6 Hz), 3.57 (2H, m), 3.73 (1H, m), 4.17 (1H, t, J=4.3 Hz), 4.36 (1H, $d_{AB}$, J=11.1 Hz), 4.38 (1H, $d_{AB}$, J=11.1 Hz), 7.27 (1H, m), 7.33–7.58 (8H), 9.46 (2H, br s), 9.75 (1H, t, J=5.1 Hz). IR $v_{max}$ (KBr): 3432, 3185, 3059, 2921, 1720 cm$^{-1}$. Elemental analysis ($C_{20}H_{22}N_2ClF_3O_2$); Calcd.: C, 57.90; H, 5.35; N, 6.75; Cl, 8.55; F, 13.74%. Found: C, 57.86; H, 5.44; N, 6.49; Cl, 8.39; F, 13.61%.

(2) 51→52

The compound (52) was obtained in a manner similar to that described in the synthesis of the compound (A-1) in Example 1 using the hydrochloride (51) as a starting material.

NMR (CDCl$_3$) δ ppm: 1.71 (1H, ddd, J=5.0, 8.4, 13.9 Hz), 2.20 (1H, m), 3.18 (1H, dd, J=4.1, 12.0 Hz), 3.26–3.40 (2H), 3.83–3.95 (2H), 4.25 (1H, $d_{AB}$, J=11.3 Hz), 4.35 (1H, $d_{AB}$, J=11.3 Hz), 4.32–4.45 (1H), 7.15 (2H, t, J=8.6 Hz), 7.24–7.61 (13H), 7.82 (2H, m), 8.42 (1H, m). IR $v_{max}$ (KBr): 3342, 1720, 1658, 1628, 1599 cm$^{-1}$. Elemental analysis ($C_{34}H_{28}N_2F_4O_2 \cdot 0.2H_2O$); Calcd.: C, 67.14; H, 4.71; N, 4.61; F, 12.49%. Found: C, 67.26; H, 4.83; N, 4.77; F, 12.30%.

(2) 52→53

To a solution of the compound (52) (610 mg, 1.009 mmol) in dimethylformamide (10 ml) was added sodium hydride (60%) (50 mg, 1.25 mmol) and the resulting mixture was stirred for 30 min at room temperature. Successively, methyl iodide (0.1 ml, 1.6 mmol) was added to this mixture and the resulting mixture was stirred for 3 h at room temperature. The reaction mixture was diluted with ethyl acetate (50 ml), washed with water and brine, dried over sodium sulphate, and concentrated in vacuo to give 454 mg(72.8%) of the compound (53).

NMR (CDCl$_3$) δ ppm: 1.89 (1H, td, J=5.8, 13.6 Hz), 2.07 (1H, m), 3.18 (3H, q, J=1.7 Hz), 3.30 (1H, m), 3.37–3.58 (3H), 4.03 (1H, m), 4.29 (1H, $d_{AB}$, J=11.4 Hz), 4.32 (1H, $d_{AB}$, J=11.4 Hz), 4.47 (1H, m), 7.10 (2H, t, J=8.6 Hz), 7.20–7.60 (13H), 7.83 (2H, m).

(3) 53→G-1

To a solution of the compound (53) (454 mg, 0.734 mmol) in methanol (15 ml) was added 1N sodium hydroxide aq. (5 ml) and the resulting mixture was stirred for 1.5 h at room temperature. After 2N hydrochloric acid aq. (2.2 ml) was added to the mixture, methanol was removed by concentrating in vacuo, and diluted with ethyl acetate (100 ml). The organic layer was washed with water and brine, dried over sodium sulfate, and concentrated in vacuo to give 420 mg(100%) of the crude compound (54). The crude compound was treated in a manner similar to that described in the synthesis of the compound (9) in Example 1, and re-precipitated with ethyl acetate and hexane to give 542 mg (98%) of the compound (G-1).

NMR (CDCl$_3$) δ ppm: 1.97 (1H, m), 2.14 (1H, m), 3.03 (3H, s), 3.24 (1H, dd, J=5.6, 13.3 Hz), 3.35 (1H, dd, J=3.5, 11.4 Hz), 3.62 (1H, dd, J=5.6, 13.3 Hz), 3.99 (1H, dd, J=8.2, 13.3 Hz), 4.21 (1H, m), 4.35 (2H, s), 4.76 (1H, m), 7.09 (2H, t, J=8.6 Hz), 7.19–7.64 (17H), (1H, s), 7.85 (2H, m), 9.26 (1H, s). IR $v_{max}$ (KBr): 3437, 1748, 1708, 1662, 1633, 1598 cm$^{-1}$. Elemental analysis ($C_{44}H_{36}N_3FSO_6 \cdot 0.3CH_3CO_2C_2H_5 \cdot 0.3C_6H_{14}$); Calcd.: C, 69.98; H, 5.40; N, 5.21; F, 2.35; S, 3.97%. Found: C, 70.14; H, 5.32; N, 5.41; F, 2.49; S, 4.10%.

Example 173 (Method G-2)

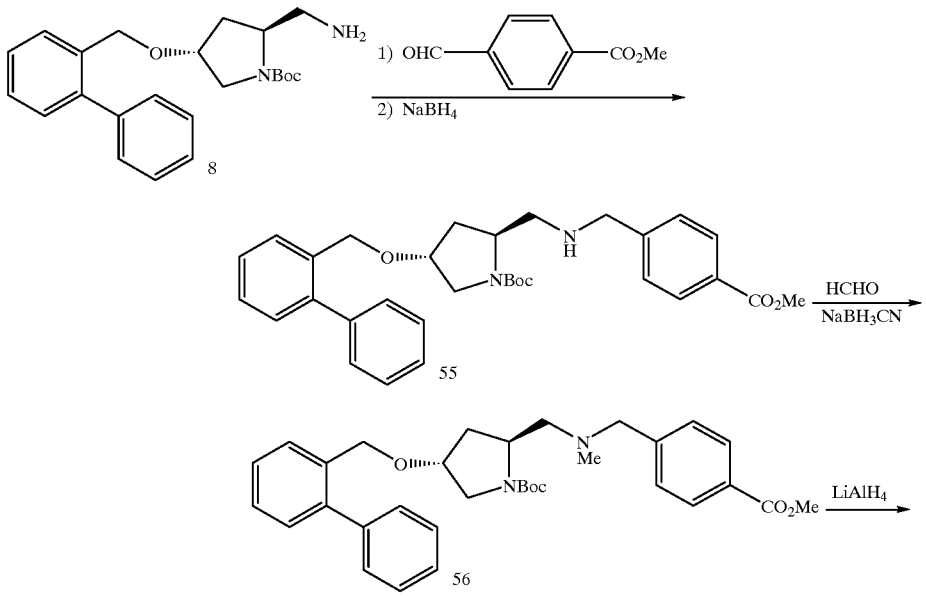

-continued

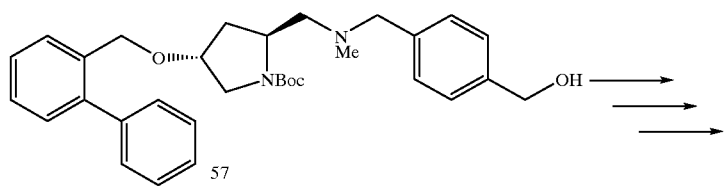

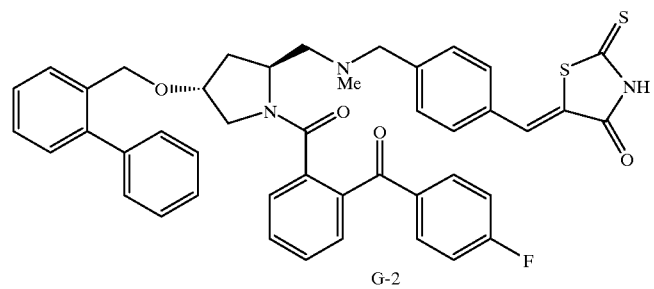

(1) 8→55

To a solution of the compound (8) (3.135 g, 8.197 mmol) in benzene (30 ml) was added 4-methoxycarbonylbenzaldehyde (1.35 g, 8.224 mmol) and the resulting mixture was heated at reflux for 3 h with removing off the generating water. The solvent was removed by concentrating in vacuo. The residue was dissolved in methanol (20 ml) and sodium borohydride (400 mg) was added to the mixture under ice-cooling. The reaction mixture was stirred for 1 h and partitioned between water and ethyl acetate. The organic layer was washed with water and brine, dried over sodium sulfate, and concentrated in vacuo to give the compound (55).

NMR (CDCl$_3$) δ ppm: 1.42 (9H, s), 1.53–2.13 (3H), 2.65–2.80 (2H), 3.29 (1H, dd, J=4.8, 11.6 Hz), 3.39–3.77 (1H), 3.78–4.10 (4H), 3.91 (3H, s), 4.37 (2H, br s), 7.25–7.51 (11H), 7.98 (2H, d, J=8.2 Hz). IR $\nu_{max}$ (Film): 1720, 1692, 1611 cm$^{-1}$. Elemental analysis ($C_{32}H_{38}N_2O_5 \cdot 1.0H_2O$); Calcd.: C, 70.05; H, 7.35; N, 5.11%. Found: C, 70.14; H, 7.13; N, 5.27%.

(2) 55→56

To a solution of the compound (55) (500.1 mg, 0.942 mmol) in acetonitrile (20 ml) was added 37% formaldehyde (0.38 ml, 4.712 mmol) and the resulting mixture was stirred for 15 min at room temperature. After sodium cyanoborohydride (59.2 mg, 0.942 mmol) was added to the mixture and the resulting mixture was stirred for 15 min, acetic acid (0.055 ml, 0.942 mmol) was added to this mixture and the resulting mixture was stirred for 45 min. The reaction mixture was partitioned between sat. sodium hydrogencarbonate aq, and ethyl acetate. The organic layer was washed with water and brine, dried over sodium sulphate, and concentrated in vacuo. The residue was subjected to silica gel column chromatography (hexane:ethyl acetate=3:1) to give 453.9 mg (88.5%) of the aimed compound (56).

NMR (CDCl$_3$) δ ppm: 1.46 (9H, s), 1.89–2.14 (2H), 2.14–2.29 (4H), 2.51–2.71 (1H), 3.18–3.73 (4H), 3.82–4.15 (2H), 3.90 (3H, s), 4.34 (2H, br s), 7.26–7.51 (11H), 7.97 (2H, d, J=8.2 Hz). IR $\nu_{max}$ (Film): 1722, 1694, 1610 cm$^{-1}$. Elemental analysis ($C_{33}H_{40}N_2O_5 \cdot 0.25H_2O$); Calcd.: C, 72.17; H, 7.43; N, 5.10%. Found: C, 72.11; H, 7.56; N, 5.40%.

(3) 56→57

To a solution of the compound (56) (377.5 mg, 0.693 mmol) in tetrahydrofuran (4 ml) was added lithium aluminum hydride (52.6 mg, 1.386 mmol) under ice-cooling and the resulting mixture was stirred for 1 h at the same temperature. Methanol (0.5 ml) was added to the reaction mixture and the resulting mixture was stirred for 15 min. The mixture was partitioned between water and ethyl acetate. The organic layer was washed with water and brine, dried over sodium sulfate, and concentrated in vacuo. The residue was subjected to silica gel column chromatography (hexane:ethyl acetate=1:1) to give 351 mg (98%) of the compound (57).

NMR (CDCl$_3$) δ ppm: 1.46 (9H, br s), 1.86 (1H, br s), 1.93–2.07 (2H), 2.16–2.29 (4H), 2.47–2.67 (1H), 3.20–3.66 (4H), 3.82–4.16 (2H), 4.32 (2H, br s), 4.63 (2H, 7.23–7.51 (13H). IR $\nu_{max}$ (Film): 3445, 1737, 1693, 1599 cm$^{-1}$. Elemental analysis ($C_{32}H_{40}N_2O_4 \cdot 0.2H_2O$); Calcd.: C, 73.87; H, 7.83; N, 5.38%. Found: C, 73.60; H, 8.02; N, 5.71%.

(4) 57→G-2

The compound (G-2) was synthesized in a manner similar to that described in the synthesis of the compound (C-1) from the compound (34) in Example 151 using the compound (57) as a starting material.

NMR (CDCl$_3$) δ ppm: 1.85–1.97 (1H, m), 2.07–2.34 (4H), 2.42–2.70 (1H), 3.19–4.05 (6H), 4.22 (1H, d$_{AB}$, J=11.2 Hz), 4.30 (1H, d$_{AB}$, J=11.2 Hz), 4.32–4.45 (1H), 7.08 (2H, t, J=8.6 Hz), 7.23–7.60(16H), 7.61 (1H, s), 7.75–7.85 (2H). IR $\nu_{max}$ (KBr): 3432, 1718, 1660, 1632, 1597 cm$^{-1}$. Elemental analysis ($C_{44}H_{38}N_3FS_2O_4 \cdot 0.4H_2O$); Calcd.: C, 69.25; H, 5.12; N, 5.51; F, 2.49; S, 8.40%. Found: C, 69.27; H, 5.15; N, 5.53; F, 2.58; S, 8.25%.

The compound (G-3) was synthesized in a manner similar to that described in the above method. The result was shown in Table 22.

Example 175
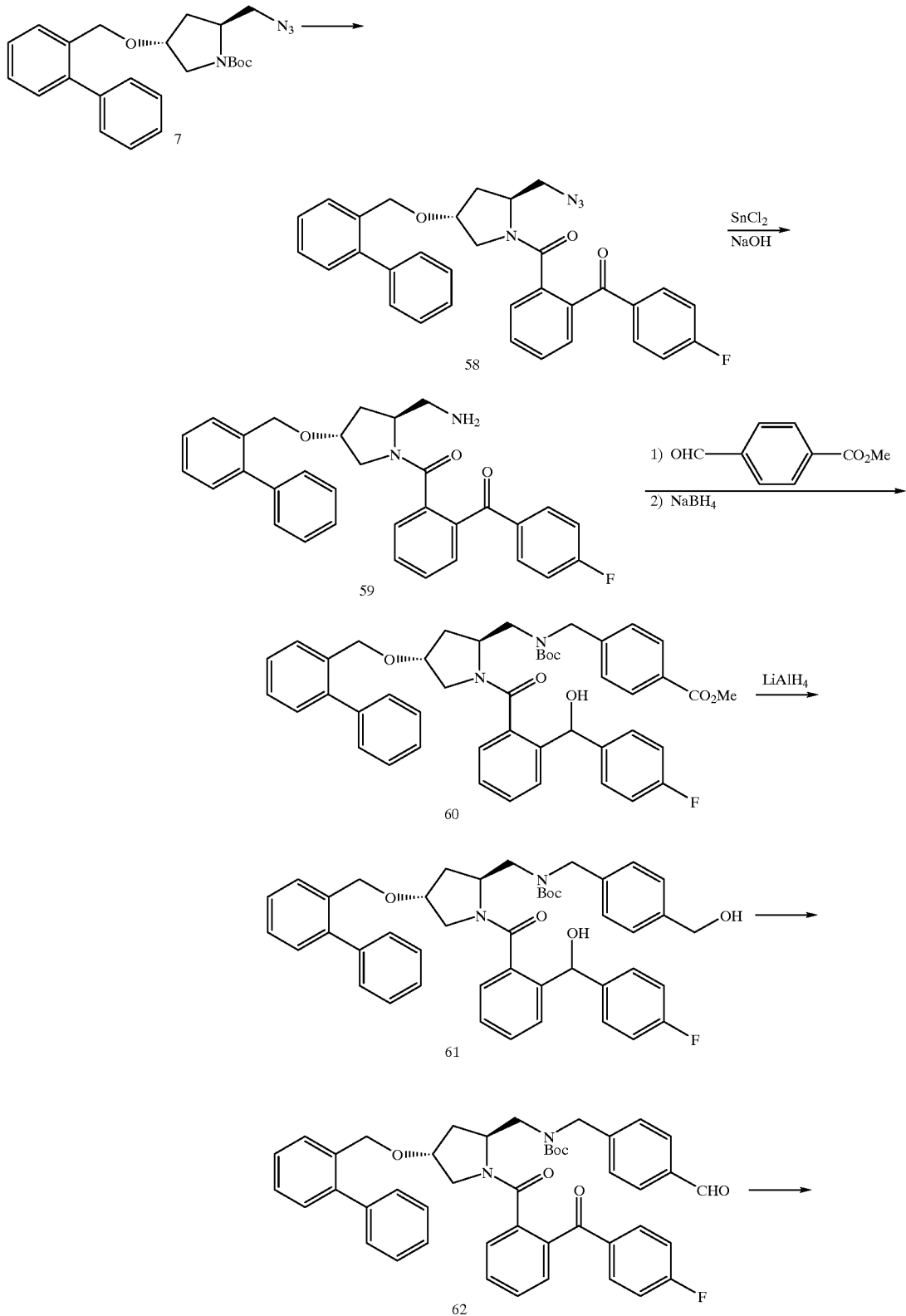

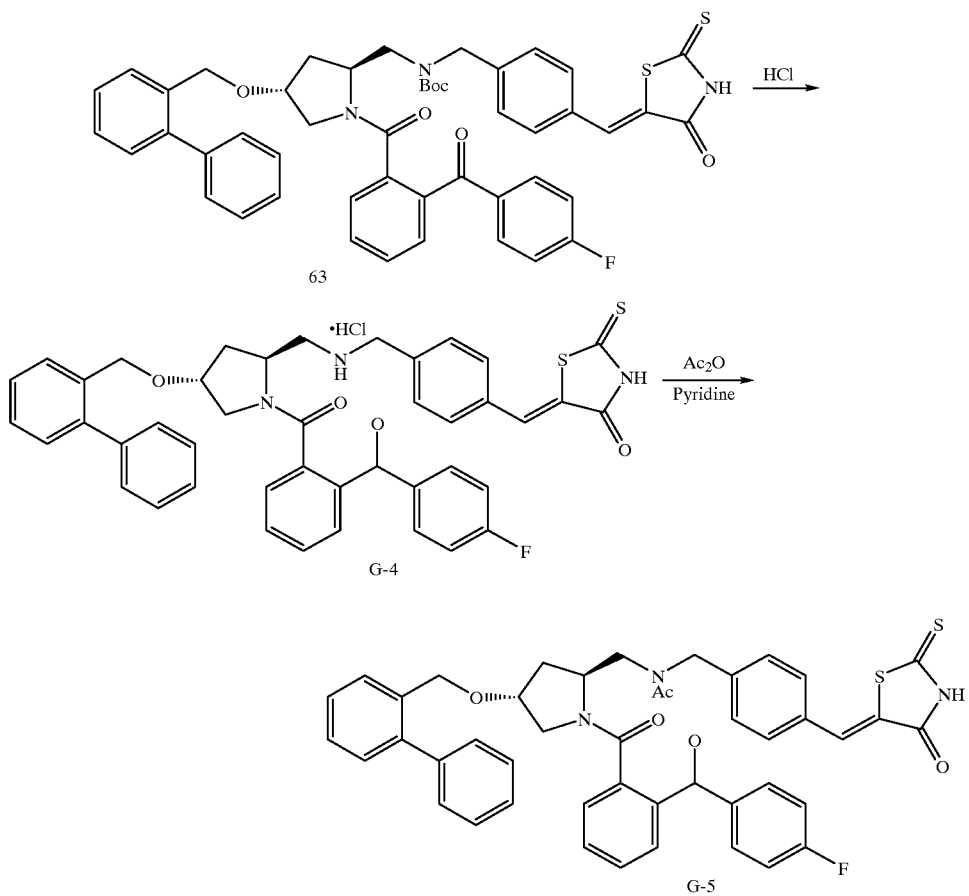

G-4

G-5

(1) 7→58

The compound (58) was synthesized in a manner similar to that described in the synthesis of the compound (A-1) form the compound (9) in Example 1 using the compound (7) as a starting material.

NMR (CDCl$_3$) δ ppm: 2.02 (2H, m), 3.31 (1H, dd, J=2.8, 12.4 Hz), 3.38 (2H, d, J=3.4 Hz), 3.67 (1H, dd, J=5.2 12.4 Hz), 3.99 (1H, m), 4.33 (2H, s), 4.40 (1H, m), 7.04–7.87 (17H). IR ν$_{max}$ (CHCl$_3$) 2106, 1730, 1663, 1630, 1598 cm$^{-1}$.

(2) 58→59

The compound (59) was obtained in a manner similar to that described in the synthesis of the compound (8) in Example 1 using the compound (58) as a starting material.

NMR (CDCl$_3$) δ ppm: 1.89 (1H, m), 2.10 (1H, m), 2.61 (1H, dd, J=4.2, 12.9 Hz), 2.94 (1H, dd, J=5.4, 12.9 Hz), 3.30 (2H, m), 3.96 (1H, m), 4.25 (1H, d$_{AB}$, J=11.4 Hz), 4.33 (1H, d$_{AB}$, J=11.4 Hz), 4.41 (1H, m), 7.07–7.86(17H). IR ν$_{max}$ (CHCl$_3$): 1661, 1624, 1598 cm$^{-1}$.

(3) 59→60

To a solution of the compound (59) (1.43 g, 2.81 mmol) in benzene (20 ml) was added 4-methoxycarbonylbenzaldehyde (461 mg, 2.81 mmol) and the resulting mixture was treated in a manner similar to that described in the synthesis of the compound (55) in Example 174 to give aminoalcohol. This aminoalcohol was dissolved in chloroform (10 ml), to this mixture was added a solution of di-t-butylcarbonate (674 mg, 3.09 mmol) in chloroform (5 ml) under ice-cooling, and the resulting mixture was stirred for 2 h at the same temperature and for 2 h at room temperature. The reaction mixture was diluted with ethyl acetate. The organic layer was washed with water and brine, dried over sodium sulfate, and concentrated in vacuo. The residue was subjected to silica gel column chromatography (hexane:ethyl acetate=3:1) to give 1.62 g (76.2%) of the compound (60).

NMR (CDCl$_3$) δ ppm: 1.33–1.50 (9H), 1.75–2.12 (2H), 2.71–3.59 (4H), 3.80–4.05 (4H), 4.16–4.95 (5H), 5.66–5.80 (1H, m), 6.78–7.50 (18H), 6.91 (2H, t, J=8.8 Hz), 8.02 (2H, t, J=8.8 Hz). IR ν$_{max}$ (KBr): 1720, 1692, 1613 cm$^{-1}$. Elemental analysis (C$_{46}$H$_{47}$N$_2$FO$_7$); Calcd.: C, 72.80; H, 6.24; N, 3.69; F, 2.50%. Found: C, 72.81; H, 6.26; N, 3.74; F, 2.29%.

(4) 60→61

The compound (61) was obtained in a manner similar to that described in the synthesis of the compound (57) in Example 174 using the compound (60) as a starting material.

NMR (CDCl$_3$) δ ppm: 1.42 (9H, br s), 1.76–2.10 (2H), 2.70–3.53 (3H), 3.78–4.71 (9H), (⅔×1H, br s), 5.76 (⅓×1H, br s), 6.71–7.46 (21H), 6.91 (2H, t, J=8.8 Hz). IR ν$_{max}$ (KBr): 1771, 1736, 1688, 1611 cm$^{-1}$. Elemental analysis (C$_{45}$H$_{47}$N$_2$FO$_6$.0.7H$_2$O); Calcd.: C, 72.70; H, 6.56; N, 3.77; F, 2.56%. Found: C, 72.65; H, 6.64; N, 3.67; F, 2.73%.

(5) 61→62

The compound (61) was reacted with 3 mol equivalents of Dess-Martin reagent and the resulting mixture was treated in a manner similar to that described in the synthesis of the compound (35) in Example 151 to give the compound (62).

NMR (CDCl$_3$) δ ppm: 1.37 (⅔×9H, s), 1.46 (⅓×9H, s), 1.96–2.10 (2H), 3.00–3.44 (4H), 3.93–4.09 (1H), 4.25 (1H, d$_{AB}$, J=11.1 Hz), 4.32 (1H, d$_{AB}$, J=11.1 Hz), 4.20–4.72 (3H, 7.01 (2H, t, J=8.5 Hz), 7.22–7.57 (15H), 7.70–7.92 (4H), 9.94–10.05 (1H). IR ν$_{max}$ (KBr): 1693, 1665, 1633, 1598 cm$^{-1}$. Elemental analysis (C$_{45}$H$_{43}$N$_2$FO$_6$); Calcd.: C, 74.36; H, 5.96; N, 3.85; F, 2.61%. Found: C, 74.09; H, 5.95; N, 3.86; F, 2.63%.

(4) 62→63

The compound (63) was synthesized in a manner similar to that described in the synthesis of the compound (15) in Example 58 using the compound (62) as a starting material.

NMR (CDCl$_3$) δ ppm: 1.38 (⅔×9H, s), 1.49 (⅓×9H, s), 1.90–2.13 (2H), 3.04–3.45(4H), 3.98–4.12 (1H), 4.21–4.75 (5H), 7.02 (2H, t, J=8.5 Hz) 7.20–7.56 (18H), 7.70–7.85 (2H), 10.40 (1H, br s). IR ν$_{max}$ (KBr): 1719, 1693, 1663, 1635, 1598 cm$^{-1}$. Elemental analysis (C$_{48}$H$_{44}$N$_3$FS$_2$O$_6$·0.3CHCl$_3$); Calcd.: C, 66.09; H, 5.09; N, 4.79; F, 2.16; S, 7.31, Cl, 3.63%. Found: C, 66.02; H, 5.06; N, 4.79; F, 2.20; S, 7.17; Cl, 3.67%.

(5) 63→G-4

To a solution of the compound (63) (209.3 mg, 0.249 mmol) in ethyl acetate (2 ml) was added 4N hydrogen chloride in ethyl acetate (2 ml) and the resulting mixture was stirred for 1 h at room temperature. The solvent was removed by concentrating in vacuo. The residue was washed with ethyl acetate to give 115.9 mg (59.8%) of the compound (G-4).

NMR (DMSO-d$_6$) δ ppm: 1.89–2.02 (1H), 2.08–2.19 (1H), 2.93–3.18 (2H), 3.24–3.36 (1H), 3.55 (1H, dd, J=3.8, 11.4 Hz), 3.95–4.03 (1H), 4.11–4.41 (3H), 4.32 (2H, s), 7.21–7.43 (10H), 7.43–7.77 (12H), 9.32 (1H, br s). IR ν$_{max}$ (KBr): 1744, 1704, 1656, 1597 cm$^{-1}$. Elemental analysis (C$_{43}$H$_{37}$N$_3$FSClO$_5$·1.0H$_2$O); Calcd.: C, 66.19; H, 5.04; N, 5.38; F, 2.43; S, 4.11; Cl, 4.54%. Found: C, 65.91; H, 5.28; N, 5.33; F, 2.76; S, 4.09; Cl, 4.63%.

(5) G-4→G-5

To a solution of the compound (G-4) (72.8 mg, 0.0935 mmol) in pyridine (0.5 ml) was added acetic anhydride (0.5 ml) and the resulting mixture was stirred for 20 h at room temperature. The reaction mixture was diluted with ethyl acetate, washed with water and brine, dried over sodium sulfate, and concentrated in vacuo. The residue was subjected to thin layer chromatography (chloroform:methanol= 30:1) to give 66 mg (90.0%) of the compound (G-5).

NMR (CDCl$_3$) δ ppm: 1.50–1.80 (1H), 1.96–2.25(1H), 2.04 (⁵⁄₇×3H, s), 2.25 (²⁄₇×3H, s), 3.18–3.32 (2H), 3.40–3.65 (2H), 3.88–3.96 (²⁄₇×1H), 3.88–3.96 (⁵⁄₇×1H), 4.23–4.85 (5H), 7.03 (2H, t, J=8.1 Hz), 7.17–7.61 (18H), 7.74–7.83 (2H), 10.18 (⁵⁄₇×1H, s), 10.30 (²⁄₇×1H, s). IR ν$_{max}$: 3444, 3185, 1718, 1636, 1597 cm$^{-1}$. Elemental analysis (C$_{45}$H$_{38}$N$_3$FS$_2$O$_5$·0.6H$_2$O); Calcd.: C, 68.01; H, 4.97; N, 5.29; F, 2.39; S, 8.07%. Found: C, 68.06; H, 4.97; N, 5.36; F, 2.34; S, 7.82%.

The compounds (G-6) to (G-9) were synthesized in a manner similar to that described in the above method. The results were shown in Table 22.

TABLE 22

| Compound No. | —X$^1$— | B | NMR(CDCl$_3$) δ ppm |
|---|---|---|---|
| G-1 | —N(Me)C(O)CH$_2$CH$_3$ group | O | 4.35(2H, s)<br>7.69(1H, s) |
| G-2 | —N(Me)CH$_2$CH$_3$ group | S | 4.22(1H, d$_{AB}$, J=11.2Hz)<br>4.30(1H, d$_{AB}$, J=11.2Hz)<br>7.61(1H, s) |
| G-3 | —N(Me)CH$_2$CH$_3$ group | O | 4.22(1H, d$_{AB}$, J=11.1Hz)<br>4.30(1H, d$_{AB}$, J=11.1Hz)<br>7.82(1H, s) |
| G-4 | —NH— · HCl | S | (DMSO-d$_6$)<br>4.32(2H, s)<br>7.61(1H, s) |
| G-5 | —N(C(O)Me)— | S | 2.04(3H, s)<br>4.28(1H, d$_{AB}$, J=11.4Hz)<br>4.33(1H, d$_{AB}$, J=11.4Hz) |
| G-6 | —NH— · HCl | O | (DMSO-d$_6$)<br>4.32(2H, s)<br>7.78(1H, s) |
| G-7 | —N(C(O)Me)— | O | 2.04(3H, s)<br>4.26(1H, d$_{AB}$, J=11.1Hz)<br>4.32(1H, d$_{AB}$, J=11.1Hz) |
| G-8 | —N(C(O)Ph)— | S | 4.32(2H, s)<br>4.66(2H, s) |
| G-9 | —N(C(O)Ph)— | O | 4.31(1H, d$_{AB}$, J=11.1Hz)<br>4.33(1H, d$_{AB}$, J=11.1Hz)<br>7.70(1H, s) |

Example 181 (Method G-3)

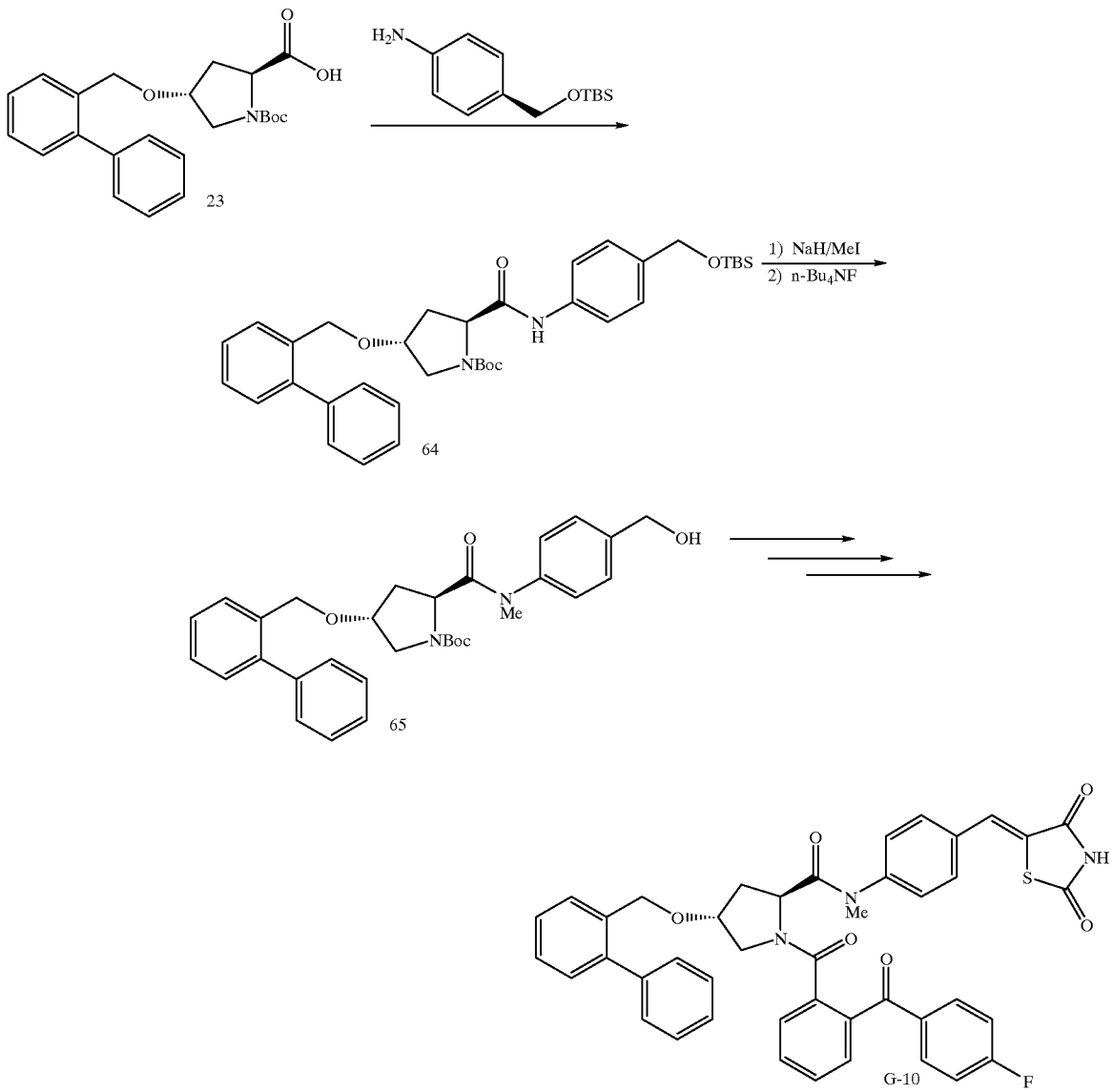

(1) 23→64

The compound (64) was obtained (380 mg, 47%) in a manner similar to that described in the synthesis of the compound (9) in Example 1 using the compound (23) (520 mg, 1.31 mmol) and t-butylsilylether of 4-aminobenzylalcohol (315 mg, 1.33 mmol).

NMR (CDCl$_3$) δ ppm: 0.08 (6H, s), 0.93 (9H, s), 1.47 (9H, br s), 1.97 (1H, m), 2.63 (1H, m), 3.42 (2H, br s), 4.12 (1H, m), 4.25–4.58 (3H), 4.69 (2H, s), 7.22–7.52 (9H), 9.29 (1H, br s).

(2) 64→65

N-methyl derivative (360 mg, 93%) was obtained in a manner similar to that described in the synthesis of the compound (53) in Example 172 using the compound (64) (380 mg, 0.616 mmol) as a starting material. This compound was dissolved in tetrahydrofuran (6 ml). A solution of 1N-tetra-n-butylammoniumfluoride in tetrahydrofuran (0.6 ml) was added to the mixture and the resulting mixture was stirred for 4 h at room temperature. The reaction mixture was diluted with ethyl acetate, washed with water and brine, dried over sodium sulfate, and concentrated in vacuo to give 317 mg (100%) of the crude compound, NMR (CDCl$_3$) δ ppm: 1.44 (½×9H, s), 1.48 (½×9H, s), 1.75–2.02 (2H), 3.25 (½×3H, s), 3.26 (½×3H, s), 3.66 (½×1H, m), 3.54–3.65 (2.5H), 3.97 (½×1H, m), 4.09 (½×1H, m), 4.19–4.39 (3H), 4.72 (½×2H, s), 4.74 (½×2H, s), 7.16–7.45 (13H).

(3) 65→G-10

The compound (G-10) was synthesized in a manner similar to that described in the synthesis of the compound (C-1) from the compound (34) in Example 151 using the compound (65) as a starting material.

NMR (CDCl$_3$) δ ppm: 1.95–2.13(2H), 3.07 (¹/₁₀×3H, s), 3.26 (⁹/₁₀×3H, s), 3.23–3.40 (1H), 3.62 (1H, dd, J=5.0, 11.4 Hz), 4.10–4.17 (1H), 4.27 (1H, d$_{AB}$, J=11.3 Hz), 4.35 (1H, d$_{AB}$, J=11.3 Hz), 4.35 (1H, d$_{AB}$, J=11.3 Hz), 4.54–4.65 (1H), 7.03 (2H, t, J=8.6 Hz), 7.21–7.63 (17H), 7.74–7.82 (2H), 7.75 (1H, s), 7.75 (1H, s), 8.70 (¹/₁₀×1H, s), 8.80 (⁹/₁₀×1H, s). IR ν$_{max}$ (KBr): 3439, 1747, 1707, 1662, 1636, 1598 cm$^{-1}$. Elemental analysis (C$_{43}$H$_{34}$N$_3$FSO$_6$.0.5H$_2$O); Calcd.: C, 68.97; H, 4.71; N, 5.61; F, 2.54; S, 4.28%. Found: C, 69.00; H, 4.83; N, 5.58; F, 2.34; S, 4.38%.

The compounds (G-11) to (G-13) were synthesized in a manner similar to that described in the above method. The results were shown in Table 23.

TABLE 23

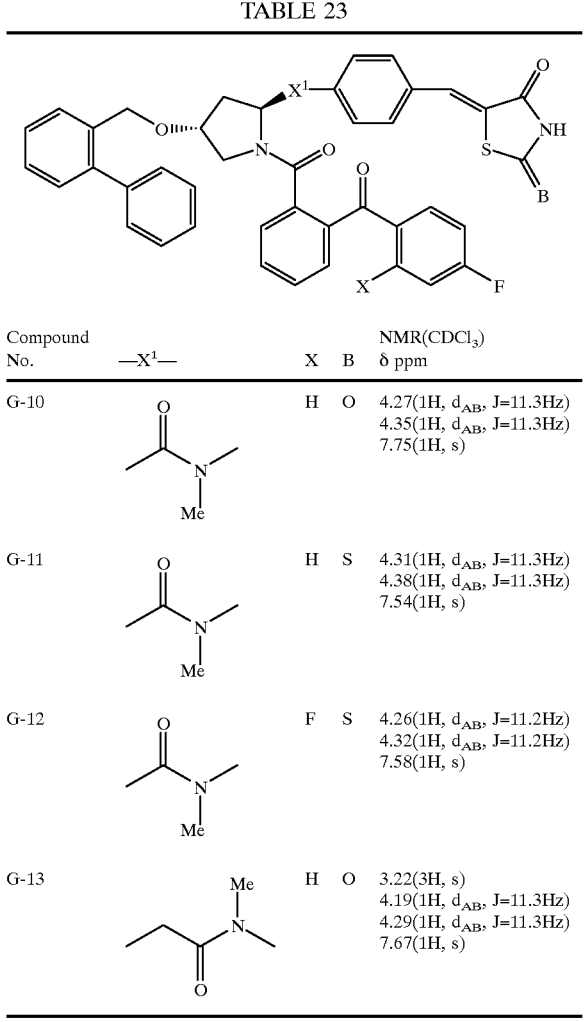

| Compound No. | —X¹— | X | B | NMR(CDCl₃) δ ppm |
|---|---|---|---|---|
| G-10 | (acetyl-N,N-dimethyl) | H | O | 4.27(1H, d$_{AB}$, J=11.3Hz)<br>4.35(1H, d$_{AB}$, J=11.3Hz)<br>7.75(1H, s) |
| G-11 | (acetyl-N,N-dimethyl) | H | S | 4.31(1H, d$_{AB}$, J=11.3Hz)<br>4.38(1H, d$_{AB}$, J=11.3Hz)<br>7.54(1H, s) |
| G-12 | (acetyl-N,N-dimethyl) | F | S | 4.26(1H, d$_{AB}$, J=11.2Hz)<br>4.32(1H, d$_{AB}$, J=11.2Hz)<br>7.58(1H, s) |
| G-13 | (propionyl-N,N-dimethyl) | H | O | 3.22(3H, s)<br>4.19(1H, d$_{AB}$, J=11.3Hz)<br>4.29(1H, d$_{AB}$, J=11.3Hz)<br>7.67(1H, s) |

Example 185 (method H)

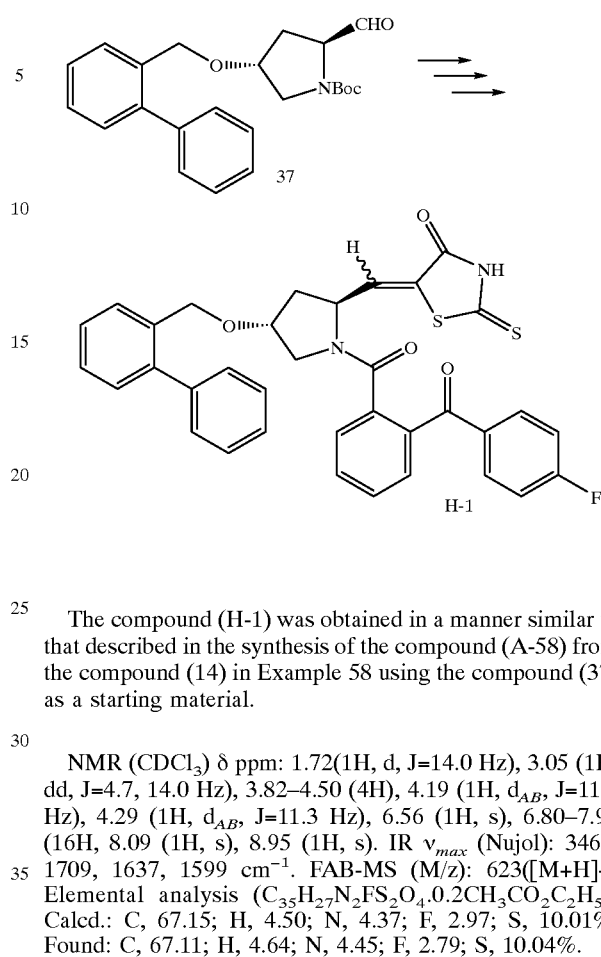

The compound (H-1) was obtained in a manner similar to that described in the synthesis of the compound (A-58) from the compound (14) in Example 58 using the compound (37) as a starting material.

NMR (CDCl₃) δ ppm: 1.72(1H, d, J=14.0 Hz), 3.05 (1H, dd, J=4.7, 14.0 Hz), 3.82–4.50 (4H), 4.19 (1H, d$_{AB}$, J=11.3 Hz), 4.29 (1H, d$_{AB}$, J=11.3 Hz), 6.56 (1H, s), 6.80–7.90 (16H, 8.09 (1H, s), 8.95 (1H, s). IR ν$_{max}$ (Nujol): 3465, 1709, 1637, 1599 cm⁻¹. FAB-MS (M/z): 623([M+H]+) Elemental analysis (C$_{35}$H$_{27}$N$_2$FS$_2$O$_4$·0.2CH$_3$CO$_2$C$_2$H$_5$); Calcd.: C, 67.15; H, 4.50; N, 4.37; F, 2.97; S, 10.01%. Found: C, 67.11; H, 4.64; N, 4.45; F, 2.79; S, 10.04%.

Example 186 (Method I-1)

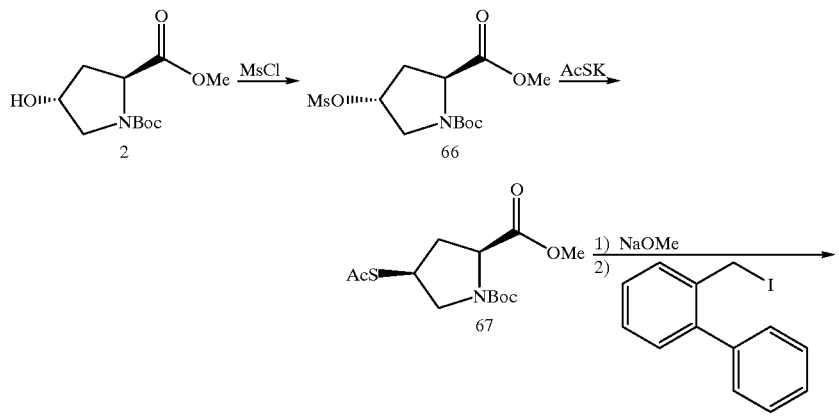

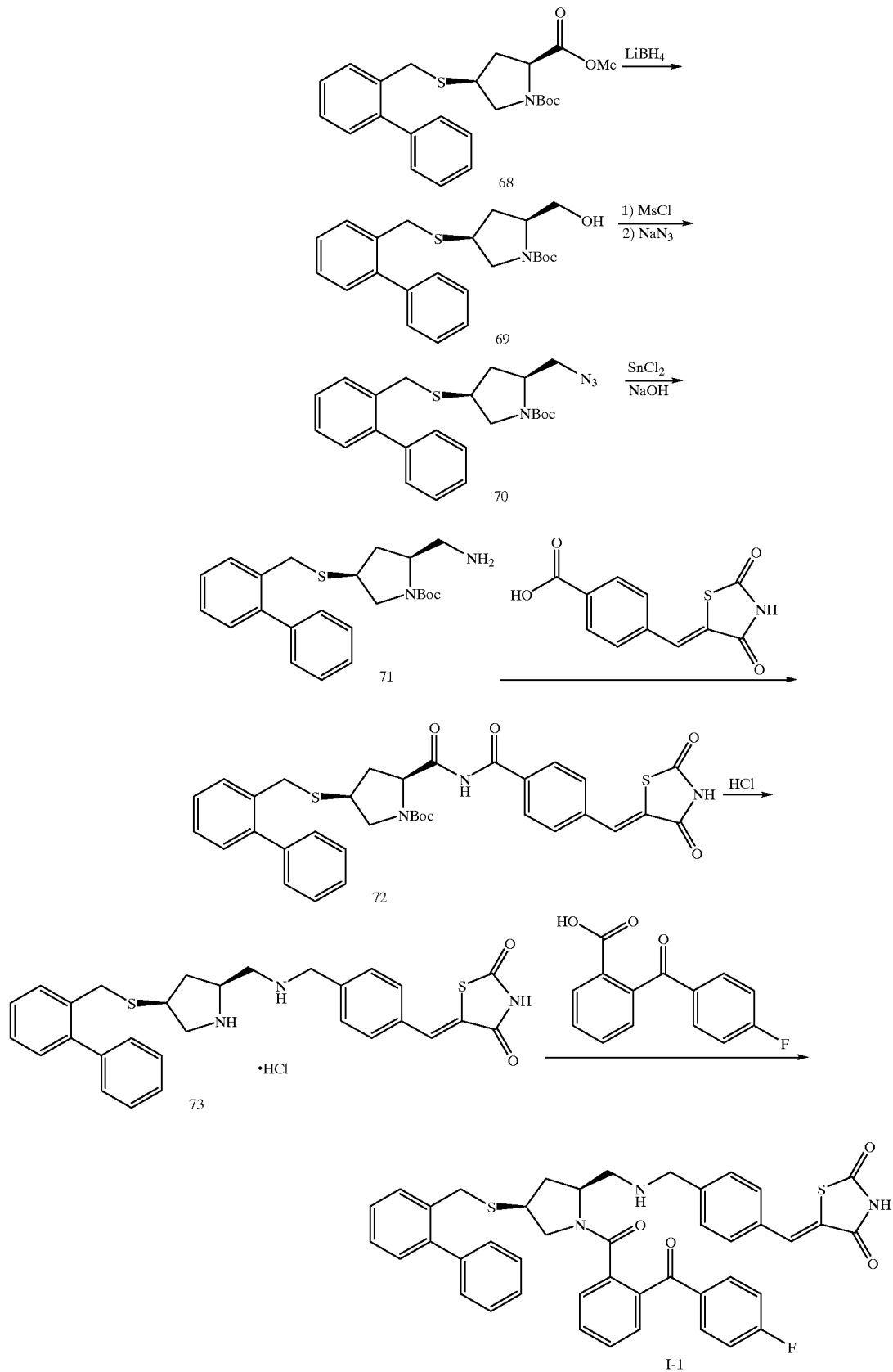

(1) 2→66

To a solution of N-Boc-4-hydroxy-L-proline methylester (2) (10.60 g, 43.22 mmol) described in Example 1 in tetrahydrofuran (80 ml) were added methanesulfonyl chloride (5.45 g, 47.58 mmol) and triethylamine (4.82 g, 47.63 mmol) under ice-cooling and the resulting mixture was stirred for 3 h. Ethyl acetate (100 ml) was added to the reaction mixture. The precipitation was filtered off and the filtrate was concentrated in vacuo. The residue was subjected to silica gel column chromatography (hexane:ethyl acetate=1:1) to give 10.20 g (73.0%) of the aimed compound (66).

(2) 66→67

To a solution of the compound (21) (10.10 g, 31.23 mmol) in N, N-dimethylformamide (31 ml) was added sodium thioacetate (4.4 g, 38.53 mmol) at 60° C. and the resulting mixture was stirred for 3 h at the same temperature. The mixture was allowed to cool to room temperature, diluted with ethyl acetate (200 ml), washed with water and brine, dried over sodium sulfate, and concentrated in vacuo. The residue was subjected to silica gel column chromatography (hexane:ethyl acetate=3:1) to give 7.10 g (75.0%) of the aimed compound (67).

NMR (CDCl$_3$) δ ppm: 1.41 (⅗×9H, s), 1.46 (⅖×9H, s), 1.97 (1H, m), 2.72 (1H, m), 3.34 (1H, m), 3.74 (3H, s), 3.97 (2H, m), 4.29 (⅗×1H, t, J=7.4 Hz), 4.37 (⅖×1H, t, J=7.4 Hz).

(3) 67→68

To a solution of the compound (67) (7.10 g, 23.40 mmol) in toluene was added dropwise 1M-sodium methylate in methanol (25 ml) over 10 min and the resulting mixture was stirred for 15 min at the same temperature. To the reaction mixture was added a solution of 2-phenylbenzyl iodide (8.0 g, 27.20 mmol) in toluene (15 ml) at −25° C. and the resulting mixture was allowed to warm to room temperature and stirred for 1.5 h. The reaction mixture was poured into ice water (100 ml) and extracted with ethyl acetate (300 ml). The organic layer was washed with water and brine, dried over sodium sulfate, and concentrated in vacuo. The residue was subjected to silica gel column chromatography (hexane:ethyl acetate=5:2) to give 9.92 g (99.1%) of the aimed compound (68).

NMR (CDCl$_3$) δ ppm: 1.39 (⅗×9H, s), 1.44 (⅖×9H, s), 1.76 (1H, m), 2.35 (1H, m), 2.59–3.19 (2H), 3.53–3.80 (1H), 3.70 (3H, s), 3.73 (2H, s), 4.15 (⅗×1H, t, J=7.9 Hz), 4.21 (⅖×1H, t, J=7.9 Hz), 7.22–7.48 (9H). IR $\nu_{max}$ (CHCl$_3$): 1750, 1692, 1403 cm$^{-1}$. Elemental analysis (C$_{24}$H$_{29}$NSO$_4$.0.1H$_2$O); Calcd.: C, 67.14; H, 6.85; N, 3.26; S, 7.47%. Found: C, 67.00; H, 6.88; N, 3.33; S, 7.48%.

(4) 68→69

The compound (69) was obtained in a manner similar to that described in the synthesis of the compound (4) in Example 1 using the compound (68) as a starting material.

NMR (CDCl$_3$) δ ppm: 1.30 (1H, m), 1.45 (9H, s), 2.12 (1H, m), 2.83–3.00 (2H), 3.50–3.65 (3H), 3.73 (1H, d$_{AB}$, J=12.7 Hz), 3.76 (1H, d$_{AB}$, J=12.7 Hz), 3.85 (1H, m), 4.91 (1H, br s), 7.22–7.49 (9H).

(5) 69→70

The compound (70) was obtained in a manner similar to that described in the synthesis of the compound (5) in Example 1 using the compound (69) as a starting material.

NMR (CDCl$_3$) δ ppm: 1.45 (9H, s), 1.69 (1H, m), 2.15 (1H, br s), 2.86–3.08 (2H), 3.25–3.90 (6H), 7.22–7.50 (9H). IR $\nu_{max}$ (CHCl$_3$): 2105, 1685, 1397 cm$^{-1}$. Elemental analysis (C$_{23}$H$_{28}$N$_4$SO$_2$); Calcd.: C, 65.07; H, 6.65; N, 13.20; S, 7.55%. Found: C, 64.95; H, 6.67; N, 13.16; S, 7.54%.

(6) 70→71

The compound (71) was obtained in a manner similar to that described in the synthesis of the compound (8) in Example 1 using the compound (70) as a starting material.

NMR (CDCl$_3$) δ ppm: 1.30–1.60 (3H), 1.45 (9H, s), 2.20 (1H, m), 2.76–3.06 (4H), 3.55–3.95 (4H), 7.22–7.49 (9H).

(7) 71→72

The compound (72) was obtained in a manner similar to that described in the synthesis of the compound (9) in Example 1 using the compound (71) as a starting material. The compound was re-precipitated with ethyl acetate and hexane and the resulting compound was washed with hexane.

NMR (CDCl$_3$) δ ppm: 1.48 (10H, s), 2.33 (1H, m), 2.91–3.01 (2H), 3.41 (1H, m), 3.66 (2H, m), 3.75 (1H, d$_{AB}$, J=13.2 Hz), 3.77 (1H, d$_{AB}$, J=13.2 Hz), 4.04 (1H, m), 7.22–7.50 (9H), 7.53 (2H, d, J=8.2 Hz), 7.82 (1H, s), 7.94 (2H, d, J=8.2 Hz), 8.66 (1H, br s). IR $\nu_{max}$ (KBr): 3396, 3116, 1751, 1709, 1664, 1610, 1540, 1405, 1161 cm$^{-1}$. Elemental analysis (C$_{34}$H$_{35}$N$_3$S$_2$O$_5$.0.05C$_6$H$_{14}$.0.8H$_2$O); Calcd.: C, 63.53; H, 5.80; N, 6.48; S, 9.89%. Found: C, 63.43; H, 6.05; N, 6.73; S, 9.91%.

(8) 72→73

The hydrochloride derivative (73) was obtained in a manner similar to that described in the synthesis of the compound (10) in Example 1 using the compound (72) as a starting material.

Melting point: 201–203° C. NMR (DMSO-d$_6$) δ ppm: 1.50 (1H, m), 2.28 (1H, m), 2.91 (1H, m), 3.33 (2H, m), 3.59 (2H, m), 3.68 (1H, m), 3.79 (2H, s), 7.22 (1H, m), 7.30–7.52 (8H), 7.71 (2H, d, J=8.5 Hz), 7.84 (1H, s), 8.03 (2H, d, J=8.5 Hz), 9.02 (1H, t, J=5.4 Hz), 9.18 (1H, br s), 9.55 (1H, br s), 12.54 (1H, br s). IR $\nu_{max}$ (KBr): 3373, 2915, 2723, 1750, 1702, 1644, 1610, 1540, 1320, 1289, 1156 cm$^{-1}$. Elemental analysis (C$_{29}$H$_{28}$N$_3$S$_2$ClO$_3$.0.8H$_2$O); Calcd.: C, 60.00; H, 5.14; N, 7.24; Cl, 6.11; S, 11.05%. Found: C, 60.02; H, 5.28; N, 7.42; Cl, 5.97; S, 11.03%.

(9) 73→I-1

The compound (I-1) was obtained in a manner similar to that described in the synthesis of the compound (A-1) in Example 1 using the hydrochloride (73) as a starting material. The compound was re-precipitated with ethyl acetate and hexane and the resulting compound was washed with hexane.

NMR (CDCl$_3$) δ ppm: 1.52 (1H, m), 2.42 (1H, m), 2.93 (1H, t, J=10.3 Hz), 3.09 (1H, m), 3.29 (1H, dd, J=6.7, 10.4 Hz), 3.44 (1H, m), 3.65 (1H, d$_{AB}$, J=12.9 Hz), 3.70 (1H, d$_{AB}$, J=12.9 Hz), 3.83 (1H, m), 4.41 (1H, m), 7.06–7.45 (13H), 7.52–7.67 (3H), 7.73 (1H, s), 7.79 (1H, m), 7.88 (2H, d, J=8.4 Hz), 8.30 (1H, t, J=4.8 Hz). IR $\nu_{max}$ (KBr): 3395, 1749, 1708, 1658, 1621, 1597, 1283, 1150 cm$^{-1}$. Elemental analysis (C$_{34}$H$_{35}$N$_3$FS$_2$O$_5$.0.2C$_6$H$_{14}$.0.4H$_2$O); Calcd.: C, 68.03; H, 4.86; N, 5.38; F, 2.43; S, 8.22%. Found: C, 68.02; H, 5.05; N, 5.63; F, 2.52; S, 8.22%.

The compound (I-2) was synthesized in a manner similar to that described in the above method. The result was shown in Table 24.

TABLE 24

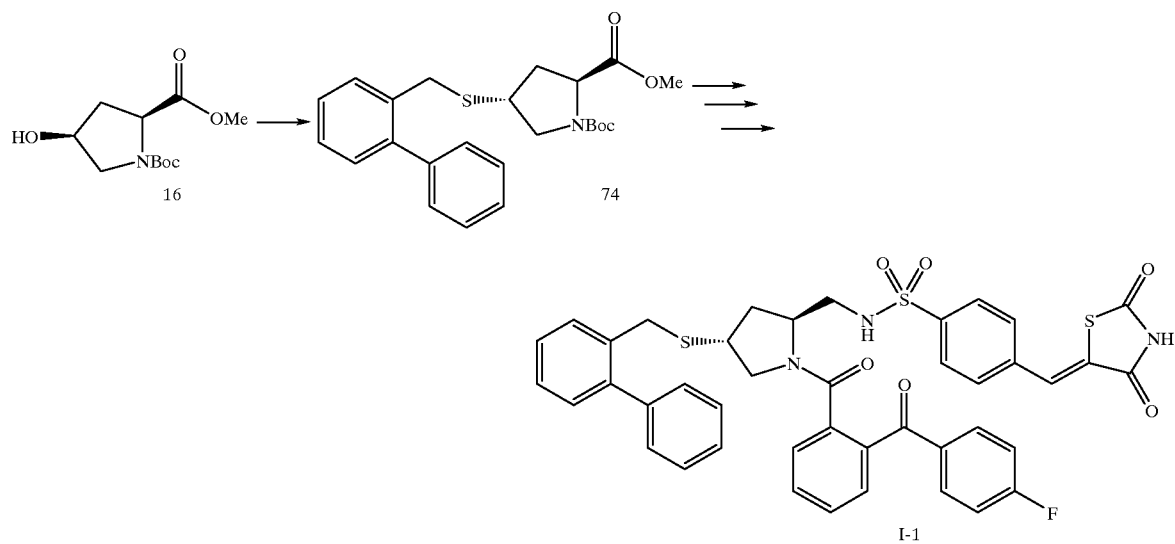

Example 188 (Method I-2)

(1) 16→74

The compound (74) was synthesized in a manner similar to that described in Example 186 using the compound (16) as a starting material.

NMR (CDCl$_3$) δ ppm: 1.39 and 1.44(9H, each s), 1.90–2.13 (2H), 3.03–3.28 (2H), 3.55–3.76 (1H), 3.71 (3H, s), 3.73 (2H, s), 7.22–7.48 (9H). IR ν$_{max}$ (CHCl$_3$): 1745, 1692, 1401 cm$^{-1}$. [α]$_D$=−9.6° (t=23° C., c=1.012, CHCl$_3$); Elemental analysis (C$_{24}$H$_{29}$NSO$_4$·0.1C$_6$H$_6$); Calcd.: C, 67.87; H, 6.85; N, 3.22; S, 7.36%. Found: C, 67.86; H, 6.95; N, 3.33; S, 7.23%.

(2) 74→1–3

The compound (1–3) was synthesized in a manner similar to that described in Example 186 using the compound (74) as a starting material.

NMR (CDCl$_3$) δ ppm: 1.90 (1H, m), 2.35 (1H, m), 2.90–3.08 (2H), 3.25–3.40 (2H), 3.60–3.75 (1H), 3.69 (2H, m), 4.30 (1H, m), 6.26 (1H, m), 7.10–8.00 (22H), 9.46 (1H, s). IR ν$_{max}$ (Nujol): 1749, 1710, 1597, 1160 cm$^{-1}$. Elemental analysis (C$_{42}$H$_{34}$N$_3$FS$_3$O$_6$·0.5H$_2$O); Calcd.: C, 62.98; H, 4.40; N, 5.25; F, 2.37; S, 12.01%. Found: C, 63.21; H, 4.61; N, 5.27; F, 2.34; S, 11.81%.

The compounds (I-4) to (I-10) were synthesized in a manner similar to that described in the above method. The results were shown in Table 25.

TABLE 25

[Structure: biphenyl-CH2-S-pyrrolidine-N-C(O)-(2-(4-fluorobenzoyl)phenyl), with X1-X2-CH= connected to thiazolidinone with =B substituent]

| Compound No. | —X¹—X² | B | NMR(CDCl₃) δ ppm |
|---|---|---|---|
| I-3 | [ethyl-NH-SO2-phenyl-CH3] | O | 3.69(2H, m)<br>6.26(1H, m) |
| I-4 | [ethyl-NH-SO2-phenyl-CH3] | S | 3.69(2H, m)<br>6.26(1H, m) |
| I-5 | [ethyl-NH-C(O)-phenyl-CH3] | O | 3.65(1H, d$_{AB}$, J=12.9Hz)<br>3.68(1H, d$_{AB}$, J=12.9Hz)<br>7.90(1H, s) |
| I-6 | [ethyl-NH-C(O)-phenyl-CH3] | S | 3.65(1H, d$_{AB}$, J=13.0Hz)<br>3.68(1H, d$_{AB}$, J=13.0Hz)<br>7.06(2H, t, J=8.4Hz)<br>7.91(2H, d, J=8.4Hz) |

TABLE 25-continued

[Structure: same as above]

| Compound No. | —X¹—X² | B | NMR(CDCl₃) δ ppm |
|---|---|---|---|
| I-7 | [ethyl-NH-C(O)-thienyl-CH3] | O | 3.66(2H, m)<br>7.89(1H, s) |
| I-8 | [ethyl-NH-C(O)-thienyl-CH3] | S | 3.67(2H, m)<br>7.67(1H, s) |
| I-9 | [ethyl-NH-SO2-thienyl-CH3] | O | 3.66(1H, d$_{AB}$, J=12.9Hz)<br>3.71(1H, d$_{AB}$, J=12.9Hz)<br>7.69(1H, s) |
| I-10 | [ethyl-NH-SO2-thienyl-CH3] | S | 3.66(1H, d$_{AB}$, J=12.9Hz)<br>3.71(1H, d$_{AB}$, J=12.9Hz)<br>7.54(1H, s) |

Example 196 (Method J-2)

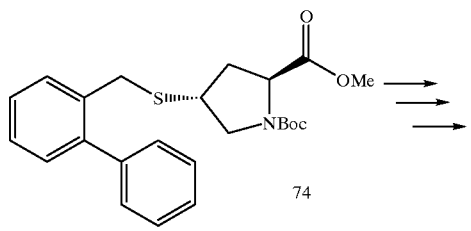

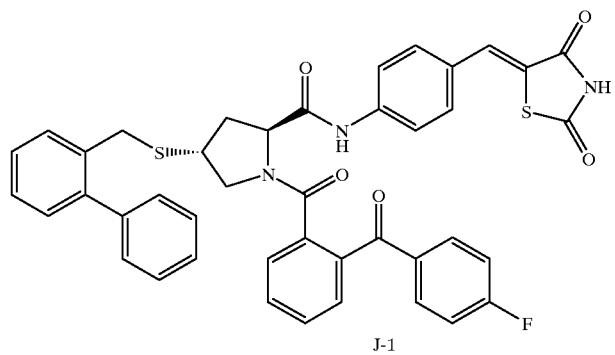

(1) 74→J-1

After the ester compound (74) was hydrolyzed, the compound (J-1) was obtained in a manner similar to that described in Example 142 or Example 149.

NMR (CDCl$_3$) δ ppm: 2.04 (1H, td, J=8.4, 13.2 Hz), 2.58 (1H, ddd, J=3.6, 6.3, 13.2 Hz), 3.08 (1H, dd, J=6.9, 10.8 Hz), 3.26 (1H, m), 3.42 (1H, dd, J=6.9, 10.8 Hz), 3.70 (2H, s), 4.89 (1H, dd, J=3.6, 8.4 Hz), 7.12–7.86 (21H), 7.81 (1H, s), 8.89 (1H, br s), 9.43 (1H, br s). IR ν$_{max}$ (CHCl$_3$): 3393, 3182, 1745, 1704, 1652, 1516, 1414 cm$^{-1}$. Elemental analysis (C$_{42}$H$_{32}$N$_3$FS$_2$O$_5$·0.2H$_2$O); Calcd.: C, 67.67; H, 4.38; N, 5.64; F, 2.55; S, 8.60%. Found: C, 67.65; H, 4.57; N, 5.82; F, 2.35; S, 8.36%.

The compounds (J-2) to (J-6) were synthesized in a manner similar to that described in the above method. The results were shown in Table 26.

TABLE 26

| Compound No. | —X$^1$—X$^2$— | B | NMR(CDCl$_3$) δ ppm |
|---|---|---|---|
| J-1 | —C(O)NH—C$_6$H$_4$— | O | 3.70(2H, s) 7.81(1H, s) |
| J-2 | —C(O)NH—C$_6$H$_4$— | S | 3.70(2H, s) 7.59(1H, s) |
| J-3 | —C(O)NH—thienyl— | O | 3.71(2H, s) 6.97(1H, d, J=4.2Hz) 7.91(1H, s) |
| J-4 | —C(O)NH—thienyl— | S | (DMSO-d$_6$) 3.76(2H, s) 6.84(1H, d, J=4.0Hz) 7.83(1H, s) |
| J-5 | —C(O)—piperidinyl— | O | 3.61–3.73(3H) 6.82–6.91(1H) 7.80–7.87(2H) |

TABLE 26-continued

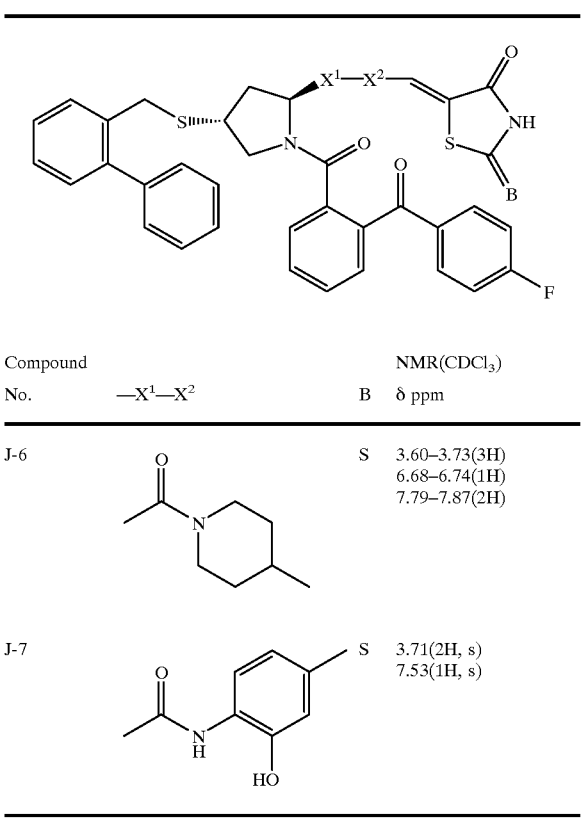

| Compound No. | —X¹—X² | B | NMR(CDCl₃) δ ppm |
|---|---|---|---|
| J-6 | (acetyl-4-methylpiperidine structure) | S | 3.60–3.73(3H) 6.68–6.74(1H) 7.79–7.87(2H) |
| J-7 | (acetamido-hydroxy-methylphenyl structure) | S | 3.71(2H, s) 7.53(1H, s) |

Example 203 (Method M)

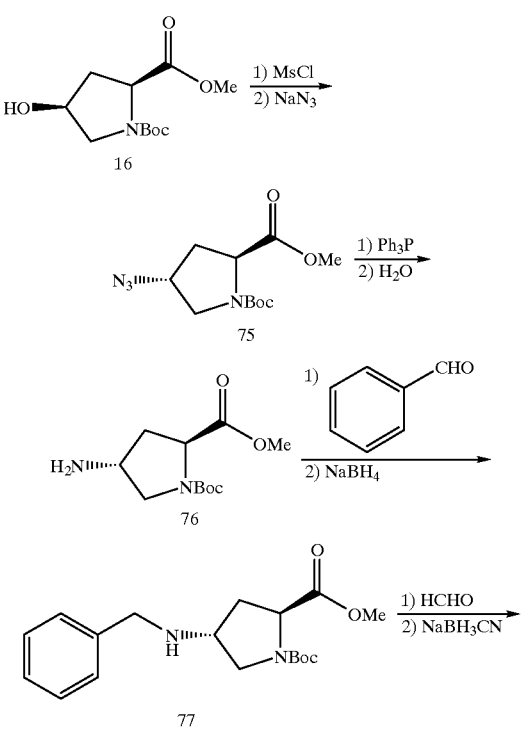

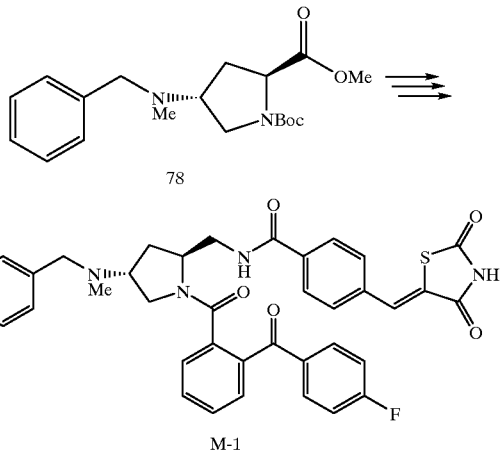

(1) 16→75

The compound (75) was synthesized in a manner similar to that described in the synthesis of the compound (5) in Example 1 using the compound (16) as a starting material.

NMR (CDCl₃) δ ppm: 1.42 and 1.47(9H, each s), 2.18 (1H, m), 2.33 (1H, m), 3.42–3.74 (2H), 3.74 and 3.75 (3H, each s), 4.19 (1H, m), 4.30–4.46 (1H).

(2) 75→76

To a solution of the compound (75) (9.25 g, 34.22 mmol) in tetrahydrofuran (130 ml) was added triphenylphosphine (9.0 g, 34.31 mmol) and the resulting mixture was stirred for 2 days at room temperature. To this mixture was added water (20 ml) and the resulting mixture was heated at reflux for 1 h. The mixture was diluted with ethyl acetate, washed with water and brine, dried over sodium sulfate, and concentrated in vacuo. The residue was subjected to silica gel column chromatography (chloroform:methanol=9:1) to give 8.79 g (>100%) of the compound (76).

NMR (CDCl₃) δ ppm: 1.41 and 1.46(9H, each s), 1.90–2.19 (2H), 3.06–3.23 (1H), (2H), 3.73 (3H, s), 4.32–4.46 (1H).

(3) 76→77

The compound (77) was obtained in a manner similar to that described in the synthesis of the compound (55) in Example 173 using the compound (76) as a starting material.

NMR (CDCl₃) δ ppm: 1.41 and 1.46(9H, each s), 2.00–2.20 (2H), 3.14–3.35 (1H), 3.60–3.80 (1H), 3.72 and 3.73 (3H, each s), 3.77 (2H, s), 4.30–4.48 (1H), 7.22–7.38 (5H). IR $v_{max}$ (KBr): 3319 1747, 1699 cm⁻¹. Elemental analysis ($C_{18}H_{26}N_2O_4$); Calcd.: C, 64.65; H, 7.84; N, 8.38%. Found: C, 64.38; H, 7.84; N, 8.36%.

(4) 77→78

The compound (78) was obtained in a manner similar to that described in the synthesis of the compound (56) in Example 173 using the compound (77) as a starting marerial.

NMR (CDCl₃) δ ppm: 1.42 and 1.47(9H, each s), 2.11 (3H, s), 2.15–2.28 (2H), 3.12–3.42 (2H), 3.48 (2H, s), 3.74 (3H, s), 3.75–3.91 (1H), 4.33–4.48 (1H), 7.30 (5H, m). IR $v_{max}$ (Film): 1749, 1702, 1397 cm⁻¹. Elemental analysis ($C_{19}H_{28}N_2O_4$); Calcd.: C, 65.49; H, 18.10; N, 8.04%. Found: C, 65.35; H, 8.13; N, 8.11%.

(5) 78→M-1

The compound (M-1) was obtained in a manner similar to that described in the synthesis of the compound (A-67) from the compound (17) in Example 67 using the compound (78) as a starting material.

NMR (CDCl₃) δ ppm: 2.08 (3H, s), 2.10–2.30 (2H), 3.22–3.87 (7H), 4.72 (1H, t, J=8.6 Hz), 7.07 (2H, t, J=8.5 Hz), 7.17–7.32 (5H), 7.61 (1H, dt, J=1.8. 7.2 Hz), 7.73 (1H, s), 7.78 (2H, m), 7.90 (2H, d, J=8.2 Hz), 8.24 (1H, t, J=4.5 Hz). IR ν$_{max}$ (KBr): 3400, 1749, 1707, 1656, 1662, 1596 cm⁻¹. Elemental analysis (C$_{38}$H$_{33}$N$_4$FSO$_5$.0.4H$_2$O); Calcd.: C, 66.73; H, 4.98; N, 8.19; F, 2.78; S, 4.69%. Found: C, 66.67; H, 5.03; N, 8.33; F, 2.59; S, 4.74%.

The compounds (M-2) to (M-21) were synthesized in a manner similar to that described in the above method. The results were shown in Tables 27 to 29.

TABLE 27

| Compound No. | R¹ | R¹⁶ | B | NMR(CDCl₃) δ ppm |
|---|---|---|---|---|
| M-1 | benzyl | Me | O | 2.08(3H, s)<br>7.36(2H, d, J=8.5Hz)<br>7.73(1H, s) |
| M-2 | benzyl | Me | S | 2.11(3H, s)<br>7.34(2H, d, J=8.5Hz)<br>7.50(1H, s) |
| M-3 | benzyl | benzyl | O | 3.51(2H, d$_{AB}$, J=13.8Hz)<br>3.61(2H, d$_{AB}$, J=13.8Hz)<br>7.73(1H, s) |
| M-4 | benzyl | isopropyl | S | 0.93(3H, d, J=6.3Hz)<br>0.99(3H, d, J=6.6Hz)<br>7.84(2H, d, J=8.1Hz) |
| M-5 | benzyl | sec-butyl | O | 0.79(3H, d, J=6.3Hz)<br>0.85(3H, d, J=6.6Hz)<br>7.84(2H, d, J=8.4Hz) |
| M-6 | 2-biphenylmethyl | Me | O | 3.33(1H, d$_{AB}$, J=13.2Hz)<br>3.45(1H, d$_{AB}$, J=13.2Hz)<br>7.67(1H, s) |
| M-7 | 2-biphenylmethyl | Me | S | 3.39(1H, d$_{AB}$, J=13.5Hz)<br>3.51(1H, d$_{AB}$, J=13.5Hz)<br>7.44(1H, s) |

TABLE 27-continued

| Compound No. | R¹ | R¹⁶ | B | NMR(CDCl₃) δ ppm |
|---|---|---|---|---|
| M-8 | 2-phenylphenyl | Et | O | 0.78(3H, t, J=6.9Hz)<br>3.40(1H, d_AB, J=14.4Hz)<br>3.57(1H, d_AB, J=14.1Hz) |
| M-9 | 2-phenylphenyl | iPr (Me₂CH) | O | 0.86(6H, t, J=6.9Hz)<br>7.85(1H, t, J=8.4Hz) |
| M-10 | 2-phenylphenyl | sec-Bu (MeCH(Et)) | O | 3.74(1H, s)<br>7.68(1H, s) |
| M-11 | 2-phenylphenyl | MeCH(Pr) | O | 0.73(3H, d_AB, J=3.6Hz)<br>0.75(3H, d_AB, J=3.9Hz)<br>7.85(2H, d, J=8.4Hz) |

TABLE 28

[Structure diagram showing the core molecule with R¹, R¹⁶, X, F substituents]

| Compound No. | R¹ | R¹⁶ | B | NMR(CDCl₃) δ ppm |
|---|---|---|---|---|
| M-12 | diphenylmethyl (CH(Ph)₂) with Me | Me | H | 4.57(1H, s)<br>7.71(1H, s) |
| M-13 | diphenylmethyl (CH(Ph)₂) with Me | sec-butyl (CH(Me)CH₂Me) | H | 4.98(1H, s)<br>7.69(1H, s) |
| M-14 | diphenylmethyl (CH(Ph)₂) with Me | cyclopropylmethyl | H | 5.19(1H, s)<br>7.70(1H, s) |
| M-15 | CH(Me)CH₂Me (sec-butyl, Me/Me) | sec-butyl (Me/Me) | H | 0.75(6H, d, J=6.6Hz)<br>0.83(6H, d, J=6.3Hz)<br>7.89(2H, d, J=8.4Hz) |
| M-16 | 2-benzoylphenyl (biphenyl with C=O, Me) | H | H | 7.67(1H, s) |
| M-17 | diphenylmethyl (CH(Ph)₂) with Me | sec-butyl (Me/Me) | F | 4.95(1H, s)<br>7.73(1H, s)<br>7.86(2H, d, J=8.2Hz) |

TABLE 29

| Compound No. | R¹ | R¹⁶ | X | NMR(CDCl₃) δ ppm |
|---|---|---|---|---|
| M-18 | benzyl (CH₂-Ph) | sec-butyl (CHMe-Et, Me,Me) | H | 0.79(6H, d, J=6.6Hz) 0.85(6H, d, J=6.6Hz) 7.74(1H, s) |
| M-19 | 2-phenylbenzyl | sec-butyl | H | 3.47(2H, s) 6.43(1H, d, J=15.8Hz) 7.72(1H, s) |
| M-20 | diphenylmethyl (CHPh₂) with Me | sec-butyl | H | 0.91(6H, d, J=6.6Hz) 5.06(1H, br s) 7.80(1H, s) |
| M-21 | diphenylmethyl with Me | sec-butyl | F | 4.98(1H, s) 6.45(1H, d, J=15.5Hz) 7.73(1H, s) |

Example 224 (Method N)

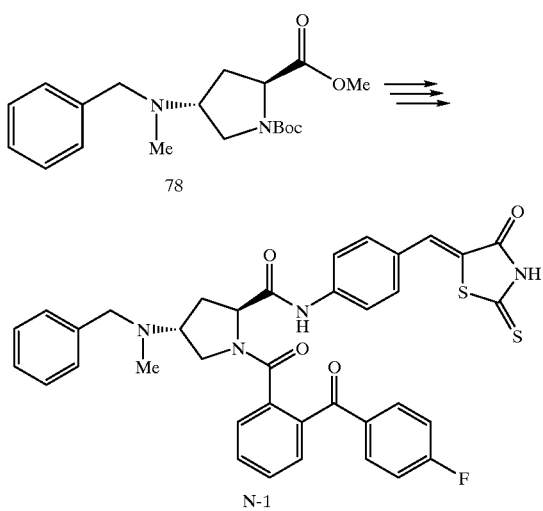

(1) 78→N-1

After the ester compound (78) was hydrolyzed, the compound (N-1) was obtained in a manner similar to that described in Example 142 or Example 149.

NMR (CDCl₃) δ ppm: 2.11 (3H, s), 2.23 (1H, m), 2.80 (1H, m), 3.22–3.48 (3H), 3.53–3.68 (2H), 5.03 (1H, d, J=7.8 Hz), 7.18 (2H, t, J=8.6 Hz), 7.22–7.31 (5H), 2H, d, J=8.6 Hz), 7.49–7.70 (5H), 7.85 (2H, d, J=8.8 Hz), 7.87 (2H, m), 9.59 (1H, s). IR $\nu_{max}$ (KBr): 3444, 3180, 1702, 1651, 1623, 1595 cm⁻¹. Elemental analysis ($C_{37}H_{31}N_4FS_2O_4 \cdot 0.5H_2O \cdot 0.07CHCl_3$); Calcd, C, 63.96; H, 4.64; N, 8.05; F, 2.73; S, 9.21; Cl, 1.07%. Found: C, 63.97; H, 4.76; N, 8.14; F, 2.72; S, 9.07; Cl, 1.11%.

The compounds (N-2) to (N-5) were synthesized in a manner similar to that described in the above method. The results were shown in Table 30.

TABLE 30

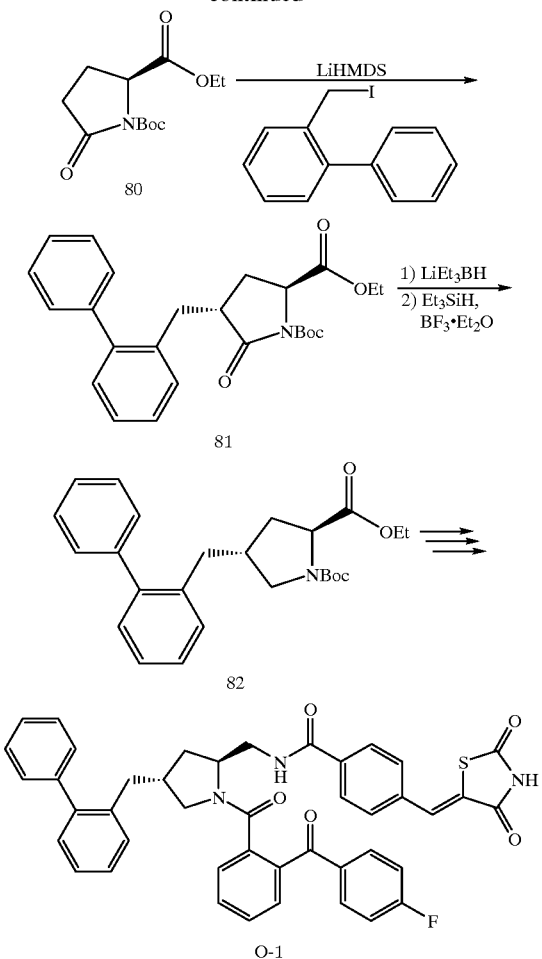

| Compound No. | $R^1$ | $R^{16}$ | B | NMR(CDCl$_3$) δ ppm |
|---|---|---|---|---|
| N-1 | benzyl | Me | S | 2.11(3H, s)<br>5.03(1H, d, J=7.8Hz)<br>7.18(2H, d, J=8.6Hz)<br>9.59(1H, s) |
| N-2 | 2-biphenylmethyl | Me | O | 3.29(1H, d$_{AB}$, J=13.5Hz)<br>3.47(1H, d$_{AB}$, J=13.5Hz)<br>7.76(1H, s) |
| N-3 | 2-biphenylmethyl | Me | S | 3.30(1H, d$_{AB}$, J=13.2Hz)<br>3.48(1H, d$_{AB}$, J=13.2Hz)<br>7.58(1H, s) |
| N-4 | 2-biphenylmethyl | Et | O | 0.78(3H, t, J=6.9Hz)<br>4.87(1H, d, J=7.5Hz)<br>9.48(1H, s) |
| N-5 | 2-biphenylmethyl | Et | S | 0.78(3H, t, J=6.9Hz)<br>4.88(1H, d, J=7.8Hz)<br>9.50(1H, s) |

Example 229 (Method O)

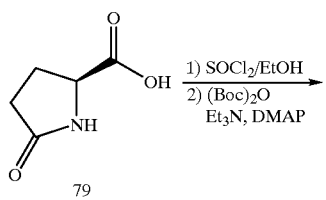

(1) 79→80

L-pyroglutamic acid (79) was converted into ethylester in a manner similar to that described in a literature (J. Org, Chem., 1980, 45, 815–818). To a solution of L-pyroglutamic acid ethylester (8.85 g) in dichloromethane (70 ml) were added triethylamine (4.71 ml), di-t-butyldicarbonate (15.5 ml), and 4-dimethylaminopyridine (4.13 g) at room temperature and the resulting mixture was stirred for 4 h. The solvent was removed by concentrating in vacuo. The residue was subjected to silica gel column chromatography to give 13.73 g (92%) of the aimed compound (80).

NMR (CDCl$_3$) δ ppm: 1.30 (3H, t, J=7.2 Hz), 1.50 (9H, s), 1.97–2.10 (1H), 2.23–2.27 (3H), 4.24 (2H, q, J=7.2 Hz), 4.60 (1H, dd, J=3.0, 9.3 Hz).

(2) 80→81

To a solution of the compound (80) (500 mg) in tetrahydrofuran (10 ml) was added lithium bis(trimithylsilyl)amide (1M tetrahydrofuran solution, 2.14 ml) at −78° C. and the resulting mixture was stirred for 1 h at the same temperature. To this solution was added a solution of 2-(iodomethyl)biphenyl (686 mg) in tetrahydrofuran (2.5 ml) and the resulting mixture was stirred for 1 h at the same temperature. To the mixture was added sat, ammonium chloride aq, and the resulting mixture was partitioned between water and ethyl acetate. The organic layer was washed with brine, dried over magunesium sulfate, and concentrated in vacuo. The residue was subjected to silica gel column chromatography to give 576 mg (70%) of the aimed trans compound (81) and 190 mg (23%) of cis compound which is diastereomer of the aimed compound, NMR (CDCl$_3$) δ ppm: 1.23 (3H, t, J=7.2 Hz), 1.46 (9H, s), 1.55–1.71 (1H), 1.74–1.86 (1H), 2.59–2.77 (2H), 3.40 (1H, d, J=9.9 Hz), 4.15 (2H, q, J=7.2 Hz), 4.34 (1H, dd, J=1.5, 9.5 Hz), 7.18–7.45 (9H). IR ν$_{max}$ (CHCl$_3$): 1788, 1742 cm$^{-1}$. HR-FAB-MS (M/z): C$_{25}$H$_{29}$NNaO$_5$[M+Na]$^+$; Calcd.: 446.1943. Found: 446.1950.

(3) 81→82

To a solution of the compound (81) (500 mg) in tetrahydrofuran (6 ml) was added lithium triethylborohydride (1M tetrahydrofuran solution, 1.42 ml) was added at −78° C., and the resulting mixture was stirred for 30 min at the same temperature. After sat, sodium hydrogencarbonate aq. (1.42 ml) was added to the mixture at the same temperature, 30% hydrogen peroxide aq. (5 drops) was added to the resulting mixture. The resulting mixture was stirred for 45 min under ice-cooling. The solvent was removed by concentrating in vacuo. The residue was dissolved in chloroform and the resulting mixture was washed with water, dried over magnesium sulfate, and concentrated in vacuo. The residue was dissolved in dichloromethane (15 ml). To the mixture were added triethylsilane (0.189 ml) and boron trifluoride etherate (0.165 ml) at −78° C., and the resulting mixture was stirred for 30 min at the same temperature. Triethylsilane (0.189 ml) and boron trifluoride etherate (0.165 ml) were added the reaction mixture again and the resulting mixture was stirred for 1 h at −78° C. To the mixture was added sat, sodium hydrogencarbonate aq. (2 ml) and the resulting mixture was poured into sat, sodium hydrogencarbonate and chloroform. The aqueous layer was extracted with chloroform. The fused chloroform layer was dried over magnesium sulfate and concentrated in vacuo. The residue was subjected to silica gel column chromatography to give 349 mg (72%) of the aimed compound (82).

NMR (CDCl$_3$) δ ppm: 1.21 (⅖×3H, t, J=7.2 Hz), 1.23 (⅗×3H, t, J=7.2 Hz), (⅗×9H, s), 1.42 (⅖×9H, s), 1.61–1.89 (2H), 2.28–2.46 (1H), 2.57–2.97 (3H), 3.40–3.57 (1H), 4.00–4.25 (3H), 7.17–7.45 (9H). IR ν$_{max}$ (CHCl$_3$): 1690, 1739 cm$^{-1}$. HR-FAB-MS (M/z): C$_{25}$H$_{32}$NO$_4$ [M+H]$^+$; Calcd.: 410.2331. Found: 410.2341.

(4) 82→O-1

The compound (O-1) was obtained in a manner similar to that described in the synthesis of the compound (A-67) from the compound (17) using the compound (82) as a starting material.

NMR (CDCl$_3$) δ ppm: 1.62–1.85 (2H), 2.38 (2H, quint, J=7.2 Hz), 2.61–2.80 (2H), 2.86 (1H, dd, J=7.1, 10.7 Hz), 3.25 (1H, dd, J=7.1, 10.7 Hz), 3.43 (1H, ddd, J=4.3, 9.5, 13.8 Hz), 3.67 (1H, ddd, J=3.0, 4.8, 13.8 Hz), 4.33–4.47 (1H), 6.99–7.65 (17H), 7.73 (2H, dd, J=5.4, 9.0 Hz), 7.85 (2H, d, J=8.4 Hz), 8.25 (1H, t, J=4.4 Hz), 8.85 (1H, br s). IR ν$_{max}$ (KBr): 1750, 1708, 1659, 1616 cm$^{-1}$. Elemental analysis (C$_{43}$H$_{34}$N$_3$FSO$_5$.0.3H$_2$O); Calcd.: C, 70.82; H, 4.78; N, 5.76; F, 2.61; S, 4.40%. Found: C, 70.87; H, 4.93; N, 5.61; F, 2.32; S, 4.33%.

Example 230 (Method O-2)

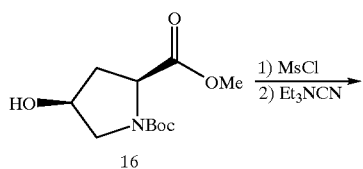

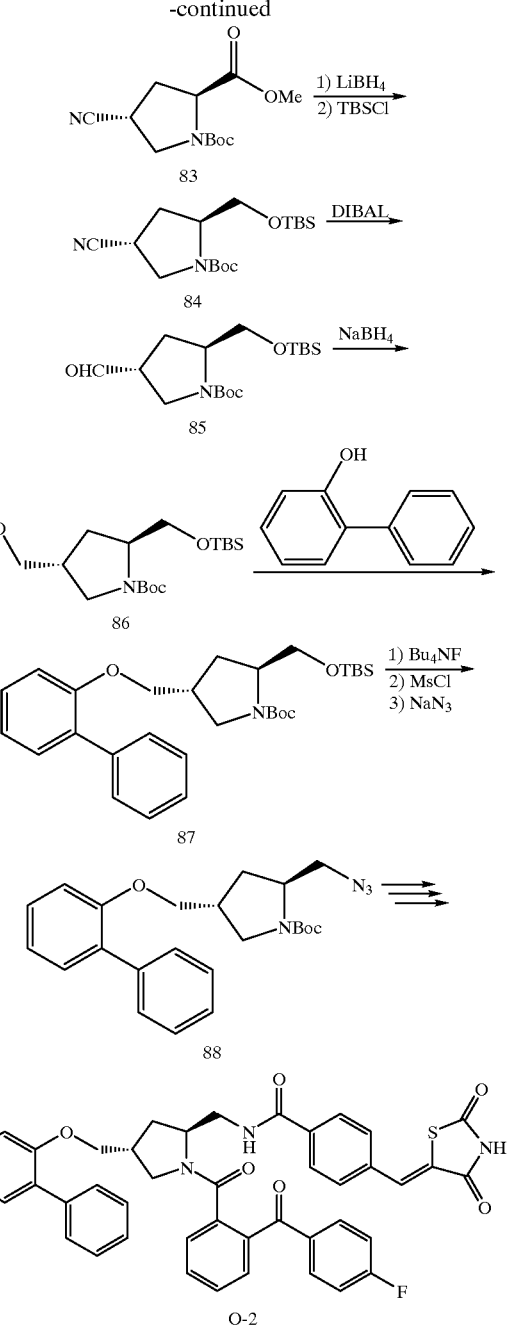

(1) 16→83

To a solution of the compound (16) (5 g) in tetrahydrofuran (60 ml) were added to triethylamine (3.69 ml) and methanesulfonyl chloride (1.89 ml) under ice-cooling and the resulting mixture was stirred for 30 min at the same temperature. The reaction mixture was filtered and the filtrate was concentrated in vacuo. The residue was subjected to silica gel column chromatography to give 6.56 g (100%) of the mesyl derivative. This mesyl derivative (1 g) was dissolved in acetonitrile (6 ml). To this solution was added tetraethylammonium cyanate (94%, 1.03 g) and the resulting mixture was stirred for 4 h at 65° C. The reaction mixture was allowed to cool and partitioned between water and ethyl acetate. The organic layer was washed with water and brine, dried over magnesium sulfate and concentrated in vacuo. The residue was subjected to silica gel column chromatography to give 395 mg (50%) of the aimed compound (83).

NMR (CDCl$_3$) δ ppm: 1.42 (⅖×9H, s), 1.47 (⅗×9H, s), 2.34 (⅖×1H, dd, J=3.3, 7.2 Hz), 2.38 (⅗×1H, dd, J=3.3, 7.2 Hz), 2.40–2.61 (1H), 3.17 –3.34 (1H), 3.17–3.34 (1H, 3.57–3.79 (1H), 3.75 (3H, s), 3.83–3.98 (1H), 4.34–4.54 (1H).

IR ν$_{max}$ (CHCl$_3$): 2250, 1747, 1699 cm$^{-1}$.

(2) 83→84

To a solution of the compound (83) (250 mg) in tetrahydrofuran (5 ml) was added lithium borohydride (43 mg) at room temperature and the resulting mixture was stirred for 1 h. The reaction mixture was partitioned between water and ethyl acetate. The organic layer was washed with sat, ammonium chloride aq, and brine, dried over magnesium sulfate, and concentrated in vacuo. The residue was dissolved in dichloromethane (5 ml). To this mixture were added imidazole (134 mg) and t-butyldimethylchlorosilane (222 mg) and the resulting mixture was stirred for 1.5 h. The reaction mixture was partitioned between water and ethyl acetate. The organic layer was washed with brine, dried over magnesium sulfate, and concentrated in vacuo. The residue was subjected to silica gel column chromatography to give 263 mg (79%) of the silyl derivative (84).

NMR (CDCl$_3$) δ ppm: 0.02 (3H, s), 0.04 (3H, s), 0.88 (9H, s), 1.47 (9H, s), 2.16–2.44 (2H), 3.23 –4.06 (6H). IR ν$_{max}$ (CHCl$_3$): 2247, 1691 cm$^{-1}$.

(3) 84→85

The compound (85) was obtained in a manner similar to that described in the synthesis of the compound (44) in Example 161 using the compound (84) as a starting material.

NMR (CDCl$_3$) δ ppm: 0.04 (3H, s), 0.05 (3H, s), 0.89 (9H, s), 1.46 (9H, s), 2.10–2.28 (2H), 3.05–3.32 (1H), 3.43–4.04 (5H), 9.65 (1H, d, J=2.1 Hz). IR ν$_{max}$ (CHCl$_3$): 1727, 1685 cm$^{-1}$.

(4) 85→86

To a solution of the compound (85) (350 mg) in tetrahydrofuran (5 ml) was added sodium borohydride (58 mg) under ice-cooling and the resulting mixture was stirred for 30 min. The reaction mixture was partitioned between water and ethyl acetate. The organic layer was washed with sat, ammonium chloride aq. and brine, dried over magnesium sulfate, and concentrated in vacuo. The residue was subjected to silica gel column chromatography to give 323 mg (92%) of the aimed compound (86).

NMR (CDCl$_3$) δ ppm: 0.04 (3H, s), 0.05 (3H, s), 0.89 (9H, s), 1.46 (9H, s), 1.55–1.85 (1H), 1.98–2.20 (1H), 2.42–2.67 (1H), 3.04–3.27 (1H), 3.39 –3.99 (6H). IR ν$_{max}$ (CHCl$_3$): 3626, 1683 cm$^{-1}$. HR-FAB-MS (M/z): C$_{17}$H$_{36}$NO$_4$Si [M+H]$^+$; Calcd.: 346.2413. Found: 346.2411.

(5) 86→87

The compound (87) was obtained in a manner similar to that described in the synthesis of the compound (17) in Example 67 using the compound (86) as a starting material.

NMR (CDCl$_3$) δ ppm: 0.02 (6H, s), 0.87 (9H, s), 1.45 (9H, s), 1.60–1.81 (1H), 1.97–2.15 (1H), 2.63–2.86 (1H), 3.03–3.25 (1H), 3.35 –4.00 (6H), 6.95 (1H, d, J=8.1 Hz), 7.04 (1H, dt, J=0.9, 7.5 Hz), 7.24–7.44 (5H), 7.51 (2H, dd, J=1.4, 8.3 Hz). IR ν$_{max}$ (CHCl$_3$): 1684 cm$^{-1}$. HR-FAB-MS (M/z): C$_{29}$H$_{44}$NO$_4$Si [M+H]$^+$; Calcd.: 498.3040. Found: 498.3032.

(6) 87→88

To a solution of the compound (87) (300 mg) in tetrahydrofuran (5 ml) was added tetra-n-butylammonium fluoride (1M solution in tetrahydrofuran, 0.90 ml) under ice-cooling and the resulting mixture was stirred for 30 min, allowed to warm to room temperature and stirred for 30 min. The reaction mixture was partitioned between water and ethyl acetate. The organic layer was washed with brine, dried over magnesium sulfate, and concentrated in vacuo. The obtained crude alcohol derivative was treated in a manner similar to that described in the synthesis of the compound (5) in Example 1 to give 223 mg (91%) of the aimed compound (88).

NMR (CDCl$_3$) δ ppm: 1.46 (9H, s), 1.60–1.98 (2H), 2.58 (1H, m), 2.95–4.06 (7H), 6.95 (1H, d, J=8.4 Hz), 7.05 (1H, dt, J=1.2. 7.5 Hz), 7.24–7.54 (7H). IR ν$_{max}$ (CHCl$_3$): 2104, 1685 cm$^{-1}$. HR-FAB-MS (M/z): C$_{23}$H$_{29}$N$_4$O$_3$ [M+H]$^+$; Calcd.: 409.2239. Found: 409.2245.

(7) 88→O-2

The compound (O-2) was obtained in a manner similar to that described in the synthesis of the compound (A-67) from the compound (19) in Example 67 using the compound (88) as a starting material.

NMR (CDCl$_3$) δ ppm: 1.89–2.18 (2H), 2.62–2.80 (1H), 3.29 (1H, dd, J=5.1, 11.0 Hz), 3.42 (1H, dd, J=7.2, 11.0 Hz), 3.54–4.06 (4H), 4.57–4.72 (1H), 6.92–7.60 (17H), 7.68 (1H, s), 7.69 (2H, dd, J=5.4, 9.0 Hz), 7.87 (2H, d, J=8.4 Hz), 8.29 (1H, t, J=4.8 Hz), 9.65 (1H, br s). IR ν$_{max}$ (KBr): 1749, 1708, 1657 cm$^{-1}$. HR-FAB-MS (M/z): C$_{43}$H$_{35}$N$_3$FSO$_6$ [M+H]$^+$; Calcd.: 740.2230. Found: 740.2213. Elemental analysis (C$_{43}$H$_{34}$N$_3$FSO$_6$.0.6H$_2$O); Calcd.: C, 69.81; H, 4.73; N, 5.60; F, 2.53; S, 4.27%. Found: C, 70.09; H, 4.78; N, 5.82; F, 2.42; S, 3.94%.

Example 231 (Method O-3)

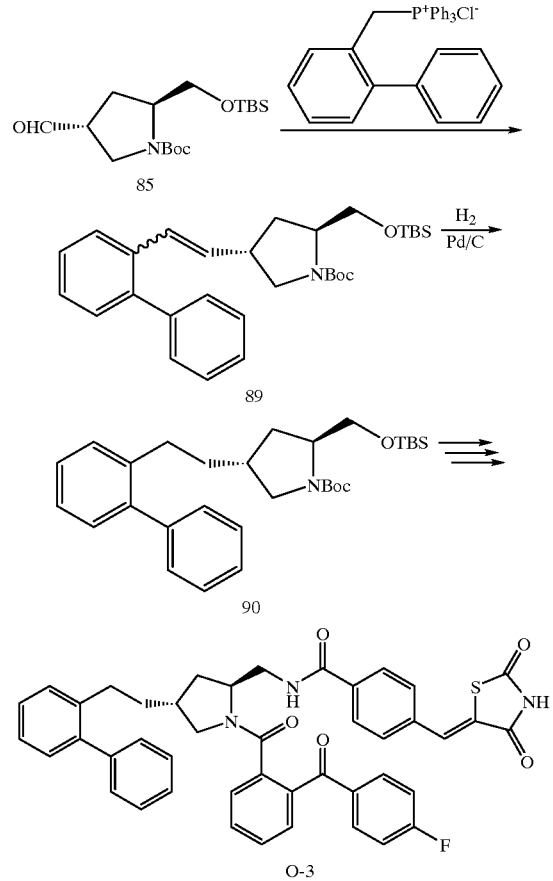

(1) 85→89

To a solution of the compound (85) (315 mg) described in Example 230 in ethanol (10 ml) were added 2-phenylbenzyltriphenylphosphonium chloride (1.71 g) and triethylamine (0.77 ml) at room temperature and the resulting mixture was heated at reflux for 16 h. The reaction mixture was concentrated in vacuo and the residue was dissolved in ethyl acetate. The precipitation was filtered off and the filtrate was concentrated in vacuo. The residue was subjected to silica gel column chromatography to give 367 mg (81%) of the aimed compound (89).

NMR (CDCl$_3$) δ ppm: 0.05–0.07 (6H), 0.78–0.92 (9H), 1.45 (½×9H, s), 1.46 (½×9H, s), 1.68–2.20 (2H), 2.66–4.02 (6H), 5.33–5.49 (½×1H), 5.94–6.07 (½×1H), 6.32 (½×1H, d, J=11.0 Hz), 6.44 (½×1H, d, J=11.0 Hz), 7.24–7.60 (9H). IR $v_{max}$ (CHCl$_3$): 1683 cm$^{-1}$. HR-FAB-MS (M/z): C$_{30}$H$_{44}$NO$_3$Si [M+H]$^+$; Calcd.: 494.3090. Found: 494.3080.

Calcd.: C, 71.10; H, 4.96; N, 5.65; F, 2.56; S, 4.31%. Found: C, 71.19; H, 4.96; N, 5.43; F, 2.47; S, 4.20%.

Example 232–236

Using the stereoisomers of the compound (2) which were prepared in a manner similar to those described in JP 5-294970 (A1) and J. Org, Chem. 1981, 46, 2954–2960. (J. K. Stille, et al.), the compound (Q-1) to (Q-5) were synthesized in a manner similar to that described in the above methods. The results were shown in Table 31.

TABLE 31

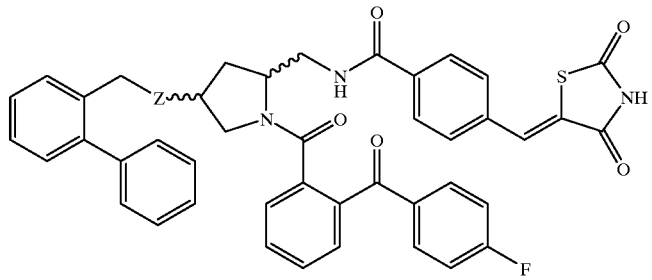

| Compound No. | Z | Configuration | [α]$_D$ (c = 1.0, CHCl$_3$) | NMR (CDCl$_3$) δ ppm |
|---|---|---|---|---|
| Q-1 | S | (2R, 4R) | +47.7° (t = 22° C.) | 3.65(1H, d$_{AB}$, J=12.9Hz) 3.70(1H, d$_{AB}$, J=12.9Hz) 7.73(1H, s) |
| Q-2 | O | (2R, 4R) | +29.6° (t = 23° C.) | 4.33(1H, d$_{AB}$, J=11.4Hz) 4.42(1H, d$_{AB}$, J=11.4Hz) 7.67(1H, s) |
| Q-3 | O | (2S, 4S) | −29.0° (t = 23.5° C.) | 4.33(1H, d$_{AB}$, J=11.4Hz) 4.42(1H, d$_{AB}$, J=11.4Hz) 7.67(1H, s) |
| Q-4 | S | (2R, 4S) | +39.2° (t = 22° C.) | 3.65(1H, d$_{AB}$, J=12.9Hz) 3.68(1H, d$_{AB}$, J=12.9Hz) 7.90(1H, s) |
| Q-5 | O | (2R, 4S) | +98.6° (t = 22° C.) | 4.25(1H, d$_{AB}$, J=11.4Hz) 4.40(1H, d$_{AB}$, J=11.4Hz) 7.78(1H, s) |

(2) 89→90

To a solution of the compound (89) (300 mg) in ethyl acetate (15 ml) was added 5% palladium-carbon (30 mg) and the resulting mixture was hydrogenated at 1 atm. The catalysts were filtered off and the filtrate was concentrated in vacuo to give 300 mg (100%) of the compound (90).

NMR (CDCl$_3$) δ ppm: 0.01 (6H, s), 0.86 (½×9H, s), 0.87 (½×9H, s), 1.20–1.66 (3H), 1.44 (9H, s), 1.75–2.25 (2H), 2.47–2.87 (3H), 3.20–3.93 (4H), 7.16–7.45 (9H). IR $v_{max}$ (CHCl$_3$): 1682 cm$^{-1}$.

(3) 90→O-3

The compound (O-3) was obtained in a manner similar to that described in the synthesis of the compound (O-2) from the compound (87) in Example 230 using the compound (90) as a starting material.

NMR (CDCl$_3$) δ ppm: 1.39–1.85 (2H), 2.08–2.25 (1H), 2.42–2.69 (2H), 2.78 (1H, dd, J=7.8, 10.8 Hz), 3.30 (1H, dd, J=7.8, 10.8 Hz), 3.42–3.56 (1H), 3.61–3.75 (1H), 4.41–4.54 (1H), 7.01–7.65 (17H), 7.69 (1H, s), 7.76 (2H, dd, J=5.4, 9.0 Hz), 7.85 (2H, d, J=8.4 Hz), 8.26 (1H, t, J=4.5 Hz), 9.42(1H, br s). IR $v_{max}$ (KBr): 1750, 1708, 1659 cm$^{-1}$. HR-FAB-MS (M/z): C$_{44}$H$_{37}$N$_3$FSO$_5$ [M+H]$^+$; Calcd.: 738.2438. Found: 738.2430. Elemental analysis (C$_{44}$H$_{36}$N$_3$FSO$_5$·0.3H$_2$O);

Test Example 1 cPLA$_2$ Inhibitory Activity

The compounds of the present invention were tested for the cPLA$_2$ inhibitory activity according to the method disclosed in R. M. Kramer, E. F. Roberts, J. Manetta, and J. E. Putnam, J. Biol. Chem., 1991, 266, 5268–5272 as outlined below.

Using the 1-palmitoyl-2-[$^{14}$C]-arachidonoyl-sn-glycero-3-phosphocholine as a substrate, liposomes (a substrate solution) containing the substrate of which concentration was 2.5 μM in the reaction mixture and sn-1,2-dioleoylglycerol of which concentration was 1.25 μM in the reaction mixture at the molar ratio of 2:1 were prepared. The reaction mixture includes 50 mM HEPES buffer (pH 7.5), 1 mM calcium chloride, 150 mM sodium chloride, 0.1 mg/ml bovine serum albumin, and 1.7 mM dithiothreitol. To the reaction mixture was added the compound of the present invention and the substrate solution. The reaction was allowed to start by adding an enzyme and continued for 15 min at 37° C. The fatty acids released by the reaction were extracted by the method described in V. P. Dole, and H. Meinertz, J. Biol. Chem., 1960, 235, 2595–2599 and its radiation activity was measured on a liquid scintillation counter. Control was obtained by conducting the experiment in the same manner except that a compound of the present invention was not added. The results were shown in Tables 32 to 35.

TABLE 32

| Compound No. | IC$_{50}$ ($\mu$M) |
|---|---|
| A-1 | 0.17 |
| A-2 | 1.2 |
| A-3 | 1.4 |
| A-4 | 0.30 |
| A-5 | 0.58 |
| A-6 | 4.8 |
| A-7 | 5.0 |
| A-8 | 24 |
| A-9 | 5.5 |
| A-10 | 3.2 |
| A-11 | 0.86 |
| A-12 | 3.1 |
| A-13 | — |
| A-14 | 0.37 |
| A-15 | — |
| A-16 | 0.079 |
| A-17 | 1.6 |
| A-18 | 1.2 |
| A-19 | 1.0 |
| A-20 | 0.30 |
| A-21 | 0.43 |
| A-22 | 0.30 |
| A-23 | 0.46 |
| A-24 | 5.8 |
| A-25 | 0.048 |
| A-26 | 1.0 |
| A-27 | 0.43 |
| A-28 | 0.28 |
| A-29 | 0.086 |
| A-30 | 0.098 |
| A-31 | 0.20 |
| A-32 | 0.067 |
| A-33 | 0.059 |
| A-34 | 0.071 |
| A-35 | 0.040 |
| A-36 | 0.048 |
| A-37 | 0.073 |
| A-38 | 0.084 |
| A-39 | 0.025 |
| A-40 | 0.036 |
| A-41 | 0.056 |
| A-42 | 0.14 |
| A-43 | 0.052 |
| A-44 | 0.057 |
| A-45 | 0.074 |
| A-46 | 0.15 |
| A-47 | 0.056 |
| A-48 | 0.090 |
| A-49 | 0.049 |
| A-50 | 0.67 |
| A-51 | 0.18 |
| A-52 | 0.053 |
| A-54 | 0.14 |
| A-56 | 2.5 |
| A-58 | 0.049 |
| A-59 | 0.047 |
| A-60 | 1.3 |
| A-62 | 0.26 |
| A-64 | 2.2 |
| A-66 | 0.21 |
| A-67 | 0.069 |
| A-69 | 0.072 |
| A-70 | 0.090 |
| A-71 | 0.19 |

TABLE 33

| Compound No. | IC$_{50}$ ($\mu$M) |
|---|---|
| A-73 | 0.11 |
| A-75 | 0.19 |

TABLE 33-continued

| Compound No. | IC$_{50}$ ($\mu$M) |
|---|---|
| A-76 | 0.072 |
| A-77 | 0.10 |
| A-79 | 0.020 |
| A-81 | 0.053 |
| A-82 | 0.050 |
| A-83 | 0.053 |
| A-84 | 0.033 |
| A-86 | 0.028 |
| A-87 | 0.18 |
| A-89 | 0.096 |
| A-91 | 0.050 |
| A-92 | 0.057 |
| A-94 | 0.024 |
| A-95 | 0.076 |
| A-97 | 0.051 |
| A-98 | 0.059 |
| A-99 | 0.037 |
| A-101 | 0.062 |
| A-102 | 0.052 |
| A-103 | 0.058 |
| A-104 | 0.038 |
| A-105 | 0.15 |
| A-106 | 0.20 |
| A-107 | 0.041 |
| A-108 | 0.044 |
| A-109 | 0.059 |
| A-110 | 0.10 |
| A-111 | 0.066 |
| A-112 | 0.065 |
| A-113 | 0.12 |
| A-114 | 0.020 |
| A-115 | 0.010 |
| A-117 | 0.015 |
| A-118 | 0.008 |
| A-119 | 0.030 |
| A-120 | 0.029 |
| A-121 | 0.065 |
| A-122 | 0.035 |
| A-124 | 0.024 |
| A-125 | 0.0066 |
| A-126 | 0.0055 |
| A-128 | 0.034 |
| A-129 | 0.013 |
| A-130 | 0.026 |
| A-132 | 0.0032 |
| A-133 | 0.0022 |
| A-135 | 0.0079 |
| A-136 | 4.7 |
| A-137 | 0.046 |
| A-139 | 0.046 |
| A-140 | 0.021 |
| A-141 | 0.014 |
| B-1 | 0.21 |
| B-2 | 0.084 |
| B-3 | 0.42 |
| B-4 | 0.13 |
| B-5 | 0.44 |
| B-6 | 0.14 |
| B-7 | 1.0 |
| B-8 | 1.0 |
| B-9 | 14 |
| C-1 | 0.35 |

TABLE 34

| Compound No. | IC$_{50}$ ($\mu$M) |
|---|---|
| C-2 | 1.1 |
| E-1 | 1.1 |
| E-2 | 0.28 |
| E-3 | 0.73 |
| E-4 | 1.1 |
| E-5 | 0.75 |
| E-6 | 1.5 |

TABLE 34-continued

| Compound No. | IC$_{50}$ ($\mu$M) |
|---|---|
| E-7 | 1.6 |
| E-8 | 1.4 |
| E-9 | 1.0 |
| E-10 | 0.79 |
| E-11 | 0.32 |
| E-12 | 0.35 |
| E-13 | 0.077 |
| E-14 | 0.098 |
| F-1 | 15 |
| F-2 | 4.7 |
| F-3 | 0.42 |
| F-4 | 0.42 |
| F-5 | 0.62 |
| G-1 | 0.78 |
| G-2 | 5.4 |
| G-3 | 3.3 |
| G-5 | 1.6 |
| G-7 | 2.8 |
| G-8 | 1.1 |
| G-9 | 1.3 |
| G-10 | 2.4 |
| G-11 | 4.0 |
| G-12 | 2.8 |
| G-13 | 5.6 |
| H-1 | 10 |
| I-1 | 0.10 |
| I-2 | 1.0 |
| I-3 | 0.055 |
| I-4 | 0.48 |
| I-5 | 0.034 |
| I-6 | 0.071 |
| I-7 | 0.039 |
| I-8 | 0.033 |
| I-9 | 0.24 |
| I-10 | 0.76 |
| J-1 | 0.084 |
| J-2 | 0.023 |
| J-3 | 0.43 |
| J-4 | 0.81 |
| J-5 | 8.6 |
| J-6 | 13 |
| J-7 | 0.50 |
| M-1 | 1.5 |
| M-2 | 1.4 |
| M-3 | 0.060 |
| M-4 | 0.14 |
| M-5 | 0.10 |
| M-6 | 0.14 |
| M-7 | 0.27 |
| M-8 | 0.060 |
| M-9 | 0.039 |
| M-10 | 0.022 |
| M-11 | 0.036 |
| M-12 | 0.094 |
| M-13 | 0.013 |
| M-14 | 0.027 |
| M-15 | 0.15 |

TABLE 35

| Compound No. | IC$_{50}$ ($\mu$M) |
|---|---|
| M-16 | 2.0 |
| M-17 | 0.0041 |
| M-18 | 0.079 |
| M-19 | 0.0031 |
| M-20 | 0.0064 |
| M-21 | 0.0021 |
| N-1 | 0.14 |
| N-2 | 0.13 |
| N-3 | 0.059 |
| N-4 | 0.069 |
| N-5 | 0.24 |
| O-1 | 0.20 |

TABLE 35-continued

| Compound No. | IC$_{50}$ ($\mu$M) |
|---|---|
| O-2 | 0.058 |
| O-3 | 0.055 |
| Q-1 | 2.51 |
| Q-2 | 1.81 |
| Q-3 | 0.20 |
| Q-4 | 1.85 |
| Q-5 | 1.92 |

Test Example 2 Inhibition of Production of Prostaglandin E$_2$ in Human Fibroblasts.

In order to examine the availability of the composition for inhibiting cytosolic phospholipase A$_2$ (cPLA$_2$) on the cells, the compounds of the present invention were tested for the effect on the production of prostaglandin E$_2$ by human fibroblasts under the stimulation with IL-1 according to the method of J. M. Dayer et al (CACHECTIN/TUMOR NECROSIS FACTOR STIMULATES COLLAGENASE AND PROSTAGLANDIN E$_2$ PRODUCTION BY HUMAN SYNOVIAL CELLS AND DERMAL FIBROBLASTS; J. M. Dayer, B, Beutler and A, Cerami, J. EXP. Med., 1985, 162, 2163–2168.).

As shown in Tables 36 to 38, the production of prostaglandin E$_2$ was significantly inhibited.

TABLE 36

| Compound No. | IC$_{50}$ ($\mu$M) |
|---|---|
| A-1 | 0.17 |
| A-2 | 0.73 |
| A-3 | 0.90 |
| A-4 | 0.21 |
| A-5 | 0.26 |
| A-6 | 8.9 |
| A-10 | 0.47 |
| A-11 | 0.23 |
| A-12 | 0.10 |
| A-13 | — |
| A-14 | 0.33 |
| A-15 | — |
| A-16 | 0.26 |
| A-17 | 0.70 |
| A-18 | 0.38 |
| A-19 | 0.16 |
| A-20 | 0.35 |
| A-21 | 0.23 |
| A-22 | 0.18 |
| A-23 | 1.2 |
| A-25 | 0.80 |
| A-26 | 0.17 |
| A-27 | 1.2 |
| A-28 | 1.4 |
| A-29 | 2.2 |
| A-30 | 0.46 |
| A-32 | 0.57 |
| A-33 | 0.46 |
| A-34 | 0.48 |
| A-35 | 0.18 |
| A-36 | 0.18 |
| A-37 | 0.28 |
| A-38 | 0.43 |
| A-39 | 0.33 |
| A-40 | 0.61 |
| A-41 | 1.2 |
| A-43 | 0.56 |
| A-44 | 0.55 |
| A-45 | 0.38 |
| A-48 | 0.62 |
| A-49 | 0.12 |
| A-52 | 0.62 |
| A-58 | 1.6 |
| A-59 | 0.94 |

TABLE 36-continued

| Compound No. | IC$_{50}$ ($\mu$M) |
|---|---|
| A-60 | 1.3 |
| A-61 | 0.97 |
| A-62 | 1.1 |
| A-63 | 0.90 |
| A-67 | 0.39 |
| A-69 | 0.19 |
| A-70 | 0.19 |
| A-71 | 0.31 |
| A-73 | 0.10 |
| A-75 | 2.2 |
| A-76 | 0.52 |
| A-77 | 0.35 |
| A-79 | 0.31 |
| A-81 | 0.35 |
| A-82 | 0.045 |
| A-83 | 0.23 |
| A-84 | 0.25 |
| A-86 | 0.093 |
| A-87 | 0.33 |
| A-89 | 0.49 |

TABLE 37

| Compound No. | IC$_{50}$ ($\mu$M) |
|---|---|
| A-91 | 0.94 |
| A-94 | 1.4 |
| A-95 | 0.39 |
| A-97 | 0.64 |
| A-98 | 0.44 |
| A-100 | 0.32 |
| A-101 | 0.35 |
| A-102 | 0.33 |
| A-103 | 0.59 |
| A-104 | 1.3 |
| A-107 | 1.1 |
| A-108 | 0.47 |
| A-109 | 1.2 |
| A-111 | 0.47 |
| A-112 | 1.7 |
| A-115 | 4.6 |
| A-117 | 0.20 |
| A-118 | 2.2 |
| A-119 | 2.8 |
| A-120 | 0.74 |
| A-122 | 1.4 |
| A-127 | 0.29 |
| A-128 | 0.44 |
| A-129 | 1.2 |
| A-130 | 0.49 |
| A-132 | 0.27 |
| A-133 | 0.24 |
| A-135 | 0.49 |
| A-137 | 0.84 |
| B-1 | 12 |
| B-2 | 4.0 |
| B-3 | 3.9 |
| B-4 | 5.6 |
| B-5 | 7.4 |
| B-6 | 7.1 |
| B-7 | 8.1 |
| B-8 | 2.7 |
| C-1 | 2.3 |
| C-2 | 2.2 |
| E-1 | 2.2 |
| E-2 | 1.1 |
| E-3 | 6.0 |
| E-4 | 1.2 |
| E-5 | 3.5 |
| E-9 | 6.5 |
| E-12 | 5.7 |
| E-14 | 5.6 |
| F-3 | 3.0 |
| F-4 | 2.8 |

TABLE 37-continued

| Compound No. | IC$_{50}$ ($\mu$M) |
|---|---|
| F-5 | 1.9 |
| G-1 | 0.98 |
| I-1 | 0.26 |
| I-2 | 0.66 |
| I-3 | 0.98 |
| I-4 | 1.3 |
| I-5 | 0.49 |
| I-6 | 0.26 |
| I-7 | 0.69 |
| I-8 | 1.0 |
| I-9 | 1.8 |
| I-10 | 0.32 |
| J-1 | 0.12 |
| J-2 | 0.96 |
| J-3 | 5.7 |

TABLE 38

| Compound No. | IC$_{50}$ ($\mu$M) |
|---|---|
| J-4 | 5.2 |
| J-7 | 6.2 |
| M-3 | 3.1 |
| M-5 | 3.0 |
| M-6 | 1.5 |
| M-7 | 1.5 |
| M-8 | 0.80 |
| M-9 | 3.6 |
| M-10 | 0.27 |
| M-11 | 0.97 |
| M-12 | 0.23 |
| M-14 | 1.4 |
| M-17 | 1.0 |
| M-18 | 8.8 |
| M-21 | 0.31 |
| N-1 | 0.76 |
| N-2 | 1.8 |
| N-3 | 1.0 |
| O-1 | 0.76 |
| O-2 | 0.23 |
| O-3 | 1.1 |
| Q-1 | 1.2 |
| Q-2 | 1.4 |
| Q-3 | 0.49 |
| Q-4 | 0.95 |
| Q-5 | 1.3 |

FORMULATION EXAMPLE

Formulation Example 1

Granules are prepared using the following ingredients.

| Ingredients | | |
|---|---|---|
| | The compound represented by the formula (I) | 10 mg |
| | Lactose | 700 mg |
| | Corn starch | 274 mg |
| | HPC-L | 16 mg |
| | | 1000 mg |

The compound represented by the formula (I) and lactose were made pass through a 60 mesh sieve. Corn starch was made pass through a 120 mesh sieve. They were mixed by a twin shell blender. An aqueous solution of HPC-L (low mucosity hydroxypropylcellulose) was added to the mixture and the resulting mixture was kneaded, granulated (by the extrusion with pore size 0.5 to 1 mm mesh), and dried. The dried granules thus obtained were sieved by a swing sieve (12/60 mesh) to yield the granules.

Formulation 2

Powders for filling capsules are prepared using the following ingredients.

| Ingredients | | |
|---|---|---|
| | The compound represented by the formula (I) | 10 mg |
| | Lactose | 79 mg |
| | Corn starch | 10 mg |
| | Magnesium stearate | 1 mg |
| | | 100 mg |

The compound represented by the formula (I) and lactose were made pass through a 60 mesh sieve. Corn starch was made pass through a 120 mesh sieve. These ingredients and magnesium stearate were mixed by a twin shell blender. 100 mg of the 10-fold trituration was filled into a No. 5 hard gelatin capsule.

Formulation 3

Granules for filling capsules are prepared using the following ingredients.

| Ingredients | | |
|---|---|---|
| | The compound represented by the formula (I) | 15 mg |
| | Lactose | 90 mg |
| | Corn starch | 42 mg |
| | HPC-L | 3 mg |
| | | 150 mg |

The compound represented by the formula (I) and lactose were made pass through a 60 mesh sieve. Corn starch was made pass through a 120 mesh sieve. After mixing them, an aqueous solution of HPC-L was added to the mixture and the resulting mixture was kneaded, granulated, and dried. After the dried granules were lubricated, 150 mg of that were filled into a No. 4 hard gelatin capsule.

Formulation 4

Tablets are prepared using the following ingredients.

| Ingredients | | |
|---|---|---|
| | The compound represented by the formula (I) | 10 mg |
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC-Na (carboxymethylcellulose sodium salt) were made pass through a 60 mesh sieve and then mixed. The resulting mixture was mixed with magnesium stearate to obtain the mixed powder for the tablet formulation. The mixed powder was compressed to yield tablets of 150 mg.

Industrial Applicability

The compounds of the present invention have cytosolic phospholipase $A_2$ inhibitory activity. Therefore, it is consider that the compounds are useful for the prevention or treatment of the inflammatory diseases.

What is claimed is:
1. A compound represented by the formula (I):

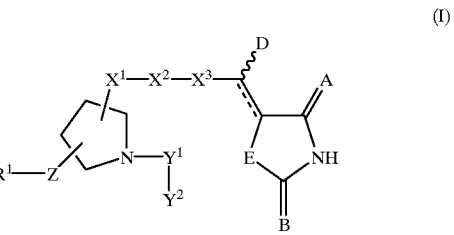

wherein $R^1$ is hydrogen atom, lower alkyl, optionally substituted aryl, aryl fused with a non-aromatic hydrocarbon ring or a non-aromatic heterocyclic ring, optionally substituted aralkyl, optionally substituted arylcarbonyl, or optionally substituted heteroaryl; Z is —S—, —SO—, —O—, —OCH$_2$—, —CONH—, CONHCH$_2$—, —N(R$^{16}$)— (wherein R$^{16}$ is hydrogen atom, alkyl, or aralkyl), or a bond; X$^1$ is —(CH$_2$)$_q$—CO— (wherein q is an integer of 0 to 3), —(CH$_2$)$_r$—CO—N(R$^{17}$)— (wherein R$^{17}$ is hydrogen atom or lower alkyl, and r is an integer of 0 to 3), —CH$_2$NSO$_2$—, —(CH$_2$)$_s$—N(R$^{18}$)—CO— (wherein R$^{18}$ is hydrogen atom or lower alkyl, s is an integer of 0 to 3), —CH$_2$NHCOCH$_2$O—, —CH$_2$N(R$^{19}$)COCH=CH— (wherein R$^{19}$ is hydrogen atom or lower alkyl), —CH$_2$NHCS—, —CH$_2$O—, —OCH$_2$—, —CH$_2$OCH$_2$—, —CH$_2$—N(R$^{20}$)—CH$_2$— (wherein R$^{20}$ is hydrogen atom, lower alkyl, or acyl), alkylene, alkenylene, or a bond; X$^2$ is optionally substituted arylene, optionally substituted heteroarylene, heterocyclediyl, —C≡C—, or a bond; X$^3$ is alkylene, alkenylene, or a bond; A, B, and E are each independently oxygen atom or sulfur atom; D is hydrogen atom or hydroxy lower alkyl; Y$^1$ is —(CH$_2$)$_m$CO—, —(CH$_2$)$_m$CONH—, —(CH$_2$)$_m$CSNH—, —(CH$_2$)$_m$SO$_2$—, —(CH$_2$)$_m$COO—, —(CH$_2$)$_n$NHCO—, —(CH$_2$)$_n$NHSO$_2$—, or a bond; m is an integer of 0 to 3; n is an integer of 1 to 3; Y$^2$ is a substituent represented by the formula:

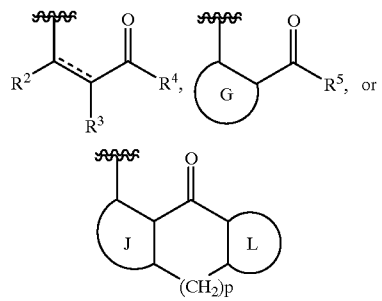

wherein $R^2$ and $R^3$ are both hydrogen atom or one is optionally substituted aryl, optionally substituted heteroaryl, or optionally substituted cycloalkyl, and the other is hydrogen atom or lower alkyl; $R^4$, $R^5$, G ring, J ring, and L ring are each independently optionally substituted aryl, optionally substituted heteroaryl, optionally substituted cycloalkyl, or cycloalkenyl; a broken line (— — —) represents the presence or absence of a bond; and p is an integer of 0 to 2; a broken line (— — — —) represents the presence or absence of a bond; a wavy line (~) represents cis or trans configuration of D to E; provided that X$^1$ is alkylene and X$^2$ and X$^3$ are both bonds when the carbon atom attached to D and the adjacent carbon atom in the ring is linked by a single bond, and Y$^1$ is not a bond when X$^1$ is —CH$_2$O—, its pharmaceutically acceptable salt, or hydrate thereof.

2. A compound represented by the formula (II):

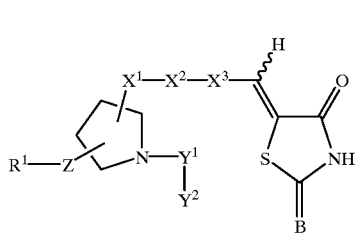
(II)

wherein $R^1$, Z, $X^1$, $X^2$, $X^3$, $Y^1$, $Y^2$, and B are as defined in claim 1, a wavy line represents cis or trans configuration of hydrogen atom to sulfur atom, provided that $Y^1$ is not a bond when $X^1$ is —CH$_2$O—, its pharmaceutically acceptable salt, or hydrate thereof.

3. A compound represented by the formula (III):

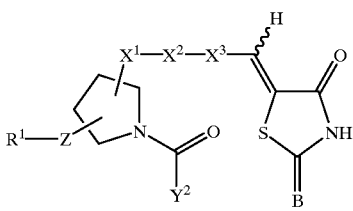
(III)

wherein $R^1$, Z, $X^1$, $X^2$, $X^3$, $Y^2$, B, and a wavy line are as defined in claim 1, its pharmaceutically acceptable salt, or hydrate thereof.

4. A compound represented by the formula (IV):

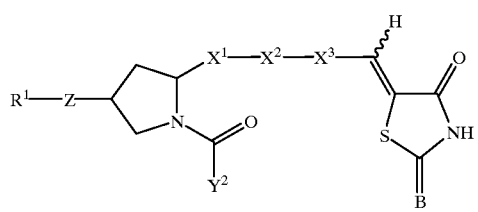
(IV)

wherein $R^1$, Z, $X^1$, $X^2$, $X^3$, $Y^2$, B, and a wavy line are as defined in claim 1, its pharmaceutically acceptable salt, or hydrate thereof.

5. A compound represented by the formula (V):

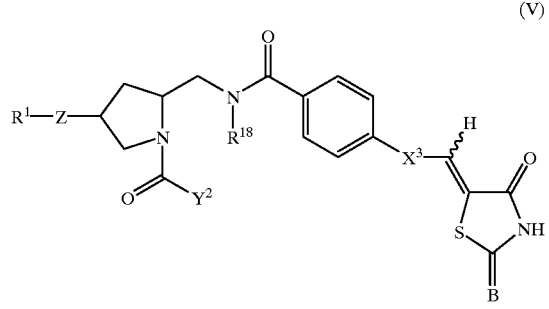
(V)

wherein $R^1$, Z, $R^{18}$, $X^3$, $Y^2$, B, and a wavy line are as defined in claim 1, its pharmaceutically acceptable salt, or hydrate thereof.

6. A compound represented by the formula (VI):

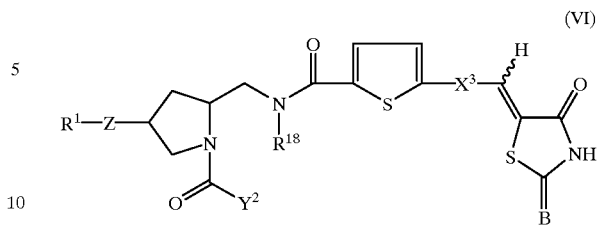
(VI)

wherein $R^1$, Z, $R^{18}$, $X^3$, $Y^2$, B, and a wavy line are as defined in claim 1, it pharmaceutically acceptable salt, or hydrate thereof.

7. A compound represented by the formula (VII):

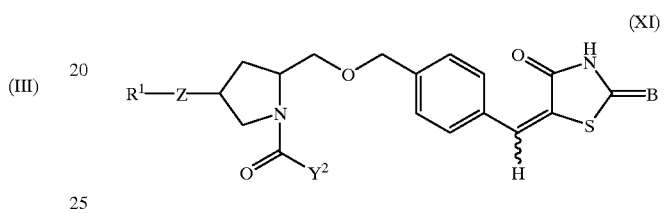
(XI)

wherein $R^1$, Z, $R^{19}$, $X^3$, $Y^2$, B, and a wavy line are as defined in claim 1, its pharmaceutically acceptable salt, or hydrate thereof.

8. A compound represented by the formula (VIII):

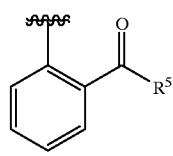

wherein $R^1$, Z, $Y^2$, B, and a wavy line are as defined in claim 1, its pharmaceutically acceptable salt, or hydrate thereof.

9. A compound represented by the formula (IX):

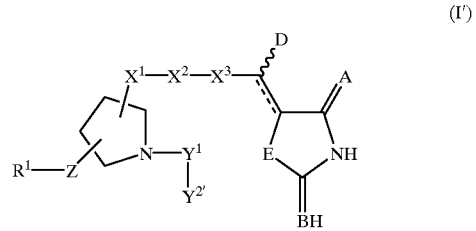
(I')

wherein $R^1$, Z, $Y^2$, B, and a wavy line are as defined in claim 1, its pharmaceutically acceptable salt, or hydrate thereof.

10. A compound represented by the formula (X):

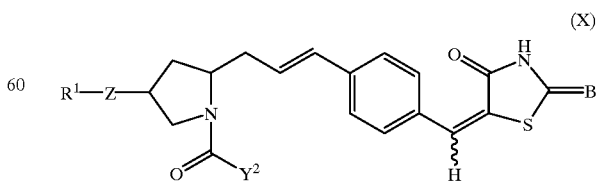
(X)

wherein $R^1$, Z, $Y^2$, B, and a wavy line are as defined in claim 1, its pharmaceutically acceptable salt, or hydrate thereof.

11. A compound represented by the formula (XI):

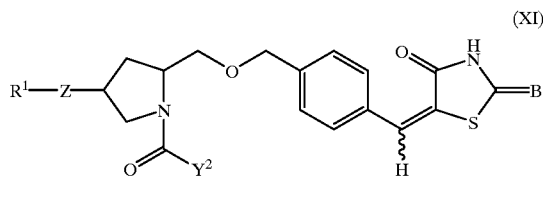

(XI)

wherein $R^1$, $Z$, $Y^2$, $B$, and a wavy line are as defined in claim 1, its pharmaceutically acceptable salt, or hydrate thereof.

12. The compound of claim 1, wherein Z is —N($R^{16}$)—, its pharmaceutically acceptable salt, or hydrate thereof.

13. The compound of claim 5, wherein $R^{18}$ is hydrogen atoms and $X^3$ is a bond, its pharmaceutically acceptable salt, or hydrate thereof.

14. The compound of claim 1, wherein $R^1$ is optionally substituted aryl, aryl fused with a non-aromatic hydrocarbon ring or a non-aromatic heterocyclic ring, optionally substituted aralkyl, its pharmaceutically acceptable salt, or hydrate thereof.

15. The compound of claim 1, wherein $Y^2$ is a substituent represented by the formula:

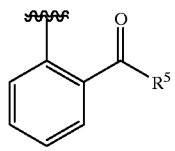

wherein $R^5$ is optionally substituted aryl, its pharmaceutically acceptable salt, or hydrate thereof.

16. A compound represented by the formula (I'):

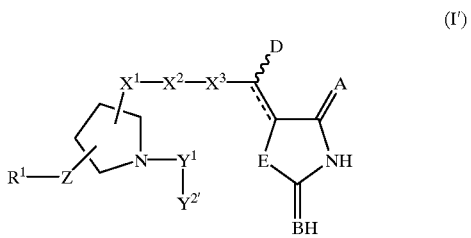

(I')

wherein Z is —N($R^{16}$)—, $Y^{2'}$ is optionally substituted aryl, and $R^1$, $X^1$, $X^2$, $X^3$, $Y^1$, A, B, a wavy line, and a broken line are as defined in claim 1, its pharmaceutically acceptable salt, or hydrate thereof.

17. A pharmaceutical composition which contains a compound of claim claim 1 as an active ingredient.

18. A composition for inhibiting phospholipase $A_2$ which contains a compound of claim 1 as an active ingredient.

19. A composition for inhibiting the production of arachidonic acid which contains a compound of claim 1 as an active ingredient.

20. A composition for inhibiting the production of prostaglandin $E_2$ which contains a compound of claim 1 as an active ingredient.

21. A composition for inhibiting the production of leukotriene $C_4$ which contains a compound of claim 1 as an active ingredient.

22. A method for the prevention or treatment of an inflammatory disease, comprising administering to a patient in need thereof an effective amount of a compound according to claim 1.

23. A method according to claim 22, wherein said inflammatory disease is rheumatoid arthritis, asthma, inflammatory bowel diseases, injury due to ischemic reperfusion, allergic rhinitis or psoriasis.

* * * * *

UNITED STATES PATENT AND TRADEMARK OFFICE
CERTIFICATE OF CORRECTION

PATENT NO. : 6,147,100
DATED : November 14, 2000
INVENTOR(S) : Kaoru Seno et al.

It is certified that error appears in the above-identified patent and that said Letters Patent is hereby corrected as shown below:

Column 184,
Line 19, please delete:

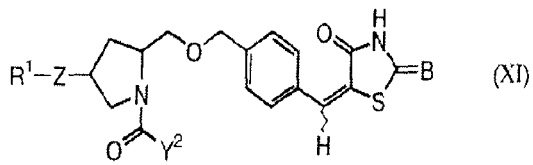 (XI)

and replace with the following:
--

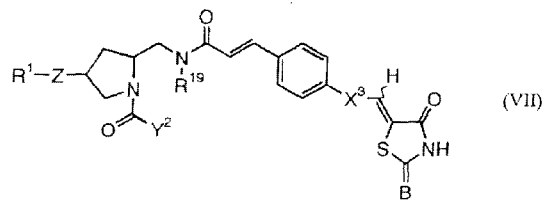 (VII)

Column 184,
Line 31, please delete:

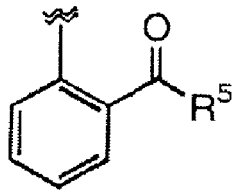

and replace with the following:
--

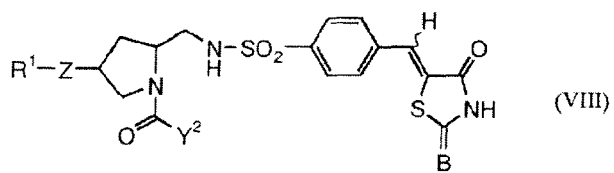 (VIII)

--

UNITED STATES PATENT AND TRADEMARK OFFICE
CERTIFICATE OF CORRECTION

PATENT NO.  : 6,147,100
DATED       : November 14, 2000
INVENTOR(S) : Kaoru Seno et al.

It is certified that error appears in the above-identified patent and that said Letters Patent is hereby corrected as shown below:

Column 184 cont'd.
Line 45, please delete:

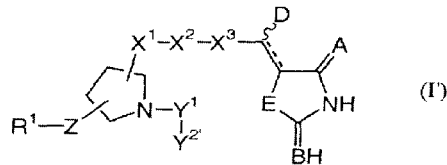

and replace with the following:

--
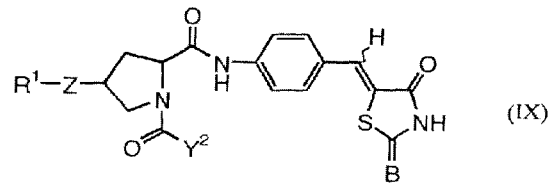
--

Column 186,
Line 5, please delete:

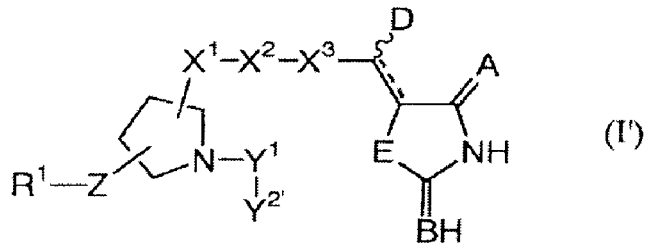

UNITED STATES PATENT AND TRADEMARK OFFICE
CERTIFICATE OF CORRECTION

PATENT NO.   : 6,147,100
DATED        : November 14, 2000
INVENTOR(S)  : Kaoru Seno et al.

It is certified that error appears in the above-identified patent and that said Letters Patent is hereby corrected as shown below:

<u>Column 186 cont'd.</u>
and replace with the following:
--

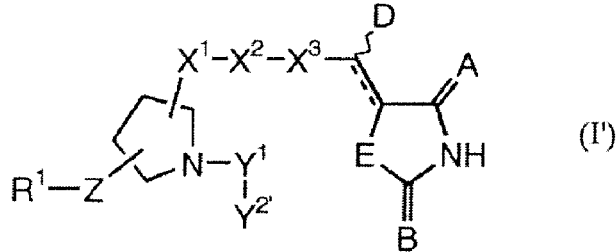

(I')

--

Signed and Sealed this

Eighth Day of October, 2002

*Attest:*

*Attesting Officer*

JAMES E. ROGAN
*Director of the United States Patent and Trademark Office*